United States Patent

Kimura et al.

[11] Patent Number: 5,908,858
[45] Date of Patent: Jun. 1, 1999

[54] 1,2-DIPHENYLPYRROLE DERIVATIVES, THEIR PREPARATION AND THEIR THERAPEUTIC USES

[75] Inventors: Tomio Kimura, Tokyo; Yasuo Noguchi, Hiratsuka; Akira Nakao, Tokyo; Keisuke Suzuki, Tokyo; Shigeru Ushiyama, Tokyo; Akihiro Kawara, Yokohama; Masaaki Miyamoto, Fujisawa, all of Japan

[73] Assignee: Sankyo Company, Limited, Tokyo, Japan

[21] Appl. No.: 08/824,775

[22] Filed: Mar. 26, 1997

[30] Foreign Application Priority Data

Apr. 5, 1996 [JP] Japan ............................ 8-083562

[51] Int. Cl.$^6$ ................ A61K 31/40; C07D 207/333; C07D 207/335; C07D 207/337
[52] U.S. Cl. ..................... 514/427; 514/422; 548/517; 548/526; 548/562; 548/563
[58] Field of Search ................... 548/562, 563, 548/526, 517; 514/422, 427

[56] References Cited

U.S. PATENT DOCUMENTS

| | | | |
|---|---|---|---|
| 3,427,305 | 2/1969 | Chinn et al. | 260/239.6 |
| 5,344,991 | 9/1994 | Reitz et al. | 568/34 |
| 5,418,254 | 5/1995 | Huang et al. | 514/604 |
| 5,434,178 | 7/1995 | Talley et al. | 514/406 |
| 5,486,534 | 1/1996 | Lee et al. | 514/406 |

FOREIGN PATENT DOCUMENTS

| | | |
|---|---|---|
| 1 938 904 | 2/1970 | Germany . |
| 2-240058 | 9/1990 | Japan . |
| 3-141261 | 6/1991 | Japan . |
| 5-1027 | 1/1993 | Japan . |
| WO 94/15932 | 7/1994 | WIPO . |
| WO 94/27980 | 12/1994 | WIPO . |
| WO 95/00501 | 1/1995 | WIPO . |
| WO 95/15316 | 6/1995 | WIPO . |
| WO 96/03387 | 2/1996 | WIPO . |
| WO 96/03388 | 2/1996 | WIPO . |
| WO 96/03392 | 2/1996 | WIPO . |
| WO 96/19463 | 6/1996 | WIPO . |
| WO 96/25405 | 8/1996 | WIPO . |

OTHER PUBLICATIONS

Chemical Abstracts, vol. 105, No. 17, Oct. 27, 1986, Columbus, Ohio, Abstract No. 152868p, LI, et al: "Synthesis and properties of 1–aryl–3–benzoyl–2–,5–diphenylpyrroles" of Gaodeng Xuexiao Huaxue Xuebao (1985), 6(10), 917–18.

Chemical Abstracts, vol. 104, No. 15, Apr. 14, 1986, Columbus, Ohio, Abstract No. 129728p, LI, et al: "Synthesis and properties of polysubstituted pyrroles, (II)" of Gaodeng Xuexiao Huaxue Xuebao (1985), 6(6), 513–14.

Primary Examiner—Laura L. Stockton
Attorney, Agent, or Firm—Frishauf, Holtz, Goodman, Langer & Chick, P.C.

[57] ABSTRACT

Compounds of formula (I) and (II):

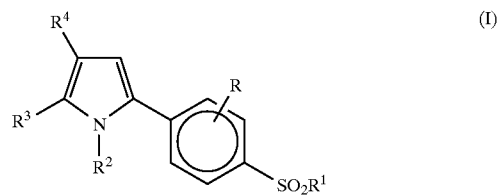

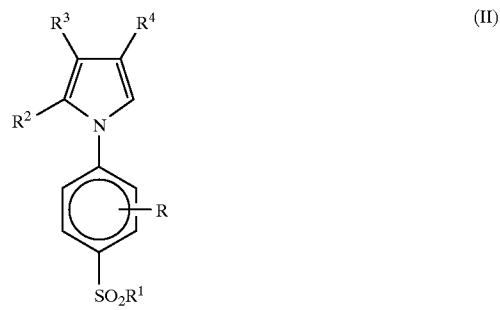

[wherein R is hydrogen, halogen or alkyl; $R^1$ is alkyl, amino or substituted amino; $R^2$ is optionally substituted phenyl; $R^3$ is hydrogen, halogen or optionally substituted alkyl; $R^4$ is hydrogen, optionally substituted alkyl, cycloalkyl, aryl, or aralkyl] have valuable analgesic, anti-inflammatory, antipyretic and anti-allergic activities and have the ability to inhibit the production of leukotrienes and to inhibit bone resorption. They are relatively free from the side effects which generally result from the administration of compounds having these kinds of activities.

43 Claims, No Drawings

1,2-DIPHENYLPYRROLE DERIVATIVES, THEIR PREPARATION AND THEIR THERAPEUTIC USES

BACKGROUND TO THE INVENTION

The present invention relates to a series of new 1,2-diphenylpyrrole derivatives which have valuable analgesic, anti-inflammatory, anti-pyretic and anti-allergic activities and have the ability to inhibit the production of leukotrienes and to inhibit bone resorption, and which are relatively free from the side effects which generally result from the administration of compounds having these kinds of activities. The invention also provides methods and compositions using these novel compounds as well as processes for their preparation.

Non-steroidal anti-inflammatory drugs (NSAIDs) have been widely used for clinical purposes for the treatment of inflammatory diseases, such as pyrexia, pain and edema. However, the adverse effects of these drugs, such as gastrointestinal disorders and renal disorders, present problems to any patient who takes the drug for an extended period of time as well as to older patients. There are two major metabolic pathways beginning with the arachidonic acids. These are the pathway leading to the production of prostaglandins (PG) and the pathway leading to the production of leukotrienes (LT).

NSAIDs are believed to act by inhibiting the action of PG cyclooxygenase (COX) which is a crucial step in the production of PG from arachidonic acid. It has recently been found that two isozymes, called COX-1 and COX-2, are present in COX.

It has been discovered that COX-1 is normally present in the stomach, the intestines, the kidneys and other tissues and serves to produce PG which functions physiologically, while COX-2 is induced by inflammatory cytokines and endotoxins, such as IL-1, TNFα, and the like, and is expressed specifically at an inflammatory site to produce PG which functions as a mediator of inflammatory reactions. With the discovery of these two isozymes, it was thought that anti-inflammatory agents which specifically inhibit COX-2 without inhibiting COX-1 would be free from the side effects caused by conventional drugs and could be a new type of anti-inflammatory agent.

On the other hand, it is known that IL-1, TNFα, IL-6 and IL-8, the inflammatory cytokines, are produced in monocytes, macrophages and synovial cells as a result of various inflammatory stimulants and influence a number of biological processes, such as the production of PG, the expression of cell adhesion molecules, the production of collagenase-protease, the activation of osteoclasts, pyrexia, the production of acute phase protein, and chemotactic activity of leukocytes.

It is said that these cytokines are associated with the progression of various diseases, such as the chronic inflammatory diseases, including chronic rheumatic arthritis. Thus, drugs which inhibit cytokine actions are useful as a new type of anti-inflammatory agent.

Recently, it has been considered that the prostaglandins, synthesised by the osteoblast cells through induction by COX-2, activate the osteoclast cells and thus induce bone resorption. Accordingly, COX-2 inhibitors are expected to be useful for the treatment and prophylaxis of diseases which are accompanied by or result from bone resorption or destruction, such as osteoporosis, rheumatoid arthritis and osteoarthritis.

Leukotrienes, on the other hand, have been demonstrated to be heavily involved in inflammation, allergy and gastric ulcer formation.

Inhibitors of both LT and PG synthesis are therefore thought to be more desirable drugs for the treatment and prophylaxis of inflammatory diseases.

Amongst the known 1,2-diphenylpyrrole derivatives having analgesic and antiphlogistic actions, a compound represented by the following formula is disclosed in German Patent No. 1938904:

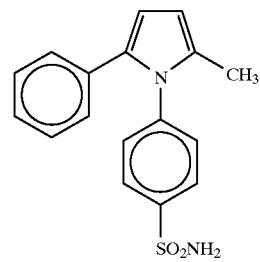

This compound is hereinafter referred to as "Compound A".

However, this compound is not sufficiently effective, and so more effective compounds would be desirable.

We have now discovered a series of new compounds which have the required activity and which do not appear to exhibit the side effects of known compounds. Moreover, the compounds also surprisingly have the ability to inhibit the production of leukotrienes and to inhibit bone resorption, both of which are of therapeutic and prophylactic value.

BRIEF SUMMARY OF THE INVENTION

It is therefore an object of the present invention to provide a series of new compounds which are useful for the treatment, prophylaxis and alleviation of pain and inflammation and which inhibit the production of leukotrienes and inhibit bone resorption.

It is a further, and more specific object of the present invention to provide such compounds which are, in general, free from or relatively less susceptible to such side effects as gastrointestinal disturbances.

Other objects and advantages will become apparent as the description proceeds.

The compounds of the present invention are those compounds of formula (I) and (II):

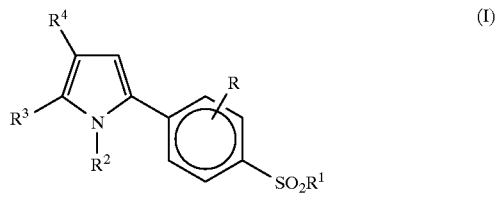

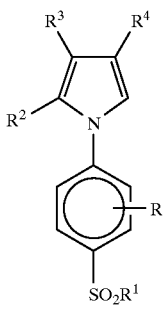

wherein:

R represents a hydrogen atom, a halogen atom or an alkyl group having from 1 to 6 carbon atoms;

$R^1$ represents an alkyl group having from 1 to 6 carbon atoms, an amino group or a group of formula —$NHR^a$, where $R^a$ represents an alkanoyl group having from 1 to 25 carbon atoms, an alkoxycarbonyl group having from 1 to 6 carbon atoms in the alkoxy part, an aralkyloxycarbonyl group in which the aralkyl part is as defined below, an alkanoyloxymethyl group having from 1 to 6 carbon atoms in the alkanoyl part, an alkoxycarbonyloxymethyl group having from 1 to 6 carbon atoms in the alkoxy part or a (2-oxo-1,3-dioxolen-4-yl)methyl group which is unsubstituted or is substituted at the 5-dioxolen position by an alkyl group having from 1 to 6 carbon atoms or by an aryl group as defined below;

$R^2$ represents a phenyl group which is unsubstituted or is substituted by at least one substituent selected from the group consisting of substituents α and substituents β, defined below;

$R^3$ represents a hydrogen atom, a halogen atom or an alkyl group which has from 1 to 6 carbon atoms and which is unsubstituted or is substituted by at least one substituent selected from the group consisting of substituents α, defined below;

$R^4$ represents a hydrogen atom, an alkyl group which has from 1 to 6 carbon atoms and which is unsubstituted or is substituted by at least one substituent selected from the group consisting of substituents α, defined below, a cycloalkyl group having from 3 to 8 carbon atoms, an aryl group which is as defined below, or an aralkyl group which is as defined below;

said aryl groups have from 6 to 14 ring carbon atoms in a carbocyclic ring and are unsubstituted or are substituted by at least one substituent selected from the group consisting of substituents α and substituents β, defined below;

said aralkyl groups and the aralkyl parts of said aralkyloxycarbonyl groups are alkyl groups having from 1 to 6 carbon atoms and which are substituted by at least one aryl group as defined above;

said substituents α are selected from the group consisting of hydroxy groups, halogen atoms, alkoxy groups having from 1 to 6 carbon atoms and alkylthio groups having from 1 to 6 carbon atoms;

said substituents β are selected from the group consisting of alkyl groups which have from 1 to 6 carbon atoms and which are unsubstituted or are substituted by at least one substituent selected from the group consisting of substituents α, defined above, alkanoyloxy groups having from 1 to 6 carbon atoms, mercapto groups, alkanoylthio groups having from 1 to 6 carbon atoms, alkylsulfinyl groups having from 1 to 6 carbon atoms, cycloalkyloxy groups having from 3 to 8 carbon atoms, haloalkoxy groups having from 1 to 6 carbon atoms and alkylenedioxy groups having from 1 to 6 carbon atoms;

and pharmaceutically acceptable salts thereof.

The invention also provides a method of treating or relieving pain or inflammation in a mammal, which may be human, suffering therefrom by the administration of an anti-inflammatory and analgesic compound selected from the group consisting of compounds of formula (I) and (II) and pharmaceutically acceptable salts thereof.

The invention also provides a method of inhibiting bone resorption in a mammal, which may be human, suffering therefrom by the administration of an active compound selected from the group consisting of compounds of formula (I) and (II) and pharmaceutically acceptable salts thereof.

The invention also provides a method of inhibiting leukotriene production in a mammal, which may be human, by the administration of an active compound selected from the group consisting of compounds of formula (I) and (II) and pharmaceutically acceptable salts thereof.

DETAILED DESCRIPTION OF THE INVENTION

In the compounds of the present invention, where R represents a halogen atom, this may be a fluorine, chlorine, bromine or iodine atom, of which the fluorine and chlorine atoms are preferred and the fluorine atom is most preferred.

Where R represents an alkyl group having from 1 to 6 carbon atoms, this may be a straight or branched chain group, and examples include the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups. Of these, we prefer those alkyl groups having from 1 to 4 carbon atoms, preferably the methyl, ethyl, propyl, isopropyl, butyl and isobutyl groups, and most preferably the methyl group.

Of the above groups and atoms, we prefer that R should represent a hydrogen atom, a fluorine atom, a chlorine atom or a methyl group, of which the hydrogen atom is most preferred.

Where $R^1$ represents an alkyl group having from 1 to 6 carbon atoms, this may be a straight or branched chain group, and examples include the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups. Of these, we prefer those alkyl groups having from 1 to 4 carbon atoms, preferably the methyl, ethyl, propyl, isopropyl, butyl and isobutyl groups, and most preferably the methyl group.

Where $R^1$ represents a group of formula —$NHR^a$, and where $R^a$ represents an alkanoyl group, this is an alkanoylamino group, which may be a straight or branched chain group having from 1 to 25 carbon atoms, more preferably from 1 to 20 carbon atoms, still more preferably from 1 to 6 carbon atoms, and most preferably from 1 to 4 carbon atoms. Examples of such alkanoylamino groups include the formylamino, acetylamino, propionylamino, butyrylamino, isobutyrylamino, pivaloylamino, valerylamino, isovalerylamino, hexanoylamino, heptanoylamino, octanoylamino, nonanoylamino, decanoylamino, undecanoylamino, lauroylamino, tridecanoylamino, myristoylamino, palmitoylamino, stearoylamino, icosanoylamino, docosanoylamino and pentacosanoylamino groups, of which those alkanoylamino groups having from 1 to 12 carbon atoms are preferred and the acetylamino group is most preferred.

Where $R^1$ represents a group of formula —$NHR^a$, and where $R^a$ represents an alkoxycarbonyl group having from 1 to 6 carbon atoms in the alkoxy part, this is an alkoxycarbonylamino group. The alkoxy part may be a straight or branched chain group having from 1 to 6 carbon atoms. Examples of such alkoxycarbonylamino groups include the methoxycarbonylamino, ethoxycarbonylamino, propoxycarbonylamino, isopropoxycarbonylamino, butoxycarbonylamino, isobutoxycarbonylamino, sec-butoxycarbonylamino, t-butoxycarbonylamino, pentyloxycarbonylamino, isopentyloxycarbonylamino, neopentyloxycarbonylamino, 2-methylbutoxycarbonylamino, 1-ethylpropoxycarbonylamino, 4-methylpentyloxycarbonylamino, 3-methylpentyloxycarbonylamino, 2-methylpentyloxycarbonylamino, 1-methylpentyloxycarbonylamino, 3,3-dimethylbutoxycarbonylamino, 2,2-dimethylbutoxycarbonylamino, 1,1-dimethylbutoxycarbonylamino, 1,2-dimethylbutoxycarbonylamino, 1,3-dimethylbutoxycarbonylamino, 2,3-dimethylbutoxycarbonylamino, 2-ethylbutoxycarbonylamino, hexyloxycarbonylamino and isohexyloxycarbonylamino groups. Of these, we prefer those alkoxycarbonylamino groups having from 1 to 4 carbon atoms in the alkoxy part, preferably the methoxycarbonylamino, ethoxycarbonylamino, propoxycarbonylamino, isopropoxycarbonylamino, butoxycarbonylamino, isobutoxycarbonylamino, sec-butoxycarbonylamino and t-butoxycarbonylamino groups, and most preferably the methoxycarbonylamino or ethoxycarbonylamino group.

Where $R^1$ represents a group of formula —$NHR^a$, and where $R^a$ represents an aralkyloxycarbonyl group, the aryl part of this group is a carbocyclic aromatic group preferably having from 6 to 14 ring carbon atoms, more preferably from 6 to 10 ring carbon atoms, and may be substituted or unsubstituted. If substituted, the substituents are preferably selected from the group consisting of substituents α and substituents β, defined and exemplified above, and there is no particular restriction on the number of such substituents, except such as may be imposed by the number of substitutable positions (5 in the case of phenyl groups and 7 in the case of naphthyl groups) and possibly by steric constraints. Examples of such aryl groups are as given below, but the unsubstituted groups, particularly the phenyl group, are preferred. The aralkyl group may contain from 1 to 3 such aryl groups, preferably one aryl group. The alkyl part of the aralkyl group may be any of the alkyl groups exemplified above in relation to R, but is preferably such a group having from 1 to 4 carbon atoms, preferably the methyl, ethyl or propyl group, and most preferably the methyl group. The most preferred aralkyl group is the benzyl group. Specific examples of the aralkyloxycarbonylamino groups which may be represented by $R^1$ are the benzyloxycarbonylamino, 1-naphthyloxycarbonylamino, 2-naphthyloxycarbonylamino, o-, m- and p-chlorobenzyloxycarbonylamino, and o-, m- and p-methylbenzyloxycarbonylamino groups, of which the benzyloxycarbonylamino group is most preferred.

Where $R^1$ represents a group of formula —$NHR^a$, and where $R^a$ represents an alkanoyloxymethyl group, this has from 1 to 6 carbon atoms in the alkanoyl part. Examples of alkanoyl groups are those alkanoyl groups having from 1 to 6 carbon atoms and included in the alkanoylamino groups exemplified above. Specific examples of alkanoyloxymethylamino groups include the formyloxymethylamino, acetoxymethylamino, propionyloxymethylamino, butyryloxymethylamino, isobutyryloxymethylamino, pivaloyloxymethylamino, valeryloxymethylamino, isovaleryloxymethylamino and hexanoyloxymethylamino groups, of which the acetoxymethylamino, propionyloxymethylamino, butyryloxymethylamino and pivaloyloxymethylamino groups are preferred.

Where $R^1$ represents a group of formula —$NHR^a$, and where $R^a$ represents an alkoxycarbonyloxymethyl group having from 1 to 6 carbon atoms in the alkoxy part, the alkoxy part may be a straight or branched chain group. Examples of such alkoxycarbonyloxymethylamino groups include the methoxycarbonyloxymethylamino, ethoxycarbonyloxymethylamino, propoxycarbonyloxymethylamino, isopropoxycarbonyloxymethylamino, butoxycarbonyloxymethylamino, isobutoxycarbonyloxymethylamino, sec-butoxycarbonyloxymethylamino, t-butoxycarbonyloxymethylamino, pentyloxycarbonyloxyrnethylamino, isopentyloxycarbonyloxymethylamino, neopentyloxycarbonyloxymethylamino, 2-methylbutoxycarbonyloxymethylamino, 1-ethylpropoxycarbonyloxymethylamino, 4-methylpentyloxycarbonyloxymethylamino, 3-methylpentyloxycarbonyloxymethylamino, 2-methylpentyloxycarbonyloxymethylamino, 1-methylpentyloxycarbonyloxymethylamino, 3,3-dimethylbutoxycarbonyloxymethylamino, 2,2-dimethylbutoxycarbonyloxymethylamino, 1,1-dimethylbutoxycarbonyloxymethylamino, 1,2-dimethylbutoxycarbonyloxymethylamino, 1,3-dimethylbutoxycarbonyloxymethylamino, 2,3-dimethylbutoxycarbonyloxymethylamino, 2-ethylbutoxycarbonyloxymethylamino, hexyloxycarbonylox-methylamino and isohexyloxycarbonyloxy-methylamino groups. Of these, we prefer those alkoxycarbonyloxymethylamino groups having from 1 to 4 carbon atoms in the alkoxy part, preferably the methoxycarbonyloxymethylamino, ethoxycarbonyloxymethylamino, propoxycarbonyloxymethylamino, isopropoxycarbonyloxymethylamino, butoxycarbonyloxymethylamino, isobutoxycarbonyloxymethylamino, sec-butoxycarbonyloxymethylamino and t-butoxycarbonyloxymethylamino groups, and most preferably the methoxycarbonyloxymethylamino or ethoxycarbonyloxymethylamino group.

Where $R^1$ represents a group of formula —$NHR^a$, and where $R^a$ represents a (2-oxo-1,3-dioxolen-4-yl)methyl group, this is unsubstituted or is substituted at the 5-dioxolen position by an alkyl group having from 1 to 6 carbon atoms or by an aryl group. Examples of such alkyl groups include those exemplified above in relation to R, preferably the methyl, ethyl or t-butyl group. Examples of such aryl groups include those exemplified below in relation to $R^4$, preferably the phenyl group. Specific examples of such (2-oxo-1,3-dioxolen-4-yl)methyl groups include the (2-oxo-1,3-dioxolen-4-yl)methyl, (5-methyl-2-oxo-1,3-dioxolen-4-yl) methyl, (5-ethyl-2-oxo-1,3-dioxolen-4-yl)methyl, (5-t-butyl-2-oxo-1,3-dioxolen-4-yl)methyl and (5-phenyl-2-oxo-1,3-dioxolen-4-yl)methyl groups.

Of the above groups and atoms, we prefer that $R^1$ should represent a methyl group, an amino group or an acetylamino group, of which the amino group and the acetylamino group are most preferred.

Where $R^2$ represents a substituted phenyl group, this may have from 1 to 5 substituents, preferably from 1 to 3 substituents, more preferably 1 or 2 substituents, and most preferably 1 substituent. Where there is more than one substituent, these may be the same as or different from each other. The substituents are selected from the group consisting of substituents α and substituents β, defined above and exemplified below, more preferably from substituents $α^1$ and substituents $β^1$, defined and exemplified below, and still more preferably from substituents $α^1$ and substituents $β^2$, defined and exemplified below.

Substituents $α^1$ are selected from the group consisting of halogen atoms, alkoxy groups having from 1 to 4 carbon atoms and alkylthio groups having from 1 to 4 carbon atoms.

Substituents $β^1$ are selected from the group consisting of alkyl groups having from 1 to 4 carbon atoms, alkyl groups which have from 1 to 4 carbon atoms and which are substituted by at least one substituent selected from the group consisting of substituents $α^1$, mercapto groups, alkanoylthio groups having from 1 to 4 carbon atoms, haloalkoxy groups having from 1 to 4 carbon atoms and alkylenedioxy groups having from 1 to 4 carbon atoms.

Substituents $β^2$ are selected from the group consisting of alkyl groups having from 1 to 4 carbon atoms, haloalkyl groups having from 1 to 4 carbon atoms, mercapto groups, alkanoylthio groups having from 1 to 4 carbon atoms, haloalkoxy groups having from 1 to 4 carbon atoms and alkylenedioxy groups having from 1 to 4 carbon atoms.

Where substituent α or substituent $α^1$ represents a halogen atom, this may be a fluorine, chlorine, bromine or iodine atom, of which the fluorine, chlorine and bromine atoms are preferred.

Where substituent α or substituent $α^1$ represents an alkoxy group having from 1 to 6 (or 4) carbon atoms, this may be a straight or branched chain group, and examples include the methoxy, ethoxy, propoxy, isopropoxy, butoxy, isobutoxy, sec-butoxy, t-butoxy, pentyloxy, isopentyloxy, neopentyloxy, 2-methylbutoxy, 1-ethylpropoxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy, 2-ethylbutoxy, hexyloxy and isohexyloxy groups. Of these, we prefer those alkoxy groups having from 1 to 4 carbon atoms, preferably the methoxy, ethoxy, propoxy, isopropoxy, butoxy, isobutoxy, sec-butoxy and t-butoxy groups, and most preferably the methoxy and ethoxy groups.

Where substituent α or substituent $α^1$ represents an alkylthio group having from 1 to 6 (or 4) carbon atoms, this may be a straight or branched chain group, and examples include the methylthio, ethylthio, propylthio, isopropylthio, butylthio, isobutylthio, sec-butylthio, t-butylthio, pentylthio, isopentylthio, neopentylthio, 2-methylbutylthio, 1-ethylpropylthio, 4-methylpentylthio, 3-methylpentylthio, 2-methylpentylthio, 1-methylpentylthio, 3,3-dimethylbutylthio, 2,2-dimethylbutylthio, 1,1-dimethylbutylthio, 1,2-dimethylbutylthio, 1,3-dimethylbutylthio, 2,3-dimethylbutylthio, 2-ethylbutylthio, hexylthio and isohexylthio groups. Of these, we prefer those alkylthio groups having from 1 to 4 carbon atoms, preferably the methylthio, ethylthio, propylthio, isopropylthio, butylthio, isobutylthio, sec-butylthio and t-butylthio groups, and most preferably the methylthio and ethylthio groups.

Where substituent β, substituent $β^1$ or substituent $β^2$ represents an alkyl group having from 1 to 6 (or 4) carbon atoms, this may be a straight or branched chain group, and examples include the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups. Of these, we prefer those alkyl groups having from 1 to 4 carbon atoms, preferably the methyl, ethyl, propyl, isopropyl, butyl, isobutyl, sec-butyl and t-butyl groups, and most preferably the methyl and ethyl groups. Such groups may be unsubstituted or they may be substituted by at least one of substituents α (or $α^1$) defined and exemplified above, particularly the halogen atoms. Specific examples of such haloalkyl groups include the fluoromethyl, difluoromethyl, trifluoromethyl, 2-fluoroethyl, 2,2-difluoroethyl, 2,2,2-trifluoroethyl, 2,2,2-trichloroethyl, 3-fluoropropyl, 4-fluorobutyl, chloromethyl, trichloromethyl, iodomethyl and bromomethyl groups, of which the fluoromethyl, difluoromethyl, trifluoromethyl, 2-fluoroethyl, 3-fluoropropyl, 4-fluorobutyl, chloromethyl, trichloromethyl and bromomethyl groups are preferred, and the fluoromethyl, difluoromethyl and trifluoromethyl groups are most preferred.

In general, where substituent β, substituent , $β^1$ or substituent $β^2$ represents a substituted alkyl group, there is no particular restriction on the number of substituents, except such as may be imposed by the number of substitutable positions or possibly by steric constraints. However, we normally prefer from 1 to 3 such substituents.

Where substituent β represents an alkanoyloxy group, this may be a straight or branched chain group having from 1 to 6 carbon atoms. Specific examples of alkanoyloxy groups include the formyloxy, acetoxy, propionyloxy, butyryloxy, isobutyryloxy, pivaloyloxy, valeryloxy, isovaleryloxy and hexanoyloxy groups, of which the acetoxy and propionyloxy groups are preferred.

Where substituent β, substituent $β^1$ or substituent $β^2$ represents an alkanoylthio group, this may be a straight or branched chain group having from 1 to 6 (or 4) carbon atoms. Specific examples of alkanoylthio groups include the formylthio, acetylthio, propionylthio, butyrylthio, isobutyrylthio, pivaloylthio, valerylthio, isovalerylthio and hexanoylthio groups, of which those groups having from 1 to 4 carbon atoms are preferred, and the acetylthio and propionylthio groups are more preferred.

Where substituent β represents an alkylsulfinyl group having from 1 to 6 carbon atoms, this may be a straight or branched chain group, and examples include the methylsulfinyl, ethylsulfinyl, propylsulfinyl, isopropylsulfinyl, butylsulfinyl, isobutylsulfinyl, sec-butylsulfinyl, t-butylsulfinyl, pentylsulfinyl, isopentylsulfinyl, neopentylsulfinyl, 2-methylbutylsulfinyl, 1-ethylpropylsulfinyl, 4-methylpentylsulfinyl, 3-methylpentylsulfinyl, 2-methylpentylsulfinyl, 1-methylpentylsulfinyl, 3,3-dimethylbutylsulfinyl, 2,2-dimethylbutylsulfinyl, 1,1-dimethylbutylsulfinyl, 1,2-dimethylbutylsulfinyl, 1,3-dimethylbutylsulfinyl, 2,3-dimethylbutylsulfinyl, 2-ethylbutylsulfinyl, hexylsulfinyl and isohexylsulfinyl groups. Of these, we prefer those alkylsulfinyl groups having from 1 to 4 carbon atoms, preferably the methylsulfinyl, ethylsulfinyl, propylsulfinyl, isopropylsulfinyl, butylsulfinyl and isobutylsulfinyl groups, and most preferably the methylsulfinyl and ethylsulfinyl groups.

Where substituent β represents a cycloalkyloxy group, this preferably has from 3 to 8 carbon atoms in a single carbocyclic ring, and examples include the cyclopropyloxy, cyclobutyloxy, cyclopentyloxy, cyclohexyloxy, cycloheptyloxy and cyclooctyloxy groups, of which the cyclopentyloxy and cyclohexyloxy groups are preferred, the cyclopentyloxy group being most preferred.

Where substituent β, substituent $β^1$ or substituent $β^2$ represents a haloalkoxy group having from 1 to 6 (or 4) carbon atoms, this may be a straight or branched chain group, and examples include the fluoromethoxy, difluoromethoxy, trifluoromethoxy, 2-fluoroethoxy, 2-chloroethoxy, 2-bromoethoxy, 2,2-difluoroethoxy, 2,2,2-trifluoroethoxy, 2,2,2-trichloroethoxy, 3-fluoropropoxy, 4-fluorobutoxy, chloromethoxy, trichloromethoxy, iodomethoxy and bromomethoxy groups, of which those groups having from 1 to 4 carbon atoms are preferred, the fluoromethoxy, difluoromethoxy, trifluoromethoxy, 2-fluoroethoxy, 2-chloroethoxy, 2-bromoethoxy, 3-fluoropropoxy, 4-fluorobutoxy, chloromethoxy, trichloromethoxy and bromomethoxy groups are more preferred, and the fluoromethoxy, difluoromethoxy and trifluoromethoxy groups are most preferred.

Where substituent β, substituent $β^1$ or substituent $β^2$ represents an alkylenedioxy group having from 1 to 6 (or 4) carbon atoms, this may be a straight or branched chain group, and examples include the methylenedioxy, ethylenedioxy, trimethylenedioxy, tetramethylenedioxy, pentamethylenedioxy, hexamethylenedioxy and propylenedioxy groups, of which those groups having from 1 to 4 carbon atoms are preferred, and the methylenedioxy and ethylenedioxy groups are more preferred.

Specific preferred examples of $R^2$ include: the phenyl group; phenyl groups having from 1 to 3 substituents selected from halogen atoms, $C_1–C_4$ alkyl, $C_1–C_4$ alkoxy, $C_1–C_4$ alkylthio, mercapto, $C_1–C_4$ alkanoylthio and $C_1–C_4$ alkylsulfinyl groups, such as the 4-fluorophenyl, 4-chlorophenyl, 4-bromophenyl, p-tolyl, 4-ethylphenyl, 4-methoxyphenyl, 4-ethoxyphenyl, 4-methylthiophenyl, 4-ethylthiophenyl, 4-mercaptophenyl, 4-acetylthiophenyl, 4-propionylthiophenyl, 4-methylsulfinylphenyl, 4-ethylsulfinylphenyl, 3,4-difluorophenyl, 2,4-difluorophenyl, 3,4-dichlorophenyl, 2,4-dichlorophenyl, 3,4-dimethylphenyl, 3,4-dimethoxyphenyl, 3-chloro-4-fluorophenyl, 3-chloro-4-methoxyphenyl, 3-fluoro-4-methoxyphenyl, 3-methyl-4-methoxyphenyl, 3,5-dichloro-4-methoxyphenyl and 4-methoxy-3,5-dimethylphenyl groups; trifluoromethyl-, difluoromethoxy- or trifluoromethoxy-substituted phenyl groups, such as the 4-trifluoromethylphenyl, 4-difluoromethoxyphenyl and 4-trifluoromethoxyphenyl groups; and methylenedioxy- or ethylenedioxy-substituted phenyl groups, such as the 3,4-methylenedioxyphenyl and 3,4-ethylenedioxyphenyl groups.

In the compounds of formula (I) and (II), $R^3$ represents a hydrogen atom, a halogen atom, an alkyl group having from 1 to 6 carbon atoms or an alkyl group having from 1 to 6 carbon atoms and substituted by at least one substituent selected from the group consisting of substituents α, and preferably by at least one substituent selected from the group consisting of substituents $α^1$, defined and exemplified above, and more preferably by at least one halogen atom.

Where $R^3$ represents a halogen atom, this may be a fluorine, chlorine, bromine or iodine atom.

Where $R^3$ represents an alkyl group having from 1 to 6 carbon atoms, this may be a straight or branched chain group, and examples include the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups. Of these, we prefer those alkyl groups having from 1 to 4 carbon atoms, preferably the methyl, ethyl, propyl, isopropyl, butyl, isobutyl, sec-butyl and t-butyl groups, and most preferably the methyl and ethyl groups.

Where $R^3$ represents a substituted alkyl group having from 1 to 6 carbon atoms, this may be a straight or branched chain group which is substituted by at least one substituent selected from the group consisting of substituents α (or $α^1$), defined and exemplified above, and particularly by a halogen atom. Examples of the alkyl part may be as given above in relation to the unsubstituted groups. Specific examples of such haloalkyl groups include the fluoromethyl, difluoromethyl, trifluoromethyl, 2-fluoroethyl, 2,2-difluoroethyl, 2,2,2-trifluoroethyl, 2,2,2-trichloroethyl, 3-fluoropropyl, 4-fluorobutyl, chloromethyl, trichloromethyl, iodomethyl and bromomethyl groups, of which the fluoromethyl, difluoromethyl, trifluoromethyl, 2-fluoroethyl, 3-fluoropropyl, 4-fluorobutyl, iodomethyl, chloromethyl, trichloromethyl, bromomethyl, 2-chloroethyl and 3-chloropropyl groups are preferred, and the fluoromethyl, difluoromethyl, trifluoromethyl, 2-fluoroethyl and 2-chloroethyl groups are most preferred.

$R^3$ preferably represents a hydrogen atom; a halogen atom (such as a fluorine, chlorine, bromine or iodine atom); a methyl group, an ethyl group, a fluoromethyl group, a difluoromethyl group, a 2-fluoroethyl group or a 2-chloroethyl group.

In the compounds of formulae (I) and (II), $R^4$ represents a hydrogen atom, an alkyl group having from 1 to 6 carbon atoms, an alkyl group having from 1 to 6 carbon atoms and substituted by at least one of substituents α, a cycloalkyl group having from 3 to 8 carbon atoms, an aryl group having from 6 to 14 carbon atoms, an aryl group having from 6 to 14 carbon atoms and substituted by at least one of substituents α or substituents β (preferably at least one of substituents $α^1$, defined and exemplified above, or substituents $β^3$, defined below and included in the groups exemplified above in relation to substituents β), an aralkyl group (having from 1 to 6 carbon atoms in the alkyl part and from 6 to 14 carbon atoms, preferably from 6 to 10 carbon atoms, in the aryl part) or an aralkyl group (having from 1 to 6 carbon atoms in the alkyl part and from 6 to 14 carbon atoms, preferably from 6 to 10 carbon atoms, in the aryl part) substituted by at least one of substituents α or substituents β (preferably at least one of substituents $α^1$ or substituents $β^3$).

Substituents $β^3$ include alkyl groups having from 1 to 6 carbon atoms, alkyl groups having from 1 to 6 carbon atoms and substituted by at least one of substituents α, and cycloalkyloxy groups having from 3 to 8 carbon atoms, all as defined and exemplified above.

In particular, we prefer that $R^4$ should represent a hydrogen atom, an alkyl group having from 1 to 4 carbon atoms, an alkyl group having from 1 to 4 carbon atoms and substituted by at least one substituent selected from the group consisting of substituents of $α^2$, defined below and included in the groups exemplified above in relation to substituents α, a cycloalkyl group having from 3 to 6 carbon atoms, an aryl group which is unsubstituted or is substituted by of substituents $α^2$ and substituents $β^4$, defined below and included in the groups exemplified above in relation to substituents β, an aralkyl group which is unsubstituted or is substituted by at least one substituent selected from the group consisting of substituents $α^2$ and substituents $β^4$.

Substituents $α^2$ include hydroxy groups, halogen atoms and alkoxy groups having from 1 to 6 carbon atoms, all as defined and exemplified above.

Substituents $β^4$ include alkyl groups having from 1 to 6 carbon atoms and which are unsubstituted or are substituted by at least one halogen atom, and cycloalkyloxy groups having from 3 to 8 carbon atoms, all as defined and exemplified above.

Where $R^4$ represents an alkyl group, this may be a straight or branched chain group having from 1 to 6, preferably from 1 to 4, carbon atoms, and examples include the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups. Of these, we prefer those alkyl groups having from 1 to 4 carbon atoms, preferably the methyl, ethyl, propyl, isopropyl and butyl groups, and most preferably the methyl group.

Where $R^4$ represents a substituted alkyl group, this may be any of the alkyl groups exemplified above, particularly the methyl, ethyl, propyl, isopropyl, butyl, isobutyl, sec-butyl, t-butyl, pentyl or hexyl group. Such groups are substituted by one or more of the substituents α defined and exemplified above, especially the hydroxy group, alkoxy groups having from 1 to 4 carbon atoms and halogen atoms, such as the fluorine, chlorine, bromine and iodine atoms. There is no particular restriction on the number of such substituents, except such as may be imposed by the number of substitutable positions, and possibly by steric constraints. However, in general, from 1 to 3 substituents are preferred. In the case of substituents other than halogen atoms, a single substituent is more preferred.

Where $R^4$ represents a cycloalkyl group, this has from 3 to 8 carbon atoms, and examples include the cyclopropyl, cyclobutyl, cyclopentyl, cyclohexyl, cycloheptyl and cyclooctyl groups, of which the cyclopropyl, cyclobutyl, cyclopentyl and cyclohexyl groups are preferred, and the cyclopropyl group is most preferred.

Where $R^4$ represents an aryl group, this is a carbocyclic aromatic group preferably having from 6 to 10 ring carbon atoms, for example a phenyl or naphthyl (e.g. 1- or 2-naphthyl) group. Such a group may be substituted or unsubstituted, and, if substituted, the substituents are selected from the group consisting of substituents α and substituents β, defined and exemplified above.

Where $R^4$ represents an aralkyl group, this is an alkyl group (which may be as defined and exemplified above in relation to R), preferably having from 1 to 4 carbon atoms, which is substituted by, preferably, from 1 to 3 (more preferably 1) aryl groups, which may be as defined and exemplified above. This aralkyl group may be substituted or unsubstituted on the aryl part, and, if substituted, the substituents are selected from the group consisting of substituents α and substituents β, defined and exemplified above. Specific examples of the unsubstituted groups include the benzyl, phenethyl, 3-phenylpropyl, 4-phenylbutyl, 1-naphthylmethyl and 2-naphthylmethyl groups.

Where these aryl and aralkyl groups are substituted, there is no particular restriction on the number of such substituents, except such as may be imposed by the number of substitutable positions (5 in the case of phenyl groups and 7 in the case of naphthyl groups) and possibly by steric constraints. Preferred examples of such substituents include: halogen atoms, such as the fluorine, chlorine, bromine and iodine atoms; alkyl groups having from 1 to 6 carbon atoms, such as the methyl, ethyl, propyl, isopropyl, butyl, isobutyl, sec-butyl and t-butyl groups; haloalkyl groups having from 1 to 6 carbon atoms, such as the fluoromethyl, difluoromethyl, trifluoromethyl, chloromethyl, trichloromethyl, chlorodifluoromethyl, 2-fluoromethyl, 2-chloroethyl, 2-bromoethyl, 2-iodoethyl, 3-fluoropropyl and 4-fluoropropyl groups; alkoxy groups having from 1 to 6 carbon atoms, such as the methoxy, ethoxy, propoxy, isopropoxy, butoxy, isobutoxy, sec-butoxy and t-butoxy groups; and cycloalkyloxy groups having from 3 to 8 carbon atoms, such as the cyclopropyloxy, cyclobutyloxy, cyclopentyloxy, cyclohexyloxy and cycloheptyloxy groups.

Preferred examples of groups which may be represented by $R^4$ include: the hydrogen atom; alkyl groups having from 1 to 4 carbon atoms, such as the methyl, ethyl, isopropyl, butyl and isobutyl groups; mono-, di- or tri-haloalkyl groups having from 1 to 4 carbon atoms, such as the fluoromethyl, difluoromethyl, chlorodifluoromethyl, bromodifluoromethyl, trifluoromethyl, 2- fluoroethyl and 2,2,2-trifluoromethyl groups; the hydroxymethyl group; alkoxymethyl groups having from 1 to 4 carbon atoms in the alkoxy part, such as the methoxymethyl and ethoxymethyl groups; cycloalkyl groups having from 3 to 6 carbon atoms, such as the cyclopropyl, cyclobutyl, cyclopentyl and cyclohexyl groups; the phenyl group; mono- or di-fluorophenyl groups, such as the 4-fluorophenyl and 2,4-difluorophenyl groups; mono- or di-methoxyphenyl groups, such as the 4-methoxyphenyl and 3,4-dimethoxyphenyl groups; tolyl groups, such as the p-tolyl and o-tolyl groups; cyclopentyloxy(methoxy)phenyl groups, such as the 3-cyclopentyloxy-4-methoxyphenyl group; trifluoromethylphenyl groups, such as the 4-trifluoromethylphenyl group; the benzyl group; substituted benzyl groups, such as the 4-methoxybenzyl and 3-cyclopentyloxy-4-methoxybenzyl groups; the phenethyl group; naphthyl groups, such as the 1-naphthyl and 2-naphthyl groups; and naphthylmethyl groups, such as the 1-naphthylmethyl and 2-naphthylmethyl groups.

Preferred classes of compounds of the present invention are those compounds of formula (I) and (II) and salts thereof in which:

(A) R represents a hydrogen atom, a halogen atom or an alkyl group having from 1 to 4 carbon atoms.

(B) $R^1$ represents a methyl group, an amino group or an acetylamino group.

(C) $R^2$ represents a phenyl group or a phenyl group which is substituted by at least one substituent selected from the group consisting of substituents $α^1$ and substituents $β^1$, defined below, substituents $\alpha^1$ are selected from the group consisting of halogen atoms, alkoxy groups having from 1 to 4 carbon atoms and alkylthio groups having from 1 to 4 carbon atoms; and substituents $\beta^1$ are selected from the group consisting of alkyl groups having from 1 to 4 carbon atoms, alkyl groups which have from 1 to 4 carbon atoms and which are substituted by at least one substituent selected from the group consisting of substituents $\alpha^1$, mercapto groups, alkanoylthio groups having from 1 to 4 carbon atoms, haloalkoxy groups having from 1 to 4 carbon atoms and alkylenedioxy groups having from 1 to 4 carbon atoms.

(D) $R^3$ represents a hydrogen atom, a halogen atom, an alkyl group having from 1 to 4 carbon atoms or a substituted alkyl group having from 1 to 4 carbon atoms and substituted by at least one substituent selected from the group consisting of substituents $\alpha^1$, defined below; substituents $\alpha^1$ are selected from the group consisting of halogen atoms, alkoxy groups having from 1 to 4 carbon atoms and alkylthio groups having from 1 to 4 carbon atoms.

(E) $R^4$ represents a hydrogen atom, an alkyl group having from 1 to 4 carbon atoms, a substituted alkyl group having from 1 to 4 carbon atoms and substituted by at least one substituent selected from the group consisting of substituents $\alpha$, defined above, a cycloalkyl group having from 3 to 6 carbon atoms, an aryl group which has from 6 to 10 ring carbon atoms and which is unsubstituted or is substituted by at least one substituent selected from the group consisting of substituents $\alpha^1$ and substituents $\beta^3$, defined below, an aralkyl group having from 1 to 4 carbon atoms in the alkyl part and containing at least one aryl group as defined above;

substituents $\alpha^1$ are selected from the group consisting of halogen atoms, alkoxy groups having from 1 to 4 carbon atoms and alkylthio groups having from 1 to 4 carbon atoms; and substituents $\beta^3$ include alkyl groups having from 1 to 6 carbon atoms, alkyl groups having from 1 to 6 carbon atoms and substituted by at least one of substituents $\alpha$, and cycloalkyloxy groups having from 3 to 8 carbon atoms.

Particularly preferred compounds of the present invention are those compounds of formula (I) and salts thereof in which R is as defined in (A) above, $R^1$ is as defined in (B) above, $R^2$ is as defined in (C) above, $R^3$ is as defined in (D) above and $R^4$ is as defined in (E) above.

More preferred classes of compounds of the present invention are those compounds of formula (I) and (II) and salts thereof in which:

(F) R represents a hydrogen atom, a fluorine atom, a chlorine atom or a methyl group.

(G) $R^1$ represents an amino group or an acetylamino group.

(H) $R^2$ represents a phenyl group or a phenyl group which is substituted by at least one substituent selected from the group consisting of substituents $\alpha^1$ and substituents $\beta^2$, defined below, and more preferably with from 1 to 3 of said substituents;

substituents $\alpha^1$ are selected from the group consisting of halogen atoms, alkoxy groups having from 1 to 4 carbon atoms and alkylthio groups having from 1 to 4 carbon atoms; and substituents $\beta^2$ are selected from the group consisting of alkyl groups having from 1 to 4 carbon atoms, haloalkyl groups having from 1 to 4 carbon atoms, mercapto groups, alkanoylthio groups having from 1 to 4 carbon atoms, haloalkoxy groups having from 1 to 4 carbon atoms and alkylenedioxy groups having from 1 to 4 carbon atoms.

(I) $R^3$ represents a hydrogen atom, a halogen atom, an alkyl group having from 1 to 4 carbon atoms or a haloalkyl group having from 1 to 4 carbon atoms.

(J) $R^4$ represents a hydrogen atom, an alkyl group having from 1 to 4 carbon atoms, a substituted alkyl group having from 1 to 4 carbon atoms and substituted by at least one substituent selected from the group consisting of substituents $\alpha^2$, defined above, a cycloalkyl group having from 3 to 6 carbon atoms, an aryl group which has from 6 to 10 ring carbon atoms and which is unsubstituted or is substituted by at least one substituent selected from the group consisting of substituents $\alpha^2$ and substituents $\beta^4$, defined below, an aralkyl group having from 1 to 4 carbon atoms in the alkyl part and containing at least one aryl group as defined above;

substituents $\alpha^2$ include hydroxy groups, halogen atoms and alkoxy groups having from 1 to 6 carbon atoms; and substituents $\beta^4$ include alkyl groups having from 1 to 6 carbon atoms and which are unsubstituted or are substituted by at least one halogen atom, and cycloalkyloxy groups having from 3 to 8 carbon atoms.

Particularly preferred compounds of the present invention are those compounds of formula (I) and (II) and salts thereof in which R is as defined in (F) above, $R^1$ is as defined in (G) above, $R^2$ is as defined in (H) above, $R^3$ is as defined in (I) above and $R^4$ is as defined in (J) above.

The most preferred classes of compounds of the present invention are those in which:

(K) R represents a hydrogen atom.

Of these, particularly preferred compounds of the present invention are those compounds of formula (I) and (II) and salts thereof in which R is as defined in (K) above, $R^1$ is as defined in (G) above, $R^2$ is as defined in (H) above, $R^3$ is as defined in (I) above and $R^4$ is as defined in (J) above.

The compounds of the present invention can exist in the form of various stereoisomers, R and S isomers, depending upon the presence of asymmetric carbon atoms. The present invention covers both the individual isomers and mixtures thereof, including racemic mixtures.

The compounds of the invention may take up water upon exposure to the atmosphere to absorb water or to produce a hydrate. The present invention covers such hydrates. Additionally, certain other solvents may be taken up by the compounds of the present invention to produce solvates, which also form part of the present invention.

The compounds of the present invention can form salts. Examples of such salts include: salts with an alkali metal, such as sodium, potassium or lithium; salts with an alkaline earth metal, such as barium or calcium; salts with another metal, such as magnesium or aluminum; ammonium salts; organic base salts, such as a salt with methylamine, dimethylamine, triethylamine, diisopropylamine, cyclohexylamine or dicyclohexylamine; and salts with a basic amino acid, such as lysine or arginine.

Specific examples of compounds of the present invention are those compounds of formula (I) and (II), in which the substituent groups are as defined in the respective one of Tables 1 [formula (I)] and 2 [formula (II)]:

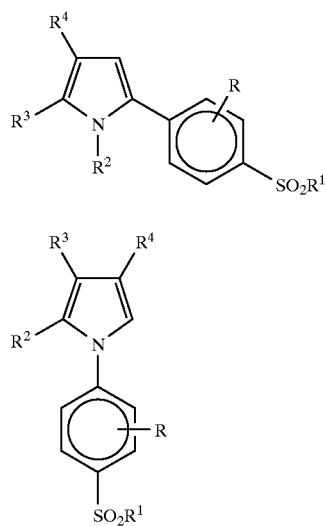

In these Tables, the following abbreviations are used:

| | |
|---|---|
| Ac | acetyl |
| Bu | butyl |
| Byr | butyryl |
| iByr | isobutyryl |
| Bz | benzyl |
| Et | ethyl |
| For | formyl |
| Me | methyl |
| Ph | phenyl |
| Piv | pivaloyl |
| cPn | cyclopentyl |
| Pr | propyl |
| cPr | cyclopropyl |
| iPr | isopropyl |
| Prn | propionyl |
| iVal | isovaleryl |
| Val | valeryl |

TABLE 1

| Cpd. No. | R | $R^1$ | $R^2$ | $R^3$ | $R^4$ |
|---|---|---|---|---|---|
| 1-1 | H | Me | Ph | H | H |
| 1-2 | H | Me | Ph | H | Me |
| 1-3 | H | Me | 4-F—Ph | H | H |
| 1-4 | H | Me | 4-F—Ph | F | H |
| 1-5 | H | Me | 4-F—Ph | Cl | H |
| 1-6 | H | Me | 4-F—Ph | Br | H |
| 1-7 | H | Me | 4-F—Ph | I | H |
| 1-8 | H | Me | 4-F—Ph | Me | H |
| 1-9 | H | Me | 4-F—Ph | Et | H |
| 1-10 | H | Me | 4-F—Ph | Pr | H |
| 1-11 | H | Me | 4-F—Ph | Bu | H |
| 1-12 | H | Me | 4-F—Ph | $CH_2F$ | H |
| 1-13 | H | Me | 4-F—Ph | $CHF_2$ | H |
| 1-14 | H | Me | 4-F—Ph | $CF_3$ | H |
| 1-15 | H | Me | 4-F—Ph | H | Me |
| 1-16 | H | Me | 4-F—Ph | F | Me |
| 1-17 | H | Me | 4-F—Ph | Cl | Me |
| 1-18 | H | Me | 4-F—Ph | Br | Me |
| 1-19 | H | Me | 4-F—Ph | I | Me |
| 1-20 | H | Me | 4-F—Ph | Me | Me |
| 1-21 | H | Me | 4-F—Ph | Et | Me |
| 1-22 | H | Me | 4-F—Ph | Pr | Me |
| 1-23 | H | Me | 4-F—Ph | H | Et |
| 1-24 | H | Me | 4-F—Ph | H | Pr |
| 1-25 | H | Me | 4-F—Ph | H | Bu |
| 1-26 | H | Me | 4-F—Ph | H | cPr |
| 1-27 | H | Me | 4-F—Ph | H | Ph |
| 1-28 | H | Me | 4-F—Ph | H | $CH_2Ph$ |
| 1-29 | H | Me | 4-F—Ph | H | $CHF_2$ |
| 1-30 | H | Me | 4-F—Ph | Me | $CHF_2$ |
| 1-31 | H | Me | 4-F—Ph | H | $CF_3$ |
| 1-32 | H | Me | 4-F—Ph | Me | $CF_3$ |
| 1-33 | H | Me | 4-MeO—Ph | H | H |
| 1-34 | H | Me | 4-MeO—Ph | H | Me |
| 1-35 | H | Me | 4-Cl—Ph | H | H |
| 1-36 | H | Me | 4-Cl—Ph | H | Me |
| 1-37 | H | Me | 4-Me-Ph | H | H |
| 1-38 | H | Me | 4-Me-Ph | H | Me |
| 1-39 | H | Me | 3-Cl-4-F—Ph | H | H |
| 1-40 | H | Me | 3-Cl-4-F—Ph | H | Me |
| 1-41 | H | Me | 3,4-methylenedioxy-Ph | H | H |
| 1-42 | H | Me | 3,4-methylenedioxy-Ph | H | Me |
| 1-43 | H | Me | 3-Cl-4-MeO—Ph | H | H |
| 1-44 | H | Me | 3-Cl-4-MeO—Ph | H | Me |

TABLE 1-continued

| Cpd. No. | R | R¹ | R² | R³ | R⁴ |
|---|---|---|---|---|---|
| 1-45 | H | Me | 4-CF₃—Ph | H | H |
| 1-46 | H | Me | 4-CF₃O—Ph | H | H |
| 1-47 | H | Me | 3-F-4-MeO—Ph | H | H |
| 1-48 | H | Me | 3-F-4-MeO—Ph | H | Me |
| 1-49 | H | Me | 3-Me-4-MeO—Ph | H | H |
| 1-50 | H | Me | 3-Me-4-MeO—Ph | H | Me |
| 1-51 | H | Me | 3,4-diF—Ph | H | H |
| 1-52 | H | Me | 3,4-diF—Ph | H | Me |
| 1-53 | H | Me | 2,4-diF—Ph | H | H |
| 1-54 | H | Me | 2,4-diF—Ph | H | Me |
| 1-55 | H | Me | 3,4-diMe-Ph | H | H |
| 1-56 | H | Me | 3,4-diMe-Ph | H | Me |
| 1-57 | H | Me | 3,4-diCl—Ph | H | H |
| 1-58 | H | Me | 3,4-diCl—Ph | H | Me |
| 1-59 | H | Me | 3,4-di(MeO)—Ph | H | H |
| 1-60 | H | Me | 3,4-di(MeO)—Ph | H | Me |
| 1-61 | H | Me | 4-F—Ph | H | CH₂OH |
| 1-62 | H | Me | 4-F—Ph | Me | CH₂OH |
| 1-63 | H | Me | 4-F—Ph | H | CH₂OMe |
| 1-64 | H | Me | 4-MeO—Ph | H | CH₂OH |
| 1-65 | H | Me | 4-MeO—Ph | H | CH₂OMe |
| 1-66 | H | Me | 4-Cl—Ph | H | CH₂OH |
| 1-67 | H | Me | 4-Cl—Ph | H | CH₂OMe |
| 1-68 | H | Me | 4-Me-Ph | H | CH₂OH |
| 1-69 | H | Me | 4-Me-Ph | H | CH₂OMe |
| 1-70 | H | NH₂ | Ph | H | H |
| 1-71 | H | NH₂ | Ph | H | Me |
| 1-72 | H | NH₂ | Ph | Me | H |
| 1-73 | H | NH₂ | 4-F—Ph | H | H |
| 1-74 | H | NH₂ | 4-F—Ph | H | Me |
| 1-75 | H | NH₂ | 4-F—Ph | Cl | Me |
| 1-76 | H | NH₂ | 4-F—Ph | Me | H |
| 1-77 | H | NH₂ | 4-F—Ph | H | Et |
| 1-78 | H | NH₂ | 4-F—Ph | H | Pr |
| 1-79 | H | NH₂ | 4-F—Ph | H | Bu |
| 1-80 | H | NH₂ | 4-F—Ph | H | cPr |
| 1-81 | H | NH₂ | 4-F—Ph | H | Ph |
| 1-82 | H | NH₂ | 4-F—Ph | H | CH₂Ph |
| 1-83 | H | NH₂ | 4-F—Ph | H | CHF₂ |
| 1-84 | H | NH₂ | 4-F—Ph | H | CF₃ |
| 1-85 | H | NH₂ | 4-MeO—Ph | H | H |
| 1-86 | H | NH₂ | 4-MeO—Ph | H | Me |
| 1-87 | H | NH₂ | 4-MeO—Ph | H | Bu |
| 1-88 | H | NH₂ | 4-MeO—Ph | Me | H |
| 1-89 | H | NH₂ | 4-EtO—Ph | H | H |
| 1-90 | H | NH₂ | 4-EtO—Ph | H | Me |
| 1-91 | H | NH₂ | 4-EtO—Ph | Me | H |
| 1-92 | H | NH₂ | 4-PrO—Ph | H | Me |
| 1-93 | H | NH₂ | 4-MeS—Ph | H | H |
| 1-94 | H | NH₂ | 4-MeS—Ph | H | Me |
| 1-95 | H | NH₂ | 4-MeS—Ph | Me | H |
| 1-96 | H | NH₂ | 4-Cl—Ph | H | H |
| 1-97 | H | NH₂ | 4-Cl—Ph | H | Me |
| 1-98 | H | NH₂ | 4-Cl—Ph | Me | H |
| 1-99 | H | NH₂ | 4-Me-Ph | H | H |
| 1-100 | H | NH₂ | 4-Me-Ph | H | Me |
| 1-101 | H | NH₂ | 4-Me-Ph | Me | H |
| 1-102 | H | NH₂ | 3-Cl-4-F—Ph | H | H |
| 1-103 | H | NH₂ | 3-Cl-4-F—Ph | H | Me |
| 1-104 | H | NH₂ | 3-Cl-4-F—Ph | Me | H |
| 1-105 | H | NH₂ | 3,4-methylenedioxy-Ph | H | H |
| 1-106 | H | NH₂ | 3,4-methylenedioxy-Ph | H | Me |
| 1-107 | H | NH₂ | 3-Cl-4-MeO—Ph | H | H |
| 1-108 | H | NH₂ | 3-Cl-4-MeO—Ph | H | Me |
| 1-109 | H | NH₂ | 3-Cl-4-MeO—Ph | Me | H |
| 1-110 | H | NH₂ | 4-CF₃—Ph | H | H |
| 1-111 | H | NH₂ | 4-CF₃O—Ph | H | H |
| 1-112 | H | NH₂ | 3-F-4-MeO—Ph | H | H |
| 1-113 | H | NH₂ | 3-F-4-MeO—Ph | H | Me |
| 1-114 | H | NH₂ | 3-F-4-MeO—Ph | Me | H |
| 1-115 | H | NH₂ | 3-Me-4-MeO—Ph | H | H |
| 1-116 | H | NH₂ | 3-Me-4-MeO—Ph | H | Me |
| 1-117 | H | NH₂ | 3-Me-4-MeO—Ph | Me | H |
| 1-118 | H | NH₂ | 3,4-diF—Ph | H | H |
| 1-119 | H | NH₂ | 3,4-diF—Ph | H | Me |
| 1-120 | H | NH₂ | 3,4-diF—Ph | Me | H |
| 1-121 | H | NH₂ | 2,4-diF—Ph | H | H |

TABLE 1-continued

| Cpd. No. | R | R¹ | R² | R³ | R⁴ |
|---|---|---|---|---|---|
| 1-122 | H | NH₂ | 2,4-diF—Ph | H | Me |
| 1-123 | H | NH₂ | 2,4-diF—Ph | Me | H |
| 1-124 | H | NH₂ | 3,4-diMe-Ph | H | H |
| 1-125 | H | NH₂ | 3,4-diMe-Ph | H | Me |
| 1-126 | H | NH₂ | 3,4-diMe-Ph | Me | H |
| 1-127 | H | NH₂ | 2,4-diCl—Ph | H | H |
| 1-128 | H | NH₂ | 2,4-diCl—Ph | H | Me |
| 1-129 | H | NH₂ | 2,4-diCl—Ph | Me | H |
| 1-130 | H | NH₂ | 3,4-diCl—Ph | H | H |
| 1-131 | H | NH₂ | 3,4-diCl—Ph | H | Me |
| 1-132 | H | NH₂ | 3,4-diCl—Ph | Me | H |
| 1-133 | H | NH₂ | 3,4-di(MeO)—Ph | H | H |
| 1-134 | H | NH₂ | 3,4-di(MeO)—Ph | H | Me |
| 1-135 | H | NH₂ | 4-F—Ph | H | CH₂OH |
| 1-136 | H | NH₂ | 4-F—Ph | H | CH₂OMe |
| 1-137 | H | NH₂ | 4-MeO—Ph | H | CH₂OH |
| 1-138 | H | NH₂ | 4-MeO—Ph | H | CH₂OMe |
| 1-139 | H | NH₂ | 4-Cl—Ph | H | CH₂OH |
| 1-140 | H | NH₂ | 4-Cl—Ph | H | CH₂OMe |
| 1-141 | H | NH₂ | 4-Me-Ph | H | CH₂OH |
| 1-142 | H | NH₂ | 4-Me-Ph | H | CH₂OMe |
| 1-143 | H | NH₂ | 4-Et-Ph | H | H |
| 1-144 | H | NH₂ | 4-Et-Ph | H | Me |
| 1-145 | H | NH₂ | 4-Et-Ph | Me | H |
| 1-146 | H | NH₂ | 2,4,6-triMe-Ph | H | Me |
| 1-147 | H | NH₂ | 4-MeO—Ph | Cl | H |
| 1-148 | H | NH₂ | 4-MeO—Ph | Br | H |
| 1-149 | H | NH₂ | 4-MeO—Ph | Cl | Me |
| 1-150 | H | NH₂ | 2-F-4-Cl—Ph | H | Me |
| 1-151 | H | NH₂ | 4-EtO—Ph | Cl | H |
| 1-152 | H | NH₂ | 4-MeS—Ph | Cl | H |
| 1-153 | H | NH₂ | 4-MeSO—Ph | H | Me |
| 1-154 | H | NH₂ | 4-EtS—Ph | H | Me |
| 1-155 | H | NH₂ | 2,4-diCl—Ph | Cl | H |
| 1-156 | H | NH₂ | 4-SH—Ph | H | Me |
| 1-157 | H | NH₂ | 4-AcS—Ph | H | Me |
| 1-158 | 3-F | NH₂ | 4-MeO—Ph | H | Me |
| 1-159 | 3-F | NH₂ | 4-EtO—Ph | H | Me |
| 1-160 | 3-F | NH₂ | 3,4-diMe-Ph | H | Me |
| 1-161 | 3-F | NH₂ | 4-Cl—Ph | H | Me |
| 1-162 | 3-F | NH₂ | 4-F—Ph | H | Me |
| 1-163 | 3-F | NH₂ | 4-SH—Ph | H | Me |
| 1-164 | 3-F | NH₂ | 4-MeS—Ph | H | Me |
| 1-165 | 3-F | NH₂ | 4-EtS—Ph | H | Me |
| 1-166 | 3-F | NH₂ | 4-AcS—Ph | H | Me |
| 1-167 | 3-Me | NH₂ | 4-MeO—Ph | H | Me |
| 1-168 | 3-Me | NH₂ | 4-EtO—Ph | H | Me |
| 1-169 | 3-Me | NH₂ | 3,4-diMe-Ph | H | Me |
| 1-170 | 3-Me | NH₂ | 4-Cl—Ph | H | Me |
| 1-171 | 3-Me | NH₂ | 4-F—Ph | H | Me |
| 1-172 | 3-Me | NH₂ | 4-MeS—Ph | H | Me |
| 1-173 | 3-F | NHFor | 4-MeS—Ph | H | Me |
| 1-174 | 3-F | NHAc | 4-MeS—Ph | H | Me |
| 1-175 | 3-F | NHPrn | 4-MeS—Ph | H | Me |
| 1-176 | 3-F | NHByr | 4-MeS—Ph | H | Me |
| 1-177 | 3-F | NHiByr | 4-MeS—Ph | H | Me |
| 1-178 | 3-F | NHVal | 4-MeS—Ph | H | Me |
| 1-179 | 3-F | NHiVal | 4-MeS—Ph | H | Me |
| 1-180 | 3-F | NHPiv | 4-MeS—Ph | H | Me |
| 1-181 | 3-F | NH(MeOCO) | 4-MeS—Ph | H | Me |
| 1-182 | 3-F | NH(EtOCO) | 4-MeS—Ph | H | Me |
| 1-183 | 3-F | NH(BzOCO) | 4-MeS—Ph | H | Me |
| 1-184 | 3-F | NH(AcOCH₂) | 4-MeS—Ph | H | Me |
| 1-185 | 3-F | NH(PrnOCH₂) | 4-MeS—Ph | H | Me |
| 1-186 | 3-F | NH(MeOCOOCH₂) | 4-MeS—Ph | H | Me |
| 1-187 | 3-F | NH(EtOCOOCH₂) | 4-MeS—Ph | H | Me |
| 1-188 | 3-F | NH[(5-Me-2-oxo-1,3-dioxolen-4-yl)CH₂] | 4-MeS—Ph | H | Me |
| 1-189 | 3-F | NH[(5-Ph-2-oxo-1,3 dioxoten-4-yl)CH₂] | 4-MeS—Ph | H | Me |

TABLE 2

| Cpd. No. | R | R¹ | R² | R³ | R⁴ |
|---|---|---|---|---|---|
| 2-1 | H | Me | Ph | H | H |
| 2-2 | H | Me | Ph | H | Me |
| 2-3 | H | Me | 4-F—Ph | H | H |
| 2-4 | H | Me | 4-F—Ph | F | H |
| 2-5 | H | Me | 4-F—Ph | Cl | H |
| 2-6 | H | Me | 4-F—Ph | Br | H |
| 2-7 | H | Me | 4-F—Ph | I | H |
| 2-8 | H | Me | 4-F—Ph | Me | H |
| 2-9 | H | Me | 4-F—Ph | Et | H |
| 2-10 | H | Me | 4-F—Ph | Pr | H |
| 2-11 | H | Me | 4-F—Ph | H | Me |
| 2-12 | H | Me | 4-F—Ph | H | Et |
| 2-13 | H | Me | 4-F—Ph | H | Pr |
| 2-14 | H | Me | 4-F—Ph | H | Bu |
| 2-15 | H | Me | 4-F—Ph | H | cPr |
| 2-16 | H | Me | 4-F—Ph | H | Ph |
| 2-17 | H | Me | 4-F—Ph | H | $CH_2Ph$ |
| 2-18 | H | Me | 4-F—Ph | H | $CHF_2$ |
| 2-19 | H | Me | 4-F—Ph | H | $CF_3$ |
| 2-20 | H | Me | 4-MeO—Ph | H | H |
| 2-21 | H | Me | 4-MeO—Ph | Me | H |
| 2-22 | H | Me | 4-MeO—Ph | H | Me |
| 2-23 | H | Me | 4-Cl—Ph | H | H |
| 2-24 | H | Me | 4-Cl—Ph | Me | H |
| 2-25 | H | Me | 4-Me-Ph | H | H |
| 2-26 | H | Me | 4-Me-Ph | Me | H |
| 2-27 | H | Me | 4-Me-Ph | H | Me |
| 2-28 | H | Me | 3-Cl-4-F—Ph | H | H |
| 2-29 | H | Me | 3-Cl-4-F—Ph | H | Me |
| 2-30 | H | Me | 3,4-methylenedioxy-Ph | H | H |
| 2-31 | H | Me | 3,4-methylenedioxy-Ph | H | Me |
| 2-32 | H | Me | 3-Cl-4-MeO—Ph | H | H |
| 2-33 | H | Me | 3-Cl-4-MeO—Ph | H | Me |
| 2-34 | H | Me | 4-$CF_3$—Ph | H | H |
| 2-35 | H | Me | 4-$CF_3$O—Ph | H | H |
| 2-36 | H | Me | 4-$CHF_2$O—Ph | H | H |
| 2-37 | H | Me | 4-$CHF_2$O—Ph | Me | H |
| 2-38 | H | Me | 3-F-4-MeO—Ph | H | H |
| 2-39 | H | Me | 3-F-4-MeO—Ph | H | Me |
| 2-40 | H | Me | 3-Me-4-MeO—Ph | H | H |
| 2-41 | H | Me | 3-Me-4-MeO—Ph | H | Me |
| 2-42 | H | Me | 3,4-diF—Ph | H | H |
| 2-43 | H | Me | 3,4-diF—Ph | H | Me |
| 2-44 | H | Me | 2,4-diF—Ph | H | H |
| 2-45 | H | Me | 2,4-diF—Ph | H | Me |
| 2-46 | H | Me | 3,4-diMe-Ph | H | H |
| 2-47 | H | Me | 3,4-diCl—Ph | H | H |
| 2-48 | H | Me | 3,4-diCl—Ph | H | Me |
| 2-49 | H | Me | 3,4-di(MeO)—Ph | H | H |
| 2-50 | H | Me | 3,4-di(MeO)—Ph | H | Me |
| 2-51 | H | Me | 4-F—Ph | H | $CH_2OH$ |
| 2-52 | H | Me | 4-F—Ph | H | $CH_2OMe$ |
| 2-53 | H | Me | 4-MeO—Ph | H | $CH_2OH$ |
| 2-54 | H | Me | 4-MeO—Ph | H | $CH_2OMe$ |
| 2-55 | H | Me | 4-Cl—Ph | H | $CH_2OH$ |
| 2-56 | H | Me | 4-Cl—Ph | H | $CH_2OMe$ |
| 2-57 | H | Me | 4-Me-Ph | H | $CH_2OH$ |
| 2-58 | H | Me | 4-Me-Ph | H | $CH_2OMe$ |
| 2-59 | H | $NH_2$ | Ph | H | H |
| 2-60 | H | $NH_2$ | Ph | H | Me |
| 2-61 | H | $NH_2$ | Ph | Me | H |
| 2-62 | H | $NH_2$ | 4-F—Ph | H | H |
| 2-63 | H | $NH_2$ | 4-F—Ph | H | Me |
| 2-64 | H | $NH_2$ | 4-F—Ph | Me | H |
| 2-65 | H | $NH_2$ | 4-F—Ph | H | Et |
| 2-66 | H | $NH_2$ | 4-F—Ph | H | Pr |
| 2-67 | H | $NH_2$ | 4-F—Ph | H | Bu |
| 2-68 | H | $NH_2$ | 4-F—Ph | H | cPr |
| 2-69 | H | $NH_2$ | 4-F—Ph | H | Ph |
| 2-70 | H | $NH_2$ | 4-F—Ph | H | $CH_2Ph$ |
| 2-71 | H | $NH_2$ | 4-F—Ph | H | $CHF_2$ |
| 2-72 | H | $NH_2$ | 4-F—Ph | H | $CF_3$ |
| 2-73 | H | $NH_2$ | 4-MeO—Ph | H | H |
| 2-74 | H | $NH_2$ | 4-MeO—Ph | H | Me |
| 2-75 | H | $NH_2$ | 4-MeO—Ph | H | Et |
| 2-76 | H | $NH_2$ | 4-MeO—Ph | Me | H |
| 2-77 | H | $NH_2$ | 4-EtO—Ph | H | H |

TABLE 2-continued

| Cpd. No. | R | R$^1$ | R$^2$ | R$^3$ | R$^4$ |
|---|---|---|---|---|---|
| 2-78 | H | NH$_2$ | 4-EtO—Ph | H | Me |
| 2-79 | H | NH$_2$ | 4-EtO—Ph | Me | H |
| 2-80 | H | NH$_2$ | 4-PrO—Ph | H | Me |
| 2-81 | H | NH$_2$ | 4-MeS—Ph | H | H |
| 2-82 | H | NH$_2$ | 4-MeS—Ph | H | Me |
| 2-83 | H | NH$_2$ | 4-MeS—Ph | Me | H |
| 2-84 | H | NH$_2$ | 4-Cl—Ph | H | H |
| 2-85 | H | NH$_2$ | 4-Cl—Ph | H | Me |
| 2-86 | H | NH$_2$ | 4-Cl—Ph | Me | H |
| 2-87 | H | NH$_2$ | 4-Me-Ph | H | H |
| 2-88 | H | NH$_2$ | 4-Me-Ph | Me | H |
| 2-89 | H | NH$_2$ | 4-Me-Ph | H | Me |
| 2-90 | H | NH$_2$ | 4-Et-Ph | H | H |
| 2-91 | H | NH$_2$ | 4-Et-Ph | H | Me |
| 2-92 | H | NH$_2$ | 4-Et-Ph | Me | H |
| 2-93 | H | NH$_2$ | 4-iPr-Ph | H | Me |
| 2-94 | H | NH$_2$ | 3-Cl-4-F—Ph | H | H |
| 2-95 | H | NH$_2$ | 3-Cl-4-F—Ph | H | Me |
| 2-96 | H | NH$_2$ | 3-Cl-4-F—Ph | Me | H |
| 2-97 | H | NH$_2$ | 3,4-methylenedioxy-Ph | H | H |
| 2-98 | H | NH$_2$ | 3,4-methylenedioxy-Ph | H | Me |
| 2-99 | H | NH$_2$ | 3-Cl-4-MeO—Ph | H | H |
| 2-100 | H | NH$_2$ | 3-Cl-4-MeO—Ph | H | Me |
| 2-101 | H | NH$_2$ | 3-Cl-4-MeO—Ph | Me | H |
| 2-102 | H | NH$_2$ | 4-CF$_3$—Ph | H | Me |
| 2-103 | H | NH$_2$ | 4-CHF$_2$O—Ph | H | Me |
| 2-104 | H | NH$_2$ | 4-CF$_3$O—Ph | H | Me |
| 2-105 | H | NH$_2$ | 2-F-4-MeO—Ph | H | Me |
| 2-106 | H | NH$_2$ | 3-F-4-MeO—Ph | H | Me |
| 2-107 | H | NH$_2$ | 3-F-4-MeO—Ph | Me | H |
| 2-108 | H | NH$_2$ | 3-Me-4-MeO—Ph | H | H |
| 2-109 | H | NH$_2$ | 3-Me-4-MeO—Ph | H | Me |
| 2-110 | H | NH$_2$ | 3-Me-4-MeO—Ph | Me | H |
| 2-111 | H | NH$_2$ | 3,4-diF—Ph | H | H |
| 2-112 | H | NH$_2$ | 3,4-diF—Ph | H | Me |
| 2-113 | H | NH$_2$ | 3,4-diF—Ph | Me | H |
| 2-114 | H | NH$_2$ | 2,4-diF—Ph | H | H |
| 2-115 | H | NH$_2$ | 2,4-diF—Ph | H | Me |
| 2-116 | H | NH$_2$ | 2,4-diF—Ph | Me | H |
| 2-117 | H | NH$_2$ | 3,4-diMe-Ph | H | H |
| 2-118 | H | NH$_2$ | 3,4-diMe-Ph | H | Me |
| 2-119 | H | NH$_2$ | 3,4-diMe-Ph | Me | H |
| 2-120 | H | NH$_2$ | 2,4-diCl—Ph | H | H |
| 2-121 | H | NH$_2$ | 2,4-diCl—Ph | H | Me |
| 2-122 | H | NH$_2$ | 2,4-diCl—Ph | Me | H |
| 2-123 | H | NH$_2$ | 3,4-diCl—Ph | H | H |
| 2-124 | H | NH$_2$ | 3,4-diCl—Ph | H | Me |
| 2-125 | H | NH$_2$ | 3,4-diCl—Ph | Me | H |
| 2-126 | H | NH$_2$ | 3,4-di(MeO)—Ph | H | H |
| 2-127 | H | NH$_2$ | 3,4-di(MeO)—Ph | H | Me |
| 2-128 | H | NH$_2$ | 4-F—Ph | H | CH$_2$OH |
| 2-129 | H | NH$_2$ | 4-F—Ph | H | CH$_2$OMe |
| 2-130 | H | NH$_2$ | 4-MeO—Ph | H | CH$_2$OH |
| 2-131 | H | NH$_2$ | 4-MeO—Ph | H | CH$_2$OMe |
| 2-132 | H | NH$_2$ | 4-Cl—Ph | H | CH$_2$OH |
| 2-133 | H | NH$_2$ | 4-Cl—Ph | H | CH$_2$OMe |
| 2-134 | H | NH$_2$ | 4-Me-Ph | H | CH$_2$OH |
| 2-135 | H | NH$_2$ | 4-Me-Ph | H | CH$_2$OMe |
| 2-136 | H | NH$_2$ | 3,5-diCl-4-MeO—Ph | H | Me |
| 2-137 | H | NH$_2$ | 3,5-diMe-4-MeO—Ph | H | Me |
| 2-138 | H | NH$_2$ | 2,3-diCl—Ph | H | Me |
| 2-139 | H | NH$_2$ | 3,5-diCl—Ph | H | Me |
| 2-140 | H | NH$_2$ | 2,4,5-triMe-Ph | H | Me |
| 2-141 | H | NH$_2$ | 3-cPnO-4-MeO—Ph | H | Me |
| 2-142 | H | NH$_2$ | 3-CF$_3$-4-Cl—Ph | H | Me |
| 2-143 | H | NH$_2$ | 3-F-4-Me-Ph | H | Me |
| 2-144 | H | NH$_2$ | 3-Me-4-Cl—Ph | H | Me |
| 2-145 | H | NH$_2$ | 2,4-diMe-Ph | H | Me |
| 2-146 | H | NH$_2$ | 4-OH—Ph | H | Me |
| 2-147 | H | NH$_2$ | 3,5-diMe-Ph | H | Me |
| 2-148 | H | NHAc | 4-MeO—Ph | H | Me |
| 2-149 | H | NHAc | 3,4-diMe-Ph | H | Me |
| 2-150 | H | NH$_2$ | 4-MeO—Ph | H | 3-cPnO-4-MeO—Bz |
| 2-151 | H | NH$_2$ | 4-MeSO—Ph | H | Me |
| 2-152 | 3-F | NH$_2$ | 4-MeO—Ph | H | Me |
| 2-153 | 3-F | NH$_2$ | 4-EtO—Ph | H | Me |
| 2-154 | 3-F | NH$_2$ | 3,4-diMe-Ph | H | Me |

TABLE 2-continued

| Cpd. No. | R | R¹ | R² | R³ | R⁴ |
|---|---|---|---|---|---|
| 2-155 | 3-F | NH₂ | 4-Cl—Ph | H | Me |
| 2-156 | 3-F | NH₂ | 4-F—Ph | H | Me |
| 2-157 | 3-F | NH₂ | 4-SH—Ph | H | Me |
| 2-158 | 3-F | NH₂ | 4-MeS—Ph | H | Me |
| 2-159 | 3-F | NH₂ | 4-EtS—Ph | H | Me |
| 2-160 | 3-F | NH₂ | 4-AcS—Ph | H | Me |
| 2-161 | 3-Me | NH₂ | 4-MeO—Ph | H | Me |
| 2-162 | 3-Me | NH₂ | 4-EtO—Ph | H | Me |
| 2-163 | 3-Me | NH₂ | 3,4-diMe-Ph | H | Me |
| 2-164 | 3-Me | NH₂ | 4-MeS—Ph | H | Me |
| 2-165 | H | NHFor | 4-MeO—Ph | H | Me |
| 2-166 | H | NHPrn | 4-MeO—Ph | H | Me |
| 2-167 | H | NHByr | 4-MeO—Ph | H | Me |
| 2-168 | H | NHiByr | 4-MeO—Ph | H | Me |
| 2-169 | H | NHVal | 4-MeO—Ph | H | Me |
| 2-170 | H | NHiVal | 4-MeO—Ph | H | Me |
| 2-171 | H | NHPiv | 4-MeO—Ph | H | Me |
| 2-172 | H | NH(MeOCO) | 4-MeO—Ph | H | Me |
| 2-173 | H | NH(EtOCO) | 4-MeO—Ph | H | Me |
| 2-174 | H | NH(BzOCO) | 4-MeO—Ph | H | Me |
| 2-175 | H | NH(AcOCH₂) | 4-MeO—Ph | H | Me |
| 2-176 | H | NH(PrnOCH₂) | 4-MeO—Ph | H | Me |
| 2-177 | H | NH(MeOCOOCH₂) | 4-MeO—Ph | H | Me |
| 2-178 | H | NH(EtOCOOCH₂) | 4-MeO—Ph | H | Me |
| 2-179 | H | NH[(5-Me-2-oxo-1,3-dioxolen-4-yl)CH₂] | 4-MeO—Ph | H | Me |
| 2-180 | H | NH[(5-Ph-2-oxo-1,3-dioxolen-4-yl)CH₂] | 4-MeO—Ph | H | Me |
| 2-181 | H | NHFor | 4-EtO—Ph | H | Me |
| 2-182 | H | NHAc | 4-EtO—Ph | H | Me |
| 2-183 | H | NHPrn | 4-EtO—Ph | H | Me |
| 2-184 | H | NHByr | 4-EtO—Ph | H | Me |
| 2-185 | H | NHiByr | 4-EtO—Ph | H | Me |
| 2-186 | H | NHVal | 4-EtO—Ph | H | Me |
| 2-187 | H | NHiVal | 4-EtO—Ph | H | Me |
| 2-188 | H | NHPiv | 4-EtO—Ph | H | Me |
| 2-189 | H | NH(MeOCO) | 4-EtO—Ph | H | Me |
| 2-190 | H | NH(EtOCO) | 4-EtO—Ph | H | Me |
| 2-191 | H | NH(BzOCO) | 4-EtO—Ph | H | Me |
| 2-192 | H | NH(AcOCH₂) | 4-EtO—Ph | H | Me |
| 2-193 | H | NH(PrnOCH₂) | 4-EtO—Ph | H | Me |
| 2-194 | H | NH(MeOCOOCH₂) | 4-EtO—Ph | H | Me |
| 2-195 | H | NH(EtOCOOCH₂) | 4-EtO—Ph | H | Me |
| 2-196 | H | NH[(5-Me-2-oxo-1,3-dioxolen-4-yl)CH₂] | 4-EtO—Ph | H | Me |
| 2-197 | H | NH[(5-Ph-2-oxo-1,3-dioxolen-4-yl)CH₂] | 4-EtO—Ph | H | Me |
| 2-198 | H | NMFor | 3,4-diMe-Ph | H | Me |
| 2-199 | H | NHPrn | 3,4-diMe-Ph | H | Me |
| 2-200 | H | NHByr | 3,4-diMe-Ph | H | Me |
| 2-201 | H | NHiByr | 3,4-diMe-Ph | H | Me |
| 2-202 | H | NHVal | 3,4-diMe-Ph | H | Me |
| 2-203 | H | NHiVal | 3,4-diMe-Ph | H | Me |
| 2-204 | H | NHPiv | 3,4-diMe-Ph | H | Me |
| 2-205 | H | NH(MeOCO) | 3,4-diMe-Ph | H | Me |
| 2-206 | H | NH(EtOCO) | 3,4-diMe-Ph | H | Me |
| 2-207 | H | NH(BzOCO) | 3,4-diMe-Ph | H | Me |
| 2-208 | H | NH(AcOCH₂) | 3,4-diMe-Ph | H | Me |
| 2-209 | H | NH(PrnOCH₂) | 3,4-diMe-Ph | H | Me |
| 2-210 | H | NH(MeOCOOCH₂) | 3,4-diMe-Ph | H | Me |
| 2-211 | H | NH(EtOCOOCH₂) | 3,4-diMe-Ph | H | Me |
| 2-212 | H | NH[(5-Me-2-oxo-1,3-dioxolen-4-yl)CH₂] | 3,4-diMe-Ph | H | Me |
| 2-213 | H | NH[(5-Ph-2-oxo-1,3-dioxolen-4-yl)CH₂] | 3,4-diMe-Ph | H | Me |

Of the compounds listed above, particularly preferred specific compounds are:
(1) 3-Methyl-2-(4-methylphenyl)-1-(4-sulfamoylphenyl)pyrrole
(2) 4-Methyl-2-(4-methylphenyl)-1-(4-sulfamoylphenyl)pyrrole
(3) 1-(4-Fluorophenyl)-2-(4-sulfamoylphenyl)pyrrole
(4) 1-(4-Fluorophenyl)-4-methyl-2-(4-sulfamoylphenyl)pyrrole
(5) 5-Fluoro-1-(4-fluorophenyl)-2-(4-methylsulfonylphenyl)pyrrole
(6) 2-(4-Methoxyphenyl)-4-methyl-1-(4-sulfamoylphenyl)pyrrole
(7) 1-(4-Methoxyphenyl)-4-Methyl-2-(4-sulfamoylphenyl)pyrrole
(8) 4-Ethyl-2-(4-methoxyphenyl)-1-(4-sulfamoylphenyl)pyrrole (9) 2-(4-Chlorophenyl)-4-methyl-1-(4-sulfamoylphenyl) pyrrole
(10) 4-Methyl-2-(4-methylthiophenyl)-1-(4-sulfamoylphenyl)pyrrole
(11) 2-(4-Ethoxyphenyl)-4-methyl-1-(4-sulfamoylphenyl) pyrrole
(12) 2-(4-Methoxy-3-methylphenyl)-4-methyl-1-(4-sulfamoylphenyl)pyrrole
(13) 2-(3-Fluoro-4-methoxyphenyl)-4-methyl-1-(4-sulfamoylphenyl)pyrrole
(14) 4-Methyl-2-phenyl-1-(4-sulfamoylphenyl)pyrrole
(15) 2-(3,4-Dimethylphenyl)-4-methyl-1-(4-sulfamoylphenyl)pyrrole
(16) 2-(3-Chloro-4-methoxyphenyl)-4-methyl-1-(4-sulfamoylphenyl)pyrrole
(17) 4-Methyl-1-(4-methylthiophenyl)-2-(4-sulfamoylphenyl)pyrrole
(18) 5-Chloro-1-(4-methoxyphenyl)-2-(4-sulfamoylphenyl) pyrrole
(19) 4-Methyl-1-(3,4-dimethylphenyl)-2-(4-sulfamoylphenyl)pyrrole
(20) 5-Chloro-1-(4-ethoxyphenyl)-2-(4-sulfamoylphenyl) pyrrole
(21) 5-Chloro-1-(4-methylthiophenyl)-2-(4-sulfamoylphenyl)pyrrole
(22) 1-(4-Ethylthiophenyl)-4-methyl-2-(4-sulfamoylphenyl) pyrrole
(23) 2-(3,5-Dimethylphenyl)-4-methyl-1-(4-sulfamoylphenyl)pyrrole
(24) 1-(4-Mercaptophenyl)-4-methyl-2-(4-sulfamoylphenyl)pyrrole
(25) 1-(4-Acetylthiophenyl)-4-methyl-2-(4-sulfamoylphenyl)pyrrole
(26) 1-(4-Acetylaminosulfonylphenyl)-4-methyl-2-(4-methoxyphenyl)pyrrole
(27) 1-(4-Acetylaminosulfonylphenyl)-4-methyl-2-(3,4-dimethylphenyl)pyrrole.

Of these, more preferred compounds are Nos. (2), (6), (9), (10), (11), (12), (13), (15), (17), (26) and (27), and compound No. (11), (15), (17), (26) and (27) are most preferred.

The compounds of the present invention may be prepared by a variety of processes well known for the preparation of compounds of this type, for example as shown in the following Methods A to L.

The following Methods A to E and K illustrate the preparation of compounds of formula (I).

Method A

This illustrates the preparation of compounds of formula (Ia) wherein $R^3$ is a hydrogen atom, an alkyl group or a substituted alkyl group having at least one substituent selected from the group consisting of substituents α.

Reaction Scheme A

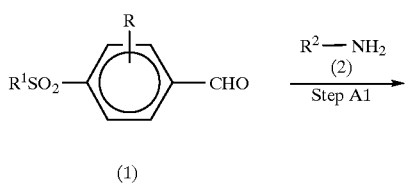

(1)

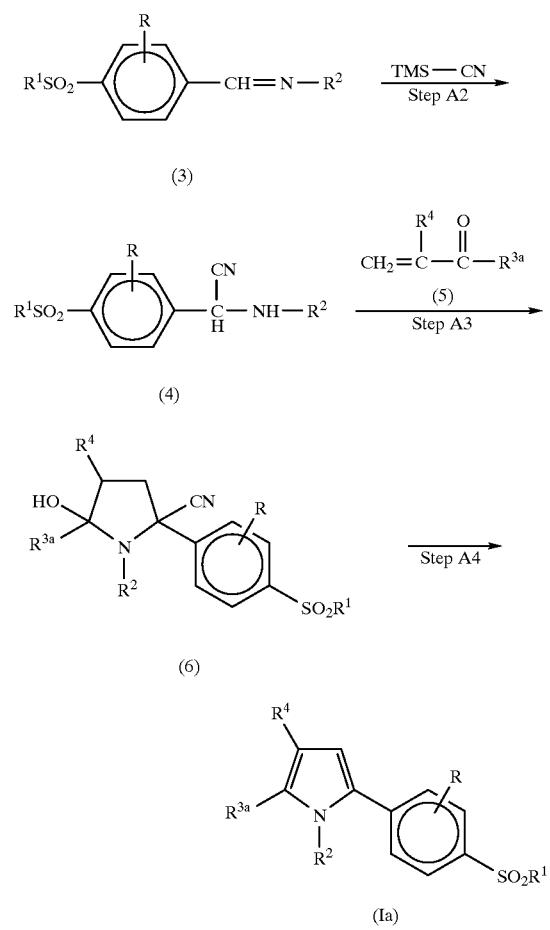

In the above formulae, R, $R^1$, $R^2$ and $R^4$ are as defined above, and $R^{3a}$ represents a hydrogen atom, an alkyl group having from 1 to 6 carbon atoms or a substituted alkyl group having from 1 to 6 carbon atoms and having at least one substituent selected from the group consisting of substituents α, as defined and exemplified above.

Step A1

In this Step, an aldimine compound of formula (3) is prepared by the dehydration condensation of a benzaldehyde compound of formula (1) with an aniline compound of formula (2) in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane and petroleum ether; aromatic hydrocarbons, such as benzene, toluene and xylene; halogenated hydrocarbons, such as methylene chloride, chloroform, carbon tetrachloride and dichloroethane; ethers, such as diethyl ether, diisopropyl ether, tetrahydrofuran and dioxane; alcohols, such as methanol, ethanol, propanol, isopropanol and butanol; and organic acids, such as acetic acid and propionic acid. Of these solvents, we prefer the alcohols.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 5° C. to 200° C., more preferably from room temperature to 150° C. The time required for the reaction may also vary widely, depending on many factors, notably the reaction temperature and the nature of the reagents and solvent employed. However, provided that the reaction is effected under the preferred conditions outlined above, a period of from 10 minutes to 20 hours, more preferably from 1 hour to 15 hours, will usually suffice.

The reaction may be carried out while the water which is produced in the reaction is removed, but the reaction will normally proceed sufficiently without any such procedure.

Step A2

In this Step, an anilinonitrile compound of formula (4) is prepared by the addition of hydrogen cyanide to the aldimine compound of formula (3), prepared as described in Step A1.

The reaction may be carried out by reacting the aldimine compound of formula (3) with trimethylsilyl cyanide (TMS-CN) in the presence of a Lewis acid, for example, aluminum chloride, tin chloride or zinc chloride.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene and nitrobenzene; halogenated hydrocarbons, such as methylene chloride, chloroform, carbon tetrachloride and 1,2-dichloroethane; and ethers, such as diethyl ether, diisopropyl ether, tetrahydrofuran and dioxane. Of these solvents, we prefer the ethers.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 5° C. to 200° C., more preferably from room temperature to 150° C. The time required for the reaction may also vary widely, depending on many factors, notably the reaction temperature and the nature of the reagents and solvent employed. However, provided that the reaction is effected under the preferred conditions outlined above, a period of from 30 minutes to 100 hours, more preferably from 1 hour to 30 hours, will usually suffice.

Step A3 and Step A4

In these Steps, the desired compound of formula (Ia), which is a compound of the present invention, is prepared by reacting the anilinonitrile compound of formula (4), prepared as described in Step A2, with an α,β-unsaturated aldehyde or ketone compound of formula (5), to obtain a pyrrolidine compound of formula (6), which is then dehydrated and dehydrogencyanated in a modification of the method of V. A. Treibs & R. Derra [Ann. Chem. 589, 176 (1954)].

Step A3

This Step is carried out in the presence of a base. There is no particular restriction on the nature of the bases used, and any base commonly used in reactions of this type may equally be used here. Examples of such bases include: alkali metal hydroxides, such as lithium hydroxide, sodium hydroxide and potassium hydroxide; alkali metal hydrides, such as lithium hydride, sodium hydride and potassium hydride; alkali metal amides, such as lithium amide, sodium amide, potassium amide and lithium bis(trimethylsilyl) amide; and alkali metal alkoxides, such as lithium ethoxide, sodium methoxide, sodium ethoxide and potassium t-butoxide. Of these, we prefer the lithium amides.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane and heptane; aromatic hydrocarbons, such as benzene, toluene and xylene; ethers, such as diethyl ether, diisopropyl ether, tetrahydrofuran and dioxane; and alcohols, such as methanol, ethanol, propanol, isopropanol and butanol. Of these, we prefer the ethers.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −78° C. to 100° C., more preferably from −78° C. to room temperature. The time required for the reaction may also vary widely, depending on many factors, notably the reaction temperature and the nature of the reagents and solvent employed. However, provided that the reaction is effected under the preferred conditions outlined above, a period of from 10 minutes to 30 hours, more preferably from 1 hour to 20 hours, will usually suffice.

Step A4

In this Step, the desired compound of formula (Ia), which is a compound of the present invention, is prepared by the dehydration and dehydrogencyanation of a compound of formula (6), prepared as described in Step A3.

This may be achieved by heating the residue obtained by distilling off the solvent from the product of Step A3, or by heating the material obtained by extracting that residue, washing it with water and distilling off the solvent, at a temperature not lower than 100° C., in the presence or absence of a solvent after completion of the reaction of Step A3. The reaction proceeds sufficiently in the absence of a solvent, but, when a solvent is used, the solvent is preferably inert and has a higher boiling point. Examples of suitable solvents include: toluene, xylene, dimethylformamide, dimethylacetamide, dimethyl sulfoxide, diglyme and diphenyl ether.

Method B

This is a modified method for preparing the compound of formula (Ia) wherein $R^3$ represents a hydrogen atom, an alkyl group having from 1 to 6 carbon atoms or a substituted alkyl group having from 1 to 6 carbon atoms and having at least one substituent selected from the group consisting of substituents α, as defined and exemplified above.

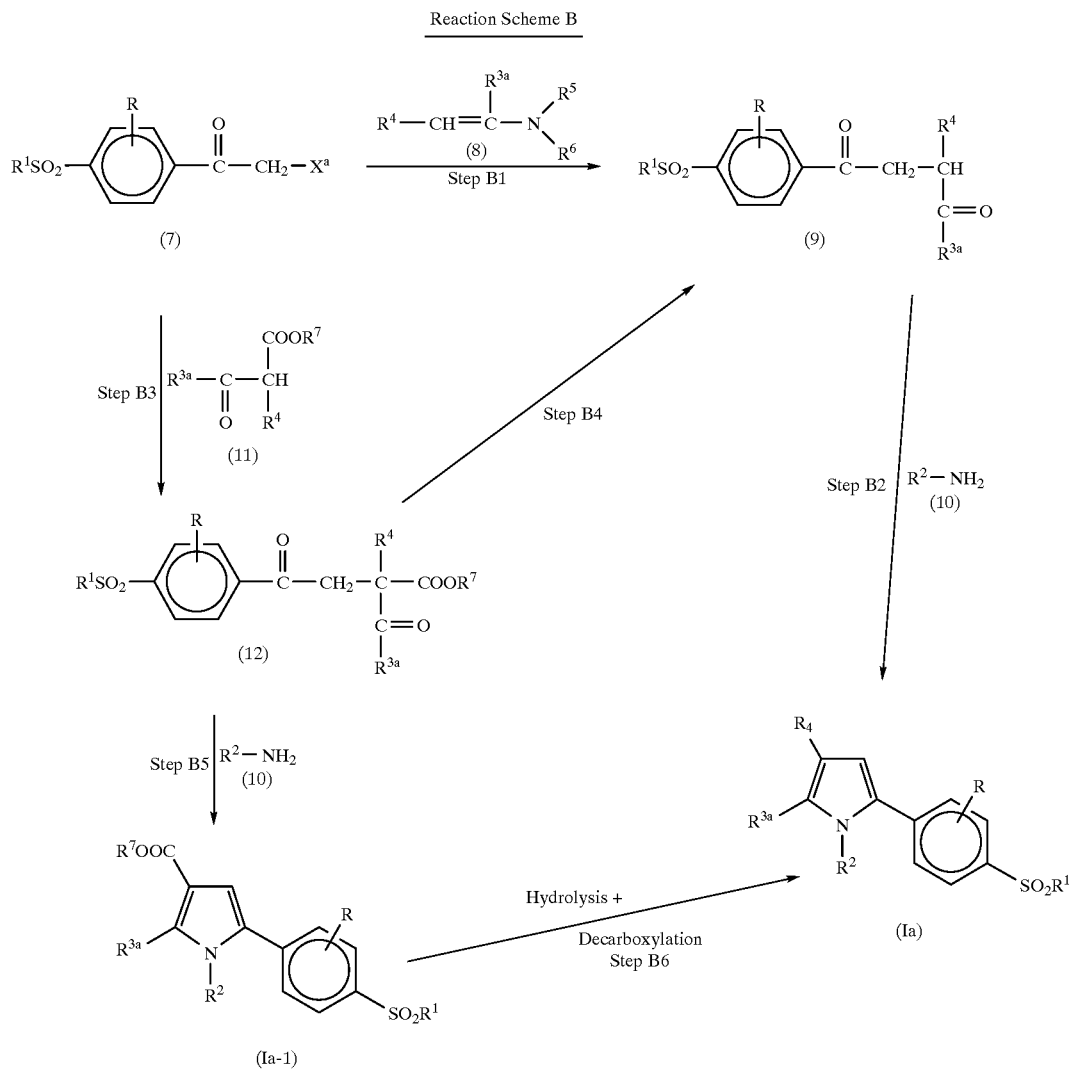

Reaction Scheme B

In the above formulae:

R, $R^1$, $R^2$, $R^{3a}$ and $R^4$ are as defined above;

each of $R^5$ and $R^6$ represents an alkyl group having from 1 to 4 carbon atoms or $R^5$ and $R^6$ together with the nitrogen atom to which they are attached, represent a heterocyclic ring containing 5 or 6 ring atoms, of which one is said nitrogen atom, 0 or 1 is an additional hetero-atom selected from the group consisting of nitrogen, oxygen and sulfur atoms, and the remaining atoms are carbon atoms;

$R^7$ represents a carboxy-protecting group; and $X^a$ represents a chlorine, bromine or iodine atom.

The term "carboxy-protecting group", as used herein, signifies a protecting group capable of being cleaved by chemical means, such as hydrogenolysis, hydrolysis, electrolysis or photolysis.

Examples of such carboxy-protecting groups include:

alkyl groups having from 1 to 20 carbon atoms, more preferably from 1 to 6 carbon atoms, such as those exemplified in relation to R and higher alkyl groups as are well known in the art, such as the heptyl, octyl, nonyl, decyl, dodecyl, tridecyl, pentadecyl, octadecyl, nonadecyl and icosyl groups, but most preferably the methyl, ethyl and t-butyl groups;

halogenated alkyl groups having from 1 to 6, preferably from 1 to 4, carbon atoms, in which the alkyl part is as defined and exemplified in relation to the alkyl groups above, and the halogen atom is chlorine, fluorine, bromine or iodine, such as the 2,2,2-trichloroethyl, 2-haloethyl (e.g. 2-chloroethyl, 2-fluoroethyl, 2-bromoethyl or 2-iodoethyl), 2,2-dibromoethyl and 2,2,2-tribromoethyl groups;

cycloalkyl groups having from 3 to 8 carbon atoms, for example the cyclopropyl, cyclobutyl, cyclopentyl, cyclohexyl and cycloheptyl groups;

aralkyl groups, in which the alkyl part has from 1 to 3 carbon atoms and the aryl part is a carbocyclic aromatic group having from 6 to 14 carbon atoms, which may be substituted or unsubstituted and, if substituted, has at least one of substituents α or substituents β defined and exemplified above, although the unsubstituted groups art preferred; examples of such aralkyl groups include the benzyl, phenethyl, 1-phenylethyl, 3-phenylpropyl, 2-phenylpropyl, 1-naphthylmethyl, 2-naphthylmethyl, 2-(1-naphthyl)ethyl, 2-(2-naphthyl)ethyl, benzhydryl (i.e. diphenylmethyl), triphenylmethyl, bis(o-nitrophenyl)methyl, 9-anthrylmethyl, 2,4,6- trimethylbenzyl, 4-bromobenzyl, 2-nitrobenzyl, 4-nitrobenzyl, 3-nitrobenzyl, 4-methoxybenzyl and piperonyl groups;

alkenyl groups having from 2 to 6 carbon atoms, such as the vinyl, allyl, 2-methylallyl, 1-propenyl, isopropenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl and 5-hexenyl groups, of which the vinyl, allyl, 2-methylallyl, 1-propenyl, isopropenyl and butenyl groups are preferred, the allyl and 2-methylallyl groups being most preferred.

substituted silylalkyl groups, in which the alkyl part is as defined and exemplified above, and the silyl group has up to 3 substituents selected from alkyl groups having from 1 to 6 carbon atoms and phenyl groups which are unsubstituted or have at least one substituent selected from substituents α and substituents β defined and exemplified above, for example a 2-trimethylsilylethyl group;

aryl groups having from 6 to 14 carbon atoms and optionally substituted by one or more of substituents α or substituents β, defined and exemplified above, for example the phenyl, α-naphthyl, β-naphthyl, indanyl and anthrenyl groups, preferably the phenyl or indanyl group and more preferably the phenyl group; any of these aryl groups may be unsubstituted or substituted, and, if substituted, preferably have at least one alkyl group having from 1 to 4 carbon atoms or acylamino group; examples of the substituted groups include the tolyl and benzamidophenyl groups;

phenacyl groups, which may be unsubstituted or have at least one of substituents α or substituents β defined and exemplified above, for example the phenacyl group itself or the p-bromophenacyl group; and cyclic and acyclic terpenyl groups, for example the geranyl, neryl, linalyl, phytyl, menthyl (especially m- and p- menthyl), thujyl, caryl, pinanyl, bornyl, notcaryl, norpinanyl, norbornyl, menthenyl, camphenyl and nor-bornenyl groups.

Step B1

In this Step, a 1,4-dioxo compound of formula (9) is prepared by alkylating the β-position of the enamine compound of formula (8) with a phenacyl halide compound of formula (7).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane and petroleum ether; aromatic hydrocarbons, such as benzene, toluene and xylene; and ethers, such as diethyl ether, diisopropyl ether, tetrahydrofuran and dioxane. Of these, we prefer the ethers.

The reaction may be carried out in the presence or absence of a base. There is likewise no particular restriction on the nature of the bases used, and any base commonly used in reactions of this type may equally be used here. Examples of such bases include: pyridine, picoline, 4-(N,N-dimethylamino)pyridine, triethylamine, tributylamine, diisopropylethylamine and N-methylpiperidine.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −30° C. to 200° C., more preferably from 0° C. to 1° C. The time required for the reaction may also vary widely, depending on many factors, notably the reaction temperature and the nature of the reagents and solvent employed. However, provided that the reaction is effected under the preferred conditions outlined above, a period of from 30 minutes to 30 hours, more preferably from 1 hour to 20 hours, will usually suffice.

At the end of this reaction, the reaction mixture is acidified, to prepare the 1,4-dioxo compound of formula (9).

Step B2

In this Step, the desired compound of formula (Ia) of the present invention is prepared by the dehydration condensation of the 1,4-dioxo compound of formula (9), prepared as described in Step B1, and an aniline compound of formula (10) to close a ring. The reaction may be carried out under the same conditions as described in Step A1 of Method A. However, it is preferred to carry out this step by heating under reflux in acetic acid for a period of from 1 hour to 10 hours.

Step B3

In this Step, a dioxo ester compound of formula (12) is prepared by alkylating the α-position of the oxo ester compound of formula (11) with a phenacyl halide compound of formula (7).

The reaction is carried out in the presence of a base. There is no particular restriction on the nature of the bases used, and any base commonly used in reactions of this type may equally be used here. Examples of such bases include: alkali metals, such as lithium, sodium and potassium; alkali metal hydrides, such as lithium hydride, sodium hydride and potassium hydride; alkali metal amides, such as lithium amide, sodium amide and potassium amide; and alkali metal alkoxides, such as lithium ethoxide, sodium methoxide, sodium ethoxide and potassium t-butoxide. Of these, we prefer the alkali metal alkoxides.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane and heptane; aromatic hydrocarbons, such as benzene, toluene and xylene; ethers, such as diethyl ether, diisopropyl ether, tetrahydrofuran and dioxane; amides, such as dimethylformamide and dimethylacetamide; and alcohols, such as methanol, ethanol, propanol, isopropanol, butanol and t-butanol. Of these, we prefer the ethers or the alcohols.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 5° C. to 200° C., more preferably from room temperature to 150° C. The time required for the reaction may also vary widely, depending on many factors, notably the reaction temperature and the nature of the reagents and solvent employed. However, provided that the reaction is effected under the preferred conditions outlined above, a period of from 10 minutes to 20 hours, more preferably from 30 minutes to 15 hours, will usually suffice.

Step B4

In this Step, which is an alternative to Step B1, the 1,4-dioxo compound of formula (9) is prepared by carrying out decarboxylation of the dioxo ester compound of formula (12), prepared as described in Step B3, at the same time as hydrolysis. The hydrolysis reaction may be carried out using any acid or alkali commonly used in organic synthesis chemistry for reactions of this type.

Step B5

This Step may be conducted when $R^4$ in the dioxo ester compound of formula (12) is a hydrogen atom. In this Step, the compound of formula (Ia-1) is prepared by reacting the dioxo ester compound of formula (12), prepared as described in Step B3, with an aniline compound of formula (10). This reaction is essentially the same as and may be carried out in the same manner as that described in Step B2.

Step B6

In this Step, the compound of formula (Ia) of the present invention is prepared by hydrolysing the ester portion of the compound of formula (Ia-1), prepared as described in Step B5, to obtain the corresponding carboxylic acid, which is then decarboxylated. The hydrolysis reaction may be carried out by conventional methods as mentioned above. The decarboxylation reaction may be carried out using an acid or an alkali, or with heating, as is well known in the field of organic synthetic chemistry [for example, the method described in the Yakugaku Zasshi, 93(5), 584–598 (1973)].

Method C

In this method, a compound of formula (Ib) wherein $R^3$ is a halogen atom is prepared by the halogenation of a corresponding compound where $R^3$ represents a hydrogen atom, as shown in the following Reaction Scheme.

Reaction Scheme C

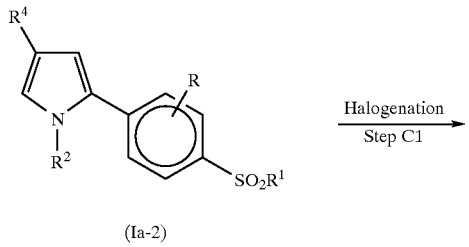

(Ia-2)

Halogenation
Step C1

-continued

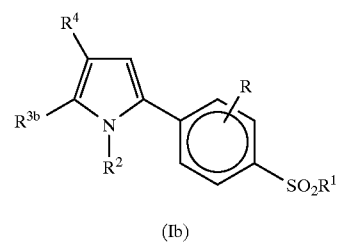

(Ib)

In the above formulae, R, $R^1$, $R^2$ and $R^4$ are as defined above, and $R^{3b}$ represents a halogen atom, for example a fluorine, chlorine, bromine or iodine atom.

Step C1

In this Step, the desired compound of formula (Ib) of the present invention is prepared by halogenating the compound of formula (Ia-2) of the present invention, which may have been prepared, for example, as described in either Method A or Method B. Examples of suitable halogenating agents include: fluorinating agents, such as xenon difluoride; chlorinating agents, such as chlorine, sulfuryl chloride or N-chlorosuccinimide; brominating agents, such as bromine or N-bromosuccinimide; and iodinating agents, such as iodine or N-iodosuccinimide. The reaction may be carried out according to the methods described in detail in "The Chemistry of Heterocyclic Compounds", Vol 48, Part 1, p348–395, published by John Wiley & Sons.

Method D

This is a method of preparing a compound of formula (Ic-1), (Ic-2) or (Ic-3) wherein $R^3$ represents a haloalkyl group having from 1 to 6 carbon atoms.

Reaction Scheme D

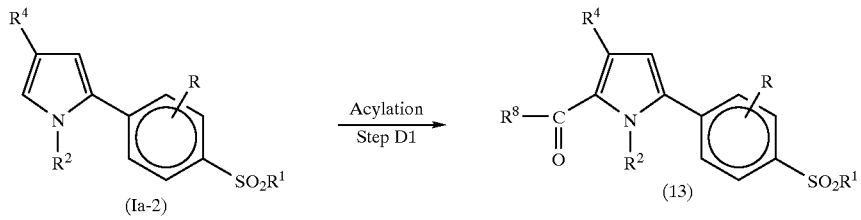

(Ia-2)   Acylation Step D1   (13)

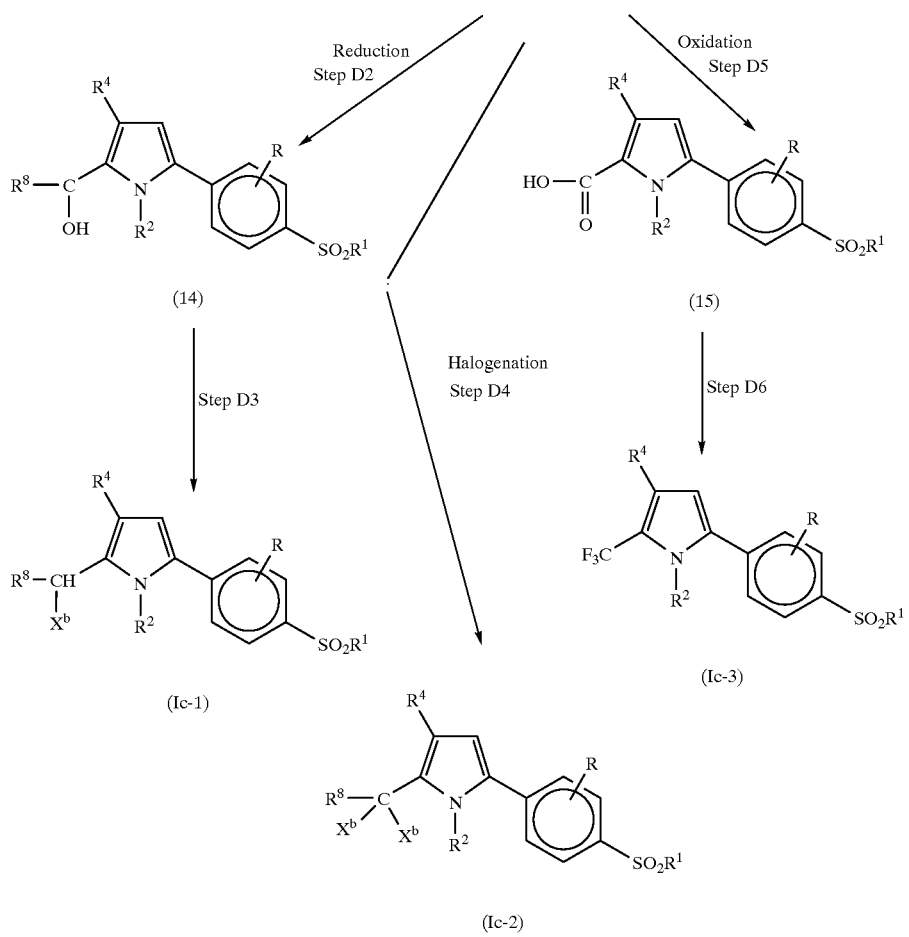

In the above formulae:

R, $R^1$, $R^2$ and $R^4$ are as defined above;

$R^8$ represents a hydrogen atom or an alkyl group having from 1 to 6 carbon atoms; and $X^b$ represents a halogen atom, for example a fluorine, chlorine, bromine or iodine atom.

Step D1

In this Step, an acylpyrrole compound of formula (13) is prepared by acylating a compound of formula (Ia-2) of the present invention, which may have been prepared, for example, as described in either Method A or Method B.

In this Step, a compound of formula (13) wherein $R^8$ represents a hydrogen atom may be prepared by reacting a Vilsmeier reagent, such as phosphorus oxychloride-dimethylformamide, phosphorus oxybromide-dimethylformamide or oxalyl chloride-dimethylformamide, with the compound of formula (Ia-2). The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, such as methylene chloride, chloroform, carbon tetrachloride and 1,2-dichloroethane; and amides, such as dimethylformamide.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −10° C. to 150° C., more preferably from 0° C. to 100° C. The time required for the reaction may also vary widely, depending on many factors, notably the reaction temperature and the nature of the reagents and solvent employed. However, provided that the reaction is effected under the preferred conditions outlined above, a period of from 15 minutes to 20 hours, more preferably from 30 minutes to 10 hours, will usually suffice.

Those compounds of formula (13) wherein $R^8$ represents an alkyl group having from 1 to 6 carbon atoms, preferably from 1 to 3 carbon atoms, may be prepared by reacting an acid anhydride or an acid halide of formula $(R^{8a}CO)_2O$ or $R^{8a}COX^a$ (wherein $X^a$ is as defined above, and $R^{8a}$ represents an alkyl group having from 1 to 6 carbon atoms, preferably from 1 to 3 carbon atoms) with the compound of formula (Ia-2) in the presence of a Lewis acid (for example, aluminum chloride, tin chloride or zinc chloride). The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene and nitrobenzene; halogenated hydrocarbons, such as methylene chloride, chloroform, carbon tetrachloride and 1,2-dichloroethane; and carbon disulfide.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −10° C. to 150° C., more preferably from 0° C. to 100° C. The time required for the reaction may also vary widely, depending on many factors, notably the reaction temperature and the nature of the reagents and solvent employed. However, provided that the reaction is effected under the preferred conditions outlined above, a period of from 10 minutes to 20 hours, more preferably from 30 minutes to 10 hours, will usually suffice.

Step D2

In this Step, a hydroxy compound of formula (14) is prepared by reducing the acyl group of the acylpyrrole compound of formula (13), prepared as described in Step D1. The reaction may be effected using a reducing agent (for example, sodium borohydride, lithium borohydride, lithium aluminum hydride, diisobutylaluminum hydride or borane) or by using catalytic reduction with hydrogen. These reactions are well known in the field of synthetic organic chemistry and may be carried out using well known techniques, for example as described in detail by J. Dale [J. Chem. Soc., (1961), 910] and by F. G. Bordwell et al. [J. Org. Chem., 33, 3385 (1968)], the disclosures of which are incorporated herein by reference.

Step D3

In this Step, the desired compound of formula (Ic-1), which is a compound of the present invention, is prepared by halogenating the hydroxy group of the hydroxy compound of formula (14), prepared as described in Step D2. Suitable halogenating agents include: fluorinating agents, such as diethylamino sulfur trifluoride (DAST); chlorinating agents, such as thionyl chloride, phosphorus trichloride, phosphorus pentachloride, phosphorus oxychloride or triphenylphosphine/carbon tetrachloride; brominating agents, such as hydrobromic acid, thionyl bromide, phosphorus tribromide or triphenylphosphine/carbon tetrabromide; and iodinating agents, such as hydroiodic acid or phosphorus triiodide. These reactions are well known in the field of synthetic organic chemistry and may be carried out using well known techniques, for example as described in detail by W. J. Middleton [J. Org. Chem., 40, 574 (1975)] and C. R. Noller & R. Dinsmore [Org. Synth., II, 358 (1943)], the disclosures of which are incorporated herein by reference.

Step D4

In this Step, the desired compound of formula (Ic-2), which is a compound of the present invention, is prepared by gem-dihalogenating the carbonyl group of the acylpyrrole compound of formula (13), prepared as described in Step D1, using a suitable halogenating agent. Suitable halogenating agents include: fluorinating agents, such as sulfur tetrafluoride and DAST; chlorinating agents, such as phosphorus pentachloride and thionyl chloride/dimethylformamide; brominating agents, such as boron tribromide; and iodinating agents, such as trimethylsilyl iodide. These reactions are well known in the field of synthetic organic chemistry and may be carried out using well known techniques, for example as described in detail by W. J. Middleton [J. Org. Chem., 40, 574 (1975)] and M. E. Jung et al. [J. Org. Chem., 43, 3698 (1978)], the disclosures of which are incorporated herein by reference.

Step D5

In this Step, a carboxylic acid compound of formula (15) is prepared by oxidizing an acylpyrrole compound of formula (13) wherein $R^8$ is a hydrogen atom, prepared as described in Step D1. Examples of suitable oxidising agents which may be used in this step include potassium permanganate, chromic acid, hydrogen peroxide, nitric acid, silver (I) oxide and silver (II) oxide. These reactions are well known in the field of synthetic organic chemistry and may be carried out using well known techniques, for example as described in detail by C. D. Hurd et al. [J. Am. Chem. Soc., 55, 1082 (1933)].

Step D6

In this Step, the desired compound of formula (Ic-3), which is a compound of the present invention, is prepared by converting the carboxy group of the carboxylic acid compound of formula (15), prepared as described in Step D5, into a trifluoromethyl group. This Step may be carried out using sulfur tetrafluoride according to the methods described by C. L. J. Wang [Org. React., 34, 319 (1985)].

Method E

This illustrates the preparation of compounds of formula (Id-1), (Id-2), (Id-3) or (Id-4) wherein $R^4$ represents a substituted alkyl group and $R^3$ represents a hydrogen atom or a halogen atom.

Reaction Scheme E

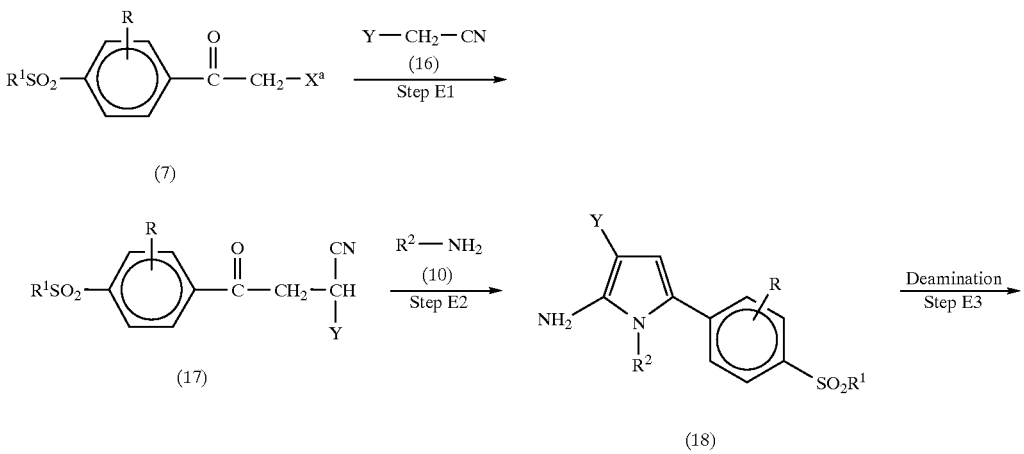

-continued

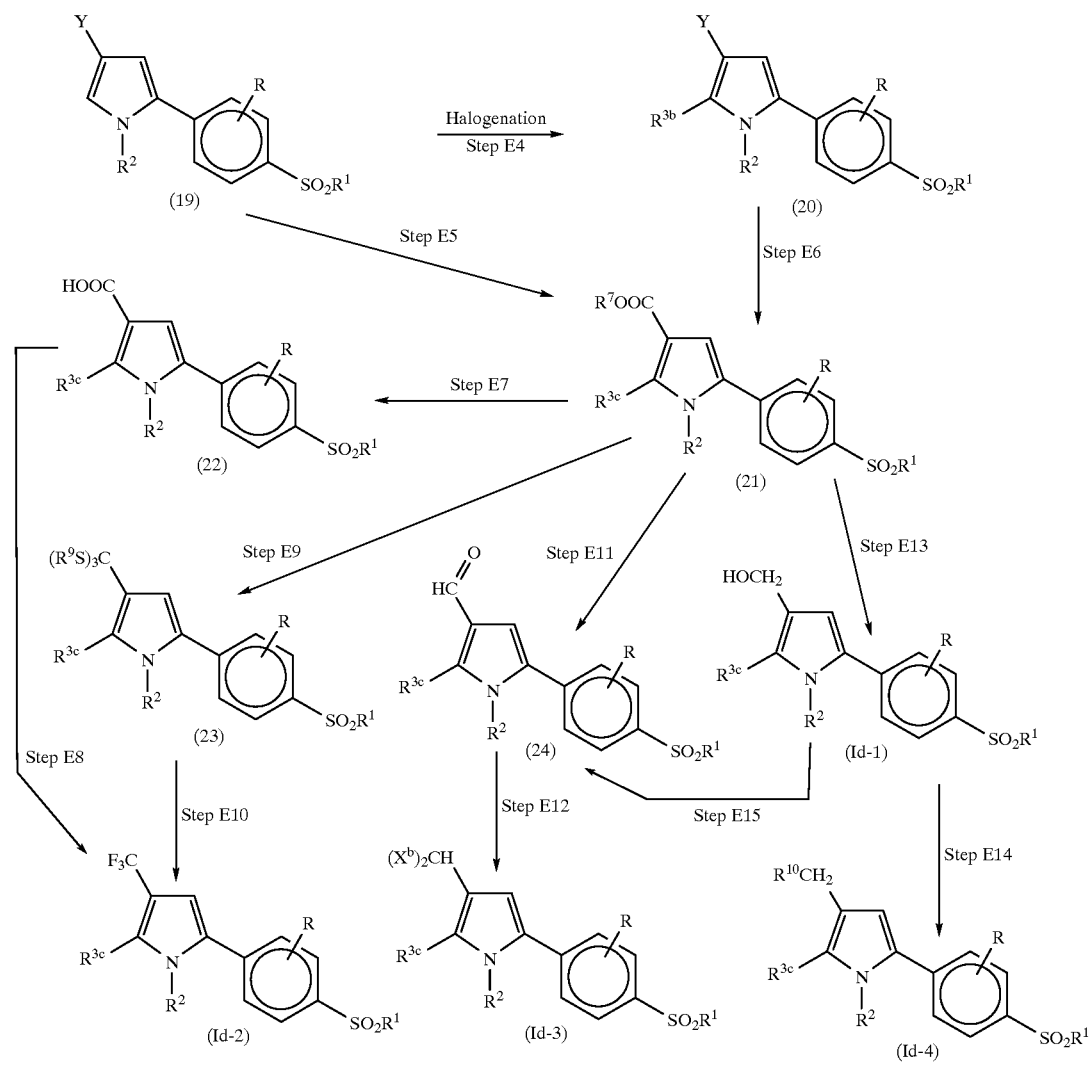

In the above formulae:

R, $R^1$, $R^2$, $R^{3b}$, $R^7$, $X^a$ and $X^b$ are as defined above;

$R^{3c}$ represents a hydrogen atom or a halogen atom;

$R^9$ represents an alkyl group having from 1 to 6 carbon atoms;

$R^{10}$ represents a halogen atom or an alkoxy group having from 1 to 6 carbon atoms; and;

Y represents a cyano group or a group of formula —$CO_2R^7$, where $R^7$ is as defined above.

Step E1

In this Step, a phenacyl acetonitrile compound of formula (17) is prepared by alkylating the cyano compound of formula (16) with a phenacyl halide compound of formula (7). This reaction is essentially the same as and may be carried out in the same manner as and using the same reagents and reaction conditions as Step B3 of Method B.

Step E2

In this Step, an aminopyrrole compound of formula (18) is prepared by reacting the phenacylacetonitrile compound of formula (17), prepared as described in Step E1, with an aniline compound of formula (10). This step may be carried out in the presence of a catalytic amount of hydrogen chloride according to the methods described by K. M. H. Hilmy & E. B. Pedersen [Liebigs Ann. Chem. (1989), 1145–1146].

Step E3

In this Step, a pyrrole compound of formula (19) is prepared by removing an amino group from the aminopyrrole compound of formula (18), prepared as described in Step E2.

This may be achieved by reacting an alkyl nitrite (for example, methyl nitrite, ethyl nitrite, propyl nitrite, butyl nitrite, t-butyl nitrite or isoamyl nitrite) with the aminopyrrole compound of formula (18). The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane or heptane; aromatic hydrocarbons, such as benzene, toluene or xylene; ethers, such as diethyl ether, diisopropyl ether, tetrahydrofuran or dioxane; and amides, such as dimethylformamide or dimethylacetamide. Of these, we prefer the ethers.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −10° C. to 200° C., more preferably from room temperature to 150° C. The time required for the reaction may also vary widely, depending on many factors, notably the reaction temperature and the nature of the reagents and solvent employed. However, provided that the reaction is effected under the preferred conditions outlined above, a period of from 10 minutes to 20 hours, more preferably from 30 minutes to 15 hours, will usually suffice.

Step E4

In this Step, a halopyrrole compound of formula (20) is prepared by halogenating the pyrrole compound of formula (19), prepared as described in Step E3. This reaction is essentially the same as and may be carried out in the same manner as and using the same reagents and reaction conditions as Step C1 of Method C.

Step E5 and Step E6

In these Steps, an ester compound of formula (21) is prepared from a compound of formula (19), prepared as described in Step E3, or (20), prepared as described in Step E4, in which Y represents a cyano group by converting the cyano group into a protected carboxy group. The steps may be carried out by using, for example, the compound of formula (19) or (20), appropriate alcohols and acids, such as hydrochloric acid, sulfuric acid, or p-toluenesulfonic acid, using the methods described R. Adams & A. F. Thal [Org. Synth., I, 270 (1941)].

Step E7

In this Step, a carboxylic acid compound of formula (22) is prepared by hydrolysing the ester compound of formula (21), prepared as described in Step E5 or E6. This reaction is essentially the same as and may be carried out in the same manner as and using the same reagents and reaction conditions as Step B4 of Method B.

Step E8

In this Step, the desired compound of formula (Id-2) of the present invention is prepared by converting the carboxy group of the carboxylic acid compound of formula (22), prepared as described in Step E7, into a trifluoromethyl group. This reaction is essentially the same as and may be carried out in the same manner as and using the same reagents and reaction conditions as Step D6 of Method D.

Step E9 and Step E10

These Steps together provide an alternative method of preparing the compound of formula (Id-2) of the present invention from the ester compound of formula (21), prepared as described in Step E5 or E6. In Step E9, first, the protected carboxy group of the ester compound of formula (21) is converted into a tri(alkylthio)methyl group. This tri(alkylthio)methyl group is then converted into a trifluoromethyl group by an oxidative fluorodesulfurization reaction in Step E10. This method is described in detail by D. P. Matthews, J. P. Whitten & J. R. McCarthy [Tetrahedron Letters, 27(40), 4861–4864, (1986)], the disclosures of which are incorporated herein by reference.

Step E11

In this Step, the corresponding aldehyde compound of formula (24) is prepared by reducing the protected carboxyl group of the ester compound of formula (21), prepared as described in Step E5 or E6. For example, this step may be carried out by using a reducing agent, such as lithium aluminum hydride, sodium aluminum hydride, lithium triethoxyaluminum hydride, diisobutylaluminum hydride, etc. according to the methods described in detail by L. I. Zakharkin & I. M. Khorlina [Tetrahedron Lett., (1962), 619], the disclosures of which are incorporated herein by reference.

Step E12

In this Step, the desired compound of formula (Id-3) is prepared by gem-dihalogenating the aldehyde compound of formula (24), prepared as described in Step E11. This reaction is essentially the same as and may be carried out in the same manner as and using the same reagents and reaction conditions as Step D4 of Method D.

Step E13

In this Step, a hydroxymethyl compound of formula (Id-1), a desired compound of the present invention, is prepared by reducing the protected carboxyl group of the ester compound of formula (21), prepared as described in Step E5 or E6. For example, this step may be carried out using a reducing agent, such as lithium aluminum hydride, lithium borohydride, or isobutylaluminum hydride, according to the methods described in detail by R. F. Nystrom et al. [J. Am. Chem. Soc., 71, 3245 (1945)], the disclosures of which are incorporated herein by reference.

Step E14

In this Step, the halomethyl compound or the alkoxymethyl compound of formula (Id-4), which are compounds of the present invention, are prepared by halogenating or etherifying a hydroxymethyl compound of formula (Id-1), prepared as described in Step E13. In this step, the halogenation reaction may be carried out in the same manner as and using the same reagents and reaction conditions as Step D3 of Method D.

The etherification reaction may be carried out by reacting the hydroxymethyl compound of formula (Id-1) with an alkyl halide. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane and petroleum ether; aromatic hydrocarbons, such as benzene, toluene and xylene; ethers, such as diethyl ether, diisopropyl ether, tetrahydrofuran and dioxane; and amides, such as dimethylformamide and dimethylacetamide. Of these, we prefer the ethers and the amides.

The reaction is carried out in the presence of a base. There is likewise no particular restriction on the nature of the bases used, and any base commonly used in reactions of this type may equally be used here. Examples of such bases include: alkali metal hydrides, such as lithium hydride, sodium hydride and potassium hydride; alkali metal alkoxides, such as sodium methoxide, sodium ethoxide, potassium t-butoxide; and tertiary amines, such as triethylamine, tributylamine, pyridine, picoline and 4-(N,N-dimethylamino)pyridine. Of these, we prefer sodium hydride or potassium t-butoxide.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −10° C. to 200° C., more preferably from 0° C. to 150° C. The time required for the reaction may also vary widely, depending on many factors, notably the reaction temperature and the nature of the reagents and solvent employed. However, provided that the reaction is effected under the preferred conditions outlined above, a period of from 30 minutes to 48 hours, more preferably from 1 hour to 24 hours, will usually suffice.

Step E15

In this Step, a compound of formula (Id-1) is oxidised to give the compound of formula (24). This may be carried out using an oxidising agent, for example, chromic acid, manganese dioxide, or dimethyl sulfoxide, according to the methods described in detail by S. Bartel & F. Bohlmann [Tetrahedron Lett., (1985), 685].

The following Methods F to J and L illustrate the preparation of compounds of formula (II).

Method F

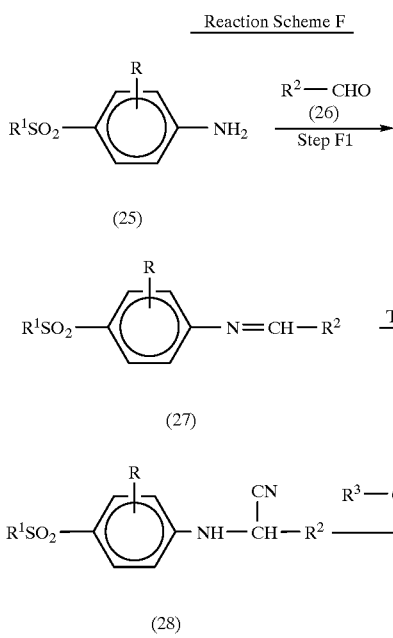

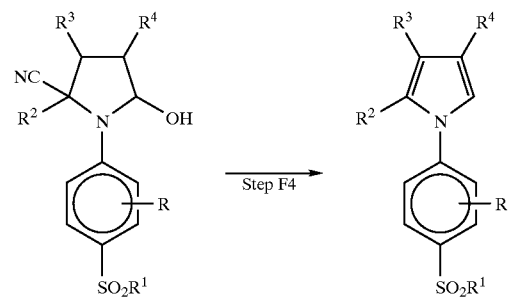

In the above formulae, R, $R^1$, $R^2$, $R^3$ and $R^4$ are as defined above.

The reactions of Step F1, Step F2, Step F3 and Step F4 are essentially the same as the reactions of Step A1, Step A2, Step A3 and Step A4, respectively, and may be carried out using the same reagents and reaction conditions.

Method G

This illustrates the preparation of a compound of formula (IIa-1) wherein $R^3$ represents a hydrogen atom, an alkyl group having from 1 to 6 carbon atoms or a substituted alkyl group having from 1 to 6 carbon atoms and having at least one substituent selected from the group consisting of substituents α, as defined and exemplified above.

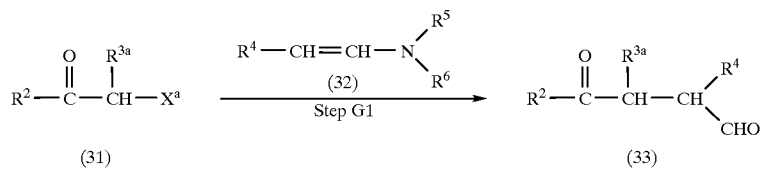

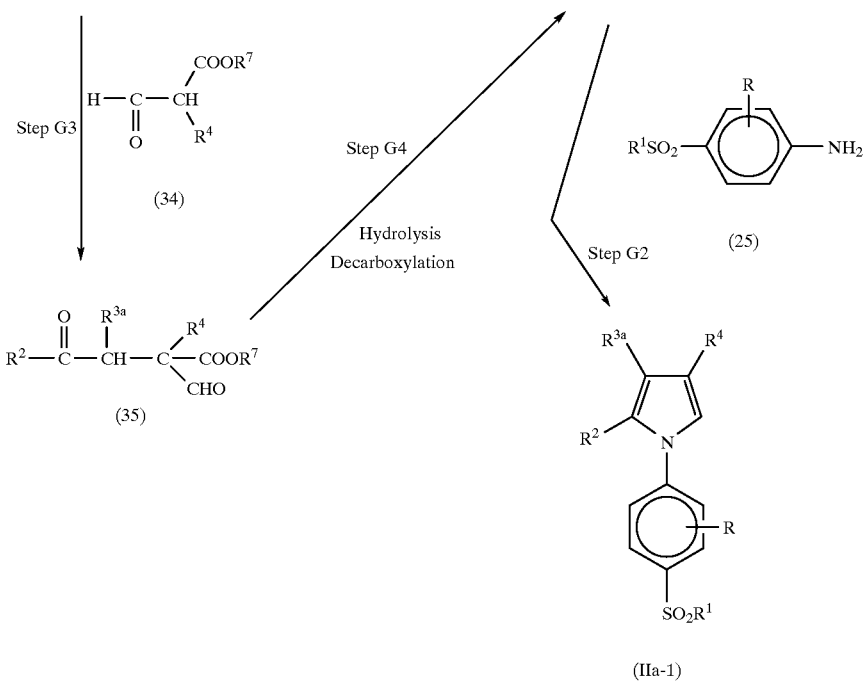

In the above formulae, R, $R^1$, $R^2$, $R^{3a}$, $R^4$, $R^5$, $R^6$, $R^7$ and $X^a$ are as defined above.

Step G1

In this Step, a 1,4-dioxo compound of formula (33) is prepared by alkylating the β-position of an enamine compound of formula (32) using a phenacyl halide compound of formula (31). This reaction is essentially the same as and may be carried out in the same manner as and using the same reagents and reaction conditions as Step B1 of Method B.

Step G2

In this Step, the compound of formula (IIa-1), which is a compound of the present invention, is prepared by the dehydration-condensation of the 1,4-dioxo compound of formula (33), prepared as described in Step G1, and the aniline compound of formula (25) to close a ring. This reaction is essentially the same as and may be carried out in the same manner as and using the same reagents and reaction conditions as Step B2 of Method B.

Step G3

In this Step, a dioxo ester compound of formula (35) is prepared by alkylating the α-position of a formyl ester compound of formula (34) with the phenacyl halide compound of formula (31). This reaction is essentially the same as and may be carried out in the same manner as and using the same reagents and reaction conditions as Step B3 of Method B.

Step G4

In this Step, the 1,4-dioxo compound of formula (33) is prepared by carrying out decarboxylation of the dioxo ester compound of formula (35), prepared as described in Step G3, at the same time as hydrolysis. This reaction is essentially the same as and may be carried out in the same manner as and using the same reagents and reaction conditions as Step B4 of Method B.

Method H

This illustrates the preparation of a compound of formula (IIb) wherein $R^3$ represents a halogen atom.

Reaction Scheme H

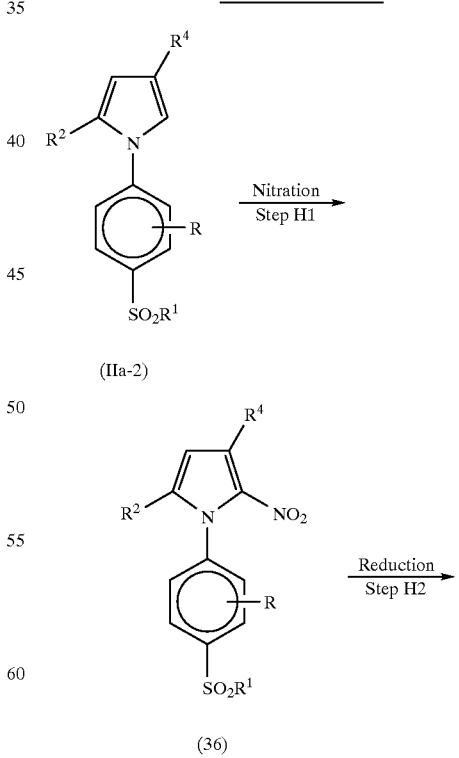

-continued

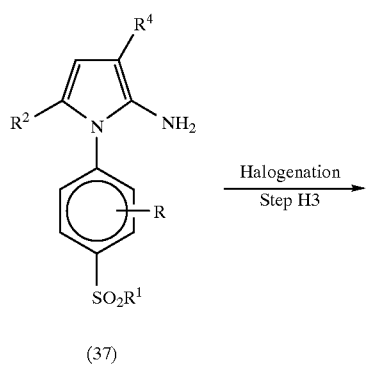

(37)

Halogenation
Step H3

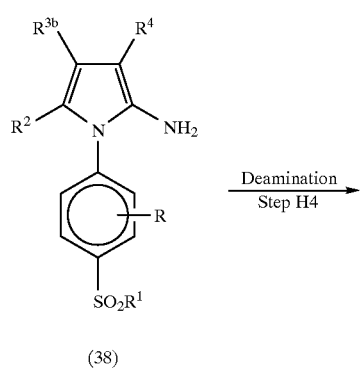

(38)

Deamination
Step H4

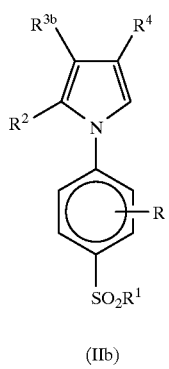

(IIb)

In the above formulae, R, $R^1$, $R^2$, $R^{3b}$ and $R^4$ are as defined above.

Step H1

In this Step, a nitropyrrole compound of formula (36) is prepared by nitrating the compound of formula (IIa-2), which may have been prepared as described in Method G [a compound of formula (IIa-1) in which $R^{3a}$ represents a hydrogen atom].

This step is carried out by using a conventional nitrating agent, for example, nitric acid, fuming nitric acid, or nitric acid/acetic anhydride, according to the methods described in detail in "The Chemistry of Heterocyclic Compounds", Vol. 48, Part 1, p330–345, published by John Wiley & Sons.

Step H2

In this Step, an aminopyrrole compound of formula (37) is prepared by reducing a nitro group of the nitropyrrole compound of formula (36), prepared as described in Step H1. Methods of reducing nitro groups to amino groups are well known in the field of organic synthetic chemistry, and any conventional method may be used.

Step H3

In this Step, an aminohalopyrrole compound of formula (38) is prepared by halogenating the aminopyrrole compound of formula (37), prepared as described in Step H2. This reaction is essentially the same as and may be carried out in the same manner as and using the same reagents and reaction conditions as Step C1 of Method C.

Step H4

In this Step, the desired compound of formula (IIb) of the present invention is prepared by removing the amino group from the aminohalopyrrole compound of formula (38), prepared as described in Step H3. This reaction is essentially the same as and may be carried out in the same manner as and using the same reagents and reaction conditions as Step E3 of Method E.

Method I

This Method illustrates the preparation of a compound of formula (IIc-1), (IIc-2), (IIc-3) or (IIc-4) wherein $R^4$ represents a substituted alkyl group having from 1 to 6 carbon atoms and substituted by at least one substituent selected from the group consisting of substitutents α, and $R^3$ represents a hydrogen atom or a halogen atom.

Reaction Scheme I

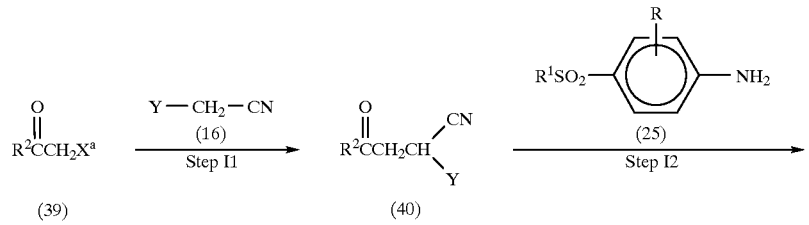

-continued
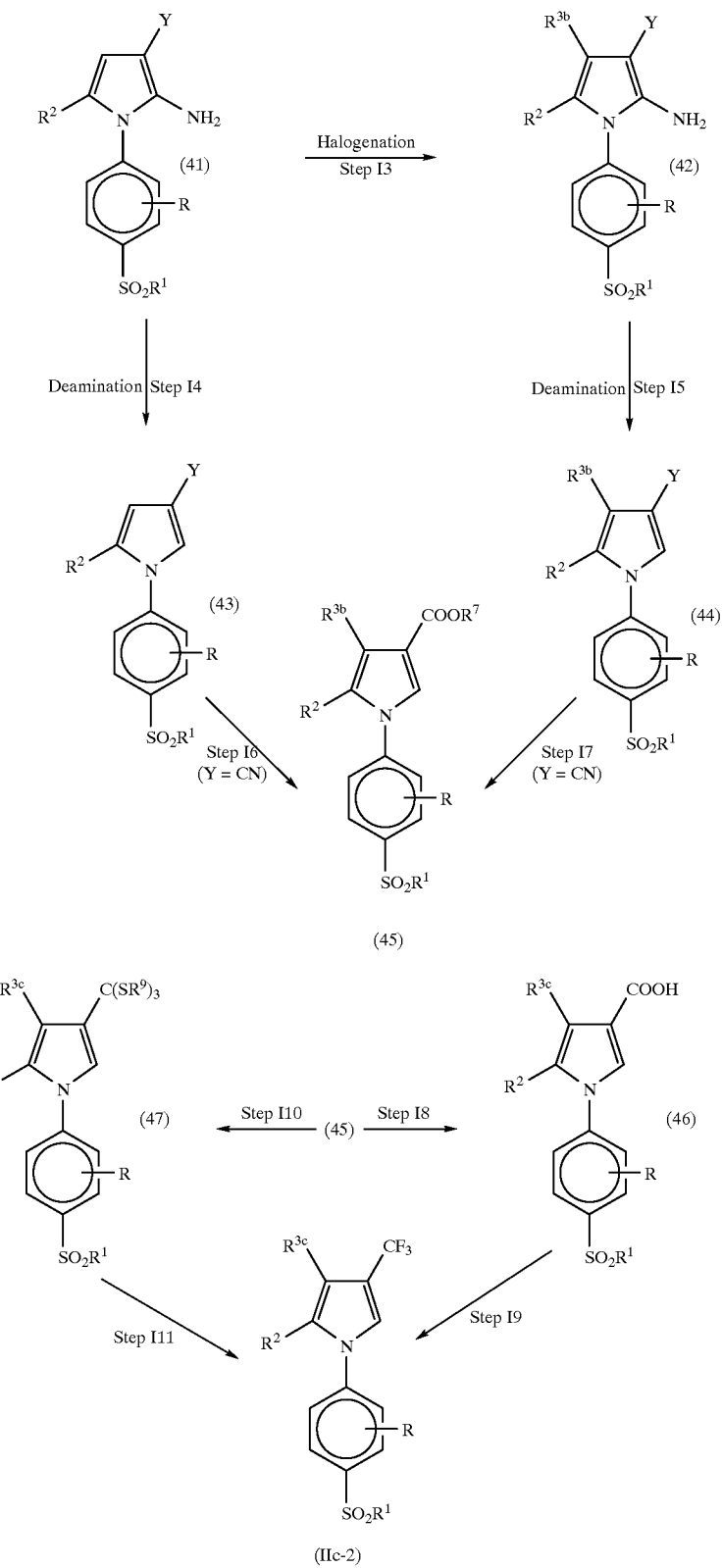

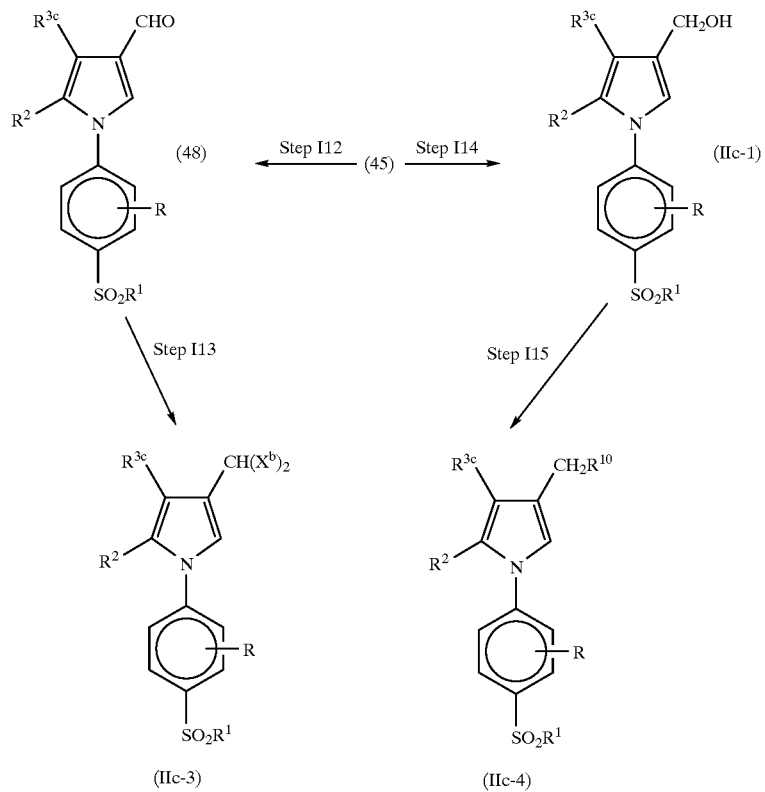

In the above formulae, R, $R^1$, $R^2$, $R^{3b}$, $R^{3c}$, $R^7$, $R^9$, $R^{10}$, $X^a$, $X^b$ and Y are as defined above.

Step I1

In this Step, a phenacylacetonitrile compound of formula (40) is prepared by alkylating the cyano compound of formula (16) with a phenacyl halide compound of formula (39). This reaction is essentially the same as and may be carried out in the same manner as and using the same reagents and reaction conditions as Step E1 of Method E.

Step I2

In this Step, an aminopyrrole compound of formula (41) is prepared by reacting the phenacylacetonitrile compound of formula (40), prepared as described in Step I1, with the aniline compound of formula (25). This reaction is essentially the same as and may be carried out in the same manner as and using the same reagents and reaction conditions as Step E2 of Method E.

Steps I3

In this Step, an aminohalogen compound of formula (42) is prepared by halogenating the aminopyrrole compound of formula (41), prepared as described in Step I2. This reaction is essentially the same as and may be carried out in the same manner as and using the same reagents and reaction conditions as Step H3 of Method H.

Step I4 and Step I5

In these Steps, a compound of formula (43) and a compound of formula (44), respectively, are prepared by removing the amino group from the aminopyrrole compound of formula (41) and the aminohalogen compound of formula (42), respectively. This reaction is essentially the same as and may be carried out in the same manner as and using the same reagents and reaction conditions as Step H4 of Method H.

Step I6 and Step I7

In these Steps, an ester compound of formula (45) is prepared from those pyrrole compounds of formulae (43) and (44) in which Y represents a cyano group by converting the cyano group to a protected carboxy group. This reaction is essentially the same as and may be carried out in the same manner as and using the same reagents and reaction conditions as Steps E5 and E6 of Method E.

Step I8 and Step I9

In these Steps, a trifluoromethyl compound of formula (IIc-2), a desired compound of the invention, is prepared from the ester compound of formula (45), prepared as described in Step I6 or I7, via a carboxylic acid compound of formula (46). This reaction is essentially the same as and may be carried out in the same manner as and using the same reagents and reaction conditions as Steps E7 and E8 of Method E.

Step I10 and Step I11

These Steps provide an alternative route for preparing the trifluoromethyl compound of formula (IIc-2) from the ester compound of formula (45), prepared as described in Step I6 or I7, via a tri(alkylthio)methyl compound of formula (47). This reaction is essentially the same as and may be carried out in the same manner as and using the same reagents and reaction conditions as Steps E9 and E10 of Method E.

Step I12 and Step I13

In these Steps, a dihalomethyl compound of formula (IIc-3), a desired compound of the present invention, is prepared from the ester compound of formula (45), prepared as described in Step I6 or I7, via an aldehyde compound of formula (48). This reaction is essentially the same as and may be carried out in the same manner as and using the same reagents and reaction conditions as Steps E11 and E12 of Method E.

Step I14 and Step I15

In these Steps, the desired compound of formula (IIc-4), which is a compound of the present invention is prepared, from the ester compound of formula (45), prepared as described in Step I6 or I7, via a hydroxymethyl compound of formula (IIc-1), which is also a compound of the present invention. This reaction is essentially the same as and may be carried out in the same manner as and using the same reagents and reaction conditions as Steps E13 and E14 of Method E.

atoms, or a substituted alkyl group having from 1 to 6 carbon atoms which is substituted by at least one substituent selected from the group consisting of substituents α, defined above, and $R^4$ represents an alkyl group having from 1 to 6 carbon atoms, a substituted alkyl group having from 1 to 6 carbon atoms and which is substituted by at least one substituent selected from the group consisting of substituents α, defined above, or an aralkyl group.

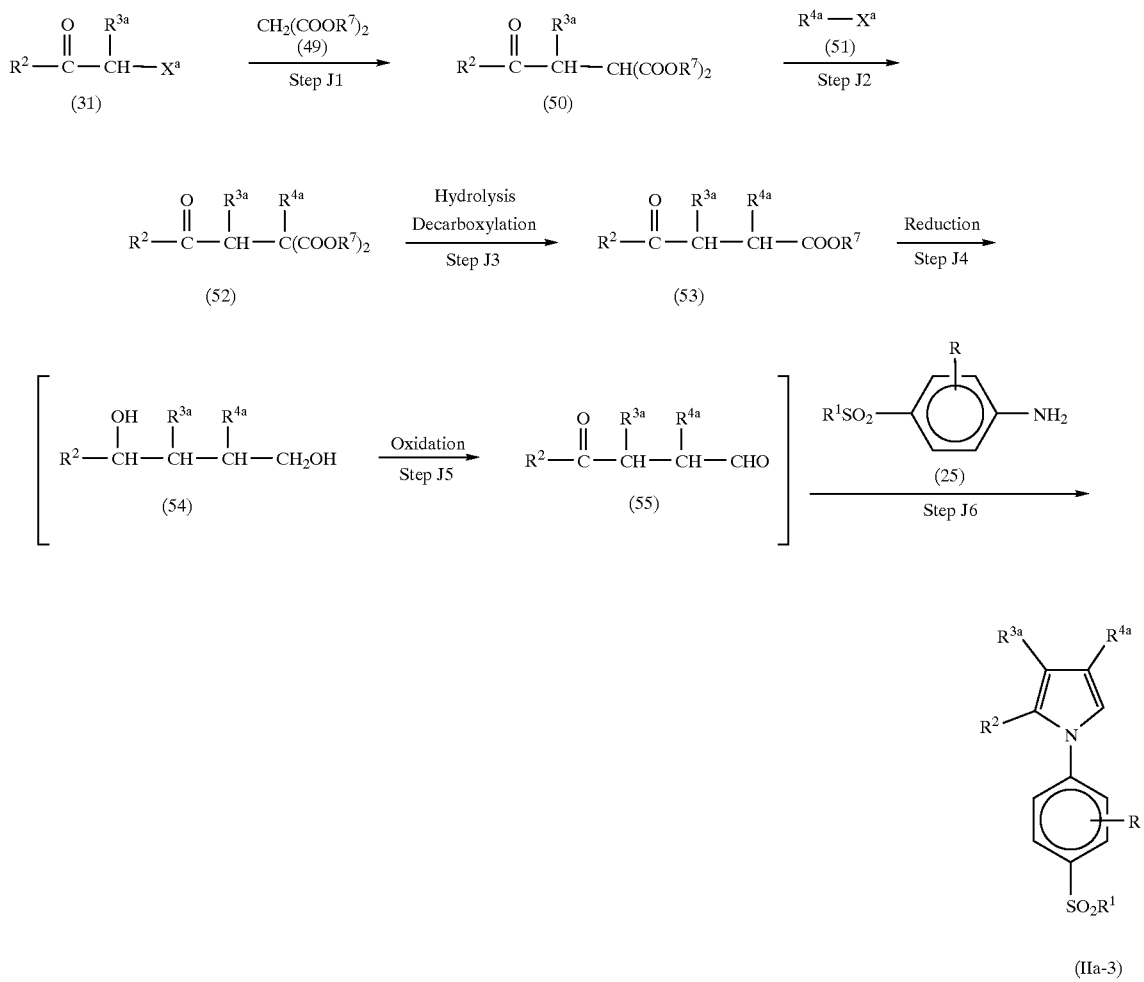

The aldehyde compound of formula (24) in Method E and the aldehyde compound of formula (48) in Method I can be also prepared from the corresponding hydroxymethyl compounds of formulae (Id-1) and (IIc-1), respectively, by converting the hydroxymethyl group to a formyl group. The reaction in which a hydroxymethyl group is converted to a formyl group may be carried out using an oxidising agent, for example, chromic acid, manganese dioxide, or dimethyl sulfoxide, according to the methods described in detail by S. Bartel & F. Bohlmann [Tetrahedron Lett., (1985), 685].

Method J

This is an alternative to Method G, and prepares a compound of formula (IIa-3) in which $R^3$ represents a hydrogen atom, an alkyl group having from 1 to 6 carbon In the above formulae:

R, $R^1$, $R^2$, $R^{3a}$, $R^7$ and $X^a$ are as defined above; and $R^{4a}$ represents an alkyl group having from 1 to 6 carbon atoms, a substituted alkyl group having from 1 to 6 carbon atoms which is substituted by at least one substituent selected from the group consisting of substituents α, defined above, or an aralkyl group.

Step J1

In this Step, a phenacylmalonic acid diester compound of formula (50) is prepared by alkylation of a malonic acid diester compound of formula (49) with a phenacyl halide of formula (31). This reaction is essentially the same as and may be carried out in the same manner as and using the same reagents and reaction conditions as Step B3 of Method B.

Step J2

In this Step, a compound of formula (52) is prepared by alkylation of the phenacylmalonic acid diester compound of formula (50), prepared as described in Step J1, with a halide compound of formula (51). This reaction is essentially the same as and may be carried out in the same manner as and using the same reagents and reaction conditions as Step B3 of Method B.

Step J3

In this Step, a β-ketoester compound of formula (53) is prepared by hydrolysis of the compound of formula (52), prepared as described in Step J2, followed by decarboxylation of the product. These reactions are essentially the same as and may be carried out in the same manner as and using the same reagents and reaction conditions as Steps B4 and B6 of Method B.

Step J4

In this Step, a diol compound of formula (54) is prepared by reduction of the ketone and ester parts of the β-ketoester compound of formula (53), prepared as described in Step J3. This reaction is essentially the same as and may be carried out in the same manner as and using the same reagents and reaction conditions as Step E13 of Method E.

Step J5

In this Step, a ketoaldehyde compound of formula (55) is prepared by oxidation of the two hydroxy groups of the diol compound of formula (54), prepared as described in Step J4. This reaction may be carried out by well known methods using an oxidising agent (such as chromic acid, manganese dioxide or dimethyl sulfoxide), for example as described by E. J. Corey, G. Schmidt et al. [Tetrahedron Lett., (1979), 399], the disclosures of which are incorporated herein by reference.

Step J6

In this Step, a compound of formula (IIa-3), which is a compound of the present invention, is prepared by cyclizing the ketoaldehyde compound of formula (55), prepared as described in Step J5, and an aniline compound of formula (25) under dehydrating condensation conditions. This reaction is essentially the same as and may be carried out in the same manner as and using the same reagents and reaction conditions as Step B2 of Method B.

Method K

In this Method, a compound of formula (Ie-1) or (Ie-2), which are compounds of formula (I) in which $R^2$ represents a phenyl group substituted by a mercapto group or by an alkanoylthio group and $R^3$ represents a hydrogen atom, an alkyl group having from 1 to 6 carbon atoms or a substituted alkyl group having from 1 to 6 carbon atoms which is substituted by at least one substituent selected from the group consisting of substituents α, defined above, is prepared.

Reaction Scheme K

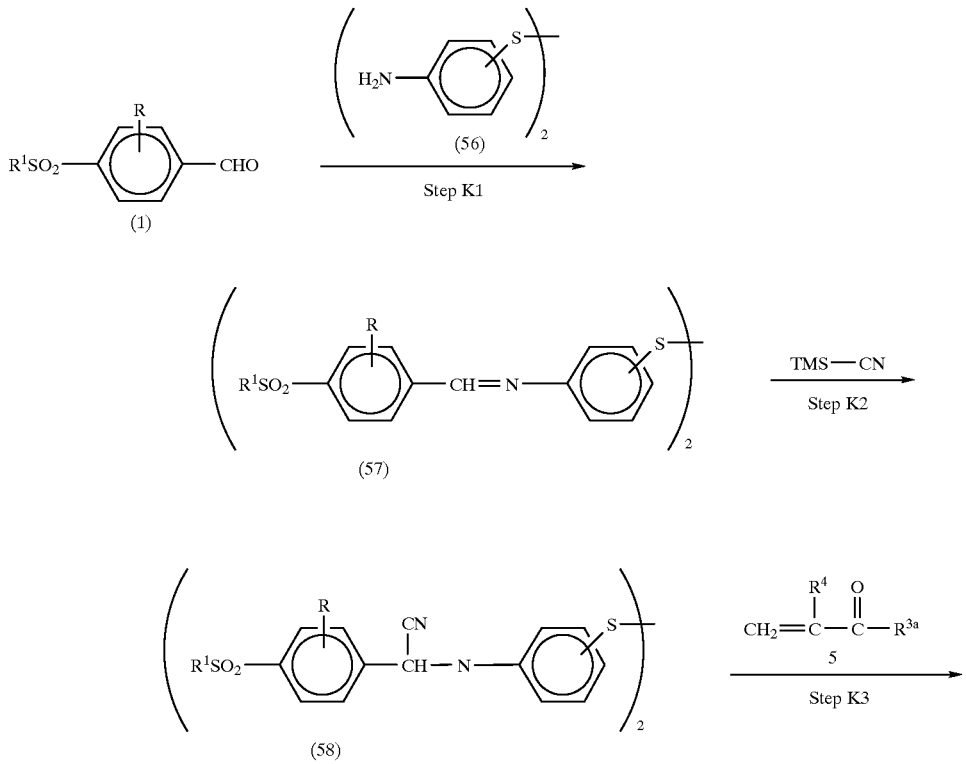

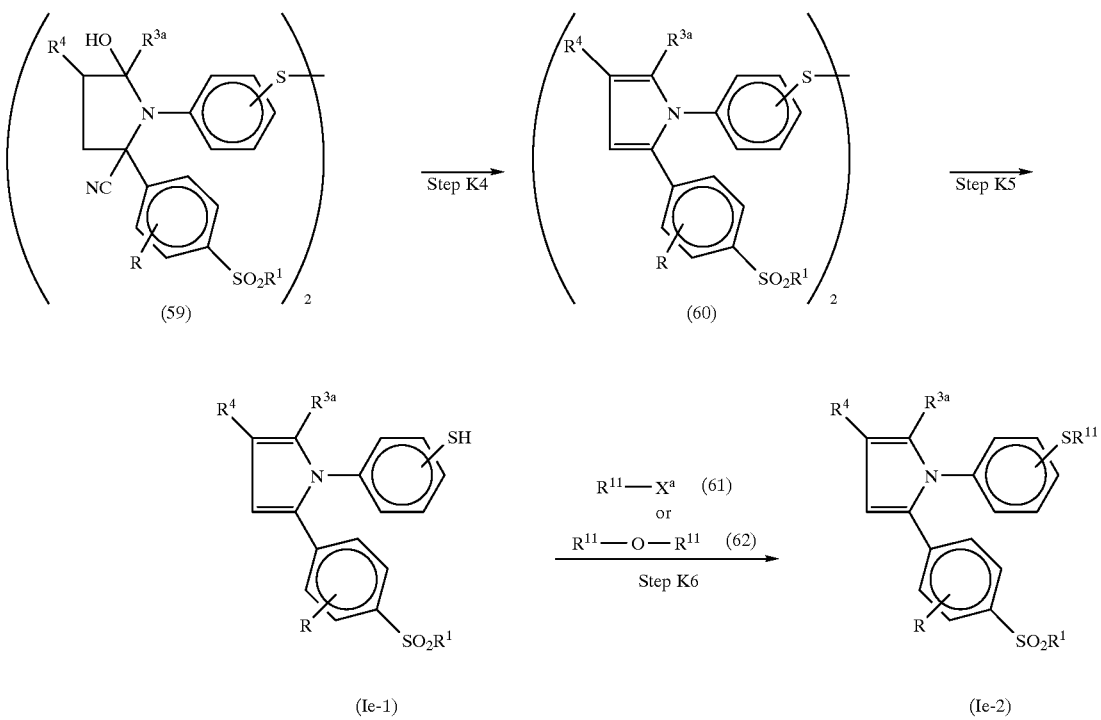

In the above formulae:

R, $R^1$, $R^{3a}$, $R^4$ and $X^a$ are as defined above; and $R^{11}$ represents an alkanoyl group having from 2 to 5 carbon atoms.

Step K1

In this Step, a compound of formula (57) is prepared by the dehydration condensation of a benzaldehyde compound of formula (1) with an aniline disulfide compound of formula (56). This reaction is essentially the same as and may be carried out in the same manner as and using the same reagents and reaction conditions as Step A1 of Method A.

Step K2

In this Step, an anilinonitrile disulfide compound of formula (58) is prepared by the addition of hydrogen cyanide to a compound of formula (57), prepared as described in Step K1. This reaction is essentially the same as and may be carried out in the same manner as and using the same reagents and reaction conditions as Step A2 of Method A.

Steps K3 and K4

In these Steps, a pyrrole disulfide compound of formula (60) is prepared by reacting an anilinonitrile disulfide compound of formula (58), prepared as described in Step K2, with an α,β-unsaturated aldehyde or ketone compound of formula (5), to give a pyrrolidine disulfide compound of formula (59), which is then dehydrated and dehydrogencyanated. These reactions are essentially the same as and may be carried out in the same manner as and using the same reagents and reaction conditions as Steps A3 and A4 of Method A.

Step K5

In this Step, a compound of formula (Ie-1), which is a compound of the present invention, is prepared by reduction of a pyrrole disulfide compound of formula (60), prepared as described in Step K4. This reaction may be carried out by well known methods using a reducing agent (such as sodium borohydride, lithium borohydride, lithium aluminum hydride, diisobutylaluminum hydride or borane), for example as described by J. J. D'Amico [J. Org. Chem., 26, 3436 (1961)].

Step K6

In this Step, a compound of formula (Ie-2), which is also a compound of the present invention, is prepared by alkanoylation of the mercapto group of the compound of formula (Ie-1), which is a compound of the present invention and which was prepared as described in Step K5. This reaction may be carried out by conventional methods, using an alkanoyl halide compound of formula (61) or the corresponding acid anhydride compound of formula (62).

Method L

This provides an alternative method to Method G for preparing a compound of formula (33).

Reaction Scheme L

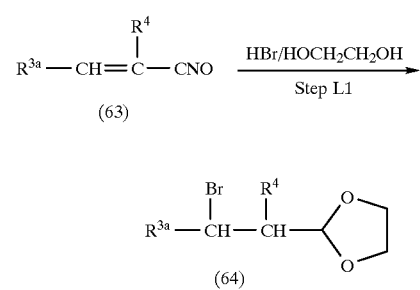

-continued

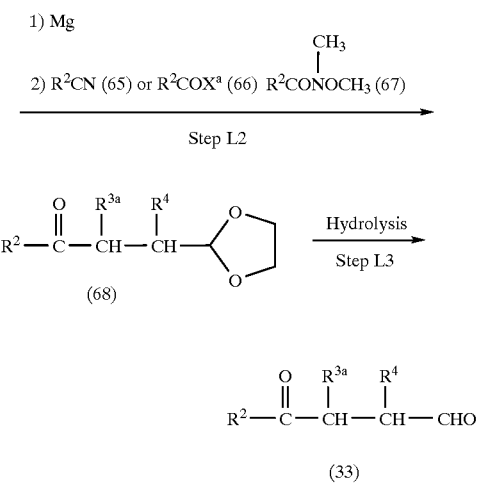

In the above formulae, $X^a$, $R^2$, $R^{3a}$ and $R^4$ are as defined above.

Step L1

In this Step, a bromoacetal compound of formula (64) is prepared by reacting an unsaturated aldehyde compound of formula (63) with hydrogen bromide gas in ethylene glycol. The reaction may be carried out by the method of Taylor et al. [J. Org. Chem., 48, 4852–4860 (1983)].

Step L2

In this Step, a ketoacetal compound of formula (68) is prepared by reacting the bromoacetal compound of formula (64), prepared as described in Step L1, with metallic magnesium to prepare a Grignard reagent and then reacting this Grignard reagent with a nitrile compound of formula (65), with an acyl halide compound of formula (66) or with an amide compound of formula (67). The reaction may be carried out by the method of Kruse et al. [Heterocycles, 26, 3141–3151 (1987)].

Step L3

In this Step, a 1,4-dioxo compound of formula (33) is prepared by the hydrolysis of the acetal moiety of the ketoacetal compound of formula (68), prepared as described in Step L2. This may be effected using any conventional hydrolysis method employing an acid.

Alternatively, the ketoacetal compound of formula (68) can be used in Step G2 in place of the compound of formula (33).

In all of the above reactions, where $R^1$ represents an alkyl group having from 1 to 6 carbon atoms, it is possible to use as a starting material a compound in which the alkylsulfonyl group (—$SO_2$-alkyl) is replaced by a alkylthio group (—S-alkyl). In all such cases, the reactions may be carried out as described above, and then the alkylthio group may be oxidised by well known and conventional methods to a alkylsulfonyl group at any stage in the reaction sequence.

For example, the oxidation of the alkylthio group to the alkylsulfonyl group may be carried out by reacting the alkylthio compound with 2 or more equivalents of an oxidising agent. There is no particular restriction on the nature of the oxidising agents used, and any oxidising agent commonly used in reactions of this type may equally be used here. Examples of such oxidising agents include: peracids, such as peracetic acid, perbenzoic acid or m-chloroperbenzoic acid; hydrogen peroxide; and alkali metal perhalogenates, such as sodium metaperchlorate, sodium metaperiodate or potassium metaperiodate. Of these, we prefer the peracids or hydrogen peroxide, particularly m-chloroperbenzoic acid.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane or petroleum ether; aromatic hydrocarbons, such as benzene, toluene or xylene; halogenated hydrocarbons, such as methylene chloride, chloroform, carbon tetrachloride or dichloroethane; alcohols, such as methanol, ethanol, propanol or butanol; esters, such as ethyl acetate, propyl acetate, butyl acetate or ethyl propionate; carboxylic acids, such as acetic acid or propionic acid; water; or a mixture of any two or more of these solvent. Of these, we prefer the halogenated hydrocarbons (particularly methylene chloride, chloroform, dichloroethane) or the carboxylic acids, (particularly acetic acid).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. to 150° C., more preferably from 0° C. to 100° C. The time required for the reaction may also vary widely, depending on many factors, notably the reaction temperature and the nature of the reagents and solvent employed. However, provided that the reaction is effected under the preferred conditions outlined above, a period of from 10 minutes to 10 hours, more preferably from 30 minutes to 5 hours, will usually suffice.

Moreover, in all of the above reactions, it is possible to use a compound in which $R^2$ represents a phenyl group substituted by an alkylthio group and then convert this to an alkylsulfinyl group at any stage in the reaction sequence, as described above. The reaction can be carried out as described above, but the amount of oxidising agent is from 0.8 to 1.2 equivalents per equivalent of the alkylthio compound.

BIOLOGICAL ACTIVITY

The 1,2-diphenylpyrrole derivatives and pharmacologically acceptable salts thereof of the present invention act as cyclooxygenase-2 selective inhibiting agents and/or as inflammatory cytokine production suppressing agents, and are thus effective for the prophylaxis and therapy of diseases mediated by cyclooxygenase-2 and/or inflammatory cytokines. In addition, they have the ability to inhibit the production of leukotrienes and to inhibit bone resorption. Accordingly, these compounds can serve as analgesics, as anti-inflammatory agents, as antipyretics and/or as anti-allergic agents. In addition, the compounds of the present invention can be used for the treatment or prophylaxis of disease involving or resulting from the resorption of bone, such as osteoporosis, rheumatoid arthritis and osteoarthritis. These types of analgesics, anti-inflammatory agents and/or antipyretics exhibit effects not only on inflammatory diseases, such as pain, pyrexia, and edema, but also on chronic inflammatory diseases, such as chronic rheumatoid arthritis and osteoarthritis, allergic inflammatory diseases, asthma, sepsis, psoriasis, various autoimmune diseases, systemic lupus erythematosus, juvenile onset diabetes, autoimmune intestinal diseases (such as ulcerative colitis, Crohn's disease), viral infection, tumors and glomerulonephritis.

The biological activity of the compounds of the present invention is illustrated by the following Experiments.

EXPERIMENT 1

Inhibitory Activity on Cyclooxygenase-1 from Ram Seminal Vesicle Microsomes (RSVM) and Human Recombinant Cyclooxygenase-2 (In Vitro Test)

In order to prepare cyclooxygenase-1 (COX-1) microsomes, ram seminal vesicles were homogenised by a blender. To prepare cyclooxygenase-2 (COX-2) microsomes, an expression vector which contains the human COX-2 gene was introduced into COS cells. The cells were homogenised by sonication after 66 hours cultivation. Microsomes were then prepared in accordance with conventional methods.

Enzyme activity was assayed as follows.

The assay mixture contained 10 $\mu$l of COX-1 or COX-2 microsomes (5 to 15 $\mu$g), 2 $\mu$l of sample dissolved in dimethyl sulfoxide, 50 $\mu$l of 200 mM Tris (pH 7.6), 10 $\mu$l of 20 mM reduced glutathione, 10 $\mu$l of 10 mM epinephrine, and 15.5 $\mu$l of distilled water. After preincubation at 37° C. for 15 minutes, 2.5 $\mu$l of 10 $\mu$M arachidonic acid (dissolved in ethanol) were then added to the mixture (final volume of 100 $\mu$l) and allowed to react at 37° C. for 30 minutes. The final dimethyl sulfoxide and ethanol concentrations were 2% and 2.5%, respectively. To the reaction mixture were then added 15 $\mu$l of ice-cooled 0.2M HCl to stop the reaction, and the mixture was cooled at 4° C. for 5 minutes. 15 $\mu$l of a 0.2M aqueous solution of sodium hydroxide were then added to the reaction mixture to neutralise the pH. The amount of $PGE_2$ in the reaction mixture was measured using a commercially available ELISA kit (Cayman). $IC_{50}$ was calculated from the regression line determined by the inhibition rates of $PGE_2$ formation and the concentrations of the compound.

The results are shown in Table 3.

TABLE 3

| Example No. | Inhibitory Effect on COX-1 [$IC_{50}$ ($\mu$M)] | Inhibitory Effect on COX-2 [$IC_{50}$ ($\mu$M)] | Selectivity (COX-1/COX-2) |
| --- | --- | --- | --- |
| 20 | 85 | 0.023 | 3696 |
| 38 | >100 | 0.023 | >4348 |
| 52 | >100 | 0.016 | >6250 |
| 56 | >100 | 0.018 | >5556 |
| 58 | 6.3 | 0.019 | 332 |
| 62 | 1.5 | 0.0097 | 153 |
| 65 | 13 | 0.015 | 867 |
| 73 | 3.0 | 0.025 | 120 |
| 80 | 25 | 0.011 | 2273 |
| 103 | 3.7 | 0.01 | 370 |
| 108 | 6.0 | <0.01 | >600 |
| 109 | 3.8 | 0.023 | 165 |
| A | >100 | >100 | |

Compound A is 5-methyl-2-phenyl-1-(4-sulfamoylphenyl)pyrrole which is disclosed in DE patent No.1938904, mentioned above.

In this test, the compound of the present invention exhibited excellent inhibitory effects selective for cyclooxygenase-2.

EXPERIMENT 2

Inhibitory Effect on Cytokine Production in Human Peripheral Monocytes (In Vitro Test)

(1) Peripheral blood was collected from healthy human volunteers in the presence of heparin. After mixing it with an equal volume of phosphate-buffered saline (PBS, Nissui Pharmaceutical), the mixture was layered onto Ficoll Paque medium (Pharmacia) at the rate of 2:1 and centrifuged at 520×g at 25° C. for 20 minutes. After centrifugation, the monocyte layer was removed and suspended in RPMI 1640 (Nissui Pharmaceutical) containing 10% fetal calf serum (FCS). The monocytes were washed once with the same medium, placed in a plastic Petri dish, pre-treated with human plasma and incubated for 2 hours in the presence of 5% $CO_2$ to cause them to adhere to the dish. After incubation, the Petri dish was washed twice with PBS to remove the non-adherent cells. Thereafter, PBS containing 5% FCS and 0.2% EDTA was added to the Petri dish and the dish was allowed to stand undisturbed for 15 minutes at 4° C. The monocytes were recovered from the dish by pipetting. The cells were finally suspended in RPMI 1640 at a concentration of $1.25 \times 10^5$ cells/ml.

(2) Culture of Human Monocytes

A 40 $\mu$l solution of the test compound and 40 $\mu$l of lipopolysaccharide (LPS; E. coli, 0.26:B6, Difco), adjusted to a final concentration of 10 $\mu$g/ml, were added to 320 $\mu$l of cell suspension. The resulting mixture was then cultured for 20 hours in the presence of 5% $CO_2$ and the supernatant was removed at the end of cultivation to assay IL-1$\beta$ and TNF$\alpha$. The test compound was dissolved in dimethyl sulfoxide and diluted by a factor of 100 with FCS to reach 10 times the final concentration (the final concentrations of dimethyl sulfoxide and FCS were 0.1% and 10%, respectively).

(3) Measurement of Cytokine in the Supernatant Medium

The amount of IL-1$\beta$ was measured with a commercially available ELISA kit (Cayman), after diluting the supernatant medium by a factor of 15 or 30 with the ELISA buffer. The amount of TNF$\alpha$ was similarly measured by a ELISA kit (Genzyme) after diluting the supernatant by a factor of 2.

The $IC_{50}$ was calculated from the regression line determined by the inhibition rates and the concentrations of the test compound. The results are summarised in Tables 4 and 5.

In this test, the compound of the present invention exhibited excellent inhibitory effects on inflammatory cytokine (IL-1$\beta$ and TNF-$\alpha$) production.

TABLE 4

| Example No. | Inhibition of IL-1$\beta$ production (%) Dose: 10 $\mu$M |
| --- | --- |
| 7 | 42.6 |
| 41 | 51.2 |
| 90 | 62.2 |
| A | 24.2 |

TABLE 5

| Example No. | Inhibition of TNF$\alpha$ production (%) Dose: 10 $\mu$M |
| --- | --- |
| 49 | 40.9 |
| 54 | 54.7 |
| 68 | 42.6 |
| 81 | 46.1 |
| 105 | 41.8 |
| 123 | 43.6 |
| A | 13.9 |

EXPERIMENT 3

Analgesic effect on yeast-inflamed pain in rats
(Randall-Selitto method) (In Vivo Test)

(1) Test Compound

The compound was suspended in 0.5% tragacanth and administered orally at a volume of 5 ml/kg. The control group was administered with 0.5% tragacanth only as a vehicle.

(2) Animals

Wistar-Imamichi rats (males, 5 week old, body weights: 80–100 g) were used in this test.

(3) Test Method

The test was conducted in accordance with the method of Winter and Flataker [J. Pharmacol. Exp. Ther. 150, 165–171, (1965)], which is a modification of the original method of Randall and Selitto [Arch. Int. Pharmacodyn. Ther. 111, 405–419, (1957)]. The rats were fasted for 16 hours prior to use. Inflammation was induced by subcutaneous injection of 0.1 ml of a suspension of 20% beer yeast (Sigma) into the right hind footpad of the animal. After 4.5 hours, increasing pressure was applied to the inflamed footpad at a constant speed using an Analgesy meter (Trade mark) (Ugo-Basile Co.). The pressure at which the animal exhibited a squeaking reaction was measured and considered to be a pain threshold (units: g). To those rats that exhibited a pain threshold of less than 200 g (mean: 60 to 120 g), the compounds were immediately administered orally and pain threshold values were measured 0.5, 1 and 2 hours after administration.

First the average of pain threshold values at each time point (0.5, 1, and 2 hr) was calculated in a control group. If a pain threshold value exceeded 2 times the control average value at the same time point even once in the drug-treated groups, then the animal was considered to indicate efficacy. Efficacy rates of the drug were estimated by the evaluation method of Blake [J. Pharm. Pharm. 19, 367–373, (1967)]. The results are shown in Table 6.

TABLE 6

Analgesic effect on yeast-inflamed pain in rats (Randall-Selitto method)

| Example No. | Efficacy Rate (No. of animals in which drug was effective/No. of animals used in test) Dose: 12.5 mg/kg |
|---|---|
| 7 | 5/5 |
| 18 | 5/5 |
| 19 | 5/5 |
| 52 | 5/5 |
| 62 | 5/5 |
| 65 | 5/5 |
| 66 | 5/5 |
| 67 | 5/5 |
| 69 | 5/5 |
| 71 | 5/5 |
| 77 | 5/5 |
| 78 | 5/5 |
| 79 | 5/5 |
| 82 | 5/5 |
| 83 | 5/5 |
| 84 | 5/5 |
| 85 | 5/5 |
| 86 | 5/5 |
| 87 | 5/5 |
| 88 | 5/5 |
| 97 | 5/5 |
| 100 | 5/5 |
| 101 | 5/5 |
| 129 | 5/5 |
| 130 | 5/5 |
| A | 1/5 |

EXPERIMENT 4

Carrageenan-induced Paw Edema Test (In Vivo Test)

The same test compounds were subjected to the test as those in the Randall-Selitto test of Experiment 3. Wistar-Imamichi rats (males, 6 week old, body weights: 110–120 g) were used in this test.

The method of Winter, et al. [Proc. Soc. Exp. Biol. Med. 111, 544–547, (1962)] was slightly modified to perform the test [Sankyo Annual Research Report 39, 77–111, (1989)]. The rats were fasted for 16 hours prior to use. Inflammatory edema was induced by the subcutaneous injection of 0.05 ml of a 1% carrageenan (Viscarin 402) solution into the right hind paw of the animal. The test compounds were administered orally 30 minutes before injection of carrageenan. The volume of the right hind foot was measured with a Plethysmometer (Trade mark) (Ugo-Basile Co.) just before administration of the test compound and 3 hours after injection of carrageenan to determine the edema intensity [(right foot volume after 3 hours/right foot volume before injection)-1]. The inhibition rate (percentage) at each dose was calculated and is shown in Table 7.

TABLE 7

Inhibitory effect on Carrageenan-induced Paw Edema in rats

| Example No | Inhibition Rate (%) Dose: 50 mg/kg |
|---|---|
| 7 | 56 |
| 17 | 67 |
| 18 | 53 |
| 19 | 65 |
| 41 | 60 |
| 52 | 65 |
| 62 | 55 |
| 64 | 60 |
| 67 | 64 |
| 69 | 55 |
| 73 | 72 |
| 75 | 57 |
| 76 | 56 |
| 78 | 66 |
| 82 | 78 |
| 83 | 70 |
| 84 | 66 |
| 85 | 73 |
| 86 | 64 |
| 88 | 61 |
| 90 | 64 |
| 96 | 60 |
| 97 | 63 |
| 98 | 55 |
| 99 | 57 |
| 100 | 57 |
| 103 | 56 |
| 104 | 69 |
| 105 | 68 |
| 108 | 58 |
| 109 | 77 |
| 120 | 62 |
| 121 | 59 |
| 129 | 62 |
| 130 | 73 |
| A | 14 |

EXPERIMENT 5

Scald-induced Pain Test (In Vivo Test)

The test was conducted in accordance with the method of Iizuka and Tanaka [Jpn. J. Pharmacol. 70, 697, (1967)]. The test compound was administered in the same manner as in Experiment 3. Male Wistar-Imamichi rats (4–5 week old, body weights: approximately 100 g) were used after fasting for 16 hours. The right hind foot of the animal was immersed in hot water at 57° C. for 6 seconds to induce scald under ether-anesthesia. Two hours later, the scald foot of the rat was irritated by immersing in hot water at 40° C. for 5 seconds, and the animal was returned to the cage.

The behaviour of the animal was observed for 30 seconds. Lifting up the scalded foot or licking it without coming in contact with the metal cage were considered to be pain responses. Pain response time was determined as the total time of the pain response during the 30-second observation period. After selecting only those animals that exhibited a favorable pain response two hours after inducing scald, the animals were given a test compound by oral administration. Pain response time was again measured 1 and 2 hours after dosing and the mean value was determined. Using the mean values, inhibition rates were calculated relative to the control group.

$ID_{50}$ was calculated from the regression line determined by the inhibition rates and the doses.

These results are shown in Table 8.

TABLE 8

Analgesic effect on scald-induced Pain in rats

| Example No. | $ID_{50}$ (mg/kg) |
| --- | --- |
| 52 | 1.1 |
| 67 | 1.6 |

EXPERIMENT 6

Antipyretic effect on yeast-induced fever (In Vivo Test)

The method of Roszkowski et al. [J. Pharmacol. Exp. Ther. 179, 114, (197 1)] was slightly modified to perform the test. The test compound was administered in the same manner as in Experiment 3. Male Wistar-Imamichi rats (6 week old, body weights: approximately 120 g) were used in the test. Yeast (Brewer's yeast, Sigma) was suspended in physiological saline to a concentration of 25%, finely crushed in an agate mortar, and injected subcutaneously into the backs of the rats under ether-anesthesia at a volume of 2 ml/rat. The rats were fasted after the injection of yeast. On the following day (19 hours after the yeast injection), a catheter-type thermistor thermometer (Japan Koden, MGA III) was inserted approximately 5 cm into the rectum to measure the temperature of the animals. Those animals, which exhibited a fever of 1.5° C. or more compared to normal animals, were selected, and grouped so that the mean fever temperatures of each group were nearly equal. Rectal temperatures were measured 1 and 2 hours after administration of the test compound, and fever temperature was calculated by subtracting the normal temperature of healthy animals measured simultaneously. Inhibition rate of the group treated with the compound relative to the control group was calculated by using the mean value at 1 and 2 hours after dosing. These results are shown in Table 9.

TABLE 9

Antipyretic effect on yeast-induced fever (In Vivo Test)

| Example No. | Inhibition Rate (%) Dose: 0.4 mg/kg |
| --- | --- |
| 52 | 82 |
| 67 | 78 |
| 84 | 64 |

EXPERIMENT 7

Irritative effect on gastric mucosa (In vivo test)

Experiments were performed according to the method described by Jahn and Adrian [Arzneim.-Forsch. 19, 36, (1969)]. Male Wistar rats weighing approximately 120 g were fasted for 16 hours before the experiment. The drugs were administered orally to rats as described in Experiment 3. Three and the half hours after dosing, the animals were killed under ether-anesthesia and the stomachs were placed into 1% of formalin. The stomach was opened by cutting along the greater curvature and the number and length of lesions were counted under a microscope (6.3×10). The ulcerogenicity in each animal was assessed according to Hitchens et. al. [Pharmacologist 9, 242, (1967)]. Incidence was determined as the rate of rats with 4 or more ulcers of more than 0.5 mm length, and $UD_{50}$'s (doses producing 50% incidence) were calculated from the incidence and the dose by probit (=probability unit) method. The results are summarised in Table 10.

TABLE 10

Irritative effect on gastric mucosa

| Example No. | $UD_{50}$ (mg/kg) |
| --- | --- |
| 65 | >100 |
| 66 | >100 |
| 67 | >100 |
| 69 | >100 |
| 70 | >100 |
| 71 | >100 |
| 76 | >100 |
| 77 | >100 |
| 78 | >100 |
| 79 | >100 |
| 80 | >100 |
| 82 | >100 |
| 84 | >100 |
| 103 | >100 |
| 119 | >100 |
| 121 | >100 |

EXPERIMENT 8

Bone resorption assay (in vitro test)

Bone resorption assays were performed according to the method of Kitamura et. al. [Bone 14, 829–834, (1993)]. Tibia and femur removed from 18- to 20-day-old ICR strain mice were minced with scissors and stirred for 30 seconds in 10 ml culture medium (D-MEM containing 10% FCS). The cell suspension stood for 2 minutes and the resulting supernatant was centrifuged at 800 rpm for 3 minutes to obtain a precipitate of unfractionated bone cells involving osteoclasts and preosteoclasts. The precipitate resuspended in the medium was incubated in the presence of $5 \times 10^{-8}$M rPTH (1–34) at 37° C. in a 5% $CO_2$ incubator for 6 days. After incubation, the cells were harvested with trypsin- EDTA, washed twice with the medium, adjusted to a density of 5×10⁵ cells/ml, and were seeded 200 μl/well in 96-well plates, each well containing an ivory slice (6 mm diameter, 0.15 mm thickness). The slices were incubated in the presence of test compounds dissolved in dimethyl sulfoxide at 37° C. in a 5% $CO_2$ incubator for 2 days. After scraping off the cells, the slices were treated with acid-hematoxilin for 10 minutes to stain pits formed and washed with water. The number of pits was counted under a light microscope and the inhibitory activity of the compound on pit formation was expressed as a percentage of the control value. In this assay, the compound of the present invention exhibited excellent inhibition on bone resorption.

EXPERIMENT 9

Effects on bone loss in ovariectomized rats (in vivo test)

Eight week-old female Sprague-Dawley rats were purchased and ovariectomy was performed at 9 weeks of age. After surgery the animals received daily oral administration of the test compound suspended in 0.5% tragacanth at a volume of 2 ml/kg for 2 weeks. On the day following the last administration, the animals were euthanized and the bilateral femurs were removed to measure bone mineral density by a bone mineral analyser using X ray. For comparison, sham-operated (Sham) and ovariectomized (OVX) rats received only 0.5% tragacanth and underwent the same measurement as the treatment group. Data will be expressed as means ±S.E.M (standard error of means). In this experiment, the compounds of the present invention exhibited excellent inhibition on the decrease in bone mineral density by OVX.

EXPERIMENT 10

Inhibitory effect on $LTB_4$ production from human peripheral monocytes (In vitro test)

(1) Isolation of human peripheral monocytes

The isolation of monocytes was carried out as described in Experiment 2-(1).

(2) Culture of human monocytes

The cell culture was carried out as described in Experiment 2-(2).

(3) Measurement of LTB4 content in the medium of monocytes culture.

The supernatant of the culture medium after incubation was subjected to the ELISA assay (Cayman). $IC_{50}$ values were calculated by the least square method from the regression line determined by the inhibition rates and the doses. The results are shown in Table 11.

TABLE 11

Inhibitory effect on $LTB_4$ production from human peripheral monocytes

| Example No. | $IC_{50}$ (μM) |
|---|---|
| 78 | 0.31 |

As can be seen from the above experiments, the compounds of the present invention have excellent analgesic, anti-inflammatory and anti-pyretic activities and also reduce the resorption of bone. They can, therefore be used in human and animal therapy.

The 1,2-diphenylpyrrole derivatives of the present invention can be administered in any conventional form, for example in the form of tablets, capsules, granules, powders or syrups, or they may be administered parenterally by injection, or as suppositories, ointments, etc. These pharmaceutical formulations can be prepared by mixing the compounds of the present invention with conventional additives, such as ordinary excipients, binders, disintegrating agents, lubricants, stabilisers, corrigents using known methods.

The dose of the compound of the present invention varies depending on the condition, age and body weight of the patient, as well as upon the administration route, the type of disease, and other factors, but the compounds of the present invention can usually be administered in a daily dose of from 0.01 to 50 mg/kg body weight, preferably from 0.1 to 10 mg/kg, in the case of adult, either as a single dose or as divided doses.

The preparation of compounds of the present invention is further illustrated by the following non-limiting Examples.

EXAMPLE 1

1-(4-Methoxyphenyl)-2-(4-methylsulfonylphenyl) pyrrole (Compound No. 1-33)

1(i) 4-Methoxy-N-(4-methylsulfonylbenzylidene)aniline 1.00 g (5.4 mmol) of 4-methylsulfonylbenzaldehyde and 0.67 g (5.4 mmol) of 4-methoxyaniline were dissolved in 15 ml of ethanol, and the solution was heated under reflux for 1 hour. At the end of this time, the reaction solution was cooled to room temperature, and the crystals which precipitated were collected by filtration and washed with ethanol, to give 1.48 g (yield 95%) of the title compound as slightly yellow prismatic crystals.

Nuclear Magnetic Resonance Spectrum (270 MHz, $CDCl_3$) δ ppm:

8.57 (1H, singlet);

8.11–8.01 (4H, multiplet);

7.33–7.26 (2H, multiplet);

6.99–6.93 (2H, multiplet);

3.85 (3H, singlet);

3.09 (3H, singlet).

1(ii) α-(4-Methoxyanilino)-α-(4-methylsulfonylphenyl) acetonitrile 1.48 g (5.1 mmol) of 4-methoxy-N-(4-methylsulfonylbenzylidene)aniline [prepared as described in step (i) above] were suspended in 15 ml of anhydrous tetrahydrofuran, and 0.80 ml (6.0 mmol) of 95% trimethylsilyl cyanide and 0.85 g (6.0 mmol) of zinc chloride were added to the resulting suspension at 0° C., whilst stirring. The temperature of the reaction mixture was then allowed to return to room temperature, and the mixture was stirred overnight. At the end of this time, water was added and the mixture was extracted with ethyl acetate. The organic extract was washed with water and dried over anhydrous sodium sulfate, after which it was concentrated by evaporation under reduced pressure and the crystals which precipitated were collected by filtration, to give 1.05 g (yield 65%) of the title compound as a slightly yellow powder.

Nuclear Magnetic Resonance Spectrum (270 MHz, hexa-deuterated dimethyl sulfoxide) δ ppm:

8.04 (1H, doublet, J=8 Hz);

7.84 (2H, doublet, J=8 Hz);

6.84 (4H, singlet);

6.45 (1H, doublet, J=10 Hz);

6.10 (1H, doublet, J=10 Hz);

3.67 (3H, singlet);

3.25 (3H, singlet).

1(iii) 1-(4-Methoxyphenyl-2-(4-methylsulfonylphenyl) pyrrole 1.00 g (3.2 mmol) of α-(4-methoxyanilino)-α-(4-methylsulfonylphenyl)-acetonitrile [prepared as described in step (ii) above] was suspended in 15 ml of anhydrous tetrahydrofuran, and 0.24 ml (3.5 mmol) of acrolein was added to the resulting suspension. 3.2 ml (3.2 mmol) of a 1.0M solution of lithium bis(trimethylsilyl)amide in tetrahydrofuran were then added dropwise to the mixture at −60° C. to −65° C., whilst stirring. The mixture was stirred at the same temperature for 1 hour, and then the temperature of the mixture was allowed to return to room temperature, and the mixture was stirred for a further 1.5 hours. At the end of this time, a saturated aqueous solution of ammonium chloride was added to the reaction solution and the mixture was extracted with ethyl acetate. The organic extract was washed with water and dried over anhydrous sodium sulfate. The solvent was then removed by distillation under reduced pressure, and the residue was heated at 200° C. for 1 hour. It was then applied to a silica gel chromatography column, and eluted with a 1:9 by volume mixture of hexane and methylene chloride, to give 0.32 g (yield 31%) of the title compound as a pale yellow powder, melting at 148–149° C.

Nuclear Magnetic Resonance Spectrum (270 MHz, CDCl$_3$) δ ppm:

7.74 (2H, doublet, J=8 Hz);
7.27 (2H, doublet, J=8 Hz);
7.13–7.07 (2H, multiplet);
6.95–6.85 (3H, multiplet);
6.58–6.57 (1H, multiplet);
6.39–6.36 (1H, multiplet);
3.84 (3H, singlet);
3.04 (3H, singlet).

EXAMPLE 2

1-(4-Chlorophenyl)-2-(4-methylsulfonylphenyl) pyrrole (Compound No. 1-35)

Following a procedure similar to that described in the three stages of Examples 1(i), 1(ii) and 1(iii), but using 4-chloroaniline as a starting material instead of 4-methoxyaniline, the title compound was obtained as a pale yellow powder, melting at 184–188° C. The yield of the compound (pale yellow prismatic crystals) in the first stage was 94%, that in the second stage (white powder) was 93%, and that in the third stage was 42%.

Nuclear Magnetic Resonance Spectrum (270 MHz, CDCl$_3$) δ ppm:

7.78 (2H, doublet, J=8 Hz);
7.37–7.26 (4H, multiplet);
7.13–7.09 (2H, multiplet);
6.97 (1H, singlet);
6.58–6.57 (1H, multiplet);
6.42–6.39 (1H, multiplet);
3.05 (3H, singlet).

EXAMPLE 3

1-(4-Trifluoromethylphenyl)-2-(4-methylsulfonylphenyl)pyrrole (Compound No. 1-45)

Following a procedure similar to that described in the three stages of Examples 1(i), 1(ii) and 1(iii), but using 4-trifluoromethylaniline as a starting material instead of 4-methoxyaniline, the title compound was obtained as a white powder, melting at 187–190° C. The yield of the compound (pale yellow prismatic crystals) in the first stage was 64%, that in the second stage (white powder) was 95%, and that in the third stage was 47%.

Nuclear Magnetic Resonance Spectrum (270 MHz, CDCl$_3$) δ ppm:

7.80 (2H, doublet, J=8 Hz);
7.64 (2H, doublet, J=8 Hz);
7.28 (4H, doublet, J=10 Hz);
7.02 (1H, singlet);
6.61–6.60 (1H, multiplet);
6.46–6.43 (1H, multiplet);
3.06 (3H, singlet).

EXAMPLE 4

1-(4-Trifluoromethoxyphenyl)-2-(4-methylsulfonylphenyl)pyrrole (Compound No. 1-46)

Following a procedure similar to that described in the three stages of Examples 1(i), 1(ii) and 1(iii), but using 4-trifluoromethoxyaniline as a starting material instead of 4-methoxyaniline, the title compound was obtained as a white powder, melting at 150–152° C. The yield of the compound (pale yellow prismatic crystals) in the first stage was 59%, that in the second stage (white powder) was 97%, and that in the third stage was 52%.

Nuclear Magnetic Resonance Spectrum (270 MHz, CDCl$_3$) δ ppm:

7.78 (2H, doublet, J=8 Hz);
7.29–7.18 (6H, multiplet);
6.98 (1H, singlet);
6.59–6.58 (1H, multiplet);
6.43–6.41 (1H, multiplet);
3.05 (3H, singlet).

EXAMPLE 5

1-(3-Chloro-4-fluorophenyl)-2-(4-methylsulfonylphenyl)pyrrole (Compound No. 1-39)

Following a procedure similar to that described in the three stages of Examples 1(i), 1(ii) and 1(iii), but using 3-chloro-4-fluoroaniline as a starting material instead of 4-methoxyaniline, the title compound was obtained as a pale yellow powder, melting at 146–149° C. The yield of the compound (white powder) in the first stage was 93%, that in the second stage (white powder) was 96%, and that in the third stage was 39%.

Nuclear Magnetic Resonance Spectrum (270 MHz, CDCl$_3$) δ ppm:

7.80 (2H, doublet, J=8 Hz);
7.33–6.95 (6H, multiplet);
6.57 (1H, doublet, J=2 Hz);
6.41–6.39 (1H, multiplet);
3.05 (3H, singlet).

EXAMPLE 6

1-(3,4-Difluorophenyl)-2-(4-methylsulfonylphenyl) pyrrole (Compound No. 1-51)

Following a procedure similar to that described in the three stages of Examples 1(i), 1(ii) and 1(iii), but using 3,4-difluoroaniline as a starting material instead of 4-methoxyaniline, the title compound was obtained as a pale yellow powder, melting at 137–139° C. The yield of the compound (pale yellow prismatic crystals) in the first stage was 66%, that in the second stage (white powder) was 92%, and that in the third stage was 46%.

Nuclear Magnetic Resonance Spectrum (270 MHz, CDCl$_3$) δ ppm:

7.80 (2H, doublet, J=8 Hz);
7.28 (2H, doublet, J=8 Hz);
7.22–6.87 (6H, multiplet);
6.58–6.56 (1H, multiplet);
6.42–6.39 (1H, multiplet);
3.06 (3H, singlet).

EXAMPLE 7

1-(2,4-Difluorophenyl)-2-(4-methylsulfonylphenyl)pyrrole (Compound No. 1-53)

Following a procedure similar to that described in the three stages of Examples 1(i), 1(ii) and 1(iii), but using 2,4-difluoroaniline as a starting material instead of 4-methoxyaniline, the title compound was obtained as a white powder, melting at 122–125° C. The yield of the compound (white powder) in the first stage was 79%, that in the second stage (white powder) was 97%, and that in the third stage was 10%.

Nuclear Magnetic Resonance Spectrum (270 MHz, CDCl$_3$) δ ppm:

7.77 (2H, doublet, J=8 Hz);
7.30–7.19 (3H, multiplet);
6.95–6.89 (3H, multiplet);
6.60–6.59 (1H, multiplet);
6.45–6.42 (1H, multiplet);
3.04 (3H, singlet).

EXAMPLE 8

1-(3,4-Dimethylphenyl)-2-(4-methylsulfonylphenyl)pyrrole (Compound No. 1-55)

Following a procedure similar to that described in the three stages of Examples 1(i), 1(ii) and 1(iii), but using 3,4-dimethylaniline as a starting material instead of 4-methoxyaniline, the title compound was obtained as a white powder, melting at 134–137° C. The yield of the compound (yellow prismatic crystals) in the first stage was 95%, that in the second stage (white powder) was 96%, and that in the third stage was 23%.

Nuclear Magnetic Resonance Spectrum (270 MHz, CDCl$_3$) δ ppm:

7.74 (2H, doublet, J=8 Hz);
7.29 (2H, doublet, J=8 Hz);
7.10–6.82 (4H, multiplet);
6.57–6.55 (1H, multiplet);
6.38–6.36 (1H, multiplet);
3.03 (3H, singlet);
2.29 (3H, singlet);
2.24 (3H, singlet).

EXAMPLE 9

1-(4-Methylphenyl)-2-(4-methylsulfonylphenyl)pyrrole (Compound No. 1-37)

Following a procedure similar to that described in the three stages of Examples 1(i), 1(ii) and 1(iii), but using 4-methylaniline as a starting material instead of 4-methoxyaniline, the title compound was obtained as a pale yellow powder, melting at 112–114° C. The yield of the compound (white powder) in the first stage was 97%, that in the second stage (white powder) was 98%, and that in the third stage was 19%.

Nuclear Magnetic Resonance Spectrum (270 MHz, CDCl$_3$) δ ppm:

7.74 (2H, doublet, J=8 Hz);
7.28 (2H, doublet, J=9 Hz);
7.16 (2H, doublet, J=8 Hz);
7.05 (2H, doublet, J=8 Hz);
6.97 (1H, multiplet);
6.57–6.56 (1H, multiplet);
6.39–6.37 (1H, multiplet);
3.03 (3H, singlet);
2.39 (3H, singlet).

EXAMPLE 10

1-(3,4-Dichlorophenyl)-2-(4-methylsulfonylphenyl)pyrrole (Compound No. 1-57)

Following a procedure similar to that described in the three stages of Examples 1(i), 1(ii) and 1(iii), but using 3,4-dichloroaniline as a starting material instead of 4-methoxyaniline, the title compound was obtained as a white powder, melting at 139–142° C. The yield of the compound (white powder) in the first stage was 91%, that in the second stage (white powder) was 93%, and that in the third stage was 41%.

Nuclear Magnetic Resonance Spectrum (270 MHz, CDCl$_3$) δ ppm:

7.83 (2H, doublet, J=8 Hz);
7.43–7.26 (4H, multiplet);
6.96–6.91 (4H, multiplet);
6.58–6.57 (1H, multiplet);
6.43–6.41 (1H, multiplet);
3.06 (3H, singlet).

EXAMPLE 11

1-(3,4-Methylenedioxyphenyl)-2-(4-methylsulfonylphenyl)pyrrole (Compound No. 1-41)

Following a procedure similar to that described in the three stages of Examples 1(i), 1(ii) and 1(iii), but using 3,4-methylenedioxyaniline as a starting material instead of 4-methoxyaniline, the title compound was obtained as a pale yellow powder, melting at 172–175° C. The yield of the compound (pale yellow powder) in the first stage was 95%, that in the second stage (grey powder) was 91%, and that in the third stage was 29%.

Nuclear Magnetic Resonance Spectrum (270 MHz, CDCl$_3$) δ ppm:

7.77 (2H, doublet, J=9 Hz);
7.31 (2H, doublet, J=9 Hz);
6.93 (1H, singlet);
6.78 (1H, doublet, J=8 Hz);
6.66 (2H, doublet, J=8 Hz);
6.55 (1H, singlet);
6.37–6.35 (1H, multiplet);

6.03 (2H, singlet);
3.05 (3H, singlet).

EXAMPLE 12

1-(4-Methoxyphenyl)-4-methyl-2-(4-methylsulfonylphenyl)pyrrole (Compound No. 1-34)

Following a procedure similar to that described in Example 1(iii), but using methacrolein instead of acrolein, the title compound was obtained as a pale yellow powder (yield 21%), melting at 154–160° C.

Nuclear Magnetic Resonance Spectrum (270 MHz, $CDCl_3$) δ ppm:
7.72 (2H, doublet, J=8 Hz);
7.25 (2H, doublet, J=8 Hz);
7.09–7.03 (2H, multiplet);
6.89–6.84 (2H, multiplet);
6.73 (1H, singlet);
6.41 (1H, doublet, J=2 Hz);
3.83 (3H, singlet);
3.03 (3H, singlet);
2.18 (3H, singlet).

EXAMPLE 13

2-(4-Fluorophenyl)-1-(4-sulfamoylphenyl)pyrrole (Compound No. 2-62)

13(i) N-(4-Fluorobenzylidene)-4-sulfamoylaniline

Following a procedure similar to that described in Example 1(i), but using 4-fluorobenzaldehyde and 4-sulfamoylaniline as starting materials, the title compound was obtained as a white powder (yield 63%).

Nuclear Magnetic Resonance Spectrum (270 MHz, hexadeuterated acetone) δ ppm:
8.64 (1H, singlet);
8.12–8.03 (2H, multiplet);
7.93 (2H, doublet, J=9 Hz);
7.40–7.28 (4H, multiplet);
6.57 (2H, singlet).

13(ii) α-(4-Fluorophenyl)-α-(4-sulfamoylanilino)acetonitrile

Following a procedure similar to that described in Example 1(ii), but using N-(4-fluorobenzylidene)-4-sulfamoylaniline [prepared as described in step (i) above] and trimethylsilyl cyanide as starting materials, the title compound was obtained as a white powder (yield 95%).

Nuclear Magnetic Resonance Spectrum (270 MHz, hexadeuterated dimethyl sulfoxide) δ ppm:
7.75 (2H, doublet, J=9 Hz);
7.66–7.55 (2H, multiplet);
7.20–7.10 (2H, multiplet);
6.81 (2H, doublet, J=9 Hz);
6.71 (1H, doublet, J=8 Hz);
6.35 (2H, singlet);
5.61 (1H, doublet, J=8 Hz).

13(iii) 2-(4-Fluorophenyl)-1-(4-sulfamoylphenyl)pyrrole

Following a procedure similar to that described in Example 1(iii), but using α-(4-fluorophenyl)-α-(4-sulfamoylanilino)acetonitrile [prepared as described in step (ii) above] and acrolein as starting materials, the title compound was obtained as a brown powder (yield 11%), melting at 198–199° C.

Nuclear Magnetic Resonance Spectrum (270 MHz, $CDCl_3$) δ ppm:
7.88 (2H, doublet, J=9 Hz);
7.26 (2H, doublet, J=9 Hz);
7.14–7.04 (2H, multiplet);
7.00–6.90 (3H, multiplet);
6.95–6.87 (2H, multiplet);
4.87 (2H, singlet).
Mass spectrum (EI) m/z: 316 [M$^+$].

EXAMPLE 14

2-(4-Fluorophenyl)-3-methyl-1-(4-sulfamoylphenyl)pyrrole (Compound No. 2-64)

Following a procedure similar to that described in Example 13(iii), but using crotonaldehyde instead of acrolein, the title compound was obtained as a white powder (yield 19%), melting at 187–188° C.

Nuclear Magnetic Resonance Spectrum (270 MHz, $CDCl_3$) δ ppm:
7.81 (2H, doublet, J=9 Hz);
7.15 (2H, doublet, J=9 Hz);
7.10–6.95 (2H, multiplet);
6.90 (2H, doublet, J=3 Hz);
6.29 (2H, doublet, J=3 Hz);
4.78 (2H, singlet);
2.14 (3H, singlet).
Mass spectrum (EI) m/z: 330 [M$^+$].

EXAMPLE 15

2-(4-Fluorophenyl)-4-methyl-1-(4-sulfamoylphenyl)pyrrole (Compound No. 2-63)

Following a procedure similar to that described in Example 13(iii), but using methacrolein instead of acrolein, the title compound was obtained as a pale yellow powder (yield 24%), melting at 168–170° C.

Nuclear Magnetic Resonance Spectrum (270 MHz, $CDCl_3$) δ ppm:
7.85 (2H, doublet, J=9 Hz);
7.21 (2H, doublet, J=9 Hz);
7.12–7.03 (2H, multiplet);
7.00–6.89 (2H, multiplet);
6.74 (1H, singlet);
6.27 (1H, singlet);
4.82 (2H, singlet);
2.18 (3H, singlet).
Mass spectrum (EI) m/z: 330 [M$^+$].

EXAMPLE 16

2-(4-Methylphenyl)-1-(4-sulfamoylphenyl)pyrrole (Compound No. 2-87)

16(i) N-(4-Methylbenzylidene)-4-sulfamoylaniline

Following a procedure similar to that described in Example 1(i), but using 4-methylbenzaldehyde and 4-sulfamoylaniline as starting materials, the title compound was obtained as a white powder (yield 91%).

Nuclear Magnetic Resonance Spectrum (270 MHz, hexadeuterated dimethyl sulfoxide) δ ppm:
8.60 (1H, singlet);
7.90–7.81 (4H, multiplet);

7.42–7.32 (4H, multiplet);
2.40 (3H, singlet).

16(ii) α-(4-Methylphenyl)-α-(4-sulfamoylanilino)acetonitrile

Following a procedure similar to that described in Example 1(ii), but using N-(4-methylbenzylidene)-4-sulfamoylaniline [prepared as described in step (i) above] and trimethylsilyl cyanide as starting materials, the title compound was obtained as a white powder (yield 94%).

Nuclear Magnetic Resonance Spectrum (270 MHz, hexadeuterated dimethyl sulfoxide) δ ppm:
7.70 (2H, doublet, J=9 Hz);
7.48 (2H, doublet, J=9 Hz);
7.26 (2H, doublet, J=9 Hz);
6.68 (1H, doublet, J=8 Hz);
6.84 (2H, doublet, J=9 Hz);
6.72 (2H, singlet);
5.67 (1H, doublet, J=8 Hz);
2.38 (3H, singlet).

16(iii) 2-(4-Methylphenyl)-1-(4-sulfamoylphenyl)pyrrole

Following a procedure similar to that described in Example 1(iii), but using α-(4-methylphenyl)-α-(4-sulfamoylanilino)acetonitrile [prepared as described in step (ii) above] and acrolein as starting materials, the title compound was obtained as a brown powder (yield 13%), melting at 183–184° C.

Nuclear Magnetic Resonance Spectrum (270 MHz, CDCl$_3$) δ ppm:
7.87 (2H, doublet, J=9 Hz);
7.28 (2H, doublet, J=9 Hz);
7.09–6.98 (4H, multiplet);
6.96–6.93 (1H, multiplet);
6.44–6.38 (2H, multiplet);
4.81 (2H, singlet);
2.33 (3H, singlet).
Mass spectrum (EI) m/z: 313 [(M+H)$^+$].

EXAMPLE 17

3-Methyl-2-(4-methylphenyl)-1-(4-sulfamoylphenyl)pyrrole (Compound No 2-88)

Following a procedure similar to that described in Example 16(iii), but using crotonaldehyde instead of acrolein, the title compound was obtained as a brown amorphous material (yield 33%).

Nuclear Magnetic Resonance Spectrum (270 MHz, CDCl$_3$) δ ppm:
7.79 (2H, doublet, J=9 Hz);
7.16 (2H, doublet, J=9 Hz);
7.09 (2H, doublet, J=9 Hz);
6.97 (2H, doublet, J=9 Hz);
6.89 (1H, doublet, J=3 Hz);
6.28 (1H, doublet, J=3 Hz);
4.83 (2H, singlet);
2.34 (3H, singlet);
2.15 (3H, singlet).
Mass spectrum (EI) m/z: 326 [M$^+$].

EXAMPLE 18

4-Methyl-2-(4-methylphenyl)-1-(4-sulfamoylphenyl)pyrrole (Compound No. 2-89)

Following a procedure similar to that described in Example 16(iii), but using methacrolein instead of acrolein as starting materials, the title compound was obtained as a pale brown powder (yield 5%), melting at 175–176° C.

Nuclear Magnetic Resonance Spectrum (270 MHz, CDCl$_3$) δ ppm:
7.84 (2H, doublet, J=9 Hz);
7.23 (2H, doublet, J=9 Hz);
7.08–6.97 (4H, multiplet);
6.73 (1H, doublet, J=2 Hz);
6.27 (1H, doublet, J=2 Hz);
4.79 (2H, singlet);
2.32 (2H, singlet);
2.18 (2H, singlet).

EXAMPLE 19

1-(4-Fluorophenyl)-2-(4-sulfamoylphenyl)pyrrole (Compound No. 1-73)

19(i) 4-Fluoro-N-(4-sulfamoylbenzylidene)aniline

Following a procedure similar to that described in Example 1(i), but using 4-sulfamoylbenzaldehyde and 4-fluoroaniline as starting materials, the title compound was obtained as white prismatic crystals (yield 25%).

Nuclear Magnetic Resonance Spectrum (270 MHz, hexadeuterated dimethyl sulfoxide) δ ppm:
8.74 (1H, singlet);
8.11 (2H, doublet, J=8 Hz);
7.96 (2H, doublet, J=8 Hz);
7.50 (2H, singlet);
7.43–7.25 (4H, multiplet).

19(ii) α-(4-Fluoroanilino)-α-(4-sulfamoylphenyl)acetonitrile

Following a procedure similar to that described in Example 1(ii), but using 4-fluoro-N-(4-sulfamoylbenzylidene)aniline [prepared as described in step (i) above] and trimethylsilyl cyanide as starting materials, the title compound was obtained as a slightly yellow powder (yield 83%).

Nuclear Magnetic Resonance Spectrum (270 MHz, hexadeuterated dimethyl sulfoxide) δ ppm:
7.93 (2H, doublet, J=8 Hz);
7.76 (2H, doublet, J=8 Hz);
7.45 (2H, singlet);
7.05 (2H, triplet, J=9 Hz);
6.73–6.85 (3H, multiplet);
6.12 (1H, doublet, J=10 Hz).
Mass spectrum (EI) m/z: 279 [M$^+$].

19(iii) 1-(4-Fluorophenyl)-2-(4-sulfamoylphenyl)pyrrole

Following a procedure similar to that described in Example 1(iii), but using α-(4-fluoroanilino)-α-(4-sulfamoylphenyl)acetonitrile [prepared as described in step (ii) above] and acrolein as starting materials, the title compound was obtained as a white powder (yield 48%), melting at 160–161° C.

Nuclear Magnetic Resonance Spectrum (270 MHz, hexadeuterated dimethyl sulfoxide) δ ppm:
7.67 (2H, doublet, J=8 Hz);
7.32–7.22 (8H, multiplet);
7.14 (1H, triplet, J=2 Hz);
6.59 (1H, doublet of doublets, J=4 & 2 Hz);
6.36 (1H, triplet, J=3 Hz).
Mass spectrum (EI) m/z: 316 [M$^+$].

EXAMPLE 20

1-(4-Fluorophenyl)-4-methyl-2-(4-sulfamoylphenyl)pyrrole (Compound No. 1-74)

Following a procedure similar to that described in Example 19(iii), but using methacrolein instead of acrolein, the title compound was obtained as a white powder (yield 62%), melting at 126–127° C.

Nuclear Magnetic Resonance Spectrum (270 MHz, CDCl$_3$) δ ppm:

7.87 (2H, doublet, J=9 Hz);
7.39–7.17 (6H, multiplet);
6.87 (1H, singlet);
6.53 (1H, singlet);
4.93 (2H, singlet);
2.31 (3H, singlet).

Mass spectrum (EI) m/z: 330 [M$^+$].

EXAMPLE 21

2-(4-Fluorophenyl)-3-methyl-1-(4-methylsulfonylphenyl)pyrrole (Compound No. 2-8)

21(i) N-(4-Fluorobenzylidene)-4-methylthioaniline

Following a procedure similar to that described in Example 1(i), but using 4-fluorobenzaldehyde and 4-methylthioaniline as starting materials, the title compound was obtained as a pale yellow needle-like crystals (yield 87%).

Nuclear Magnetic Resonance Spectrum (270 MHz, CDCl$_3$) δ ppm:

8.43 (1H, singlet);
7.94–7.86 (2H, multiplet);
7.33–7.27 (2H, multiplet);
7.21–7.12 (4H, multiplet);
2.52 (3H, singlet).

21(ii) α-(4-Fluorophenyl)-α-(4-methylthioanilino)acetonitrile

Following a procedure similar to that described in Example 1(ii), but using N-(4-fluorobenzylidene)-4-methylthioaniline [prepared as described in step (i) above] and trimethylsilyl cyanide as starting materials, the title compound was obtained as a pale yellow powder (yield 96%).

Nuclear Magnetic Resonance Spectrum (270 MHz, CDCl$_3$) δ ppm:

7.63–7.54 (2H, multiplet);
7.27 (2H, doublet, J=9 Hz);
7.21–7.12 (2H, multiplet);
6.73 (2H, doublet, J=9 Hz);
5.40 (1H, doublet, J=9 Hz);
4.01 (1H, doublet, J=9 Hz);
2.45 (3H, singlet).

21(iii) 2-(4-Fluorophenyl)-3-methyl-1-(4-methylsulfonylphenyl)pyrrole

A solution of 2.00 g (7.3 mmol) of α-(4-fluorophenyl)-(-(4-methylthioanilino)acetonitrile [prepared as described in step (ii) above] in 15 ml of tetrahydrofuran was cooled to −78° C. under a stream of nitrogen, and 0.67 ml (8.1 mmol) of crotonaldehyde was added to the resulting solution. 8.10 ml (8.1 mmol) of a 1.0M solution of lithium bis(trimethylsilyl)amide were then added dropwise to the mixture, and the resulting mixture was stirred at −78° C., after which the mixture was stirred overnight whilst allowing its temperature to rise naturally. The tetrahydrofuran was then removed by distillation under reduced pressure, and ethyl acetate was added to the residue. The resulting mixture was washed with a saturated aqueous solution of ammonium chloride, with water and with a saturated aqueous solution of sodium chloride, in that order. The organic layer was separated and dried over anhydrous magnesium sulfate, and the solvent was then removed by distillation under reduced pressure. The resulting residue was dissolved in 20 ml of dichloroethane, and 3.98 g (16.2 mmol) of 70% m-chloroperbenzoic acid were added to the resulting solution in several portions, whilst ice-cooling. The mixture was then stirred, whilst ice-cooling for 30 minutes. At the end of this time, the reaction mixture was diluted with methylene chloride and then washed with a 10% w/v aqueous solution of sodium thiosulfate and with a saturated aqueous solution of sodium hydrogencarbonate twice each, in that order. Thereafter, the organic layer was separated and dried over anhydrous magnesium sulfate. The solvent was then removed by distillation under reduced pressure. The residue was heated at 150° C. for 2 hours, after which it was applied to a silica gel chromatography column and eluted, using a 2:1 by volume mixture of hexane and ethyl acetate as the eluent, to give 0.36 g (yield 15%) of the title compound as a white powder, melting at 157–158° C.

Nuclear Magnetic Resonance Spectrum (270 MHz, CDCl$_3$) δ ppm:

7.83 (2H, doublet, J=9 Hz);
7.20 (2H, doublet, J=9 Hz);
7.10–6.95 (4H, multiplet);
6.91 (1H, doublet, J=3 Hz);
6.30 (1H, doublet, J=3 Hz);
3.06 (3H, singlet);
2.14 (3H, singlet).

Mass spectrum (EI) m/z: 329 [M$^+$].

EXAMPLE 22

2-(4-Fluorophenyl)-1-(4-methylsulfonylphenyl)pyrrole (Compound No. 2-3)

Following a procedure similar to that described in Example 21(iii), but using acrolein instead of crotonaldehyde, the title compound was obtained as a white powder (yield 7%), melting at 195–196° C.

Nuclear Magnetic Resonance Spectrum (270 MHz, CDCl$_3$) δ ppm:

7.90 (2H, doublet, J=9 Hz);
7.31 (2H, doublet, J=9 Hz);
7.13–7.05 (2H, multiplet);
7.01–6.92 (3H, multiplet);
6.46–6.40 (2H, multiplet);
3.08 (3H, singlet).

Mass spectrum (EI) m/z: 315 [M$^+$].

EXAMPLE 23

2-(4-Fluorophenyl)-4-methyl-1-(4-methylsulfonylphenyl)pyrrole (Compound No. 2-11)

Following a procedure similar to that described in Example 21(iii), but using methacrolein instead of crotonaldehyde, the title compound was obtained as a white powder (yield 36%), melting at 151–154° C.

Nuclear Magnetic Resonance Spectrum (270 MHz, CDCl$_3$) δ ppm:

7.87 (2H, doublet, J=9 Hz);
7.26 (2H, doublet, J=9 Hz);
7.12–7.03 (2H, multiplet);
7.00–6.92 (2H, multiplet);
6.76 (1H, doublet, J=2 Hz);

6.28 (1H, doublet, J=2 Hz);
3.08 (3H, singlet);
2.18 (3H, singlet).
Mass spectrum (EI) m/z: 329 [M$^+$].

EXAMPLE 24

3-Ethyl-2-(4-fluorophenyl)-1-(4-methylsulfonylphenyl)pyrrole (Compound No. 2-9)

Following a procedure similar to that described in Example 21(iii), but using 2-pentenal instead of crotonaldehyde, the title compound was obtained as a white powder (yield 15%), melting at 107–108° C.

Nuclear Magnetic Resonance Spectrum (270 MHz, CDCl$_3$) δ ppm:

7.82 (2H, doublet, J=9 Hz);
7.21–6.93 (7H, multiplet);
6.36 (1H, doublet, J=3 Hz);
3.05 (3H, singlet);
2.50 (2H, quartet, J=8 Hz);
1.19 (3H, triplet, J=8 Hz).
Mass spectrum (EI) m/z: 343 [M$^+$].

EXAMPLE 25

2-(4-Fluorophenyl)-1-(4-methylsulfonylphenyl)-3-propylpyrrole (Compound No. 2-10)

Following a procedure similar to that described in Example 21(iii), but using 2-hexenal instead of crotonaldehyde, the title compound was obtained as white prismatic crystals (yield 20%), melting at 116–117° C.

Nuclear Magnetic Resonance Spectrum (270 MHz, CDCl$_3$) δ ppm:

7.82 (2H, doublet, J=9 Hz);
7.19 (2H, doublet, J=9 Hz);
7.06–6.92 (5H, multiplet);
6.33 (1H, doublet, J=3 Hz);
3.05 (3H, singlet);
2.44 (2H, triplet, J=8 Hz);
1.63–1.56 (2H, multiplet);
0.92 (3H, triplet, J=7 Hz).
Mass spectrum (EI) m/z: 357 [M$^+$].

EXAMPLE 26

2-(4-Chlorophenyl)-1-(4-methylsulfonylphenyl)pyrrole (Compound No. 2-23)

26(i) N-(4-Chlorobenzylidene)-4-methylthioaniline

Following a procedure similar to that described in Example 1(i), but using 4-chlorobenzaldehyde and 4-methylthioaniline as starting materials, the title compound was obtained as pale yellow needle-like crystals (yield 94%).

Nuclear Magnetic Resonance Spectrum (270 MHz, CDCl$_3$) δ ppm:

8.43 (1H, singlet);
7.83 (2H, doublet, J=9 Hz);
7.45 (2H, doublet, J=9 Hz);
7.30 (2H, doublet, J=9 Hz);
7.18 (2H, doublet, J=9 Hz);
2.51 (3H, singlet).

26(ii) α-(4-Chlorophenyl)-α-(4-methylthioanilino)acetonitrile

Following a procedure similar to that described in Example 1(ii), but using N-(4-chlorobenzylidene)-4-methylthioaniline [prepared as described in step (i) above] and trimethylsilyl cyanide as starting materials, the title compound was obtained as a pale yellow powder (yield 84%).

Nuclear Magnetic Resonance Spectrum (270 MHz, CDCl$_3$) δ ppm:

7.55 (2H, doublet, J=9 Hz);
7.44 (2H, doublet, J=9 Hz);
7.27 (2H, doublet, J=9 Hz);
6.72 (2H, doublet, J=9 Hz);
5.40 (1H, doublet, J=9 Hz);
4.02 (1H, doublet, J=9 Hz);
2.45 (3H, singlet).

26(iii) 2-(4-Chlorophenyl)-1-(4-methylsulfonylphenyl)pyrrole

Following a procedure similar to that described in Example 21(iii), but using α-(4-chlorophenyl)-α-(4-methylthioanilino)acetonitrile [prepared as described in step (ii) above] and acrolein as starting materials, the title compound was obtained as an orange-colored powder (yield 32%), melting at 203–205° C.

Nuclear Magnetic Resonance Spectrum (270 MHz, CDCl$_3$) δ ppm:

7.91 (2H, doublet, J=9 Hz);
7.32 (2H, doublet, J=9 Hz);
7.23 (2H, doublet, J=9 Hz);
7.05 (2H, doublet, J=9 Hz);
7.00–6.97 (1H, multiplet);
6.48–6.45 (1H, multiplet);
6.44–6.40 (1H, multiplet);
3.09 (3H, singlet).
Mass spectrum (EI) m/z: 331 [M$^+$].

EXAMPLE 27

2-(4-Chlorophenyl)-3-methyl-1-(4-methylsulfonylphenyl)pyrrole (Compound No. 2-24)

Following a procedure similar to that described in Example 26(iii), but using crotonaldehyde instead of acrolein, the title compound was obtained as a pale yellow powder (yield 21%), melting at 173–174° C.

Nuclear Magnetic Resonance Spectrum (270 MHz, CDCl$_3$) δ ppm:

7.84 (2H, doublet, J=9 Hz);
7.27 (2H, doublet, J=9 Hz);
7.21 (2H, doublet, J=9 Hz);
7.01 (2H, doublet, J=9 Hz);
6.92 (1H, doublet, J=3 Hz);
6.30 (1H, doublet, J=3 Hz);
3.07 (3H, singlet);
2.15 (3H, singlet).
Mass spectrum (EI) m/z: 345 [M$^+$].

EXAMPLE 28

2-(4-Methoxyphenyl)-1-(4-methylsulfonylphenyl)pyrrole (Compound No. 2-20)

28(i) N-(4-Methoxybenzylidene)-4-methylthioaniline

Following a procedure similar to that described in Example 1(i), but using 4-methoxybenzaldehyde and 4-methylthioaniline as starting materials, the title compound was obtained as a slightly yellow powder (yield 100%).

Nuclear Magnetic Resonance Spectrum (270 MHz, CDCl$_3$) δ ppm:

8.39 (1H, singlet);
7.84 (2H, doublet, J=9 Hz);
7.29 (2H, doublet, J=9 Hz);
7.16 (2H, doublet, J=9 Hz);
6.98 (2H, doublet, J=9 Hz);
3.88 (3H, singlet);
2.51 (3H, singlet).

28(ii) α-(4-Methoxyphenyl)-α-(4-methylthioanilino)acetonitrile

Following a procedure similar to that described in Example 1(ii), but using N-(4-methoxybenzylidene)-4-methylthioaniline [prepared as described in step (i) above] and trimethylsilyl cyanide as starting materials, the title compound was obtained as a pale brown powder (yield 92%).

Nuclear Magnetic Resonance Spectrum (270 MHz, CDCl$_3$) δ ppm:

7.47 (2H, doublet, J=9 Hz);
7.27 (2H, doublet, J=9 Hz);
6.97 (2H, doublet, J=9 Hz);
6.73 (2H, doublet, J=9 Hz);
5.34 (1H, doublet, J=9 Hz);
3.97 (1H, doublet, J=9 Hz);
3.84 (3H, singlet);
2.45 (3H, singlet).

28(iii) 2-(4-Methoxyphenyl)-1-(4-methylsulfonylphenyl)pyrrole

Following a procedure similar to that described in Example 21 (iii), but using α-(4-methoxyphenyl)-α-(4-methylthioanilino)acetonitrile [prepared as described in step (ii) above] and acrolein as starting materials, the title compound was obtained as a white powder (yield 9%), melting at 183–184° C.

Nuclear Magnetic Resonance Spectrum (270 MHz, CDCl$_3$) δ ppm:

7.88 (2H, doublet, J=9 Hz);
7.32 (2H, doublet, J=9 Hz);
7.05 (2H, doublet, J=9 Hz);
7.98–7.93 (1H, multiplet);
6.80 (2H, doublet, J=9 Hz);
6.43–6.37 (2H, multiplet);
3.80 (3H, singlet);
3.08 (3H, singlet).
Mass spectrum (EI) m/z: 327 [M$^+$].

EXAMPLE 29

2-(4-Methylphenyl)-1-(4-methylsulfonylphenyl)pyrrole (Compound No. 2-25)

29(i) N-(4-Methylbenzylidene)-4-methylthioaniline

Following a procedure similar to that described in Example 1(i), but using 4-methylbenzaldehyde and 4-methylthioaniline as starting materials, the title compound was obtained as a slightly yellow powder (yield 96%).

Mass spectrum (EI) m/z: 241 [M$^+$].

29(ii) α-(4-Methylphenyl)-α-(4-methylthioanilino)acetonitrile

Following a procedure similar to that described in Example 1(ii), but using N-(4-methylbenzylidene)-4-methylthioaniline [prepared as described in step (i) above] and trimethylsilyl cyanide as starting materials, the title compound was obtained as a pale yellow powder (yield 73%).

Nuclear Magnetic Resonance Spectrum (270 MHz, CDCl$_3$) δ ppm:

7.47 (2H, doublet, J=9 Hz);
7.27 (4H, doublet, J=9 Hz);
6.73 (2H, doublet, J=9 Hz);
5.36 (1H, doublet, J=8 Hz);
3.99 (1H, doublet, J=8 Hz);
2.44 (3H, singlet);
2.40 (3H, singlet).

29(iii) 2-(4-Methylphenyl)-1-(4-methylsulfonylphenyl)pyrrole

Following a procedure similar to that described in Example 21(iii), but using α-(4-methylphenyl)-α-(4-methylthioanilino)acetonitrile [prepared as described in step (ii) above] and acrolein as starting materials, the title compound was obtained as a yellow powder (yield 16%), melting at 186–187° C.

Nuclear Magnetic Resonance Spectrum (270 MHz, CDCl$_3$) δ ppm:

7.88 (2H, doublet, J=9 Hz);
7.32 (2H, doublet, J=9 Hz);
7.10–6.94 (5H, multiplet);
6.45–6.39 (2H, multiplet);
3.08 (3H, singlet);
2.33 (3H, singlet).
Mass spectrum (EI) m/z: 311 [M$^+$].

EXAMPLE 30

2-(4-Methoxyphenyl)-3-methyl-1-(4-methylsulfonylphenyl)pyrrole (Compound No. 2-21)

30(i) α-(4-Methoxyphenyl)-α-(4-methylsulfonylanilino)acetonitrile 6.41 g (20.3 mmol) of α-(4-methoxyphenyl)-α-(4-methylthioanilino)acetonitrile [prepared as described in Example 28(ii)] were dissolved in 160 ml of dichloroethane, and 12.23 g (49.8 mmol) of 70% m-chloroperbenzoic acid were added to the resulting solution in several portions, whilst ice-cooling. The mixture was then stirred for 30 minutes, after which the reaction mixture was diluted with methylene chloride and then washed once with a 10% w/v aqueous solution of sodium thiosulfate and once with a saturated aqueous solution of sodium hydrogencarbonate, in that order; the two washings were then repeated in the same order. The organic layer was separated and dried over anhydrous magnesium sulfate and the solvent was then removed by distillation under reduced pressure. The resulting residue was applied to a silica gel chromatography column and eluted with a 1:2 by volume mixture of ethyl acetate and hexane, to give 3.65 g of the title compound as a pale yellow powder (yield 51%).

Nuclear Magnetic Resonance Spectrum (270 MHz, CDCl$_3$) δ ppm:

7.83 (2H, doublet, J=9 Hz);
7.50 (2H, doublet, J=9 Hz);
6.99 (2H, doublet, J=9 Hz);
6.83 (2H, doublet, J=9 Hz);
5.43 (1H, doublet, J=8 Hz);
4.56 (1H, doublet, J=8 Hz);

3.85 (3H, singlet);
3.03 (3H, singlet).

30(ii) 2-(4-Methoxyphenyl)-3-methyl-1-(4-methylsulfonylphenyl)pyrrole

Following a procedure similar to that described in Example 1(iii), but using α-(4-methoxyphenyl)-α-(4-methylsulfonylanilino)acetonitrile [prepared as described in step (i) above] and crotonaldehyde as starting materials, the title compound was obtained as an orange-colored powder (yield 40%), melting at 131–132° C.

Nuclear Magnetic Resonance Spectrum (270 MHz, $CDCl_3$) δ ppm:

7.81 (2H, doublet, J=9 Hz);
7.21 (2H, doublet, J=9 Hz);
7.01 (2H, doublet, J=9 Hz);
6.89 (1H, doublet, J=3 Hz);
6.84 (1H, doublet, J=3 Hz);
6.29 (1H, doublet, J=3 Hz);
3.81 (3H, singlet);
3.05 (3H, singlet);
2.14 (3H, singlet).
Mass spectrum (EI) m/z: 341 [M+].

EXAMPLE 31

3-Methyl-2-(4-methylphenyl)-1-(4-methylsulfonylphenyl)pyrrole (Compound No. 2-26)

31(i) α-(4-Methylphenyl)-α-(4-methylsulfonylanilino)acetonitrile

Following a procedure similar to that described in Example 30(i), but using α-(4-methylphenyl)-α-(4-methylthioanilino)acetonitrile [prepared as described in Example 29(ii)] and m-chloroperbenzoic acid as starting materials, the title compound was obtained as a white powder (yield 93%).

Nuclear Magnetic Resonance Spectrum (270 MHz, $CDCl_3$) δ ppm:

7.83 (2H, doublet, J=9 Hz);
7.47 (2H, doublet, J=9 Hz);
7.30 (2H, doublet, J=9 Hz);
6.84 (2H, doublet, J=9 Hz);
5.45 (1H, doublet, J=8 Hz);
4.55 (1H, doublet, J=8 Hz);
3.03 (3H, singlet);
2.41 (3H, singlet).

31(ii) 3-Methyl-2-(4-methylphenyl)-1-(4-methylsulfonylphenyl)pyrrole

Following a procedure similar to that described in Example 1(iii), but using α-(4-methylphenyl)-α-(4-methylsulfonylanilino)acetonitrile [prepared as described in step (i) above] and crotonaldehyde as starting materials, the title compound was obtained as a pale brown powder (yield 46%), melting at 158–160° C.

Nuclear Magnetic Resonance Spectrum (270 MHz, $CDCl_3$) δ ppm:

7.81 (2H, doublet, J=9 Hz);
7.21 (2H, doublet, J=9 Hz);
7.10 (2H, doublet, J=9 Hz);
6.97 (2H, doublet, J=9 Hz);
6.90 (1H, doublet, J=3 Hz);
6.29 (1H, doublet, J=3 Hz);
3.05 (3H, singlet);
2.35 (3H, singlet);
2.15 (3H, singlet).
Mass spectrum (FAB) m/z: 326 [(M+H)+].
"FAB" means "Fast Atom Bombardment".

EXAMPLE 32

2-(4-Difluoromethoxyphenyl)-3-methyl-1-(4-methylsulfonylphenyl)pyrrole (Compound No. 2-37)

32(i) α-(4-Difluoromethoxyphenyl)-α-(4-methylthioanilino)acetonitrile

Following a procedure similar to that described in Example 1(i), but using 4-difluoromethoxybenzaldehyde and 4-methylthioaniline as starting materials, N-(4-difluoromethoxybenzylidene)-4-methylthioaniline was obtained in a yield of 91%. This aniline compound and trimethylsilyl cyanide were then reacted together in a similar manner to that described in Example 1(ii), to give the title compound as a slightly yellow powder (yield 80%).

Nuclear Magnetic Resonance Spectrum (270 MHz, $CDCl_3$) δ ppm:

7.61 (2H, doublet, J=9 Hz);
7.27 (2H, doublet, J=9 Hz);
7.22 (2H, doublet, J=9 Hz);
6.73 (2H, doublet, J=9 Hz);
6.56 (1H, triplet, J=73 Hz);
5.41 (1H, doublet, J=9 Hz);
4.01 (1H, doublet, J=9 Hz);
2.45 (3H, singlet).

32(ii) α-(4-Difluoromethoxyphenyl)-α-(4-methylsulfonylanilino)acetonitrile

Following a procedure similar to that described in Example 30(i), but using α-(4-difluoromethoxyphenyl)-α-(4-methylthioanilino)acetonitrile [prepared as described in step (i) above] and m-chloroperbenzoic acid as starting materials, the title compound was obtained as a pale yellow powder (yield 89%).

Nuclear Magnetic Resonance Spectrum (270 MHz, $CDCl_3$) δ ppm:

7.84 (2H, doublet, J=9 Hz);
7.61 (2H, doublet, J=9 Hz);
7.25 (2H, doublet, J=9 Hz);
6.84 (2H, doublet, J=9 Hz);
6.57 (1H, triplet, J=73 Hz);
5.51 (1H, doublet, J=8 Hz);
4.60 (1H, doublet, J=8 Hz);
3.03 (3H, singlet).

32(iii) 2-(4-Difluoromethoxyphenyl)-3-methyl-1-(4-methylsulfonylphenyl)pyrrole

Following a procedure similar to that described in Example 1(iii), but using α-(4-difluoromethoxyphenyl)-α-(4-methylsulfonylanilino)acetonitrile [prepared as described in step (ii) above] and crotonaldehyde as starting materials, the title compound was obtained as a white powder (yield 31%), melting at 98–99° C.

Nuclear Magnetic Resonance Spectrum (270 MHz, $CDCl_3$) δ ppm:

7.83 (2H, doublet, J=9 Hz);
7.21 (2H, doublet, J=9 Hz);
7.12–7.02 (4H, multiplet);
6.91 (1H, doublet, J=3 Hz);
6.54 (1H, triplet, J=74 Hz);

6.30 (1H, doublet, J=3 Hz);
3.06 (3H, singlet);
2.15 (3H, singlet).
Mass spectrum (EI) m/z: 377 [M+].

EXAMPLE 33

1-(4-Fluorophenyl)-2-(4-methylsulfonylphenyl) pyrrole (Compound No. 1-3)

33(i) α-(4-Fluoroanilino)-α-(4-methylthiophenyl) acetonitrile

Following a procedure similar to that described in Example 1(i), but using 4-methylthiobenzaldehyde and 4-fluoroaniline as starting materials, 4-fluoro-N-(4-methylthiobenzylidene)aniline was obtained in a yield of 89%. This aniline compound and trimethylsilyl cyanide were then reacted together in a similar manner to that described in Example 1(ii), to give the title compound as a slightly yellow powder (yield 47%).

Nuclear Magnetic Resonance Spectrum (270 MHz, CDCl$_3$) δ ppm:

7.50 (2H, doublet, J=9 Hz);
7.31 (2H, doublet, J=9 Hz);
6.98 (2H, triplet, J=9 Hz);
6.73 (2H, doublet of doublets, J=9 & 4 Hz);
5.33 (1H, doublet, J=9 Hz);
3.92 (1H, doublet, J=9 Hz);
2.51 (3H, singlet).

33(ii) 1-(4-Fluorophenyl)-2-(4-methylsulfonylphenyl) pyrrole

Following a procedure similar to that described in Example 21(iii), but using α-(4-fluoroanilino)-α-(4-methylthiophenyl)acetonitrile [prepared as described in step (i) above] and acrolein as starting materials, the title compound was obtained as a yellow powder (yield 7%), melting at 145–147° C.

Nuclear Magnetic Resonance Spectrum (270 MHz, CDCl$_3$) δ ppm:

7.77 (2H, doublet, J=9 Hz);
7.27 (2H, doublet, J=9 Hz);
7.18–7.04 (4H, multiplet);
6.96 (1H, doublet of doublets, J=3 & 2 Hz);
6.58 (1H, doublet of doublets, J=4 & 2 Hz);
6.40 (1H, doublet of doublets, J=4 & 3 Hz);
3.04 (3H, singlet).
Mass spectrum (EI) m/z: 315 [M+].

EXAMPLE 34

1-(4-Fluorophenyl)-4-methyl-2-(4-methylsulfonylphenyl)pyrrole (Compound No. 1-15)

Following a procedure similar to that described in Example 33(ii), but using methacrolein instead of acrolein, the title compound was obtained as a white powder (yield 4%), melting at 127–130° C.

Nuclear Magnetic Resonance Spectrum (270 MHz, CDCl$_3$) δ ppm:

7.75 (2H, doublet, J=9 Hz);
7.24 (2H, doublet, J=9 Hz);
7.15–7.03 (4H, multiplet);
6.74 (1H, doublet, J=2 Hz);
6.42 (1H, doublet, J=2 Hz);
3.04 (3H, singlet);
2.18 (3H, singlet).
Mass spectrum (EI) m/z: 329 [M+].

EXAMPLE 35

5-Bromo-1-(4-fluorophenyl)-2-(4-methylsulfonylphenyl)pyrrole (Compound No. 1-6)

0.32 g (1.0 mmol) of 1-(4-fluorophenyl)-2-(4-methylsulfonylphenyl)pyrrole (prepared as described in Example 33) was dissolved in 10 ml of anhydrous tetrahydrofuran, and 0.18 g (1.0 mmol) of N-bromosuccinimide was added to the resulting solution, whilst ice-cooling. The mixture was then stirred, whilst ice-cooling for 1 hour and then at room temperature for a further 1 hour. At the end of this time, water was added to the mixture, and the resulting mixture was extracted with methylene chloride. The organic extract was dried over anhydrous magnesium sulfate, and the solvent was then removed by distillation under reduced pressure. The resulting residue was applied to a silica gel chromatography column and eluted with a 1:3 by volume mixture of ethyl acetate and hexane, to give 0.28 g of the title compound as a white powder (yield 70%), melting at 174–176° C.

Nuclear Magnetic Resonance Spectrum (270 MHz, CDCl$_3$) δ ppm:

7.73 (2H, doublet, J=9 Hz);
7.23–7.09 (6H, multiplet);
6.57 (1H, doublet, J=4 Hz);
6.44 (1H, doublet, J=4 Hz);
3.02 (3H, singlet).
Mass spectrum (EI) m/z: 393 [M+].

EXAMPLE 36

5-Bromo-1-(4-fluorophenyl)-4-methyl-2-(4-methylsulfonylphenyl)pyrrole (Compound No. 1-18)

Following a procedure similar to that described in Example 35, but using 1-(4-fluorophenyl)-4-methyl-2-(4-methylsulfonylphenyl)pyrrole (prepared as described in Example 34) and N-bromosuccinimide as starting materials, the title compound was obtained as a white powder (yield 30%), melting at 158–159° C.

Nuclear Magnetic Resonance Spectrum (270 MHz, CDCl$_3$) δ ppm:

7.71 (2H, doublet, J=9 Hz);
7.19–7.11 (6H, multiplet);
6.49 (1H, singlet);
3.02 (3H, singlet);
2.15 (3H, singlet).
Mass spectrum (EI) m/z: 407 [M+].

EXAMPLE 37

5-Chloro-1-(4-fluorophenyl)-4-methyl-2-(4-methylsulfonylphenyl)pyrrole (Compound No. 1-17)

Following a procedure similar to that described in Example 35, but using N-chlorosuccinimide instead of N-bromosuccinimide, the title compound was obtained as a white powder (yield 58%), melting at 151–154° C.

Nuclear Magnetic Resonance Spectrum (270 MHz, CDCl$_3$) δ ppm:

7.71 (2H, doublet, J=9 Hz);
7.20–7.05 (6H, multiplet);
6.44 (1H, singlet);
3.02 (3H, singlet).
Mass spectrum (EI) m/z: 363 [M$^+$].

EXAMPLE 38

5-Chloro-1-(4-fluorophenyl)-4-methyl-2-(4-sulfamoylphenyl)pyrrole (Compound No. 1-75)

1-(4-Fluorophenyl)-4-methyl-2-(4-sulfamoylphenyl)pyrrole (prepared as described in Example 20) was chlorinated in the same manner as described in Example 37, to give the title compound as white prismatic crystals (yield 67%), melting at 119–120° C.

Nuclear Magnetic Resonance Spectrum (270 MHz, hexadeuterated dimethyl sulfoxide) δ ppm:
7.63 (2H, doublet, J=8 Hz);
7.33–7.17 (8H, multiplet);
6.55 (1H, singlet);
2.10 (3H, singlet).
Mass spectrum (EI) m/z: 364 [M$^+$].

EXAMPLE 39

5-Chloro-1-(4-fluorophenyl)-2-(4-methylsulfonylphenyl)pyrrole (Compound No. 1-5)

1-(4-Fluorophenyl)-2-(4-methylsulfonylphenyl)pyrrole (prepared as described in Example 33) was chlorinated in the same manner as described in Example 37, to give the title compound as a white powder (yield 86%), melting at 180–182° C.

Nuclear Magnetic Resonance Spectrum (270 MHz, CDCl$_3$) δ ppm:
7.73 (2H, doublet, J=9 Hz);
7.23–7.09 (6H, multiplet);
6.54 (1H, doublet, J=4 Hz);
6.32 (1H, doublet, J=4 Hz);
3.02 (3H, singlet).
Mass spectrum (EI) m/z: 349 [M$^+$].

EXAMPLE 40

1-(4-Fluorophenyl)-5-iodo-2-(4-methylsulfonylphenyl)pyrrole (Compound No. 1-7)

Following a procedure similar to that described in Example 35, but using N-iodosuccinimide instead of N-bromosuccinimide, the title compound was obtained as a yellow powder (yield 51%), melting at 174–176° C.

Nuclear Magnetic Resonance Spectrum (270 MHz, CDCl$_3$) δ ppm:
7.73 (2H, doublet, J=9 Hz);
7.22–7.12 (6H, multiplet);
6.63 (1H, doublet, J=4 Hz);
6.59 (1H, doublet, J=4 Hz);
3.02 (3H, singlet).
Mass spectrum (EI) m/z: 441 [M$^+$].

EXAMPLE 41

5-Fluoro-1-(4-fluorophenyl)-2-(4-methylsulfonylphenyl)pyrrole (Compound No. 1-4)

0.90 g (2.7 mmol) of 1-(4-fluorophenyl)-2-(4-methylsulfonylphenyl)pyrrole (prepared as described in Example 33) was dissolved in 10 ml of acetonitrile in a reaction vessel made of polyethylene, and 0.46 g (2.7 mmol) of xenon difluoride was added to the resulting solution at 0° C., whilst stirring. The temperature of the reaction mixture was then allowed to return to room temperature, and the mixture was stirred at room temperature for 20 hours. At the end of this time, 20 ml of a saturated aqueous solution of sodium carbonate was added to the mixture, which was then extracted with ethyl acetate. The organic layer was washed with a saturated aqueous solution of sodium carbonate and then with water, after which it was dried over anhydrous magnesium sulfate. The solvent was then removed by distillation under reduced pressure. The resulting residue was applied to a silica gel chromatography column and eluted with a 3:1 by volume mixture of hexane and ethyl acetate, to give 0.32 g of the title compound as white prismatic crystals (yield 34%), melting at 140–141° C.

Nuclear Magnetic Resonance Spectrum (270 MHz, CDCl$_3$) δ ppm:
7.74 (2H, doublet, J=9 Hz);
7.26–7.15 (6H, multiplet);
6.41 (1H, doublet of doublets, J=6 & 4 Hz);
5.76 (1H, triplet, J=4 Hz);
3.03 (3H, singlet).
Mass spectrum (EI) m/z: 333 [M$^+$].

EXAMPLE 42

5-Fluoro-1-(4-fluorophenyl)-4-methyl-2-(4-methylsulfonylphenyl)pyrrole (Compound No. 1-16)

Following a procedure similar to that described in Example 41, but using 1-(4-fluorophenyl)-4-methyl-2-(4-methylsulfonylphenyl)pyrrole (prepared as described in Example 34), the title compound was obtained as a white powder (yield 10%), melting at 109–110° C.

Nuclear Magnetic Resonance Spectrum (270 MHz, CDCl$_3$) δ ppm:
7.71 (2H, doublet, J=9 Hz);
7.19–7.10 (6H, multiplet);
6.30 (1H, doublet, J=6 Hz);
3.02 (3H, singlet);
2.08 (3H, singlet).
Mass spectrum (EI) m/z: 347 [M$^+$].

EXAMPLE 43

1-(4-Fluorophenyl)-5-methyl-2-(4-methylsulfonylphenyl)pyrrole (Compound No. 1-8)

43(i) Methyl 2-(4-methylthiophenacyl)acetoacetate 2.28 g (19.7 mmol) of methyl acetoacetate were dissolved in 40 ml of 2-methyl-2-propanol, and 2.21 g (19.7 mmol) of potassium t-butoxide were added to the resulting solution under a nitrogen atmosphere. The mixture was then stirred at room temperature for 1 hour, after which a solution of 4.82 g (19.7 mmol) of 4-methylthiophenacyl bromide in 30 ml of benzene was added dropwise to the resulting mixture. The mixture was then stirred at 60° C. for 3 hours, after which it was cooled. It was then poured into ice-water and extracted with ethyl acetate. The organic extract was washed with a saturated aqueous solution of sodium chloride, and then dried over anhydrous magnesium sulfate. The solvent was then removed by distillation under reduced pressure. The resulting residue was applied to a silica gel chromatography column and eluted with a 1:4 by volume mixture of ethyl acetate and hexane, to give 4.42 g (yield 80%) of the title compound as a slightly yellow powder.

Nuclear Magnetic Resonance Spectrum (270 MHz, CDCl$_3$) δ ppm:

7.89 (2H, doublet, J=9 Hz);
7.27 (2H, doublet, J=9 Hz);
4.23 (1H, doublet of doublets, J=8 & 6 Hz);
3.78 (3H, singlet);
3.69 (1H, doublet of doublets, J=18 & 8 Hz);
3.48 (1H, doublet of doublets, J=18 & 6 Hz);
2.53 (3H, singlet);
2.44 (3H, singlet).

43(ii) Methyl 2-(4-methylsulfonylphenacyl)acetoacetate 4.42 g (15.8 mmol) of methyl 2-(4-methylthiophenacyl) acetoacetate [prepared as described in step (i) above] were dissolved in 150 ml of methylene chloride, and 7.77 g (31.5 mmol) of 70% m-chloroperbenzoic acid were added to the resulting solution, whilst ice-cooling. The mixture was then stirred at room temperature for 1 hour. 30 ml of a 10% w/v aqueous solution of sodium thiosulfate were added to the mixture, and the mixture was vigorously shaken, after which it separated into liquid phases. The organic layer was separated and washed with a saturated aqueous solution of sodium hydrogencarbonate and with a saturated aqueous solution of sodium chloride, in that order, after which it was dried over anhydrous magnesium sulfate and the solvent was then removed by distillation under reduced pressure. The residue was applied to a silica gel chromatography column and eluted with a 1:1 by volume mixture of ethyl acetate and hexane, to give 3.65 g (yield 74%) of the title compound as a slightly yellow powder.

Nuclear Magnetic Resonance Spectrum (270 MHz, CDCl$_3$) δ ppm:

8.16 (2H, doublet, J=9 Hz);
8.07 (2H, doublet, J=9 Hz);
4.26 (1H, doublet of doublets, J=8 & 6 Hz);
3.80 (3H, singlet);
3.75 (1H, doublet of doublets, J=19 & 8 Hz);
3.52 (1H, doublet of doublets, J=19 & 6 Hz);
3.09 (3H, singlet);
2.46 (3H, singlet).

43(iii) 1-(4-Fluorophenyl)-4-methoxycarbonyl-5-methyl-2-(4-methylsulfonylphenyl)pyrrole 3.00 g (9.6 mmol) of methyl 2-(4-methylsulfonylphenacyl)acetoacetate [prepared as described in step (ii) above] were dissolved in 100 ml of acetic acid and 0.97 g (8.7 mmol) of 4-fluoroaniline was added to the resulting solution. The resulting mixture was then heated under reflux for 5 hours. At the end of this time, the solvent was removed by distillation under reduced pressure, a saturated aqueous solution of sodium hydrogencarbonate was added to the residue and the mixture was extracted with ethyl acetate. The organic extract was washed with a saturated aqueous solution of sodium chloride and then dried over anhydrous magnesium sulfate. The solvent was then removed by distillation under reduced pressure. The residue was applied to a silica gel chromatography column and eluted with a 1:2 by volume mixture of ethyl acetate and hexane, to give 3.10 g of the title compound as a white powder (yield 92%), melting at 154–155° C.

Nuclear Magnetic Resonance Spectrum (270 MHz, CDCl$_3$) δ ppm:

7.73 (2H, doublet, J=9 Hz);
7.21–7.12 (6H, multiplet);
6.94 (1H, singlet);
3.87 (3H, singlet);
3.02 (3H, singlet);
2.41 (3H, singlet).

Mass spectrum (EI) m/z: 387 [M$^+$].

43(iv) 1-(4-Fluorophenyl)-5-methyl-2-(4-methylsulfonylphenyl)pyrrole 1.00 g (2.6 mmol) of 1-(4-fluorophenyl)-4-methoxycarbonyl-5-methyl-2-(4-methylsulfonylphenyl)pyrrole [prepared as described in step (iii) above] was suspended in 20 ml of ethanol, and 2.5 ml of a 20% w/v aqueous solution of potassium hydroxide were added to the resulting suspension. The mixture was then heated under reflux for 15 hours. At the end of this time, the mixture was cooled, and diethyl ether was added. The mixture was then shaken and the liquid phases were separated. 3N aqueous hydrochloric acid was added to the aqueous layer to make it acidic, and then the layer was extracted with ethyl acetate. The organic extract was washed with a saturated aqueous solution of sodium chloride, after which it was dried over anhydrous magnesium sulfate and the solvent was then removed by distillation under reduced pressure, to give 0.92 g of a carboxylic acid, a hydrolysed product.

0.92 g of this carboxylic acid was suspended in 12 ml of glycerol and the resulting suspension was stirred at 200° C. for 30 minutes. At the end of this time, the reaction mixture was poured into ice-water and the resulting mixture was extracted with ethyl acetate. The organic extract was washed with a saturated aqueous solution of sodium chloride, after which it was dried over anhydrous magnesium sulfate and the solvent was then removed by distillation under reduced pressure. The residue was applied to a silica gel chromatography column and eluted with a 1:4 by volume mixture of ethyl acetate and hexane, to give 0.55 g (yield 65%) of the title compound as a white powder, melting at 110–112° C.

Nuclear Magnetic Resonance Spectrum (270 MHz, CDCl$_3$) δ ppm:

7.68 (2H, doublet, J=9 Hz);
7.20–7.08 (6H, multiplet);
6.51 (1H, doublet, J=4 Hz);
6.13 (1H, doublet, J=4 Hz);
3.01 (3H, singlet);
2.13 (3H, singlet).

Mass spectrum (EI) m/z: 329 [M$^+$].

EXAMPLE 44

5-Trifluoromethyl-1-(4-fluorophenyl)-2-(4-methylsulfonylphenyl)pyrrole (Compound No. 1-14)

44(i) Ethyl 4,4,4-trifluoro-2-(4-methylthiophenacyl) acetoacetate

Following a procedure similar to that described in Example 43(i), but using ethyl 4,4,4-trifluoroacetoacetate instead of methyl acetoacetate, the title compound was obtained as a slightly yellow powder (yield 30%).

Nuclear Magnetic Resonance Spectrum (270 MHz, CDCl$_3$) δ ppm:

7.87 (2H, doublet, J=9 Hz);
7.28 (2H, doublet, J=9 Hz);
4.54 (1H, doublet of doublets, J=10 & 5 Hz);
4.26 (2H, quartet, J=7 Hz);
3.84 (1H, doublet of doublets, J=18 & 10 Hz);
3.68 (1H, doublet of doublets, J=18 & 5 Hz);

2.53 (3H, singlet);

1.29 (3H, triplet, J=7 Hz).

44(ii) 5,5,5-Trifluoro-1-(4-methylthiophenyl)pentane-1,4-dione 1.65 g (4.7 mmol) of ethyl 4,4,4-trifluoro-2-(4-methylthiophenacyl)acetoacetate [prepared as described in step (i) above] were dissolved in 15 ml of dimethylformamide, and 85 μl (4.7 mmol) of water and 0.20 g (4.7 mmol) of lithium chloride were added to the resulting solution. The mixture was then stirred at 140° C. for 1 hour, after which it was poured into ice-water and the resulting mixture was extracted with ethyl acetate. The organic extract was washed with water and dried over anhydrous magnesium sulfate, and the solvent was then removed by distillation under reduced pressure. The resulting residue was applied to a silica gel chromatography column and eluted with a 3:1 by volume mixture of hexane and ethyl acetate, to give 0.26 g (yield 20%) of the title compound as a slightly yellow powder.

Nuclear Magnetic Resonance Spectrum (270 MHz, $CDCl_3$) δ ppm:

7.89 (2H, doublet, J=9 Hz);

7.28 (2H, doublet, J=9 Hz);

3.38 (2H, triplet, J=6 Hz);

3.14 (2H, triplet, J=6 Hz).

44(iii) 5-Trifluoromethyl-1-(4-fluorophenyl)-2-(4-methylthiophenyl)pyrrole

Following a procedure similar to that described in Example 43(iii), but using 5,5,5-trifluoro-1-(4-methylthiophenyl)pentane-1,4-dione [prepared as described in step (ii) above] and 4-fluoroaniline as starting materials, the title compound was obtained as a pale brown oily substance (yield 42%).

Nuclear Magnetic Resonance Spectrum (270 MHz, $CDCl_3$) δ ppm:

7.25 (8H, multiplet);

6.76 (1H, doublet, J=4 Hz);

6.36 (1H, doublet, J=4 Hz);

2.44 (3H, singlet).

44(iv) 5-Trifluoromethyl-1-(4-fluorophenyl)-2-(4-methylsulfonylphenyl)pyrrole

5-Trifluoromethyl-1-(4-fluorophenyl)-2-(4-methylsulfonylphenyl)pyrrole [prepared as described in step (iii) above] was oxidized in the same manner as described in Example 43(ii), to give the title compound as a white powder (yield 69%), melting at 136–139° C.

Nuclear Magnetic Resonance Spectrum (270 MHz, $CDCl_3$) δ ppm:

7.87 (2H, doublet, J=9 Hz);

7.30–7.22 (4H, multiplet);

7.15–7.06 (2H, multiplet);

6.81 (1H, doublet, J=4 Hz);

6.52 (1H, doublet, J=4 Hz);

3.03 (3H, singlet).

Mass spectrum (EI) m/z: 383 [M$^+$].

EXAMPLE 45

1-(4-Fluorophenyl)-4,5-dimethyl-2-(4-methylsulfonylphenyl)pyrrole (Compound No. 1-20)

45(i) Methyl 2-methyl-2-(4-methylsulfonylphenacyl)acetoacetate 0.65 g (2.1 mmol) of methyl 2-(4-methylsulfonylphenacyl)acetoacetate [prepared as described in Example 43(ii)] was dissolved in 20 ml of anhydrous tetrahydrofuran, and 92 mg (2.3 mmol) of sodium hydride (as a 60% w/w dispersion in mineral oil) were added to the resulting solution, whilst ice-cooling and under a nitrogen atmosphere. The mixture was stirred for 10 minutes, after which 1.1 ml (2.5 mmol) of methyl iodide were added, whilst ice-cooling, and the mixture was stirred for 2 hours. At the end of this time, water was added to the mixture, which was then extracted with ethyl acetate. The organic extract was washed with a saturated aqueous solution of sodium chloride, after which it was dried over anhydrous magnesium sulfate and the solvent was removed by distillation under reduced pressure. The residue was applied to a silica gel chromatography column and eluted with a 2:3 by volume mixture of ethyl acetate and hexane, to give 0.54 g (yield 80%) of the title compound as a slightly yellow powder.

Nuclear Magnetic Resonance Spectrum (270 MHz, $CDCl_3$) δ ppm:

8.14 (2H, doublet, J=9 Hz);

8.06 (2H, doublet, J=9 Hz);

3.77 (3H, singlet);

3.69 (1H, doublet, J=18 Hz);

3.58 (1H, doublet, J=18 Hz);

3.08 (3H, singlet);

2.35 (3H, singlet);

1.60 (3H, singlet).

45(ii) 1-(4-Fluorophenyl)-4,5-dimethyl-2-(4-methylsulfonylphenyl)pyrrole

Hydrolysis and decarboxylation of methyl 2-methyl-2-(4-methylsulfonylphenacyl)acetoacetate [prepared as described in step (i) above] were carried out in the same manner as described in Example 44(ii), to give 3-methyl-1-(4-methylsulfonylphenyl)pentane-1,4-dione. This dione compound and 4-fluoroaniline were then reacted in the same manner as described in Example 43(iii), to give the title compound as a yellow powder (yield 11%), melting at 159–162° C.

Nuclear Magnetic Resonance Spectrum (270 MHz, $CDCl_3$) δ ppm:

7.67 (2H, doublet, J=9 Hz);

7.18–7.09 (6H, multiplet);

6.41 (1H, singlet);

3.01 (3H, singlet);

2.12 (3H, singlet);

2.04 (3H, singlet).

Mass spectrum (FAB) 344 [(M+H)$^+$]

EXAMPLE 46

1-(4-Fluorophenyl)-4-hydroxymethyl-2-(4-methylsulfonylphenyl)pyrrole (Compound No. 1-61)

46(i) Methyl 2-(4-methylthiophenacyl)cyanoacetate 5.70 g (57.6 mmol) of methyl cyanoacetate were dissolved in 150 ml of anhydrous tetrahydrofuran, and 7.10 g (63.3 mmol) of potassium t-butoxide were added to the resulting solution, whilst ice-cooling, and the mixture was then stirred for 30 minutes. At the end of this time, a solution of 14.11 g (57.6 mmol) of 4-methylthiophenacyl bromide in 50 ml of tetrahydrofuran was slowly added dropwise to the mixture, whilst ice-cooling. The mixture was stirred, whilst ice-cooling for 2 hours, and then a saturated aqueous solution of ammonium chloride and ethyl acetate were added. The insolubles were then filtered off. Water was added to the filtrate, and the mixture was extracted with ethyl acetate. The organic extract was dried over anhydrous magnesium sulfate and the solvent was then removed by distillation under reduced pressure. The residue was applied to a silica gel chromatography column and eluted with a 1:2 by volume mixture of ethyl acetate and hexane, to give 3.11 g (yield 21%) of the title compound as a slightly yellow powder.

Nuclear Magnetic Resonance Spectrum (270 MHz, CDCl$_3$) δ ppm:

7.87 (2H, doublet, J=9 Hz);
7.27 (2H, doublet, J=9 Hz);
4.16 (1H, doublet, J=7 & 6Hz);
3.83 (3H, singlet);
3.74 (1H, doublet, J=18 & 7 Hz);
3.53 (1H, doublet, J=18 & 6 Hz);
2.54 (3H, singlet).

46(ii) 5-Amino-1-(4-fluorophenyl)-4-methoxycarbonyl-2-(4-methylsulfonylphenyl)pyrrole 3.11 g (11.8 mmol) of methyl 2-(4-methylthiophenacyl) cyanoacetate [prepared as described in step (i) above] were dissolved in 150 ml of methylene chloride, and 5.83 g (23.6 mmol) of 70% m-chloroperbenzoic acid were added to the mixture, whilst ice-cooling. The resulting mixture was then stirred at room temperature for 1 hour. At the end of this time, 50 ml of a 10% w/v aqueous solution of sodium thiosulfate were added to the mixture and the mixture was vigorously shaken, after which it was separated into liquid phases. The organic phase was washed with a saturated aqueous solution of sodium hydrogencarbonate and with a saturated aqueous solution of sodium chloride, in that order, after which it was dried over anhydrous magnesium sulfate and the solvent was removed by distillation under reduced pressure, to give 3.15 g of methyl 2-(4-methylsulfonylphenacyl) cyanoacetate as a pale brown powder.

3.15 g of the powder thus obtained were dissolved in 100 ml of ethanol, and 1.58 g (14.2 mmol) of 4-fluoroaniline and 12 drops of concentrated aqueous hydrochloric acid were added to the resulting solution. The mixture was then heated under reflux for 3 days. At the end of this time, the reaction mixture was concentrated by evaporation under reduced pressure, methylene chloride was added to the residue, and then the insolubles were filtered off. The filtrate was concentrated by evaporation under reduced pressure, and the residue was applied to a silica gel chromatography column and eluted with a 1:1 by volume mixture of ethyl acetate and hexane, to give 2.10 g (yield 46%) of the title compound as a white powder.

Nuclear Magnetic Resonance Spectrum (270 MHz, CDCl$_3$) δ ppm:

7.68 (2H, doublet, J=9 Hz);
7.26–7.11 (6H, multiplet);
6.76 (1H, singlet);
5.15 (2H, broad singlet);
3.85 (3H, singlet);
3.01 (3H, singlet).

46(iii) 1-(4-Fluorophenyl)-4-methoxycarbonyl-2-(4-methylsulfonylphenyl)pyrrole 2.00 g (5.2 mmol) of 5-amino-1-(4-fluorophenyl)-4-methoxycarbonyl-2-(4-methylsulfonylphenyl)pyrrole [prepared as described in step (ii) above] were dissolved in 50 ml of anhydrous tetrahydrofuran, and 6.38 g (61.8 mmol) of t-butyl nitrite were added to the resulting solution at room temperature and under a nitrogen atmosphere. The mixture was then stirred at room temperature for 30 minutes, after which it was heated under reflux for 2 hours. The solvent was then removed by distillation under reduced pressure and the residue was applied to a silica gel chromatography column and eluted with a 2:3 by volume mixture of ethyl acetate and hexane, to give 1.30 g (yield 68%) of the title compound as a yellow powder, melting at 144–146° C.

Nuclear Magnetic Resonance Spectrum (270 MHz, CDCl$_3$) δ ppm:

7.95 (2H, doublet, J=9 Hz);
7.56 (1H, doublet, J=2 Hz);
7.27 (1H, doublet, J=9 Hz);
7.21–7.06 (4H, multiplet);
6.96 (1H, doublet, J=2 Hz);
3.87 (3H, singlet);
3.05 (3H, singlet).

Mass spectrum (EI) m/z: 373 [M$^+$].

46(iv) 1-(4-Fluorophenyl)-4-hydroxymethyl-2-(4-methylsulfonylphenyl)pyrrole 0.15 g (4.0 mmol) of lithium aluminum hydride was suspended in 25 ml of diethyl ether, and a solution of 0.98 g (2.6 mmol) of 1-(4-fluorophenyl)-4-methoxycarbonyl-2-(4-methylsulfonylphenyl)pyrrole [prepared as described in step (iii) above] in 20 ml of methylene chloride was added dropwise to the suspension whilst it was heated under reflux in a nitrogen atmosphere. The mixture was stirred under reflux for 1 hour, and then 0.15 ml of water, 0.15 ml of a 15% w/v aqueous solution of sodium hydroxide and 0.45 ml of water were added to the mixture, in that order. The mixture was then stirred at room temperature for 30 minutes. At the end of this time, the mixture was dehydrated by adding anhydrous magnesium sulfate, and it was filtered over a Celite (trade mark) filter aid. The solvent was then removed from the filtrate by distillation under reduced pressure. The residue was applied to a silica gel chromatography column and eluted with a 2:1 by volume mixture of ethyl acetate and hexane, to give 0.69 g (yield 76%) of the title compound as a white powder, melting at 88–90° C.

Nuclear Magnetic Resonance Spectrum (270 MHz, CDCl$_3$) δ ppm:

7.77 (2H, doublet, J=9 Hz);
7.26 (2H, doublet, J=9 Hz);
7.28–7.05 (4H, multiplet);
6.97 (1H, doublet, J=2 Hz);
6.60 (1H, doublet, J=2 Hz);
4.65 (2H, doublet, J=5 Hz);
3.04 (2H, singlet).

EXAMPLE 47

1-(4-Fluorophenyl)-4-hydroxymethyl-5-methyl-2-(4-methylsulfonylphenyl)pyrrole (Compound No. 1-62)

1-(4-Fluorophenyl)-4-methoxycarbonyl-5-methyl-2-(4-methylsulfonylphenyl)pyrrole [prepared as described in Example 43(iii)] was reduced in the same manner as described in Example 46(iv), to give the title compound as a yellow powder (yield 84%), melting at 140–142° C.

Nuclear Magnetic Resonance Spectrum (270 MHz, CDCl$_3$) δ ppm:

7.69 (2H, doublet, J=9 Hz);
7.20–7.12 (6H, multiplet);
6.58 (1H, singlet);
4.63 (2H, doublet, J=5 Hz);

3.01 (3H, singlet);
2.13 (3H, singlet).
Mass spectrum (FAB) m/z: 360 [(M+H)$^+$].

EXAMPLE 48

5-Difluoromethyl-1-(4-fluorophenyl)-2-(4-methylsulfonylphenyl)pyrrole (Compound No. 1-13)

48(i) 1-(4-Fluorophenyl)-5-formyl-2-(4-methylsulfonylphenyl)pyrrole 1.67 g (5.3 mmol) of 1-(4-fluorophenyl)-2-(4-methylsulfonylphenyl)pyrrole (prepared as described in Example 33) were dissolved in 30 ml of dimethylformamide, 0.50 ml (5.3 mmol) of phosphorous oxychloride was added to the resulting solution, and the mixture was then stirred at 60° C. for 2 hours. At the end of this time, the reaction mixture was gradually added to ice-water and the pH of the mixture was adjusted to a value of 8–9 by the addition of sodium carbonate. The mixture was then extracted with ethyl acetate. The organic extract was washed with water and dried over anhydrous sodium sulfate, after which the solvent was removed by distillation under reduced pressure. The residue was applied to a silica gel chromatography column and eluted with a 5:1 by volume mixture of hexane and ethyl acetate, to give 0.90 g (yield 50%) of the title compound as a white powder, melting at 135–137° C.

Nuclear Magnetic Resonance Spectrum (270 MHz, CDCl$_3$) δ ppm:
9.55 (1H, singlet);
7.80 (2H, doublet, J=9 Hz);
7.32–7.19 (5H, multiplet);
7.16–7.08 (2H, multiplet);
6.64 (1H, doublet, J=4 Hz);
3.04 (3H, singlet).

48(ii) 5-Difluoromethyl-1-(4-fluorophenyl)-2-(4-methylsulfonylphenyl)pyrrole 0.50 g (1.5 mmol) of 1-(4-fluorophenyl)-5-formyl-2-(4-methylsulfonylphenyl)pyrrole [prepared as described in step (i) above] was dissolved in 3 ml of anhydrous diglyme, and 0.17 ml (2.9 mmol) of diethylaminosulfur trifluoride was added to the resulting solution. The mixture was then stirred at 100° C. for 6 hours. At the end of this time, water was added to the reaction solution, and the mixture was extracted with ethyl acetate. The organic extract was washed with water and dried over anhydrous sodium sulfate, and the solvent was then removed by distillation under reduced pressure. The resulting residue was applied to a silica gel chromatography column and eluted with a 7:3 by volume mixture of hexane and ethyl acetate, to give 0.12 g (yield 23%) of the title compound as a slightly yellow powder, melting at 111–112° C.

Nuclear Magnetic Resonance Spectrum (270 MHz, CDCl$_3$) δ ppm:
7.76 (2H, doublet, J=9 Hz);
7.27–7.21 (5H, multiplet);
7.15–7.08 (2H, multiplet);
6.71–6.69 (1H, multiplet);
6.56–6.54 (1H, multiplet);
6.42 (1H, triplet, J=54 Hz);
3.03 (3H, singlet).
Mass spectrum (EI) m/z: 365 [M$^+$].

EXAMPLE 49

1-(4-Fluorophenyl)-4-difluoromethyl-2-(4-methylsulfonylphenyl)pyrrole (Compound No. 1-29)

49(i) 1-(4-Fluorophenyl)-4-formyl-2-(4-methylsulfonylphenyl)pyrrole 0.58 g (1.7 mmol) of 1-(4-fluorophenyl)-4-hydroxymethyl-2-(4-methylsulfonylphenyl)pyrrole (prepared as described in Example 46) was dissolved in 30 ml of methylene chloride, and 2.40 g of manganese dioxide were added to the resulting solution. The mixture was then stirred at room temperature for 3 hours. At the end of this time, the reaction mixture was filtered using a Celite (trade mark) filter aid and the filtrate was concentrated by evaporation under reduced pressure. The resulting residue was applied to a silica gel chromatography column and eluted with a 2:3 by volume mixture of ethyl acetate and hexane, to give 0.52 g (yield 90%) of the title compound as a white powder, melting at 169–171° C.

Nuclear Magnetic Resonance Spectrum (270 MHz, CDCl$_3$) δ ppm:
9.89 (1H, singlet);
7.82 (2H, doublet, J=9 Hz);
7.56 (1H, doublet, J=2 Hz);
7.29 (2H, doublet, J=9 Hz);
7.22–7.08 (4H, multiplet);
6.99 (1H, doublet, J=2 Hz);
3.06 (3H, singlet).

49(ii) 1-(4-Fluorophenyl)-4-difluoromethyl-2-(4-methylsulfonylphenyl)pyrrole

Following a procedure similar to that described in Example 48(ii), but using 1-(4-fluorophenyl)-4-formyl-2-(4-methylsulfonylphenyl)pyrrole [prepared as described in step (i) above] and diethylaminosulfur trifluoride as starting materials, the title compound was obtained as a white powder (yield 16%), melting at 98–100° C.

Nuclear Magnetic Resonance Spectrum (270 MHz, CDCl$_3$) δ ppm:
7.80 (2H, doublet, J=9 Hz);
7.28 (2H, doublet, J=9 Hz);
7.18–7.04 (5H, multiplet);
6.74 (1H, triplet, J=57 Hz);
6.69 (1H, singlet);
3.05 (3H, singlet).

EXAMPLE 50

1-(4-Fluorophenyl)-4-difluoromethyl-5-methyl-2-(4-methylsulfonylphenyl)pyrrole (Compound No. 1-30)

50(i) 1-(4-Fluorophenyl)-4-formyl-5-methyl-2-(4-methylsulfonylphenyl)pyrrole

Following a procedure similar to that described in Example 49(i), but using 1-(4-fluorophenyl)-4-hydroxymethyl-5-methyl-2-(4-methylsulfonylphenyl)pyrrole (prepared as described in Example 47) and manganese dioxide as starting materials, the title compound was obtained as a white powder (yield 98%), melting at 167–169° C.

Nuclear Magnetic Resonance Spectrum (270 MHz, CDCl$_3$) δ ppm:
9.99 (1H, singlet);
7.75 (2H, doublet, J=9 Hz);
7.24–7.16 (6H, multiplet);
6.94 (1H, singlet);
3.03 (3H, singlet);
2.42 (3H, singlet).
Mass spectrum (FAB) m/z: 358 [(M+H)$^+$].

50(ii) 1-(4-Fluorophenyl)-4-difluoromethyl-5-methyl-2-(4-methylsulfonylphenyl)pyrrole Following a procedure similar to that described in Example 48(ii), but using 1-(4-fluorophenyl)-4-formyl-5-methyl-2-(4-methylsulfonylphenyl)pyrrole [prepared as described in step (i) above] and diethylaminosulfur trifluoride as starting materials, the title compound was obtained as a white powder (yield 70%), melting at 136–138° C.

Nuclear Magnetic Resonance Spectrum (270 MHz, CDCl$_3$) δ ppm:

7.72 (2H, doublet, J=9 Hz);

7.22–7.08 (6H, multiplet);

6.73 (1H, triplet, J=56 Hz);

6.66 (1H, singlet);

3.02 (3H, singlet);

2.18 (3H, singlet).

Mass spectrum (EI) m/z: 379 [M$^+$].

EXAMPLE 51

2-(4-Fluorophenyl)-4-phenyl-1-(4-sulfamoylphenyl)pyrrole (Compound No. 2-69)

51(i) 3-(4-Fluorobenzoyl)-2-phenylpropionaldehyde

A 45% w/v solution of phenylacetoaldehyde in diethyl phthalate containing 25.00 g (94 mmol) of phenylacetoaldehyde was dissolved in 50 ml of toluene, and 7.96 g (94 mmol) of piperidine was added to the resulting solution. The mixture was then heated under reflux, while the water produced was removed, until the production of water stopped (about 1 hour). At the end of this time, the solvent was removed by distillation under reduced pressure, to give 31.78 g of a mixture of β-piperidinostyrene and diethyl phthalate as a red oily substance.

4.68 g of the β-piperidinostyrene/diethyl phthalate mixture were dissolved in 70 ml of anhydrous tetrahydrofuran, and 1.01 g (10 mmol) of triethylamine were added to the resulting solution. 2.60 g (12 mmol) of 4-fluorophenacyl bromide were then added to the resulting mixture, which was then stirred at room temperature for 3 hours. At the end of this time, 30 ml of 1N aqueous hydrochloric acid were added to the reaction mixture, and the mixture was stirred at room temperature for a further 1 hour. It was then extracted with diethyl ether. The organic extract was washed with water and dried over anhydrous sodium sulfate. The solvent was then removed by distillation under reduced pressure and the residue was applied to a silica gel chromatography column and eluted with a 95:5 by volume mixture of hexane and ethyl acetate, to give 0.50 g of the title compound as a slightly yellow oily substance.

Nuclear Magnetic Resonance Spectrum (270 MHz, CDCl$_3$) δ ppm:

9.80 (1H, singlet);

8.03–7.98 (2H, multiplet);

7.42–7.25 (5H, multiplet);

7.16–7.10 (2H, multiplet).

Mass spectrum (FAB) m/z: 257 [(M+H)$^+$].

51(ii) 2-(4-Fluorophenyl)-4-phenyl-1-(4-sulfamoylphenyl)pyrrole 0.32 g (1.25 mmol) of 3-(4-fluorobenzoyl)-2-phenylpropionaldehyde [prepared as described in step (i) above] and 0.26 g (1.5 mmol) of 4-sulfamoylaniline were dissolved in 20 ml of acetic acid, and the mixture was heated under reflux for 4 hours. The solvent was then removed by distillation under reduced pressure and water was added to the residue, which was then extracted with ethyl acetate. The organic extract was washed with water and dried over anhydrous sodium sulfate. The solvent was then removed by distillation under reduced pressure, and the residue was applied to a silica gel chromatography column and eluted with a 3:2 by volume mixture of hexane and ethyl acetate, to give 0.35 g (yield 60%) of the title compound as a slightly yellow powder, melting at 192–194° C.

Nuclear Magnetic Resonance Spectrum (270 MHz, CDCl$_3$) δ ppm:

7.91 (2H, doublet, J=9 Hz);

7.58 (2H, doublet, J=7 Hz);

7.39–7.22 (6H, multiplet);

7.18–7.12 (2H, multiplet);

6.99 (2H, triplet, J=9 Hz);

6.73 (1H, doublet, J=2 Hz);

4.84 (2H, singlet).

Mass spectrum (EI) m/z: 392 [M$^+$].

EXAMPLE 52

2-(4-Methoxyphenyl)-4-methyl-1-(4-sulfamoylphenyl)pyrrole (Compound No. 2-74)

52(i) N-(4-Methoxybenzylidene)-4-sulfamoylaniline

Following a procedure similar to that described in Example 1(i), but using 4-methoxybenzaldehyde and 4-sulfamoylaniline as starting materials, the title compound was obtained as a pale yellow powder (yield 95%).

Nuclear Magnetic Resonance Spectrum (270 MHz, CDCl$_3$) δ ppm:

8.35 (1H, singlet);

7.94 (2H, doublet, J=9 Hz);

7.86 (2H, doublet, J=9 Hz);

7.23 (2H, doublet, J=9 Hz);

7.00 (2H, doublet, J=9 Hz);

5.98 (2H, singlet);

3.90 (3H, singlet).

52(ii) α-(4-Methoxyphenyl)-α-(4-sulfamoylanilino)acetonitrile

Following a procedure similar to that described in Example 1(ii), but using N-(4-methoxybenzylidene)-4-sulfamoylaniline [prepared as described in step (i) above] and trimethylsilyl cyanide as starting materials, the title compound was obtained as a pale yellow powder (yield 98%).

Nuclear Magnetic Resonance Spectrum (270 MHz, hexa-deuterated dimethyl sulfoxide) δ ppm:

7.74 (2H, doublet, J=9 Hz);

7.51 (2H, doublet, J=9 Hz);

6.97 (2H, doublet, J=9 Hz);

6.82 (2H, doublet, J=9 Hz);

6.60 (1H, doublet, J=8 Hz);

6.41 (2H, singlet);

5.54 (1H, doublet, J=8 Hz);

3.84 (3H, singlet).

52(iii) 2-(4-Methoxyphenyl)-4-methyl-1-(4-sulfamoylphenyl)pyrrole

Following a procedure similar to that described in Example 1(iii), but using α-(4-methoxyphenyl)-α-(4-sulfamoylanilino)acetonitrile [prepared as described in step (ii) above] and methacrolein as starting materials, the title compound was obtained as a pale brown powder (yield 6%), melting at 163–166° C.

Nuclear Magnetic Resonance Spectrum (270 MHz, CDCl$_3$) δ ppm:

7.84 (2H, doublet, J=9 Hz);

7.23 (2H, doublet, J=9 Hz);

7.03 (2H, doublet, J=9 Hz);
6.79 (2H, doublet, J=9 Hz);
6.73 (1H, singlet);
6.23 (1H, singlet);
4.78 (2H, singlet);
3.79 (3H, singlet);
2.18 (3H, singlet).
Mass spectrum (EI) m/z: 342 [M⁺].

EXAMPLE 53

1-(3,4-Dimethoxyphenyl)-2-(4-methylsulfonylphenyl)pyrrole (Compound No. 1-59)

Following a procedure similar to that described in the three stages of Examples 1(i), 1(ii) and 1(iii), but using 3,4-dimethoxyaniline as a starting material instead of 4-methoxyaniline, the title compound was obtained as a white powder, melting at 124–126° C. The yield of the compound (yellow powder) in the first stage was 96%, that in the second stage (brown prismatic crystals) was 48%, and that in the third stage was 15%.

Nuclear Magnetic Resonance Spectrum (270 MHz, CDCl$_3$) δ ppm:
7.75 (2H, doublet, J=7 Hz);
7.30 (2H, doublet, J=7 Hz);
6.98 (1H, multiplet);
6.84 (1H, doublet, J=8 Hz);
6.74–6.70 (2H, multiplet);
6.57 (1H, multiplet);
6.39–6.37 (1H, multiplet);
3.92 (3H, singlet);
3.74 (3H, singlet);
3.03 (3H, singlet).
Mass spectrum (EI) m/z: 357 [M⁺].

EXAMPLE 54

1-(3-Fluoro-4-methoxyphenyl)-2-(4-methylsulfonylphenyl)pyrrole (Compound No. 1-47)

Following a procedure similar to that described in the three stages of Examples 1(i), 1(ii) and 1(iii), but using 3-fluoro-4-methoxyaniline as a starting material instead of 4-methoxyaniline, the title compound was obtained as a pale yellow powder, melting at 116–118° C. The yield of the compound (pale yellow powder) in the first stage was 94%, that in the second stage (white powder) was 87%, and that in the third stage was 16%.

Nuclear Magnetic Resonance Spectrum (270 MHz, CDCl$_3$) δ ppm:
7.77 (2H, doublet, J=9 Hz);
7.29 (2H, doublet, J=9 Hz);
7.00–6.84 (4H, multiplet);
6.56–6.55 (1H, multiplet);
6.39–6.37 (1H, multiplet);
3.92 (3H, singlet);
3.05 (3H, singlet).
Mass spectrum (EI) m/z: 345 [M⁺].

EXAMPLE 55

1-Phenyl-2-(4-methylsulfonylphenyl)pyrrole (Compound No. 1-1)

Following a procedure similar to that described in the three stages of Examples 1(i), 1(ii) and 1(iii), but using aniline as a starting material instead of 4-methoxyaniline, the title compound was obtained as white prismatic crystals, melting at 140–142° C. The yield of the compound (pale yellow powder) in the first stage was 76%, that in the second stage (pale yellow powder) was 95%, and that in the third stage was 16%.

Nuclear Magnetic Resonance Spectrum (270 MHz, CDCl$_3$) δ ppm:
7.74 (2H, doublet, J=8 Hz);
7.40–7.33 (3H, multiplet);
7.27 (2H, doublet, J=8 Hz);
7.18–7.15 (2H, multiplet);
7.00 (1H, multiplet);
6.59–6.58 (1H, multiplet);
6.41–6.39 (1H, multiplet);
3.03 (3H, singlet).

EXAMPLE 56

4-Methyl-1-(3,4-dimethylphenyl)-2-(4-methylsulfonylphenyl)pyrrole (Compound No. 1-56)

Following a procedure similar to that described in Example 8, but using methacrolein instead of acrolein in the third stage, the title compound was obtained as a pale yellow powder (yield 58%), melting at 126–128° C.

Nuclear Magnetic Resonance Spectrum (270 MHz, CDCl$_3$) δ ppm:
7.72 (2H, doublet, J=9 Hz);
7.27–7.24 (2H, multiplet);
7.08–7.05 (1H, multiplet);
6.96 (1H, singlet);
6.83–6.79 (1H, multiplet);
6.74 (1H, singlet);
6.41 (1H, singlet);
3.03 (3H, singlet);
2.27 (3H, singlet);
2.23 (3H, singlet);
2.18 (3H, singlet).
Mass spectrum (EI) m/z: 339 [M⁺].

EXAMPLE 57

1-(4-Methylphenyl)-2-(4-sulfamoylphenyl)pyrrole (Compound No. 1-99)

57(i) N-(4-Sulfamoylbenzylidene)-4-methylaniline

Following a procedure similar to that described in Example 1(i), but using 4-sulfamoylbenzaldehyde and 4-methylaniline as starting materials, the title compound was obtained as a yellow powder (yield 82%).

Nuclear Magnetic Resonance Spectrum (270 MHz, hexadeuterated dimethyl sulfoxide) δ ppm:
8.56 (1H, singlet);
8.01 (4H, singlet);
7.27–7.12 (6H, multiplet);
2.38 (3H, singlet).

57(ii) α-(4-Methylanilino)-α-(4-sulfamoylphenyl)acetonitrile

Following a procedure similar to that described in Example 1(ii), but using N-(4-sulfamoylbenzylidene)-4-methylaniline [prepared as described in step (i) above] and trimethylsilyl cyanide as starting materials, the title compound was obtained as a pale yellow powder (yield 60%).

Nuclear Magnetic Resonance Spectrum (270 MHz, hexadeuterated dimethyl sulfoxide) δ ppm:

7.99 (2H, doublet, J=8 Hz);
7.75 (2H, doublet, J=8 Hz);
7.03 (2H, doublet, J=8 Hz);
6.89 (2H, singlet);
6.69 (2H, doublet, J=8 Hz);
5.70–5.55 (2H, multiplet);
2.25 (3H, singlet).

57(iii) 1-(4-Methylphenyl)-2-(4-sulfamoylphenyl)pyrrole

Following a procedure similar to that described in Example 1(iii), but using α-(4-methylanilino)-α-(4-sulfamoylphenyl)acetonitrile [prepared as described in step (ii) above] and acrolein as starting materials, the title compound was obtained as a pale brown powder (yield 28%), melting at 131–134° C.

Nuclear Magnetic Resonance Spectrum (270 MHz, CDCl$_3$) δ ppm:

7.73 (2H, doublet, J=8 Hz);
7.24 (2H, doublet, J=8 Hz);
7.16 (2H, doublet, J=8 Hz);
7.04 (2H, doublet, J=8 Hz);
6.96 (1H, triplet, J=2 Hz);
6.55 (1H, doublet of doublets, J=3 & 2 Hz);
6.38 (1H, triplet, J=3 Hz);
4.74 (2H, singlet);
2.38 (3H, singlet).

Mass spectrum (EI) m/z: 312 [M$^+$].

EXAMPLE 58

4-Methyl-1-(4-methylphenyl)-2-(4-sulfamoylphenyl)pyrrole (Compound No.1-100)

Following a procedure similar to that described in Example 57(iii), but using methacrolein instead of acrolein, the title compound was obtained as a yellow powder (yield 42%), melting at 144–147° C.

Nuclear Magnetic Resonance Spectrum (270 MHz, CDCl$_3$) δ ppm:

7.71 (2H, doublet, J=8 Hz);
7.21 (2H, doublet, J=8 Hz);
7.14 (2H, doublet, J=8 Hz);
7.01 (2H, doublet, J=8 Hz);
6.74 (1H, singlet);
6.39 (1H, singlet);
4.71 (2H, singlet);
2.37 (3H, singlet);
2.18 (3H, singlet).

Mass spectrum (EI) m/z: 326 [M$^+$].

EXAMPLE 59

1-(4-Chlorophenyl)-2-(4-sulfamoylphenyl)pyrrole (Compound No. 1-96)

59(i) 4-Chloro-N-(4-sulfamoylbenzylidene)aniline

Following a procedure similar to that described in Example 1(i), but using 4-sulfamoylbenzaldehyde and 4-chloroaniline as starting materials, the title compound was obtained as a pale yellow powder (yield 72%).

Nuclear Magnetic Resonance Spectrum (270 MHz, CDCl$_3$) δ ppm:

8.52 (1H, singlet);
8.02 (4H, singlet);
7.38 (2H, doublet, J=9 Hz);
7.20 (2H, doublet, J=9 Hz);
6.87 (2H, singlet).

59(ii) α-(4-Chloroanilino)-α-(4-sulfamoylphenyl)acetonitrile

Following a procedure similar to that described in Example 1(ii), but using 4-chloro-N-(4-sulfamoylbenzylidene)aniline [prepared as described in step (i) above] and trimethylsilyl cyanide as starting materials, the title compound was obtained as a white powder (yield 93%).

Nuclear Magnetic Resonance Spectrum (270 MHz, hexadeuterated dimethyl sulfoxide) δ ppm:

7.99 (2H, doublet, J=8 Hz);
7.74 (2H, doublet, J=8 Hz);
7.14 (2H, doublet, J=9 Hz);
7.12 (2H, singlet);
6.74 (2H, doublet, J=9 Hz);
6.52 (1H, doublet, J=9 Hz);
5.69 (1H, doublet, J=9 Hz).

59(iii) 1-(4-Chlorophenyl)-2-(4-sulfamoylphenyl)pyrrole

Following a procedure similar to that described in Example 1(iii), but using α-(4-chloroanilino)-α-(4-sulfamoylphenyl)acetonitrile [prepared as described in step (ii) above] and acrolein as starting materials, the title compound was obtained as a pale yellow powder (yield 38%), melting at 179–181° C.

Nuclear Magnetic Resonance Spectrum (270 MHz, CDCl$_3$) δ ppm:

7.77 (2H, doublet, J=9 Hz);
7.34 (2H, doublet, J=9 Hz);
7.23 (2H, doublet, J=9 Hz);
7.10 (2H, doublet, J=9 Hz);
6.96 (1H, triplet, J=2 Hz);
6.56 (1H, doublet of doublets, J=3 & 2 Hz);
6.40 (1H, triplet, J=3 Hz);
4.78 (2H, singlet).

Mass spectrum (EI) m/z: 332 [M$^+$].

EXAMPLE 60

1-(4-Chlorophenyl)-4-methyl-2-(4-sulfamoylphenyl)pyrrole (Compound No. 1-97)

Following a procedure similar to that described in Example 59(iii), but using methacrolein instead of acrolein, the title compound was obtained as a pale yellow powder (yield 53%), melting at 171–173° C.

Nuclear Magnetic Resonance Spectrum (270 MHz, CDCl$_3$) δ ppm:

7.75 (2H, doublet, J=8 Hz);
7.31 (2H, doublet, J=8 Hz);
7.21 (2H, doublet, J=8 Hz);
7.06 (2H, doublet, J=8 Hz);
6.74 (1H, singlet);
6.41 (1H, singlet);
4.80 (2H, singlet);
2.18 (3H, singlet).

Mass spectrum (EI) m/z: 346 [M$^+$].

EXAMPLE 61

1-(4-Methoxyphenyl)-2-(4-sulfamoylphenyl)pyrrole (Compound No. 1-85)

61(i) 4-Methoxy-N-(4-sulfamoylbenzylidene)aniline

Following a procedure similar to that described in Example 1(i), but using 4-sulfamoylbenzaldehyde and 4-methoxyaniline as starting materials, the title compound was obtained as a pale yellow powder (yield 85%).

Nuclear Magnetic Resonance Spectrum (270 MHz, hexadeuterated dimethyl sulfoxide) δ ppm:

8.74 (1H, singlet);
8.09 (2H, doublet, J=8 Hz);
7.95 (2H, doublet, J=8 Hz);
7.48 (2H, singlet);
7.37 (2H, doublet, J=9 Hz);
7.01 (2H, doublet, J=9 Hz);
3.80 (3H, singlet).

61 (ii) α-(4-Methoxyanilino)-α-(4-sulfamoylphenyl)acetonitrile

Following a procedure similar to that described in Example 1(ii), but using 4-methoxy-N-(4-sulfamoylbenzylidene)aniline [prepared as described in step (i) above] and trimethylsilyl cyanide as starting materials, the title compound was obtained as a white powder (yield 68%).

Nuclear Magnetic Resonance Spectrum (270 MHz, CDCl$_3$) δ ppm:

7.91 (2H, doublet, J=8 Hz);
7.76 (2H, doublet, J=8 Hz);
7.43 (2H, singlet);
6.80 (4H, multiplet);
6.40 (1H, doublet, J=10 Hz);
6.03 (1H, doublet, J=10 Hz);
3.67 (3H, singlet).

61(iii) 1-(4-Methoxyphenyl)-2-(4-sulfamoylphenyl)pyrrole

Following a procedure similar to that described in Example 1(iii), but using α-(4-methoxyanilino)-α-(4-sulfamoylphenyl)acetonitrile [prepared as described in step (ii) above] and acrolein as starting materials, the title compound was obtained as a yellow powder (yield 9%), melting at 112–114° C.

Nuclear Magnetic Resonance Spectrum (270 MHz, CDCl$_3$) δ ppm:

7.78–7.68 (2H, multiplet);
7.26–6.85 (7H, multiplet);
6.53–6.51 (1H, multiplet);
6.37–6.35 (1H, multiplet);
5.07 (2H, singlet);
3.81 (3H, singlet).
Mass spectrum (EI) m/z: 328 [M$^+$].

EXAMPLE 62

1-(4-Methoxyphenyl)-4-methyl-2-(4-sulfamoylphenyl)pyrrole (Compound No. 1-86)

Following a procedure similar to that described in Example 61(iii), but using methacrolein instead of acrolein, the title compound was obtained as a pale yellow powder (yield 35%), melting at 63–64° C.

Nuclear Magnetic Resonance Spectrum (270 MHz, CDCl$_3$) δ ppm:

7.69 (2H, doublet, J=8 Hz);
7.18 (2H, doublet, J=8 Hz);
7.05 (2H, doublet, J=9 Hz);
6.85 (2H, doublet, J=9 Hz);
6.72 (1H, singlet);
6.38 (1H, singlet);
5.04 (2H, singlet);
3.80 (3H, singlet);
2.18 (3H, singlet).
Mass spectrum (EI) m/z: 342 [M$^+$].

EXAMPLE 63

4-Butyl-1-(4-methoxyphenyl)-2-(4-sulfamoylphenyl)pyrrole (Compound No. 1-87)

Following a procedure similar to that described in Example 61(iii), but using 2-butylacrolein instead of acrolein, the title compound was obtained as a pale yellow powder (yield 85%), melting at 115–117° C.

Nuclear Magnetic Resonance Spectrum (270 MHz, CDCl$_3$) δ ppm:

7.70 (2H, doublet, J=8 Hz);
7.26–7.19 (2H, multiplet);
7.08–7.05 (2H, multiplet);
6.88–6.87 (2H, multiplet);
6.72 (1H, singlet);
6.41–6.40 (1H, multiplet);
4.89 (2H, singlet);
3.82 (3H, singlet);
2.53 (2H, triplet, J=8 Hz);
1.68–1.57 (2H, multiplet);
1.49–1.36 (2H, multiplet);
0.95 (3H, triplet, J=7 Hz).
Mass spectrum (EI) m/z: 384 [M$^+$].

EXAMPLE 64

4-Ethyl-2-(4-methoxyphenyl)-1-(4-sulfamoylphenyl)pyrrole (Compound No. 2-75)

64(i) 1-(N,N-Diisopropylamino)-1-butene 6.25 ml (69.3 mmol) of butyraldehyde and 19.44 ml (139 mmol) of diisopropylamine were dissolved in 30 ml of benzene, and the mixture was heated under reflux, while removing the water produced, until the production of water stopped (about 15 hours). The solvent was then removed by distillation under reduced pressure, and the residue was distilled under atmospheric pressure. Those fractions of the distillate having a boiling point of from 140 to 160° C. were collected, to give 6.95 g of the title compound as a pale yellow oily substance (yield 65%).

Nuclear Magnetic Resonance Spectrum (270 MHz, CDCl$_3$) δ ppm:

5.94 (1H, doublet, J=14 Hz);
4.05 (1H, doublet of triplets, J=14 & 7 Hz);
3.50–3.34 (2H, multiplet);
2.01–1.88 (2H, multiplet);
1.03 (6H, doublet, J=7 Hz);
0.91 (3H, triplet, J=7 Hz).

64(ii) 2-(4-Methoxyphenacyl)butyraldehyde 1.00 g (6.4 mmol) of 1-(N,N-diisopropylamino)-1-butene [prepared as described in step (i) above] was dissolved in 10 ml of benzene, and 0.98 g (4.3 mmol) of 4-methoxyphenacyl bromide was added dropwise to the resulting solution with stirring, whilst ice-cooling. The reaction mixture was stirred, whilst ice-cooling, for 15 minutes, and then at room temperature for 48 hours. At the end of this time, 9 ml of 1N aqueous hydrochloric acid was added to the mixture, and the mixture was stirred for 15 minutes. It was then neutralised, by the addition of concentrated aqueous ammonia, and extracted with ethyl acetate. The organic extract was washed with water and dried over anhydrous magnesium sulfate, after which the solvent was removed by distillation under reduced pressure. The residue was applied to a silica gel chromatography column and eluted with a 4:1 by volume mixture of hexane and ethyl acetate, to give 0.47 g (yield 49%) of the title compound as a pale yellow oily substance.

Nuclear Magnetic Resonance Spectrum (270 MHz, CDCl$_3$) δ ppm:

9.83 (1H, singlet);
7.96 (2H, doublet, J=9 Hz);
6.94 (2H, doublet, J=9 Hz);
3.88 (3H, singlet);
3.49–3.33 (1H, multiplet);
3.09–2.93 (1H, multiplet);
1.92–1.74 (1H, multiplet);
1.70–1.54 (1H, multiplet);
1.01 (3H, triplet, J=7 Hz).

64(iii) 4-Ethyl-2-(4-methoxyphenyl)-1-(4-sulfamoylphenyl) pyrrole 0.47 g (2.1 mmol) of 2-(4-methoxyphenacyl) butyraldehyde [prepared as described in step (ii) above] and 0.44 g (2.5 mmol) of 4-sulfamoylaniline were dissolved in 5 ml of acetic acid, and the resulting solution was heated under reflux for 2 hours. At the end of this time, the mixture was cooled to room temperature, concentrated aqueous ammonia was added to adjust its pH to a value of 8.0 and the mixture was extracted with ethyl acetate. The organic extract was washed with water, dried over anhydrous magnesium sulfate and then concentrated by evaporation under reduced pressure. The residue was applied to a silica gel chromatography column, eluted with a 3:2 by volume mixture of hexane and ethyl acetate, to give 0.57 g (yield 76%) of the title compound as a pale yellow powder, melting at 154–156° C.

Nuclear Magnetic Resonance Spectrum (270 MHz, CDCl$_3$) δ ppm:

7.84 (2H, doublet, J=9 Hz);
7.24 (2H, doublet, J=9 Hz);
7.04 (2H, doublet, J=9 Hz);
6.79 (2H, doublet, J=9 Hz);
6.74 (1H, singlet);
6.27 (1H, singlet);
4.78 (2H, singlet);
3.79 (3H, singlet);
2.57 (2H, quartet, J=8 Hz);
1.26 (3H, triplet, J=8 Hz).

EXAMPLE 65

2-(4-Chlorophenyl)-4-methyl-1-(4-sulfamoylphenyl) pyrrole (Compound No. 2-85)

65(i) 1-(N,N-Diisobutylamino)-1-propene

Following a procedure similar to that described in Example 64(i), but using propionaldehyde and diisobutylamine as starting materials, the title compound was obtained as a colorless oily substance (yield 29%), boiling at 63–66° C./10 mmHg Nuclear Magnetic Resonance Spectrum (270 MHz, CDCl$_3$) δ ppm:

5.89 (1H, doublet, J=14 Hz);
3.92–3.79 (1H, multiplet);
2.66 (2H, doublet, J=7 Hz);
1.92–1.74 (2H, multiplet);
1.54 (3H, doublet, J=7 Hz);
0.80 (12H, doublet, J=7 Hz).

65(ii) 2-(4-Chlorophenacyl)propionaldehyde

Following a procedure similar to that described in Example 64(ii), but using 1-(N,N-diisobutylamino)-1-propene [prepared as described in step (i) above] and 4-chlorophenacyl bromide as starting materials, the title compound was obtained as a pale brown oily substance (yield 39%).

Nuclear Magnetic Resonance Spectrum (270 MHz, CDCl$_3$) δ ppm:

9.79 (1H, singlet);
7.92 (2H, doublet, J=9 Hz);
7.45 (2H, doublet, J=9 Hz);
3.47 (1H, doublet of doublets, J=18 & 7 Hz);
3.22–3.04 (1H, multiplet);
2.95 (1H, doublet of doublets, J=18 & 7 Hz);
1.25 (3H, doublet, J=7 Hz).

65(iii) 2-(4-Chlorophenyl)-4-methyl-1-(4-sulfamoylphenyl) pyrrole

Following a procedure similar to that described in Example 64(iii), but using 2-(4-chlorophenacyl) propionaldehyde [prepared as described in step (ii) above] and 4-sulfamoylaniline as starting materials, the title compound was obtained as a pale brown powder (yield 35%), melting at 196–198° C.

Nuclear Magnetic Resonance Spectrum (270 MHz, CDCl$_3$) δ ppm:

7.85 (2H, doublet, J=9 Hz);
7.36 (2H, doublet, J=9 Hz);
7.22 (2H, doublet, J=9 Hz);
7.03 (2H, doublet, J=9 Hz);
6.75 (1H, singlet);
6.30 (1H, singlet);
4.80 (2H, singlet);
2.17 (3H, singlet).

Mass spectrum (EI) m/z: 342 [M$^+$].

EXAMPLE 66

4-Methyl-2-(4-methylthiophenyl)-1-(4-sulfamoylphenyl)pyrrole (Compound No. 2-82)

66(i) N-(4-Methylthiobenzylidene)-4-sulfamoylaniline

Following a procedure similar to that described in Example 1(i), but using 4-methylthiobenzaldehyde and 4-sulfamoylaniline as starting materials, the title compound was obtained as a yellow powder (yield 88%).

Nuclear Magnetic Resonance Spectrum (270 MHz, hexadeuterated dimethyl sulfoxide) δ ppm:

8.46 (1H, singlet);
7.90 (2H, doublet, J=9 Hz);
7.84 (2H, doublet, J=8 Hz);
7.33 (2H, doublet, J=9 Hz);
7.27 (2H, doublet, J=8 Hz);
7.15 (2H, broad singlet);
2.55 (3H, singlet).

66(ii) α-(4-Methylthiophenyl)-α-(4-sulfamoylanilino) acetonitrile

Following a procedure similar to that described in Example 1(ii), but using N-(4-methylthiobenzylidene)-4-sulfamoylaniline [prepared as described in step (i) above]

and trimethylsilyl cyanide as starting materials, the title compound was obtained as a yellow powder (yield 100%).

Nuclear Magnetic Resonance Spectrum (270 MHz, hexadeuterated dimethyl sulfoxide) δ ppm:

7.66 (2H, doublet, J=9 Hz);
7.52 (2H, doublet, J=8 Hz);
7.31 (2H, doublet, J=8 Hz);
7.25–7.13 (1H, multiplet);
6.90 (2H, broad singlet);
6.86 (2H, doublet, J=9 Hz);
5.89–5.83 (1H, multiplet);
2.50 (3H, singlet).

66(iii) 4-Methyl-2-(4-methylthiophenyl)-1-(4-sulfamoylphenyl)pyrrole

Following a procedure similar to that described in Example 1(iii), but using α-(4-methylthiophenyl)-α-(4-sulfamoylanilino)acetonitrile [prepared as described in step (ii) above] and methacrolein as starting materials, the title compound was obtained as pale brown scaly crystals (yield 31%), melting at 172–173° C.

Nuclear Magnetic Resonance Spectrum (270 MHz, CDCl$_3$) δ ppm:

7.85 (2H, doublet, J=9 Hz);
7.24 (2H, doublet, J=9 Hz);
7.12 (2H, doublet, J=9 Hz);
7.02 (2H, doublet, J=8 Hz);
6.74 (1H, doublet, J=2 Hz);
6.29 (1H, doublet, J=2 Hz);
4.82 (2H, broad singlet);
2.47 (3H, singlet).
Mass spectrum (EI) m/z: 358 [M$^+$].

EXAMPLE 67

2-(4-Ethoxyphenyl)-4-methyl-1-(4-sulfamoylphenyl)pyrrole (Compound No. 2-78)

67(i) N-(4-Ethoxybenzylidene)-4-sulfamoylaniline

Following a procedure similar to that described in Example 1(i), but using 4-ethoxybenzaldehyde and 4-sulfamoylaniline as starting materials, the title compound was obtained as a pale yellow powder (yield 76%).

Nuclear Magnetic Resonance Spectrum (270 MHz, hexadeuterated dimethyl sulfoxide) δ ppm:

8.38 (1H, singlet);
7.88 (2H, doublet, J=9 Hz);
7.85 (2H, doublet, J=9 Hz);
7.24 (2H, doublet, J=9 Hz);
6.98 (2H, doublet, J=9 Hz);
4.12 (2H, quartet, J=7 Hz);
1.45 (3H, triplet, J=7 Hz).

67(ii) α-(4-Ethoxyphenyl)-α-(4-sulfamoylanilino)acetonitrile

Following a procedure similar to that described in Example 1(ii), but using N-(4-ethoxybenzylidene)-4-sulfamoylaniline [prepared as described in step (i) above] and trimethylsilyl cyanide as starting materials, the title compound was obtained as a slightly yellow powder (yield 88%).

Nuclear Magnetic Resonance Spectrum (270 MHz, hexadeuterated dimethyl sulfoxide) δ ppm:

7.65 (2H, doublet, J=8 Hz);
7.48 (2H, doublet, J=8 Hz);
7.20–7.03 (1H, multiplet);
6.99–6.80 (6H, multiplet);
5.88–5.76 (1H, multiplet);
4.04 (2H, quartet, J=7 Hz);
1.38 (3H, triplet, J=7 Hz).

67(iii) 2-(4-Ethoxyphenyl)-4-methyl-1-(4-sulfamoylphenyl)pyrrole

Following a procedure similar to that described in Example 1(iii), but using α-(4-ethoxyphenyl)-α-(4-sulfamoylanilino)acetonitrile [prepared as described in step (ii) above] and methacrolein as starting materials, the title compound was obtained as a brown powder (yield 3%), melting at 135–139° C.

Nuclear Magnetic Resonance Spectrum (270 MHz, CDCl$_3$) δ ppm:

7.83 (2H, doublet, J=9 Hz);
7.22 (2H, doublet, J=9 Hz);
7.02 (2H, doublet, J=9 Hz);
6.77 (2H, doublet, J=9 Hz);
6.72 (1H, broad singlet);
6.23 (1H, doublet, J=2 Hz);
4.79 (2H, broad singlet);
4.03 (2H, quartet, J=7 Hz);
2.17 (3H, singlet);
1.41 (3H, triplet, J=7 Hz).
Mass spectrum (EI) m/z: 356 [M$^+$].

EXAMPLE 68

4-Methyl-2-(4-propoxyphenyl)-1-(4-sulfamoylphenyl)pyrrole (Compound No. 2-80)

68(i) N-(4-Propoxybenzylidene)-4-sulfamoylaniline

Following a procedure similar to that described in Example 1(i), but using 4-propoxybenzaldehyde and 4-sulfamoylaniline as starting materials, the title compound was obtained as a pale yellow powder (yield 84%)

Nuclear Magnetic Resonance Spectrum (270 MHz, hexadeuterated dimethyl sulfoxide) δ ppm:

8.38 (1H, singlet);
7.92 (2H, doublet, J=9 Hz);
7.85 (2H, doublet, J=9 Hz);
7.23 (2H, doublet, J=8 Hz);
6.99 (2H, doublet, J=8 Hz);
6.81 (2H, broad singlet);
4.01 (2H, triplet, J=6 Hz);
1.91–1.78 (2H, multiplet);
1.07 (3H, triplet, J=7 Hz).

68(ii) α-(4-Propoxyphenyl)-α-(4-sulfamoylanilino)acetonitrile

Following a procedure similar to that described in Example 1(ii), but using N-(4-propoxybenzylidene)-4-sulfamoylaniline [prepared as described in step (i) above] and trimethylsilyl cyanide as starting materials, the title compound was obtained as a pale yellow powder (yield 80%).

Nuclear Magnetic Resonance Spectrum (270 MHz, hexadeuterated dimethyl sulfoxide) δ ppm:

7.68 (2H, doublet, J=9 Hz);
7.51 (2H, doublet, J=8 Hz);
7.20–7.14 (1H, broad doublet, J=8 Hz);
6.98 (2H, doublet, J=9 Hz);
6.92 (2H, broad singlet);
6.88 (2H, doublet, J=9 Hz);

5.83–5.80 (1H, broad doublet, J=8 Hz);

3.96 (2H, triplet, J=6 Hz);

1.87–1.74 (2H, multiplet);

1.04 (3H, triplet, J=7 Hz).

68(iii) 4-Methyl-2-(4-propoxyphenyl)-1-(4-sulfamoylphenyl)pyrrole

Following a procedure similar to that described in Example 1(iii), but using α-(4-propoxyphenyl)-α-(4-sulfamoylanilino)acetonitrile [prepared as described in step (ii) above] and methacrolein as starting materials, the title compound was obtained as a pale brown powder (yield 5%), melting at 142–145° C.

Nuclear Magnetic Resonance Spectrum (270 MHz, CDCl$_3$) δ ppm:

7.83 (2H, doublet, J=9 Hz);

7.23 (2H, doublet, J=9 Hz);

7.02 (2H, doublet, J=9 Hz);

6.78 (2H, doublet, J=9 Hz);

6.72 (1H, doublet, J=2 Hz);

6.23 (1H, doublet, J=2 Hz);

5.86 (2H, broad singlet);

3.90 (2H, triplet, J=7 Hz);

1.89–1.84 (2H, multiplet);

1.03 (3H, triplet, J=7 Hz).

Mass spectrum (EI) m/z: 370 [M$^+$].

EXAMPLE 69

4-Methyl-2-(4-methoxy-3-methylphenyl)-1-(4-sulfamoylphenyl)pyrrole (Compound No. 2-109)

69(i) N-(4-Methoxy-3-methylbenzylidene)-4-sulfamoylaniline

Following a procedure similar to that described in Example 1(i), but using 4-methoxy-3-methylbenzaldehyde and 4-sulfamoylaniline as starting materials, the title compound was obtained as a yellow powder (yield 92%).

Nuclear Magnetic Resonance Spectrum (270 MHz, CDCl$_3$) δ ppm:

8.85 & 8.31 (total: 1H, each singlet);

7.93 (1H, doublet, J=8 Hz);

7.77–7.65 (2H, multiplet);

7.26–7.23 (2H, multiplet);

6.91–6.86 (1H, multiplet);

6.71–6.88 (1H, multiplet);

4.77 & 4.14 (total:1H, each singlet);

3.92 (3H, singlet);

2.28 & 2.21 (total:3H, each singlet).

69(ii) α-(4-Methoxy-3-methylphenyl)-α-(4-sulfamoylanilino)acetonitrile

Following a procedure similar to that described in Example 1(ii), but using N-(4-methoxy-3-methylbenzylidene)-4-sulfamoylaniline [prepared as described in step (i) above] and trimethylsilyl cyanide as starting materials, the title compound was obtained as a white powder (yield 63%).

Nuclear Magnetic Resonance Spectrum (270 MHz, hexa-deuterated dimethyl sulfoxide) δ ppm:

7.62 (2H, doublet, J=8 Hz);

7.39–7.34 (2H, multiplet);

7.26 (1H, doublet, J=9 Hz);

7.04–7.02 (3H, multiplet);

6.90 (2H, doublet, J=8 Hz);

5.97 (1H, doublet, J=9 Hz);

3.81 (3H, singlet);

3.33 (3H, singlet).

69(iii) 4-Methyl-2-(4-methoxy-3-methylphenyl)-1-(4-sulfamoylphenyl)pyrrole

Following a procedure similar to that described in Example 1(iii), but using α-(4-methoxy-3-methylphenyl)-α-(4-sulfamoylanilino)acetonitrile [prepared as described in step (ii) above] and methacrolein as starting materials, the title compound was obtained as a pale yellow powder (yield 39%), melting at 149–151° C.

Nuclear Magnetic Resonance Spectrum (270 MHz, CDCl$_3$) δ ppm:

7.82 (2H, doublet, J=9 Hz);

7.26–7.20 (2H, multiplet);

6.99 (1H, singlet);

6.81–6.65 (3H, multiplet);

6.22 (1H, singlet);

4.90 (2H, singlet);

3.79 (3H, singlet);

2.17 (3H, singlet);

2.14 (3H, singlet).

Mass spectrum (EI) m/z: 332 [M$^+$].

EXAMPLE 70

2-(3,4-Dichlorophenyl)-4-methyl-1-(4-sulfamoylphenyl)pyrrole (Compound No. 2-124)

70(i) N-(3,4-Dichlorobenzylidene)-4-sulfamoylaniline

Following a procedure similar to that described in Example 1(i), but using 3,4-dichlorobenzaldehyde and 4-sulfamoylaniline as starting materials, the title compound was obtained as a white powder (yield 52%).

Nuclear Magnetic Resonance Spectrum (270 MHz, hexa-deuterated dimethyl sulfoxide) δ ppm:

8.49 (1H, singlet);

8.09 (1H, doublet, J=2 Hz);

7.94 (1H, doublet, J=9 Hz);

7.82 (1H, doublet of doublets, J=2 & 8 Hz);

7.63 (1H, doublet, J=8 Hz);

7.30 (2H, doublet, J=9 Hz);

7.10 (2H, broad singlet).

70(ii) α-(3,4-Dichlorophenyl)-α-(4-sulfamoylanilino)acetonitrile

Following a procedure similar to that described in Example 1(ii), but using N-(3,4-dichlorobenzylidene)-4-sulfamoylaniline [prepared as described in step (i) above] and trimethylsilyl cyanide as starting materials, the title compound was obtained as a white powder (yield 91%).

Nuclear Magnetic Resonance Spectrum (270 MHz, hexa-deuterated dimethyl sulfoxide) δ ppm:

7.76 (1H, doublet, J=2 Hz);

7.70 (2H, doublet, J=9 Hz);

7.60 (1H, doublet, J=8 Hz);

7.53 (1H, doublet of doublets, J=2 & 8 Hz);

7.24 (1H, broad doublet, J=9 Hz);

6.84 (2H, broad singlet);

6.83 (2H, doublet, J=9 Hz);

5.92 (1H, broad doublet, J=9 Hz).

70(iii) 2-(3,4-Dichlorophenyl)-4-methyl-1-(4-sulfamoylphenyl)pyrrole

Following a procedure similar to that described in Example 1(iii), but using α-(3,4-dichlorophenyl)-α-(4- sulfamoylanilino)acetonitrile [prepared as described in step (ii) above] and methacrolein as starting materials, the title compound was obtained as a pale brown powder (yield 33%), melting at 136–138° C.

Nuclear Magnetic Resonance Spectrum (270 MHz, CDCl$_3$) δ ppm:

7.89 (2H, doublet, J=9 Hz);
7.30 (1H, doublet, J=3 Hz);
7.29 (1H, doublet, J=9 Hz);
7.24 (2H, doublet, J=9 Hz);
6.79 (1H, doublet of doublets, J=2 & 9 Hz);
6.76 (1H, doublet, J=2 Hz);
6.34 (1H, doublet, J=2 Hz);
4.83 (2H, broad singlet);
2.17 (3H, singlet).

Mass spectrum (El) m/z: 380 [M$^+$].

EXAMPLE 71

2-(3-Fluoro-4-methoxylphenyl)-4-methyl-1-(4-sulfamoylphenyl)pyrrole (Compound No. 2-106)

71(i) N-(3-Fluoro-4-methoxybenzylidene)-4-sulfamoylaniline

Following a procedure similar to that described in Example 1(i), but using 3-fluoro-4-methoxybenzaldehyde and 4-sulfamoylaniline as starting materials, the title compound was obtained as a slightly yellow powder (yield 57%).

Nuclear Magnetic Resonance Spectrum (270 MHz, hexadeuterated dimethyl sulfoxide) δ ppm:

8.40 (1H, singlet);
7.92 (2H, doublet, J=9 Hz);
7.74 (1H, doublet of doublets, J=2 & 9 Hz);
7.62 (1H, doublet, J=9 Hz);
7.25 (2H, doublet, J=9 Hz);
7.12 (1H, triplet, J=8 Hz);
7.02 (2H, broad singlet);
3.97 (3H, singlet).

71(ii) α-(3-Fluoro-4-methoxyphenyl)-α-(4-sulfamoylanilino)acetonitrile

Following a procedure similar to that described in Example 1(ii), but using N-(3-fluoro-4-methoxybenzylidene)-4-sulfamoylaniline [prepared as described in step (i) above] and trimethylsilyl cyanide as starting materials, the title compound was obtained as a slightly yellow powder (yield 98%).

Nuclear Magnetic Resonance Spectrum (270 MHz, hexadeuterated dimethyl sulfoxide) δ ppm:

7.69 (2H, doublet, J=9 Hz);
7.37–7.33 (2H, multiplet);
7.13–7.05 (1H, broad singlet);
7.12 (1H, triplet, J=9 Hz);
6.83 (2H, doublet, J=9 Hz);
6.79 (2H, broad singlet);
5.77–5.73 (1H, multiplet);
3.91 (3H, singlet).

71(iii) 2-(3-Fluoro-4-methoxyphenyl)-4-methyl-1-(4-sulfamoylphenyl)pyrrole

Following a procedure similar to that described in Example 1(iii), but using α-(3-fluoro-4-methoxyphenyl)-α-(4-sulfamoylanilino) acetonitrile [prepared as described in step (ii) above] and methacrolein as starting materials, the title compound was obtained as a white powder (yield 28%), melting at 170–173° C.

Nuclear Magnetic Resonance Spectrum (270 MHz, CDCl$_3$) δ ppm:

7.86 (2H, doublet, J=9 Hz);
7.23 (2H, doublet, J=9 Hz);
6.90–6.81 (3H, multiplet);
6.79 (1H, doublet, J=2 Hz);
6.74 (1H, doublet, J=2 Hz);
4.82 (2H, broad singlet);
3.87 (3H, singlet);
2.17 (3H, singlet).

Mass spectrum (EI) m/z: 360 [M$^+$].

EXAMPLE 72

2-(2,4-Difluorophenyl)-4-methyl-1-(4-sulfamoylphenyl)pyrrole (Compound No. 2-115)

72(i) N-(2,4-Difluorobenzylidene)-4-sulfamoylaniline

Following a procedure similar to that described in Example 1(i), but using 2,4-difluorobenzaldehyde and 4-sulfamoylaniline as starting materials, the title compound was obtained as a pale yellow powder (yield 52%).

Nuclear Magnetic Resonance Spectrum (270 MHz, CDCl$_3$) δ ppm:

8.67 (1H, singlet);
8.20 (1H, doublet of triplets, J=7 & 9 Hz);
7.97 (2H, doublet of doublets, J=2 & 7 Hz);
7.28 (2H, doublet of doublets, J=2 & 7 Hz);
7.05–6.98 (1H, multiplet);
6.95–6.87 (1H, multiplet);
4.88 (2H, broad singlet).

72(ii) α-(2,4-Difluorophenyl)-α-(4-sulfamoylanilino) acetonitrile

Following a procedure similar to that described in Example 1(ii), but using N-(2,4-difluorobenzylidene)-4-sulfamoylaniline [prepared as described in step (i) above] and trimethylsilyl cyanide as starting materials, the title compound was obtained as a pale yellow powder (yield 88%).

Nuclear Magnetic Resonance Spectrum (270 MHz, hexadeuterated dimethyl sulfoxide) δ ppm:

7.76 (2H, doublet, J=9 Hz);
7.71–7.65 (1H, multiplet);
7.05–6.92 (2H, multiplet);
6.82 (2H, doublet, J=9 Hz);
6.79 (1H, multiplet);
6.37 (2H, broad singlet);
5.73 (1H, doublet, J=9 Hz).

72(iii) 2-(2,4-Difluorophenyl)-4-methyl-1-(4-sulfamoylphenyl)pyrrole

Following a procedure similar to that described in Example 1(iii), but using α-(2,4-difluorophenyl)-α-(4-sulfamoylanilino)acetonitrile [prepared as described in step (ii) above] and methacrolein as starting materials, the title compound was obtained as a pale brown powder (yield 32%), melting at 170–172° C.

Nuclear Magnetic Resonance Spectrum (270 MHz, CDCl$_3$) δ ppm:

7.84 (2H, doublet, J=9 Hz);
7.20 (2H, doublet, J=9 Hz);
7.21–7.13 (1H, multiplet);
6.87–6.67 (2H, multiplet);
6.80 (1H, broad singlet);

6.31 (1H, broad singlet);

4.85 (2H, broad singlet);

2.19 (3H, singlet).

Mass spectrum (EI) m/z: 348 [M$^+$].

EXAMPLE 73

2-(4-Methoxyphenyl)-3-methyl-1-(4-sulfamoylphenyl)pyrrole (Compound No. 2-76)

Following a procedure similar to that described in Example 52(iii), but using crotonaldehyde instead of methacrolein, the title compound was obtained as a brown amorphous powder (yield 21%).

Nuclear Magnetic Resonance Spectrum (270 MHz, CDCl$_3$) δ ppm:

7.79 (2H, doublet, J=9 Hz);

7.16 (2H, doublet, J=9 Hz);

7.01 (2H, doublet, J=9 Hz);

6.88 (1H, doublet, J=3 Hz);

6.83 (2H, doublet, J=9 Hz);

6.28 (1H, doublet, J=3 Hz);

4.86 (2H, singlet);

3.80 (3H, singlet);

2.14 (3H, singlet).

Mass spectrum (EI) m/z: 342 [M$^+$].

EXAMPLE 74

2-(3,4-Difluorophenyl)-4-methyl-1-(4-sulfamoylphenyl)pyrrole (Compound No. 2-112)

74(i) N-(3,4-Difluorobenzylidene)-4-sulfamoylaniline

Following a procedure similar to that described in Example 1(i), but using 3,4-difluorobenzaldehyde and 4-sulfamoylaniline as starting materials, the title compound was obtained as a slightly yellow powder (yield 67%).

Nuclear Magnetic Resonance Spectrum (270 MHz, hexadeuterated dimethyl sulfoxide) δ ppm:

8.40 (1H, singlet);

7.96 (2H, doublet of doublets, J=7 & 2 Hz);

7.89–7.81 (1H, multiplet);

7.67–7.62 (1H, multiplet);

7.37–7.24 (1H, multiplet);

7.25 (2H, doublet of doublets, J=7 & 2 Hz);

6.71 (2H, broad singlet).

74(ii) α-(3,4-Difluorophenyl)-α-(4-sulfamoylanilino)acetonitrile

Following a procedure similar to that described in Example 1(ii), but using N-(3,4-difluorobenzylidene)-4-sulfamoylaniline [prepared as described in step (i) above] and trimethylsilyl cyanide as starting materials, the title compound was obtained as a slightly yellow powder (yield 92%). Nuclear Magnetic Resonance Spectrum (270 MHz, hexadeuterated dimethyl sulfoxide) δ ppm:

7.76 (2H, doublet, J=9 Hz);

7.52–7.24 (3H, multiplet);

6.82–6.79 (3H, multiplet);

6.28 (2H, broad singlet);

5.64 (1H, doublet, J=8 Hz).

74(iii) 2-(3,4-Difluorophenyl)-4-methyl-1-(4-sulfamoylphenyl)pyrrole

Following a procedure similar to that described in Example 1(iii), but using α-(3,4-difluorophenyl)-α-(4-sulfamoylanilino)acetonitrile [prepared as described in step (ii) above] and methacrolein as starting materials, the title compound was obtained as a pale yellow powder (yield 51%), melting at 177–179° C.

Nuclear Magnetic Resonance Spectrum (270 MHz, CDCl$_3$) δ ppm:

7.88 (2H, doublet of doublets, J=2 & 7 Hz);

7.23 (2H, doublet of doublets, J=2 & 7 Hz);

7.08–6.89 (2H, multiplet);

6.81–6.76 (1H, multiplet);

6.74 (1H, doublet, J=2 Hz);

6.29 (1H, doublet, J=2 Hz);

4.99 (2H, broad singlet);

2.17 (3H, singlet).

Mass spectrum (EI) m/z: 348 [M$^+$].

EXAMPLE 75

1-(2,4-Difluorophenyl)-4-methyl-2-(4-sulfamoylphenyl)pyrrole (Compound No. 1-122)

75(i) 2,4-Difluoro-N-(4-sulfamoylbenzylidene)aniline

Following a procedure similar to that described in Example 1(i), but using 4-sulfamoylbenzaldehyde and 2,4-difluoroaniline as starting materials, the title compound was obtained as a white powder (yield 47%).

Nuclear Magnetic Resonance Spectrum (270 MHz, hexadeuterated dimethyl sulfoxide) δ ppm:

8.79 (1H, singlet);

8.12 (2H, doublet, J=8 Hz);

7.97 (2H, doublet, J=8 Hz);

7.58–7.34 (4H, multiplet);

7.21–7.13 (1H, multiplet).

75(ii) α-(2,4-Difluoroanilino)-α-(4-sulfamoylphenyl)acetonitrile

Following a procedure similar to that described in Example 1(ii), but using 2,4-difluoro-N-(4-sulfamoylbenzylidene)aniline [prepared as described in step (i) above] and trimethylsilyl cyanide as starting materials, the title compound was obtained as a white powder (yield 100%).

Nuclear Magnetic Resonance Spectrum (270 MHz, hexadeuterated dimethyl sulfoxide) δ ppm:

7.91 (2H, doublet, J=8 Hz);

7.76 (2H, doublet, J=8 Hz);

7.44 (2H, singlet);

7.25–7.17 (1H, multiplet);

6.97–6.94 (2H, multiplet);

6.73 (1H, doublet, J=10 Hz);

6.17 (1H, doublet, J=10 Hz).

75(iii) 1-(2,4-Difluorophenyl)-4-methyl-2-(4-sulfamoylphenyl)pyrrole

Following a procedure similar to that described in Example 1(iii), but using α-(2,4-difluoroanilino)-α-(4-sulfamoylphenyl)acetonitrile [prepared as described in step (ii) above] and methacrolein as starting materials, the title compound was obtained as a white powder (yield 63%), melting at 140–141° C.

Nuclear Magnetic Resonance Spectrum (270 MHz, CDCl$_3$) δ ppm:

7.75 (2H, doublet, J=8 Hz);

7.23–7.16 (3H, multiplet);

6.94–6.88 (2H, multiplet);

6.69 (1H, singlet);

6.43 (1H, singlet);
4.99 (2H, singlet);
2.20 (3H, singlet).
Mass spectrum (EI) m/z: 348 [M+].

EXAMPLE 76

2-(4-Methoxyphenyl)-1-(4-sulfamoylphenyl)pyrrole (Compound No. 2-73)

Following a procedure similar to that described in Example 52(iii), but using acrolein instead of methacrolein, the title compound was obtained as a pale brown powder (yield 10%), melting at 183–184° C.

Nuclear Magnetic Resonance Spectrum (270 MHz, CDCl$_3$) δ ppm:
7.92–7.84 (2H, multiplet);
7.39–7.23 (2H, multiplet);
7.11–7.04 (2H, multiplet);
6.95–6.93 (1H, multiplet);
6.82–6.78 (2H, multiplet);
6.39 (2H, multiplet);
4.84 (2H, singlet);
3.80 (3H, singlet).
Mass spectrum (EI) m/z: 342 [M+].

EXAMPLE 77

4-Methyl-2-phenyl-1-(4-sulfamoylphenyl)pyrrole (Compound No. 2-60)

77(i) N-Benzylidene-4-sulfamoylaniline

Following a procedure similar to that described in Example 1(i), but using benzaldehyde and 4-sulfamoylaniline as starting materials, the title compound was obtained as a pale yellow powder (yield 91%).

Nuclear Magnetic Resonance Spectrum (270 MHz, hexadeuterated dimethyl sulfoxide) δ ppm:
8.45 (1H, singlet);
7.97–7.90 (2H, multiplet);
7.95 (2H, doublet, J=9 Hz);
7.57–7.47 (3H, multiplet);
7.25 (2H, doublet, J=9 Hz);
6.74 (2H, broad singlet).

77(ii) α-Phenyl-α-(4-sulfamoylanilino)acetonitrile

Following a procedure similar to that described in Example 1(ii), but using N-benzylidene-4-sulfamoylaniline [prepared as described in step (i) above] and trimethylsilyl cyanide as starting materials, the title compound was obtained as a slightly yellow powder (yield 96%).

Nuclear Magnetic Resonance Spectrum (270 MHz, hexadeuterated dimethyl sulfoxide) δ ppm:
7.78 (2H, doublet, J=9 Hz);
7.64–7.61 (2H, multiplet);
7.55–7.47 (3H, multiplet);
6.85 (2H, doublet, J=9 Hz);
6.52 (1H, broad doublet, J=8 Hz);
6.24 (2H, broad singlet);
5.66 (1H, broad doublet, J=8 Hz).

77(iii) 4-Methyl-2-phenyl-1-(4-sulfamoylphenyl pyrrole

Following a procedure similar to that described in Example 1(iii), but using α-phenyl-α-(4-sulfamoylanilino)acetonitrile [prepared as described in step (ii) above] and methacrolein as starting materials, the title compound was obtained as a pale yellow powder (yield 47%), melting at 165–168° C.

Nuclear Magnetic Resonance Spectrum (270 MHz, CDCl$_3$) δ ppm:
7.84 (2H, doublet of doublets, J=2 & 7 Hz);
7.23 (2H, doublet of doublets, J=2 & 7 Hz);
7.28–7.20 (3H, multiplet);
7.12–7.09 (2H, multiplet);
6.75 (1H, doublet, J=2 Hz);
6.31 (1H, doublet, J=2 Hz);
4.88 (2H, broad singlet);
2.18 (3H, singlet).
Mass spectrum (EI) m/z: 312 [M+].

EXAMPLE 78

4-Methyl-2-(3,4-dimethylphenyl)-1-(4-sulfamoylphenyl)pyrrole (Compound No. 2-118)

78(i) N-(3,4-Dimethylbenzylidene)-4-sulfamoylaniline

Following a procedure similar to that described in Example 1(i), but using 3,4-dimethylbenzaldehyde and 4-sulfamoylaniline as starting materials, the title compound was obtained as a pale yellow powder (yield 45%).

Nuclear Magnetic Resonance Spectrum (270 MHz, hexadeuterated dimethyl sulfoxide) δ ppm:
8.36 (1H, singlet);
7.92 (2H, doublet, J=9 Hz);
7.69 (1H, doublet, J=2 Hz);
7.59 (1H, doublet of doublets, J=1 & 7 Hz);
7.26–7.08 (1H, multiplet);
7.22 (2H, doublet, J=9 Hz);
6.46 (2H, broad singlet);
2.34 (6H, singlet).

78(ii) α-(3,4-Dimethylphenyl)-α-(4-sulfamoylanilino)acetonitrile

Following a procedure similar to that described in Example 1(ii), but using N-(3,4-dimethylbenzylidene)-4-sulfamoylaniline [prepared as described in step (i) above] and trimethylsilyl cyanide as starting materials, the title compound was obtained as a slightly yellow powder (yield 91%).

Nuclear Magnetic Resonance Spectrum (270 MHz, hexadeuterated dimethyl sulfoxide) δ ppm:
7.72 (2H, doublet, J=9 Hz);
7.34 (1H, singlet);
7.30 (1H, doublet, J=8 Hz);
7.20 (1H, doublet, J=8 Hz);
6.82 (2H, doublet, J=9 Hz);
6.74–6.70 (1H, broad multiplet);
6.56 (2H, broad multiplet);
5.54 (1H, broad doublet, J=8 Hz);
2.30 (3H, singlet);
2.29 (3H, singlet).

78(iii) 4-Methyl-2-(3,4-dimethylphenyl)-1-(4-sulfamoylphenyl)pyrrole

Following a procedure similar to that described in Example 1(iii), but using α-(3,4-dimethylphenyl)-α-(4-sulfamoylanilino)acetonitrile [prepared as described in step (ii) above] and methacrolein as starting materials, the title compound was obtained as a slightly brown amorphous powder (yield 69%).

Nuclear Magnetic Resonance Spectrum (270 MHz, CDCl$_3$) δ ppm:
7.83 (2H, doublet, J=9 Hz);

7.22 (2H, doublet, J=9 Hz);
6.98–6.95 (2H, multiplet);
6.75 (1H, multiplet);
6.72 (1H, broad multiplet);
6.25 (1H, doublet, J=2 Hz);
4.84 (2H, broad singlet);
2.23 (3H, singlet);
2.19 (3H, singlet);
2.17 (3H, singlet).
Mass spectrum (EI) m/z: 340 [M$^+$].

EXAMPLE 79

2-(3-Chloro-4-methoxyphenyl)-4-methyl-1-(4-sulfamoylphenyl)pyrrole (Compound No. 2-100)

79(i) N-(3-Chloro-4-methoxybenzylidene)-4-sulfamoylaniline

Following a procedure similar to that described in Example 1(i), but using 3-chloro-4-methoxybenzaldehyde and 4-sulfamoylaniline as starting materials, the title compound was obtained as a pale yellow powder (yield 72%).

Nuclear Magnetic Resonance Spectrum (270 MHz, hexadeuterated dimethyl sulfoxide) δ ppm:
8.37 (1H, singlet);
8.00 (1H, doublet, J=2 Hz);
7.93 (2H, doublet, J=9 Hz);
7.77 (1H, doublet of doublets, J=2 & 9 Hz);
7.24 (2H, doublet, J=9 Hz);
7.09 (1H, doublet, J=9 Hz);
6.90 (2H, broad doublet, J=5 Hz);
3.99 (3H, singlet).

79(ii) α-(3-Chloro-4-methoxyphenyl)-α-(4-sulfamoylanilino)acetonitrile

Following a procedure similar to that described in Example 1(ii), but using N-(3-chloro-4-methoxybenzylidene)-4-sulfamoylaniline [prepared as described in step (i) above] and trimethylsilyl cyanide as starting materials, the title compound was obtained as a slightly yellow powder (yield 64%).

Nuclear Magnetic Resonance Spectrum (270 MHz, hexadeuterated dimethyl sulfoxide) δ ppm:
7.76–7.46 (4H, multiplet);
7.02 (1H, doublet, J=9 Hz);
6.80 (2H, doublet, J=9 Hz);
6.71–6.58 (1H, broad multiplet);
6.44–6.27 (2H, broad multiplet);
5.57 (1H, broad doublet, J=8 Hz);
3.94 (3H, singlet).

79(iii) 2-(3-Chloro-4-methoxyphenyl)-4-methyl-1-(4-sulfamoylphenyl)pyrrole

Following a procedure similar to that described in Example 1(iii), but using α-(3-chloro-4-methoxyphenyl)-α-(4-sulfamoylanilino)acetonitrile [prepared as described in step (ii) above] and methacrolein as starting materials, the title compound was obtained as a slightly yellow powder (yield 37%), melting at 160–163° C.

Nuclear Magnetic Resonance Spectrum (270 MHz, CDCl$_3$) δ ppm:
7.86 (2H, doublet, J=9 Hz);
7.23 (1H, doublet, J=2 Hz);
7.23 (2H, doublet, J=9 Hz);
6.84 (1H, doublet of doublets, J=2 & 9 Hz);
6.78 (1H, doublet, J=9 Hz);
6.73 (1H, broad multiplet);
6.25 (1H, doublet, J=2 Hz);
4.83 (2H, broad singlet);
3.88 (3H, singlet);
2.17 (3H, singlet).
Mass spectrum (EI) m/z: 376 [M$^+$].

EXAMPLE 80

2-(4-Methoxyphenyl)-4-methyl-1-(4-methylsulfonylphenyl)pyrrole (Compound No. 2-22)

Following a procedure similar to that described in Example 28(iii), but using methacrolein instead of acrolein, the title compound was obtained as a white powder (yield 36%), melting at 159–161° C.

Nuclear Magnetic Resonance Spectrum (270 MHz, CDCl$_3$) δ ppm:
7.85 (2H, doublet, J=9 Hz);
7.27 (2H, doublet, J=9 Hz);
7.03 (2H, doublet, J=9 Hz);
6.79 (2H, doublet, J=9 Hz);
6.74 (1H, singlet);
6.24 (1H, singlet);
3.80 (3H, singlet);
3.07 (3H, singlet);
2.18 (3H, singlet).
Mass spectrum (FAB) m/z: 341 [M$^+$].

EXAMPLE 81

4-(3-Cyclopentyloxy-4-methoxybenzyl)-2-(4-methoxyphenyl)-1-(4-sulfamoylphenyl)pyrrole (Compound No. 2-150)

81(i) Diethyl α-(4-methoxyphenacyl)malonate 3.50 g (21.8 mmol) of diethyl malonate were dissolved in 60 ml of anhydrous tetrahydrofuran, and 2.70 g (24.0 mmol) of potassium t-butoxide were added to the resulting solution, whilst ice-cooling. The mixture was then stirred for 1 hour. At the end of this time, a solution of 5.00 g (21.8 mmol) of 4-methoxyphenacyl bromide in 40 ml of anhydrous tetrahydrofuran was slowly added dropwise to the mixture, whilst ice-cooling. The mixture was stirred, whilst ice-cooling for 1 hour, and then a saturated aqueous solution of ammonium chloride was added, and the mixture was extracted with ethyl acetate. The organic extract was washed with water and dried over anhydrous magnesium sulfate, and then the solvent was removed by distillation under reduced pressure. The residue thus obtained was applied to a silica gel chromatography column and eluted with a 1:4 by volume mixture of ethyl acetate and hexane, to give 4.87 g of the title compound as a slightly yellow oily substance (yield 73%).

Nuclear Magnetic Resonance Spectrum (270 MHz, CDCl$_3$) δ ppm:
7.97 (2H, doublet, J=9 Hz);
6.94 (2H, doublet, J=9 Hz);
4.25 (4H, quartet of doublets, J=7 & 2 Hz);
4.04 (1H, triplet, J=7 Hz);
3.88 (3H, singlet);
3.58 (2H, doublet, J=7 Hz);
1.29 (6H, triplet, J=7 Hz).

81(ii) Diethyl α-(3-cyclopentyloxy-4-methoxybenzyl)-α-(4-methoxyphenacyl)malonate 0.29 g (7.1 mmol) of sodium hydride (as a 60% w/w dispersion in mineral oil) was added to 50 ml of anhydrous tetrahydrofuran, whilst ice-cooling, and then the mixture was stirred for 10 minutes. At the end of this time, a solution of 2.00 g (6.5 mmol) of diethyl α-(4-methoxyphenacyl) malonate [prepared as described in step (i) above] in 20 ml of anhydrous tetrahydrofuran was slowly added dropwise to the mixture, whilst ice-cooling. The mixture was then stirred for 30 minutes. A solution of 1.72 g (7.1 mmol) of 3-cyclopentyloxy-4-methoxybenzyl chloride in 20 ml of anhydrous tetrahydrofuran and 0.97 g (6.5 mmol) of sodium iodide were then added to the mixture, and the resulting mixture was heated under reflux for 2 hours. At the end of this time, the mixture was cooled to room temperature and was then acidified by the addition of 3N aqueous hydrochloric acid and extracted with ethyl acetate. The organic extract was washed with water and dried over anhydrous magnesium sulfate, and then the solvent was removed by distillation under reduced pressure. The residue thus obtained was applied to a silica gel chromatography column and eluted with a 1:4 by volume mixture of ethyl acetate and hexane, to give 2.45 g of the title compound as a pale yellow oily substance.

Nuclear Magnetic Resonance Spectrum (270 MHz, $CDCl_3$) δ ppm:

7.91 (2H, doublet, J=9 Hz);
6.91 (2H, doublet, J=9 Hz);
6.68 (1H, doublet, J=8 Hz);
6.45 (1H, doublet of doublets, J=8 & 2 Hz);
6.36 (1H, doublet, J=2 Hz);
4.31–4.22 (1H, multiplet);
4.24 (4H, quartet, J=7 Hz);
3.86 (3H, singlet);
3.77 (3H, singlet);
3.49 (2H, singlet);
3.44 (2H, singlet);
1.72–1.45 (8H, multiplet);
1.27 (6H, triplet, J=7 Hz).

81(iii) Ethyl α-(3-cyclopentyloxy-4-methoxybenzyl)-α-(4-methoxyphenacyl)acetate 2.43 g (4.7 mmol) of diethyl α-(3-cyclopentyloxy-4-methoxybenzyl)-α-(4-methoxyphenacyl)malonate [prepared as described in step (ii) above] and 1.26 g (4.7 mmol) of 18-crown-6 were dissolved in 50 ml of benzene, and 4.70 ml (4.7 mmol) of a 1.1M solution of potassium hydroxide in ethanol were added to the resulting solution. The mixture was then stirred for 30 minutes, after which the ethanol in the reaction mixture was removed by distillation under reduced pressure. The remaining reaction solution was heated under reflux for 14 hours and then the reaction mixture was cooled to room temperature. The mixture was then acidified by the addition of 3N aqueous hydrochloric acid, and the resulting mixture was extracted with ethyl acetate. The organic extract was washed with water and dried over anhydrous magnesium sulfate, and then the solvent was removed by distillation under reduced pressure. The residue thus obtained was applied to a silica gel chromatography column and eluted with a 1:4 by volume mixture of ethyl acetate and hexane, to give 1.68 g of the title compound as slightly yellow crystals (yield 81%).

Nuclear Magnetic Resonance Spectrum (270 MHz, $CDCl_3$) δ ppm:

7.92 (2H, doublet, J=9 Hz);
6.90 (2H, doublet, J=9 Hz);
6.78 (1H, doublet, J=8 Hz);
6.74–6.67 (2H, multiplet);
4.76–4.67 (1H, multiplet);
4.12 (2H, quartet, J=7 Hz);
3.86 (3H, singlet);
3.82 (3H, singlet);
3.39–3.22 (2H, multiplet);
3.07–2.92 (2H, multiplet);
2.83–2.72 (1H, multiplet);
1.97–1.53 (8H, multiplet);
1.19 (3H, triplet, J=7 Hz).

81(iv) 4-(3-Cyclopentyloxy-4-methoxybenzyl)-2-(4-methoxyphenyl)-1-(4-sulfamoylphenyl)pyrrole 200 mg (0.46 mmol) of ethyl α-(3-cyclopentyloxy-4-methoxybenzyl)-α-(4-methoxyphenacyl)acetate [prepared as described in step (iii) above] were dissolved in 10 ml of anhydrous diethyl ether, and 20 mg (0.68 mmol) of lithium aluminum hydride were added to the resulting solution, whilst ice-cooling. The mixture was then stirred for 1 hour, whilst ice-cooling. At the end of this time, 30 μl of water, 30 μl of a 15% w/v aqueous solution of sodium hydroxide and 80 μl of water were added to the mixture, in that order, and the resulting mixture was stirred at room temperature for 10 minutes. Anhydrous magnesium sulfate was then added to the reaction mixture to dehydrate it, and then the mixture was filtered using a Celite (trade mark) filter aid. The filtrate was then concentrated by evaporation under reduced pressure, to give 140 mg of a residue.

The whole of this residue was dissolved in 20 ml of methylene chloride, and 1.70 g (4.59 mmol) of pyridinium dichromate were added to the resulting solution, which was then stirred at room temperature overnight. The reaction mixture was then filtered using a Celite (trade mark) filter aid, and the filtrate was concentrated by evaporation under reduced pressure, to give a residue. The residue thus obtained was applied to a silica gel chromatography column and eluted with a 4:6 by volume mixture of ethyl acetate and hexane, to give 60 mg of crude α-(3-cyclopentyloxy-4-methoxybenzyl)-α-(4-methoxyphenacyl)acetaldehyde as a pale brown oily substance. The whole of the product thus obtained was dissolved in 3 ml of acetic acid, and 26 mg (0.15 mmol) of 4-sulfamoylaniline were added to the resulting solution. The mixture was then heated under reflux for 1 hour, after which acetic acid was removed by distillation under reduced pressure. Water was added to the residue and the mixture was neutralized with a saturated aqueous solution of sodium hydrogencarbonate. The mixture was then extracted with ethyl acetate. The organic extract was washed with water and dried over anhydrous magnesium sulfate, and then the solvent was removed by distillation under reduced pressure, to give a residue. The residue thus obtained was applied to a silica gel chromatography column and eluted with a 1:2 by volume mixture of ethyl acetate and hexane, to give 20 mg of the title compound as a yellow powder (yield 9%), melting at 81–84° C.

Nuclear Magnetic Resonance Spectrum (270 MHz, $CDCl_3$) δ ppm:

7.82 (2H, doublet, J=9 Hz);
7.20 (2H, doublet, J=9 Hz);
7.02 (2H, doublet, J=9 Hz);
6.87–6.72 (5H, multiplet);
6.63 (1H, broad singlet);
6.24 (1H, doublet, J=2 Hz);
4.84 (2H, broad singlet);

4.80–4.70 (1H, multiplet);
3.83 (3H, singlet);
3.80 (2H, singlet);
3.78 (3H, singlet);
1.95–1.53 (8H, multiplet).

EXAMPLE 82

1-(4-Acetylaminosulfonylphenyl)-2-(4-methoxyphenyl)-4-methylpyrrole (Compound No. 2-148)

82(i) 3-(4-Methoxybenzoyl)-2-methylpropionaldehyde 4.36 g (75 mmol) of propionaldehyde were added dropwise under a stream of nitrogen to a solution of 6.46 g (50 mmol) of diisopropylamine, 39 g of molecular sieves 4 Å and 10 mg of 2,6-di-t-butyl-4-methylphenol in 50 ml of tetrahydrofuran, and the mixture was left to stand for 3 hours. At the end of this time, 5.73 g (25 mmol) of 4'-methoxy-2-bromoacetophenone were added to the mixture, and the mixture was left to stand at room temperature overnight. The reaction mixture was then filtered, and 55 ml of 1N aqueous hydrochloric acid were added to the filtrate to separate it into liquid phases. The aqueous layer was separated and extracted twice with ethyl acetate. The organic extracts were combined and washed with water and with a saturated aqueous solution of sodium chloride, in that order. The resulting solution was then dried over anhydrous magnesium sulfate and concentrated by evaporation under reduced pressure. The residue thus obtained was applied to a silica gel chromatography column and eluted with a 2:1 by volume mixture of hexane and ethyl acetate, to give 2.82 g (yield 26%) of the title compound as a pale yellow oily substance.

Nuclear Magnetic Resonance Spectrum (270 MHz, CDCl$_3$) δ ppm:

9.80 (1H, singlet);
7.96 (2H, doublet, J=9 Hz);
6.94 (2H, doublet, J=9 Hz);
3.88 (3H, singlet);
3.44 (1H, doublet of doublets, J=6 & 17 Hz);
3.17–3.03 (1H, multiplet);
2.97 (1H, doublet of doublets, J=6 & 17 Hz);
1.23 (3H, doublet, J=7 Hz).

82(ii) 1-(4-Acetylaminosulfonylphenyl)-2-(4-methoxyphenyl)-4-methylpyrrole

A solution of 2.82 g (12.8 mmol) of 3-(4-methoxybenzoyl)-2-methylpropionaldehyde [prepared as described in step (i) above] and 2.74 g (12.8 mmol) of 4-acetylaminosulfonylaniline in 30 ml of acetic acid was heated under reflux for 3 hours, after which the acetic acid was removed by distillation under reduced pressure. The residue thus obtained was dissolved in chloroform and a saturated aqueous solution of sodium hydrogencarbonate was added to the resulting solution to separate it into liquid phases. The organic extract was washed with water and with a saturated aqueous solution of sodium chloride, in that order, and dried over anhydrous magnesium sulfate, after which it was concentrated by evaporation under reduced pressure. The residue thus obtained was applied to a silica gel chromatography column and eluted with a 2:3 by volume mixture of hexane and ethyl acetate. It was then recrystallized from ethanol, to give 0.79 g (yield 16%) of the title compound as a white powder, melting at 215–217° C.

Nuclear Magnetic Resonance Spectrum (270 MHz, CDCl$_3$) δ ppm:

8.07–7.91 (1H, broad singlet);
7.95 (2H, doublet, J=9 Hz);
7.24 (2H, doublet, J=9 Hz);
7.03 (2H, doublet, J=9 Hz);
6.79 (2H, doublet, J=9 Hz);
6.73 (1H, singlet);
6.23 (1H, singlet);
3.80 (3H, singlet);
2.17 (3H, singlet);
2.09 (3H, singlet).
Mass spectrum (FAB) m/z: 384 [M$^+$].

EXAMPLE 83

1-(4-Acetylaminosulfonylphenyl)-2-(3,4-dimethylphenyl)-4-methylpyrrole (Compound No. 2-149)

83(i) 3-Bromo-2-methylpropionaldehyde ethylene acetal 16.03 ml (0.12 mol) of tetralin were charged into a flask, and 24.27 ml (0.47 mol) of bromine were added dropwise thereto, whilst ice-cooling. The hydrogen bromide gas thus produced was bubbled through a tube into 55.21 ml (0.99 mol) of ethylene glycol, whilst ice-cooling. After 4 hours, 25 ml (0.30 mol) of methacrolein were added dropwise to the mixture, which was then stirred at room temperature for 1 hour. The reaction solution was then extracted twice with pentane, and the organic extract was washed with a 5% aqueous solution of sodium hydrogencarbonate and with a saturated aqueous solution of sodium chloride, in that order. It was then dried over anhydrous magnesium sulfate and concentrated by evaporation under reduced pressure. The residue thus obtained was distilled under reduced pressure, to give 29.81 g (yield 51%) of the title compound as a colorless oily substance, boiling at 65–68° C./2 mmHg Nuclear Magnetic Resonance Spectrum (270 MHz, CDCl$_3$) δ ppm:

4.83 (1H, doublet, J=5 Hz);
4.03–3.84 (4H, multiplet);
3.53 (1H, doublet of doublets, J=5 & 10 Hz);
3.37 (1H, doublet of doublets, J=7 & 10 Hz);
2.18–2.01 (1H, multiplet);
1.11 (3H, doublet, J=7 Hz).

83(ii) 3-(3,4-Dimethylbenzoyl)-2-methylpropionaldehyde ethylene acetal 0.29 ml (3.4 mmol) of 1,2-dibromoethane was added to a suspension of 1.66 g (68.1 mmol) of magnesium in 5 ml of anhydrous tetrahydrofuran under a stream of nitrogen. 9.96 g (51.1 mmol) of 3-bromo-2-methylpropionaldehyde ethylene acetal [prepared as described in step (i) above] were then added dropwise to the resulting mixture, whilst ice-cooling, after which the mixture was stirred for 1 hour. A solution of 6.58 g (34.1 mmol) of N-methoxy-N-methyl-3,4-dimethylbenzamide in 30 ml of tetrahydrofuran was then added dropwise to the mixture, and the resulting mixture was stirred, whilst ice-cooling for 1 hour. A saturated aqueous solution of ammonium chloride was then added to the mixture, and the resulting mixture was extracted twice with ethyl acetate. The organic extracts were combined and washed with a saturated aqueous solution of sodium chloride, after which they were dried over anhydrous magnesium sulfate and concentrated by evaporation under reduced pressure. The residue thus obtained was applied to a silica gel chromatography column and eluted with a 6:1 by volume mixture of hexane and ethyl acetate, to give 3.26 g (yield 39%) of the title compound as a colorless oily substance.

Nuclear Magnetic Resonance Spectrum (270 MHz, CDCl$_3$) δ ppm:

7.75 (1H, singlet);
7.71 (1H, doublet, J=8 Hz);
7.20 (1H, doublet, J=8 Hz);
4.82 (1H, doublet, J=4 Hz);
4.01–3.83 (4H, multiplet);
3.18 (1H, doublet of doublets, J=5 & 16 Hz);
2.76 (1H, doublet of doublets, J=9 & 16 Hz);
2.62–2.47 (1H, multiplet);
2.31 (6H, singlet);
1.02 (3H, doublet, J=7 Hz).

83(iii) 1-(4-Acetylaminosulfonylphenyl)-2-(3,4-dimethylphenyl)-4-methylpyrrole 3.26 g (13.1 mmol) of 3-(3,4-dimethylbenzoyl)-2-methylpropionaldehyde ethylene acetal [prepared as described in step (ii) above] and 2.81 g (13.1 mmol) of 4-acetylaminosulfonylaniline were dissolved in a mixture of 52 ml (52 mmol) of 1N aqueous hydrochloric acid and 16 ml of tetrahydrofuran, and the mixture was heated at 70° C. for 1 hour. At the end of this time, the mixture was left to stand to allow it to cool. The mixture was then extracted three times with ethyl acetate. The organic extracts were combined and washed with a saturated aqueous solution of sodium chloride. The resulting solution was then dried over anhydrous magnesium sulfate, after which it was concentrated by evaporation under reduced pressure. The residue thus obtained was applied to a silica gel chromatography column and eluted with a 3:2 by volume mixture of hexane and ethyl acetate and crystallised from diisopropyl ether, to give 1.27 g (yield 25%) of the title compound as a white powder, melting at 192–193° C.

Nuclear Magnetic Resonance Spectrum (270 MHz, CDCl$_3$) δ ppm:

7.95 (2H, doublet, J=9 Hz);
8.05–7.93 (1H, broad singlet);
7.25 (2H, doublet, J=9 Hz);
6.98 (1H, doublet, J=8 Hz);
6.93 (1H, singlet);
6.76 (1H, doublet, J=8 Hz);
6.74 (1H, singlet);
6.26 (1H, singlet);
2.23 (3H, singlet);
2.17 (6H, singlet);
2.08 (3H, singlet).
Mass spectrum (EI) m/z: 382 [M$^+$].

EXAMPLE 84

4-Methyl-1-(4-methylthiophenyl)-2-(4-sulfamoylphenyl)pyrrole (Compound No. 1-164)

84(i) 4-Methylthio-N-(4-sulfamoylbenzylidene)aniline

Following a procedure similar to that described in Example 1(i), but using 4-sulfamoylbenzaldehyde and 4-methylthioaniline as starting materials, the title compound was obtained as a yellow powder (yield 95%).

Nuclear Magnetic Resonance Spectrum (270 MHz, hexadeuterated dimethyl sulfoxide) δ ppm:

8.76 (1H, singlet);
8.10 (2H, doublet, J=8 Hz);
7.95 (2H, doublet, J=8 Hz);
7.50 (2H, singlet);
7.33 (4H, multiplet);
2.50 (3H, singlet).

84(ii) α-(4-Methylthioanilino)-α-(4-sulfamoylphenyl)acetonitrile

Following a procedure similar to that described in Example 1(ii), but using 4-methylthio-N-(4-sulfamoylbenzylidene)aniline [prepared as described in step (i) above] and trimethylsilyl cyanide as starting materials, the title compound was obtained as a yellow powder (yield 100%).

Nuclear Magnetic Resonance Spectrum (270 MHz, hexadeuterated dimethyl sulfoxide) δ ppm:

7.92 (2H, doublet, J=8 Hz);
7.75 (2H, doublet, J=8 Hz);
7.45 (2H, singlet);
7.18 (2H, doublet, J=9 Hz);
6.92–6.78 (3H, multiplet);
6.15 (1H, doublet, J=9 Hz);
2.38 (3H, singlet).

84(iii) 4-Methyl-1-(4-methylthiophenyl)-2-(4-sulfamoylphenyl)pyrrole

Following a procedure similar to that described in Example 1(iii), but using α-(4-methylthioanilino)-α-(4-sulfamoylphenyl)acetonitrile [prepared as described in step (ii) above] and methacrolein as starting materials, the title compound was obtained as a slightly yellow powder (yield 33%), melting at 194–196° C.

Nuclear Magnetic Resonance Spectrum (270 MHz, hexadeuterated dimethyl sulfoxide) δ ppm:

7.54 (2H, doublet, J=8 Hz);
7.29–7.20 (6H, multiplet);
7.10 (2H, doublet, J=9 Hz);
6.88 (1H, singlet);
6.41 (1H, multiplet);
2.48 (3H, singlet);
2.10 (3H, singlet).
Mass spectrum (EI) m/z: 358 [M$^+$].

EXAMPLE 85

1-(4-Ethylthiophenyl)-4-methyl-2-(4-sulfamoylphenyl)pyrrole (Compound No. 1-165)

85(i) 4-Ethylthio-N-(4-sulfamoylbenzylidene)aniline

Following a procedure similar to that described in Example 1(i), but using 4-sulfamoylbenzaldehyde and 4-ethylthioaniline as starting materials, the title compound was obtained as a yellow powder (yield 56%).

Nuclear Magnetic Resonance Spectrum (270 MHz, hexadeuterated dimethyl sulfoxide) δ ppm:

8.76 (1H, singlet);
8.10 (2H, doublet, J=8 Hz);
7.95 (2H, doublet, J=8 Hz);
7.50 (2H, singlet);
7.40–7.30 (4H, multiplet);
3.01 (2H, quartet, J=7 Hz);
1.27–1.22 (3H, multiplet).

85(ii) α-(4-Ethylthioanilino)-α-(4-sulfamoylphenyl)acetonitrile

Following a procedure similar to that described in Example 1(ii), but using 4-ethylthio-N-(4- sulfamoylbenzylidene)aniline [prepared as described in step (i) above] and trimethylsilyl cyanide as starting materials, the title compound was obtained as a yellow powder (yield 100%).

Nuclear Magnetic Resonance Spectrum (270 MHz, hexa-deuterated dimethyl sulfoxide) δ ppm:

7.91 (2H, doublet, J=8 Hz);
7.54 (2H, doublet, J=8 Hz);
7.44 (2H, singlet);
7.23 (2H, doublet, J=8 Hz);
6.93 (1H, doublet, J=9 Hz);
6.80 (2H, doublet, J=8 Hz);
6.14 (1H, doublet, J=9 Hz);
2.79 (2H, quartet, J=7 Hz);
1.14 (3H, triplet, J=7 Hz).

85(iii) 1-(4-Ethylthiophenyl)-4-methyl-2-(4-sulfamoylphenyl)pyrrole

Following a procedure similar to that described in Example 1(iii), but using α-(4-ethylthioanilino)-α-(4-sulfamoylphenyl)acetonitrile [prepared as described in step (ii) above] and methacrolein as starting materials, the title compound was obtained as a slightly yellow powder (yield 69%), melting at 139–141° C.

Nuclear Magnetic Resonance Spectrum (270 MHz, hexa-deuterated dimethyl sulfoxide) δ ppm:

7.65 (2H, doublet, J=8 Hz);
7.34–7.31 (4H, multiplet);
7.21 (2H, doublet, J=9 Hz);
7.10 (2H, doublet, J=8 Hz);
6.90 (1H, singlet);
6.42–6.41 (1H, multiplet);
2.99 (2H, quartet, J=7 Hz);
2.10 (3H, singlet);
1.24 (3H, triplet, J=7 Hz).
Mass spectrum (EI) m/z: 372 [M+].

EXAMPLE 86

4-Methyl-1-(3,4-dimethylphenyl)-2-(4-sulfamoylphenyl)pyrrole (Compound No. 1-160)

86(i) 3,4-Dimethyl-N-(4-sulfamoylbenzylidene)aniline

Following a procedure similar to that described in Example 1(i), but using 4-sulfamoylbenzaldehyde and 3,4-dimethylaniline as starting materials, the title compound was obtained as a yellow powder (yield 60%).

Nuclear Magnetic Resonance Spectrum (270 MHz, hexa-deuterated dimethyl sulfoxide) δ ppm:

8.94 (2H, doublet, J=8 Hz);
8.72 (1H, singlet);
7.94 (2H, doublet, J=8 Hz);
7.48 (2H, singlet);
7.21–7.06 (3H, multiplet);
2.27 (3H, singlet);
2.24 (3H, singlet).

86(ii) α-(3,4-Dimethylanilino)-α-(4-sulfamoylphenyl)acetonitrile

Following a procedure similar to that described in Example 1(ii), but using 3,4-dimethyl-N-(4-sulfamoylbenzylidene)aniline [prepared as described in step (i) above] and trimethylsilyl cyanide as starting materials, the title compound was obtained as a yellow powder (yield 100%).

Nuclear Magnetic Resonance Spectrum (270 MHz, hexa-deuterated dimethyl sulfoxide) δ ppm:

7.91 (2H, doublet, J=8 Hz);
7.53 (2H, doublet, J=8 Hz);
7.44 (2H, singlet);
6.93 (1H, doublet, J=8 Hz);
6.66 (1H, multiplet);
6.57–6.49 (3H, multiplet);
6.07 (1H, doublet, J=10 Hz);
2.14 (3H, singlet);
2.10 (3H, singlet).

86(iii) 4-Methyl-1-(3,4-dimethylphenyl)-2-(4-sulfamoylphenyl)pyrrole

Following a procedure similar to that described in Example 1(iii), but using α-(3,4-dimethylanilino)-α-(4-sulfamoylphenyl)acetonitrile [prepared as described in step (ii) above] and methacrolein as starting materials, the title compound was obtained as a slightly yellow powder (yield 43%), melting at 118–120° C.

Nuclear Magnetic Resonance Spectrum (270 MHz, $CDCl_3$) δ ppm:

7.82 (2H, doublet, J=8 Hz);
7.19 (2H, doublet, J=8 Hz);
7.05 (1H, doublet, J=8 Hz);
6.97 (1H, singlet);
6.79 (1H, doublet, J=8 Hz);
6.73 (1H, singlet);
6.38 (1H, singlet);
5.02 (2H, singlet);
2.25 (3H, singlet);
2.22 (3H, singlet);
2.17 (3H, singlet).
Mass spectrum (EI) m/z: 340 [M+].

EXAMPLE 87

4-Methyl-2-(3,5-dimethylphenyl)-1-(4-sulfamoylphenyl)pyrrole (Compound No. 2-147)

87(i) N-(3,5-Dimethylbenzylidene)-4-sulfamoylaniline

Following a procedure similar to that described in Example 1(i), but using 3,5-dimethylbenzaldehyde and 4-sulfamoylaniline as starting materials, the title compound was obtained as a pale yellow powder (yield 59%).

Nuclear Magnetic Resonance Spectrum (270 MHz, hexa-deuterated dimethyl sulfoxide) δ ppm:

8.55 (1H, singlet);
7.85 (2H, doublet, J=8 Hz);
7.57 (2H, singlet);
7.37 (4H, doublet, J=8 Hz);
7.22 (1H, singlet);
2.35 (6H, singlet).

87(ii) α-(3,5-Dimethylphenyl)-α-(4-sulfamoylanilino)acetonitrile

Following a procedure similar to that described in Example 1(ii), but using N-(3,5-dimethylbenzylidene)-4-sulfamoylaniline [prepared as described in step (i) above] and trimethylsilyl cyanide as starting materials, the title compound was obtained as a pale yellow powder (yield 90%).

Nuclear Magnetic Resonance Spectrum (270 MHz, hexa-deuterated dimethyl sulfoxide) δ ppm:

7.61 (2H, doublet, J=8 Hz);
7.29 (1H, doublet, J=8 Hz);
7.16 (2H, singlet);

7.04 (3H, singlet);
6.89 (2H, doublet, J=8 Hz);
6.00 (1H, doublet, J=8 Hz);
2.30 (6H, singlet).

87(iii) 4-Methyl-2-(3,5-dimethylphenyl)-1-(4-sulfamoylphenyl)pyrrole

Following a procedure similar to that described in Example 1(iii), but using α-(3,5-dimethylphenyl)-α-(4-sulfamoylanilino)acetonitrile [prepared as described in step (ii) above] and methacrolein as starting materials, the title compound was obtained as a slightly brown powder (yield 28%), melting at 163–166° C.

Nuclear Magnetic Resonance Spectrum (270 MHz, CDCl$_3$) δ ppm:
7.83 (2H, doublet, J=9 Hz);
7.23 (2H, doublet, J=9 Hz);
6.85 (1H, singlet);
6.73 (3H, singlet);
6.27 (1H, doublet, J=2 Hz);
4.85 (2H, singlet);
2.21 (6H, singlet);
2.17 (3H, singlet).
Mass spectrum (EI) m/z: 340 [M$^+$].

EXAMPLE 88

3-Methyl-2-(4-methylthiophenyl)-1-(4-sulfamoylphenyl)pyrrole (Compound No. 2-83)

Following a procedure similar to that described in Example 66(iii), but using crotonaldehyde instead of methacrolein, the title compound was obtained as a pale yellow powder (yield 24%), melting at 132–134° C.

Nuclear Magnetic Resonance Spectrum (270 MHz, CDCl$_3$) δ ppm:
7.81 (2H, doublet, J=9 Hz);
7.18 (2H, doublet, J=4 Hz);
7.15 (2H, doublet, J=4 Hz);
7.00 (2H, doublet, J=9 Hz);
6.89 (1H, doublet, J=3 Hz);
6.26 (1H, doublet, J=3 Hz);
4.78 (2H, singlet);
2.48 (3H, singlet);
2.15 (3H, singlet).
Mass spectrum (EI) m/z: 358 [M$^+$].

EXAMPLE 89

1-(4-Methoxyphenyl)-5-methyl-2-(4-sulfamoylphenyl)pyrrole (Compound No. 1-88)

Following a procedure similar to that described in Example 61(iii), but using methyl vinyl ketone instead of acrolein, the title compound was obtained as a pale yellow powder (yield 39%), melting at 196–197° C.

Nuclear Magnetic Resonance Spectrum (270 MHz, hexa-deuterated dimethyl sulfoxide) δ ppm:
7.56 (2H, doublet, J=7 Hz);
7.22 (2H, singlet);
7.16–7.13 (4H, multiplet);
6.99 (2H, doublet, J=7 Hz);
6.46–6.44 (1H, multiplet);
6.07 (1H, multiplet);
3.33 (3H, singlet);
2.03 (3H, singlet).
Mass spectrum (EI) m/z: 342 [M$^+$].

EXAMPLE 90

5-Methyl-1-(4-methylthiophenyl)-2-(4-sulfamoylphenyl)pyrrole (Compound No. 1-95)

Following a procedure similar to that described in Example 84(iii), but using methyl vinyl ketone instead of methacrolein, the title compound was obtained as a yellow powder (yield 65%), melting at 139–141° C.

Nuclear Magnetic Resonance Spectrum (270 MHz, hexa-deuterated dimethyl sulfoxide) δ ppm:
7.59 (2H, doublet, J=8 Hz);
7.34–7.15 (8H, m, 3 Hz);
6.48 (1H, doublet, J=3 Hz);
6.10 (1H, doublet, J=3 Hz);
2.50 (3H, singlet);
2.07 (3H, singlet).
Mass spectrum (EI) m/z: 358

EXAMPLE 91

1-(4-Chlorophenyl)-5-methyl-2-(4-sulfamoylphenyl)pyrrole (Compound No. 1-98)

Following a procedure similar to that described in Example 59(iii), but using methyl vinyl ketone instead of acrolein, the title compound was obtained as a pale yellow powder (yield 44%), melting at 152–154° C.

Nuclear Magnetic Resonance Spectrum (270 MHz, hexa-deuterated dimethyl sulfoxide) δ ppm:
7.61 (2H, doublet, J=8 Hz);
7.53 (2H, doublet, J=8 Hz);
7.28–7.20 (4H, multiplet);
7.15 (2H, doublet, J=8 Hz);
6.49 (1H, doublet, J=3 Hz);
6.12 (1H, doublet, J=3 Hz);
2.08 (3H, singlet).
Mass spectrum (EI) m/z: 346 [M$^+$].

EXAMPLE 92

1-(4-Methylthiophenyl)-2-(4-sulfamoylphenyl)pyrrole (Compound No. 1-93)

Following a procedure similar to that described in Example 84(iii), but using acrolein instead of methacrolein, the title compound was obtained as a pale yellow powder (yield 15%), melting at 159–161° C.

Nuclear Magnetic Resonance Spectrum (270 MHz, CDCl$_3$) δ ppm:
7.75 (2H, doublet, J=9 Hz);
7.26–7.21 (4H, multiplet);
7.10–7.07 (2H, multiplet);
6.97–6.95 (1H, multiplet);
6.55 (1H, doublet of doublets, J=4 & 2 Hz);
6.39 (1H, triplet, J=4 Hz);
4.82 (2H, singlet);
2.50 (3H, singlet).
Mass spectrum (EI) m/z: 344 [M$^+$].

EXAMPLE 93

1-(2,4-Dichlorophenyl)-2-(4-sulfamoylphenyl)pyrrole (Compound No. 1-127)

Following a procedure similar to that described in the three stages of Examples 19(i), 19(ii) and 19(iii), but using 2,4-dichloroaniline as a starting material instead of 4-fluoroaniline, the title compound was obtained as a white powder, melting at 147–149° C. The total yield of the compound over the three stages was 15%.

Nuclear Magnetic Resonance Spectrum (270 MHz, CDCl$_3$) δ ppm:

7.79 (2H, doublet, J=9 Hz);
7.42–7.36 (2H, multiplet);
7.26–7.23 (2H, multiplet);
6.96–6.90 (2H, multiplet);
6.50 (1H, doublet of doublets, J=3 & 1 Hz);
6.40 (1H, triplet, J=3 Hz);
4.87 (2H, singlet).
Mass spectrum (EI) m/z: 366 [M$^+$].

EXAMPLE 94

1-(4-Ethoxyphenyl)-2-(4-sulfamoylphenyl)pyrrole (Compound No. 1-89)

Following a procedure similar to that described in the three stages of Examples 19(i), 19(ii) and 19(iii), but using 4-ethoxyaniline as a starting material instead of 4-fluoroaniline, the title compound was obtained as a white powder, melting at 126–128° C. The total yield of the compound over the three stages was 16%.

Nuclear Magnetic Resonance Spectrum (270 MHz, hexadeuterated dimethyl sulfoxide) δ ppm:

7.65 (2H, doublet, J=8 Hz);
7.30–7.22 (4H, multiplet);
7.14–7.06 (3H, multiplet);
6.96 (2H, doublet, J=9 Hz);
6.56 (1H, doublet of doublets, J=3 & 1 Hz);
6.32 (1H, triplet, J=3 Hz);
4.04 (2H, quartet, J=7 Hz);
1.33 (3H, triplet, J=7 Hz).

EXAMPLE 95

4-Methyl-2-(4-methylsulfinylphenyl)-1-(4-sulfamoylphenyl)pyrrole (Compound No. 2-151)

0.35 g (1.0 mmol) of 4-methyl-2-(4-methylthiophenyl)-1-(4-sulfamoylphenyl)pyrrole (prepared as described in Example 66) was dissolved in 50 ml of chloroform, and 0.27 g (1.1 mmol) of 70% m-chloroperbenzoic acid was added to the resulting solution in several portions, whilst ice-cooling, after which the mixture was stirred for 1 hour, whilst ice-cooling. The reaction mixture was then diluted with chloroform and was washed with a 10% w/v aqueous solution of sodium thiosulfate and with a saturated aqueous solution of sodium hydrogencarbonate twice each, in that order. The organic layer was then dried over anhydrous magnesium sulfate, and the solvent was removed by distillation under reduced pressure. The residue thus obtained was applied to a silica gel chromatography column and eluted with a 95:5 by volume mixture of methylene chloride and methanol, to give 0.23 g (yield 63%) of the title compound as a pale orange-colored powder, melting at 222–226° C.

Nuclear Magnetic Resonance Spectrum (270 MHz, CDCl$_3$) δ ppm:

7.88 (2H, doublet, J=9 Hz);
7.52 (2H, doublet, J=8 Hz);
7.26 (2H, doublet, J=3 Hz);
7.25 (2H, doublet, J=3 Hz);
6.79 (1H, singlet);
6.39 (1H, doublet, J=2 Hz);
4.90 (2H, singlet);
2.74 (3H, singlet);
2.22 (3H, singlet).
Mass spectrum (EI) m/z: 374 [M$^+$].

EXAMPLE 96

4-Methyl-1-(4-methylsulfinylphenyl)-2-(4-sulfamoylphenyl)pyrrole (Compound No. 1-153)

4-Methyl-1-(4-methylthiophenyl)-2-(4-sulfamoylphenyl) pyrrole (prepared as described in Example 84) was oxidised in the same manner as described in Example 95, to give the title compound as a white powder (yield 84%), melting at 249–251° C.

Nuclear Magnetic Resonance Spectrum (270 MHz, hexadeuterated dimethyl sulfoxide) δ ppm:

7.73–7.66 (4H, multiplet);
7.37–7.31 (4H, multiplet);
7.23 (2H, doublet, J=8 Hz);
7.00 (1H, multiplet);
6.46 (1H, multiplet);
2.78 (3H, singlet);
2.12 (3H, singlet).
Mass spectrum (EI) m/z: 374 [M$^+$].

EXAMPLE 97

5-Chloro-1-(4-methoxyphenyl)-2-(4-sulfamoylphenyl)pyrrole (Compound No. 1-147)

1-(4-Methoxyphenyl)-2-(4-sulfamoylphenyl)pyrrole (prepared as described in Example 61) was chlorinated in the same manner as described in Example 37, to give the title compound as a pale yellow powder (yield 80%), melting at 119–120° C.

Nuclear Magnetic Resonance Spectrum (270 MHz, CDCl$_3$) δ ppm:

7.69 (2H, doublet, J=8 Hz);
7.17 (2H, doublet, J=8 Hz);
7.11 (2H, doublet, J=9 Hz);
6.92 (2H, doublet, J=9 Hz);
6.50 (1H, doublet, J=4 Hz);
6.29 (1H, doublet, J=4 Hz);
4.82 (2H, singlet);
3.85 (3H, singlet).
Mass spectrum (EI) m/z: 362 [M$^+$].

EXAMPLE 98

5-Bromo-1-(4-methoxyphenyl)-2-(4-sulfamoylphenyl)pyrrole (Compound No.1-148)

1-(4-Methoxyphenyl)-2-(4-sulfamoylphenyl)pyrrole (prepared as described in Example 61) was brominated in the same manner as described in Example 35, to give the title compound as a pale yellow powder (yield 76%), melting at 121–123° C.

Nuclear Magnetic Resonance Spectrum (270 MHz, hexadeuterated dimethyl sulfoxide) δ ppm:

7.62 (2H, doublet, J=8 Hz);

7.28–7.17 (6H, multiplet);
7.02 (2H, doublet, J=9 Hz);
6.63 (1H, doublet, J=4 Hz);
6.48 (1H, doublet, J=4 Hz);
3.80 (3H, singlet).
Mass spectrum (EI) m/z: 406 [M⁺].

EXAMPLE 99

5-Chloro-1-(4-methoxyphenyl)-4-methyl-2-(4-sulfamoylphenyl)pyrrole (Compound No. 1-149)

1-(4-Methoxyphenyl)-4-methyl-2-(4-sulfamoylphenyl)pyrrole (prepared as described in Example 62) was chlorinated in the same manner as described in Example 37, to give the title compound as a pale yellow powder (yield 80%), melting at 155–156° C.

Nuclear Magnetic Resonance Spectrum (270 MHz, CDCl₃) δ ppm:
7.67 (2H, doublet, J=9 Hz);
7.16–7.06 (4H, multiplet);
6.90 (2H, doublet, J=9 Hz);
6.40 (1H, singlet);
4.94 (2H, singlet);
3.84 (3H, singlet);
2.14 (3H, singlet).
Mass spectrum (EI) m/z: 376 [M⁺].

EXAMPLE 100

5-Chloro-1-(4-ethoxyphenyl)-2-(4-sulfamoylphenyl)pyrrole (Compound No. 1-151)

1-(4-Ethoxyphenyl)-2-(4-sulfamoylphenyl)pyrrole (prepared as described in Example 94) was chlorinated in the same manner as described in Example 37, to give the title compound as a white powder (yield 93%), melting at 124–125° C.

Nuclear Magnetic Resonance Spectrum (270 MHz, CDCl₃) δ ppm:
7.70 (2H, doublet, J=9 Hz);
7.11–7.07 (4H, multiplet);
6.90 (2H, doublet, J=9 Hz);
6.50 (1H, doublet, J=4 Hz);
6.29 (1H, doublet, J=4 Hz);
4.75 (2H, singlet);
4.06 (2H, quartet, J=7 Hz);
1.45 (3H, triplet, J=7 Hz).
Mass spectrum (EI) m/z: 376 [M⁺].

EXAMPLE 101

5-Chloro-1-(4-methylthiophenyl)-2-(4-sulfamoylphenyl)pyrrole (Compound No 1-152)

1-(4-Methylthiophenyl)-2-(4-sulfamoylphenyl)pyrrole (prepared as described in Example 92) was chlorinated in the same manner as described in Example 37, to give the title compound as a white powder (yield 68%), melting at 141–142° C.

Nuclear Magnetic Resonance Spectrum (270 MHz, CDCl₃) δ ppm:
7.71 (2H, doublet, J=9 Hz);
7.26–7.07 (6H, multiplet);
6.50 (1H, doublet, J 4 Hz);
6.31 (1H, doublet, J=4 Hz);
4.78 (2H, singlet);
2.52 (3H, singlet).
Mass spectrum (EI) m/z: 378 [M⁺].

EXAMPLE 102

5-Chloro-1-(2,4-dichlorophenyl)-2-(4-sulfamoylphenyl)pyrrole (Compound No. 1-155)

1-(2,4-Dichlorophenyl)-2-(4-sulfamoylphenyl)pyrrole (prepared as described in Example 93) was chlorinated in the same manner as described in Example 37, to give the title compound as a white powder (yield 73%), melting at 186–187° C.

Nuclear Magnetic Resonance Spectrum (270 MHz, hexadeuterated dimethyl sulfoxide) δ ppm:
7.78–7.67 (4H, multiplet);
7.32–7.25 (5H, multiplet);
6.63 (1H, doublet, J=4 Hz);
6.48 (1H, doublet, J=4 Hz).
Mass spectrum (EI) m/z: 400 [M⁺].

EXAMPLES 103–111

A procedure similar to that described in Example 19, steps (i) and (ii) was repeated, but using 4-sulfamoylbenzaldehyde and various kinds of anilines as starting materials, to give the corresponding α-anilino-α-(4-sulfamoylphenyl)acetonitriles, which were then reacted in the same manner as described in Example 18, to give the compounds having the following formula:

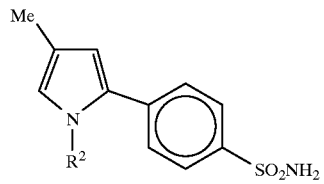

in which R² has the various meanings shown in Table 12. The abbreviations used in Tables 12 and 13 for substituent groups are as given above for Tables 1 and 2, and the abbreviation "m.p." means "melting point".

TABLE 12

| Example | Cpd. No. | R² | appearance | m.p.(° C.) |
|---|---|---|---|---|
| 103 | 1-131 | 3,4-diCl—Ph | white powder | 127–129 |
| 104 | 1-159 | 4-EtO—Ph | pale yellow powder | 122–123 |
| 105 | 1-113 | 3-F-4-MeO—Ph | pale yellow powder | 116–117 |
| 106 | 1-109 | 3-Cl-4-MeO—Ph | slightly green powder | 132–134 |
| 107 | 1-71 | Ph | white powder | 91–93 |
| 108 | 1-103 | 3-Cl-4-F—Ph | white powder | 142–144 |
| 109 | 1-106 | 3,4-methylenedioxy-Ph | slightly brown powder | 147–149 |
| 110 | 1-146 | 2,4,6-triMe-Ph | pale yellow powder | 125–126 |
| 111 | 1-150 | 4-Cl-2-F—Ph | white powder | 161–162 |

EXAMPLES 112–128

A procedure similar to that described in Example 13, steps (i) and (ii) was repeated, using 4-sulfamoylaniline and various kinds of benzaldehydes as starting materials, to give α-phenyl-α-(4-sulfamoylanilino)acetonitriles, which were then reacted in the same manner as described in Example 15, to give the compounds having the following formula:

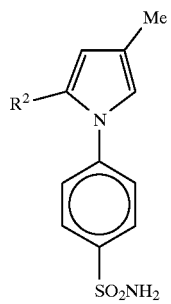

in which R² has the various meanings shown in Table 13.

TABLE 13

| Example | Cpd. No. | R² | appearance | m.p.(° C.) |
|---|---|---|---|---|
| 112 | 2-91 | 4-Et-Ph | slightly brown powder | 121–126 |
| 113 | 2-93 | 4-iPr—Ph | slightly brown powder | 135–139 |
| 114 | 2-102 | 4-CF₃—Ph | pale yellow powder | 180–185 |
| 115 | 2-95 | 3-Cl-4-F—Ph | pale yellow powder | 155–157 |
| 116 | 2-103 | 4-CHF₂O—Ph | greyish white powder | 137–140 |
| 117 | 2-104 | 4-CF₃O—Ph | white powder | 188–189 |
| 118 | 2-121 | 2,4-diCl—Ph | slightly brown powder | 197–199 |
| 119 | 2-138 | 2,3-diCl—Ph | slightly brown powder | 167–170 |
| 120 | 2-137 | 4-MeO-3,5-diMe-Ph | slightly green amorphous | — |
| 121 | 2-139 | 3,5-diCl—Ph | slightly brown powder | 157–159 |
| 122 | 2-140 | 2,4,5-triMe-Ph | orange-colored powder | 114–115 |
| 123 | 2-141 | 3-cPnO-4-MeO—Ph | slightly brown powder | 147–149 |
| 124 | 2-142 | 4-Cl-3-CF₃—Ph | slightly brown amorphous | — |
| 125 | 2-143 | 3-F-4-Me-Ph | pale yellow powder | 171–178 |
| 126 | 2-144 | 4-Cl-3-Me-Ph | pale yellow powder | 166–168 |
| 127 | 2-145 | 2,4-diMe-Ph | yellow powder | 178–182 |
| 128 | 2-146 | 4-OH—Ph | pale brown amorphous | — |

EXAMPLE 129

1-(4-Mercaptophenyl)-4-methyl-2-(4-sulfamoylphenyl)pyrrole (Compound No. 1-156)

129(i) Bis(4-aminophenyl) disulfide 7.42 g (40 mmol) of 4-acetamidothiophenol were dissolved in 100 ml of methylene chloride, and 40 ml (40 mmol) of a 10% w/v aqueous potassium hydrogencarbonate solution was added to the resulting solution. 3.20 g (20 mmol) of bromine were then slowly added dropwise to the mixture, whilst stirring and ice-cooling. The mixture was stirred at room temperature for 15 minutes, and then the resulting white precipitate was collected by filtration and washed with water, to give bis(4-acetamidophenyl) disulfide as a white powder.

The whole of this product was then dissolved in 100 ml of ethanol, and 50 ml of concentrated aqueous hydrochloric acid were added to the resulting solution. The mixture was then stirred at 80° C. for 6 hours. At the end of this time, the reaction solution was concentrated by evaporation under reduced pressure, and the residue was dissolved in 200 ml of water. The pH of the mixture was then adjusted to a value of at least 9 by the addition of a 1N w/v aqueous solution of sodium hydroxide. The resulting yellow precipitate was collected by filtration and washed with water, to give 3.92 g (yield 39%) of the title compound as a yellow powder, melting at 75–77° C.

Mass spectrum (EI) m/z: 248 [M⁺].

129(ii) Bis[4-(4-sulfamoylbenzylideneamino)phenyl] disulfide

Following a procedure similar to that described in Example 1(i), but using bis(4-aminophenyl) disulfide [prepared as described in step (i) above] and 4-sulfamoylbenzaldehyde as starting materials, the title compound was obtained as a slightly yellow powder (yield 58%), melting at 200–230° C.

129(iii) Bis[4-(α-cyano-4-sulfamoylbenzylamino)phenyl] disulfide

Following a procedure similar to that described in Example 1(ii), but using bis[4-(4-sulfamoylbenzylideneamino)phenyl] disulfide [prepared as described in step (ii) above] and trimethylsilyl cyanide as starting materials, the title compound was obtained as a yellow amorphous powder (yield 92%).

Nuclear Magnetic Resonance Spectrum (400 MHz, hexa-deuterated dimethyl sulfoxide) δ ppm:

7.95–7.91 (2H, multiplet);
7.75 (2H, doublet, J=8 Hz);
7.45 (2H, singlet);
7.31 (2H, doublet, J=8 Hz);
7.19 (1H, doublet, J=9 Hz);
6.82–6.79 (2H, multiplet);
6.19 (1H, doublet, J=9 Hz).

Mass spectrum (FAB) m/z: 636 [M⁺].

129(iv) Bis {4-[4-methyl-2-(4-sulfamoylphenyl)pyrrol-1-yl]phenyl} disulfide

Following a procedure similar to that described in Example 1(iii), but using bis[4-(α-cyano-4-sulfamoylbenzylamino)phenyl] disulfide [prepared as described in step (iii) above] and methacrolein as starting materials, the title compound was obtained as a pale yellow powder (yield 42%), melting at 251–255° C.

Nuclear Magnetic Resonance Spectrum (270 MHz, CDCl₃) δ ppm:

7.73 (4H, doublet, J=9 Hz);
7.46 (4H, doublet, J=9 Hz);
7.18 (4H, doublet, J=9 Hz);
7.10 (4H, doublet, J=9 Hz);
6.75 (2H, singlet);
6.46 (4H, singlet);
6.35 (2H, singlet);
2.16 (6H, singlet).

Mass spectrum (FAB) m/z: 686 [M⁺].

129(v) 1-(4-Mercaptophenyl)-4-methyl-2-(4-sulfamoylphenyl)pyrrole 1.00 g (1.5 mmol) of bis{4-[4-methyl-2-(4-sulfamoylphenyl)pyrrol-1-yl]-phenyl} disulfide [prepared as described in step (iv) above] was dissolved in a mixture of 40 ml of tetrahydrofuran and 10 ml of methanol, and 55 mg (1.5 mmol) of sodium borohydride was added to the resulting solution. The mixture was then stirred at room temperature for 15 minutes, after which 5% w/v aqueous sulfuric acid was added to acidify the mixture, followed by 25 ml of water. The resulting mixture was then extracted with ethyl acetate. The organic extract was washed with water and dried over anhydrous magnesium sulfate. The solvent was then removed by distillation under reduced pressure, to give 1.07 g (yield 100%) of the title compound as a pale yellow amorphous powder.

Nuclear Magnetic Resonance Spectrum (270 MHz, CDCl₃) δ ppm:

7.74 (2H, doublet, J=9 Hz);
7.24 (2H, doublet, J=9 Hz);
7.21 (2H, doublet, J=9 Hz);
6.98 (2H, doublet, J=9 Hz);
6.73 (1H, singlet);
6.40 (1H, singlet);
4.76 (2H, singlet);
3.50 (1H, singlet);
2.17 (3H, singlet).
Mass spectrum (EI) m/z: 344 [M⁺].

EXAMPLE 130

1-(4-Acetylthiophenyl)-4-methyl-2-(4-sulfamoylphenyl)pyrrole (Compound No. 1-157)

0.90 g (2.6 mmol) of 1-(4-mercaptophenyl)-4-methyl-2-(4-sulfamoylphenyl)-pyrrole (prepared as described in Example 129) was dissolved in 15 ml of tetrahydrofuran, and 0.27 ml (2.9 mmol) of acetic anhydride was added to the resulting solution. 0.53 ml (6.5 mmol) of pyridine was then added to the mixture, which was then stirred at room temperature overnight. The reaction mixture was then concentrated by evaporation under reduced pressure, and a saturated aqueous solution of sodium hydrogencarbonate was added to the residue. The resulting mixture was then extracted with ethyl acetate. The organic extract was washed with water and dried over anhydrous magnesium sulfate, after which it was concentrated by evaporation under reduced pressure. The residue thus obtained was applied to a silica gel chromatography column and eluted with a 3:2 by volume mixture of hexane and ethyl acetate, to give 0.44 g (yield 43%) of the title compound as a white powder, melting at 149–152° C.

Nuclear Magnetic Resonance Spectrum (270 MHz, CDCl₃) δ ppm:

7.75 (2H, doublet, J=9 Hz);
7.38 (2H, doublet, J=9 Hz);
7.22 (2H, doublet, J=9 Hz);
7.16 (2H, doublet, J=9 Hz);
6.80 (1H, singlet);
6.41 (1H, singlet);
4.78 (2H, singlet);
2.44 (3H, singlet);
2.18 (3H, singlet).
Mass spectrum (FAB) m/z: 386 [M⁺].

We claim:

1. A compound of formula (I) or (II):

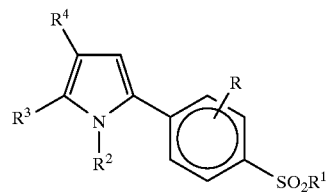

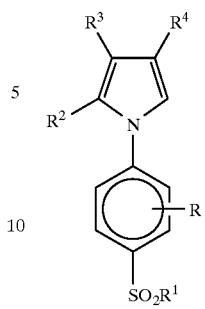

wherein:
R represents a hydrogen atom, a halogen atom or an alkyl group having from 1 to 6 carbon atoms;
$R^1$ represents an alkyl group having from 1 to 6 carbon atoms, an amino group or a group of formula —NHR$^a$, where R$^a$ represents an alkanoyl group having from 1 to 25 carbon atoms, an alkoxycarbonyl group having from 1 to 6 carbon atoms in the alkoxy part, an aralkyloxycarbonyl group in which the aralkyl part is as defined below, an alkanoyloxymethyl group having from 1 to 6 carbon atoms in the alkanoyl part, an alkoxycarbonyloxymethyl group having from 1 to 6 carbon atoms in the alkoxy part or a (2-oxo-1,3-dioxolen-4-yl)methyl group which is unsubstituted or substituted at the 5-dioxolen position by an alkyl group having from 1 to 6 carbon atoms or by an aryl group as defined below;
$R^2$ represents a phenyl group which is unsubstituted or is substituted by at least one substituent selected from the group consisting of substituents α and substituents β defined below;
$R^3$ represents a hydrogen atom, a halogen atom or an alkyl group which has from 1 to 6 carbon atoms and which is unsubstituted or is substituted by at least one substituent selected from the group consisting of a hydroxy group, a halogen atom, an alkoxy group having from 1 to 6 carbon atoms and an alkylthio group having from 1 to 6 carbon atoms;
$R^4$ represents a hydrogen atom; an alkyl group which has from 1 to 6 carbon atoms and which is unsubstituted or is substituted by at least one substituent selected from the group consisting of a hydroxy group, a halogen atom, an alkoxy group having from 1 to 6 carbon atoms and an alkylthio group having from 1 to 6 carbon atoms; a cycloalkyl group having from 3 to 8 carbon atoms, an aryl group which is as defined below, or an aralkyl group which is as defined below;
said aryl group having from 6 to 14 ring carbon atoms in a carbocyclic ring and are unsubstituted or are substituted by at least one substituent selected from the group consisting of substituents α and substituents β, defined below;
said aralkyl group and the aralkyl part of said aralkyloxycarbonyl group are an alkyl group having from 1 to 6 carbon atoms and which are substituted by at least one aryl group as defined above;
said substituents α are selected from the group consisting of a hydroxy group, a halogen atom, an alkoxy group having from 1 to 6 carbon atoms and an alkylthio group having from 1 to 6 carbon atoms; said substituents β are selected from the group consisting of an alkyl group which has from 1 to 6 carbon atoms and which is unsubstituted or are substituted by at least one substituent selected from the group consisting of a hydroxy group, a halogen atom, an alkoxy group having from 1 to 6 carbon atoms and an alkythio group having from 1 to 6 carbon atoms; an alkanoyloxy group having from 1 to 6 carbon atoms; a mercapto group; an alkanoylthio group having from 1 to 6 carbon atoms; an alkylsulfinyl group having from 1 to 6 carbon atoms; a cycloalkyloxy group having from 3 to 8 carbon atoms; a haloalkoxy group having from 1 to 6 carbon atoms; and an alkylenedioxy group having from 1 to 6 carbon atoms;

or a pharmaceutically acceptable salt thereof.

2. The compound of claim 1, wherein R represents a hydrogen atom, a halogen atom or an alkyl group having from 1 to 4 carbon atoms.

3. The compound of claim 1, wherein R represents a hydrogen atom, a fluorine atom, a chlorine atom or a methyl group.

4. The compound of claim 1, wherein R represents a hydrogen atom.

5. The compound of claim 1, wherein $R^1$ represents a methyl group, an amino group or an acetylamino group.

6. The compound of claim 1, wherein $R^1$ represents an amino group or an acetylamino group.

7. The compound of claim 1, wherein $R^2$ represents a phenyl group or a phenyl group which is substituted by at least one substituent selected from the group consisting of a halogen atom; an alkoxy group having from 1 to 4 carbon atoms; an alkylthio group having from 1 to 4 carbon atoms;

an unsubstituted alkyl group having from 1 to 4 carbon atoms; an alkyl group which has from 1 to 4 carbon atoms and which is substituted by at least one substituent selected from the group consisting of a halogen atom, an alkoxy group having from 1 to 4 carbon atoms and an alkylthio group having from 1 to 4 carbon atoms; a mercapto group; an alkanoylthio group having from 1 to 4 carbon atoms; a haloalkoxy group having from 1 to 4 carbon atoms and an alkylenedioxy group having from 1 to 4 carbon atoms.

8. The compound of claim 1, wherein $R^2$ represents a phenyl group or a phenyl group which is substituted by at least one substituent selected from the group consisting of a halogen atom, an alkoxy group having from 1 to 4 carbon atoms, an alkylthio group having from 1 to 4 carbon atoms, an alkyl group having from 1 to 4 carbon atoms, a haloalkyl group having from 1 to 4 carbon atoms, a mercapto group, an alkanoylthio group having from 1 to 4 carbon atoms, a haloalkoxy group having from 1 to 4 carbon atoms and an alkylenedioxy group having from 1 to 4 carbon atoms.

9. The compound of claim 1, wherein $R^3$ represents a hydrogen atom, a halogen atom, an unsubstituted alkyl group having from 1 to 4 carbon atoms or a substituted alkyl group having from 1 to 4 carbon atoms and substituted by at least one substituent selected from the group consisting of a halogen atom, an alkoxy group having from 1 to 4 carbon atoms, an alkylthio group having from 1 to 4 carbon atoms.

10. The compound of claim 1, wherein $R^3$ represents a hydrogen atom, a halogen atom, an alkyl group having from 1 to 4 carbon atoms or a haloalkyl group having from 1 to 4 carbon atoms.

11. The compound of claim 1, wherein $R^4$ represents a hydrogen atom; an unsubstituted alkyl group having from 1 to 4 carbon atoms; a substituted alkyl group having from 1 to 4 carbon atoms and substituted by at least one substituent selected from the group consisting of a hydroxy group, a halogen atom, an alkoxy group having from 1 to 6 carbon atoms and an alkylthio group having from 1 to 6 carbon atoms; a cycloalkyl group having from 3 to 6 carbon atoms; an aryl group which has from 6 to 10 ring carbon atoms and which is unsubstituted or is substituted by at least one substituent selected from the group consisting of a halogen atom, an alkoxy group having from 1 to 4 carbon atoms, an alkylthio group having from 1 to 4 carbon atoms, an unsubstituted alkyl group having from 1 to 6 carbon atoms, an alkyl group having from 1 to 6 carbon atoms and substituted by at least one substituent selected from the group consisting of a hydroxy group, a halogen atom, an alkoxy having from 1 to 6 carbon atoms, and an alkylthio group having from 1 to 6 carbon atoms; a cycloalkyloxy group having from 3 to 8 carbon atoms; and an aralkyl group having from 1 to 4 carbon atoms in the alkyl part and containing at least one aryl group as defined in claim 1.

12. The compound of claim 1, wherein $R^4$ represents a hydrogen atom; an unsubstituted alkyl group having from 1 to 4 carbon atoms; a substituted alkyl group having from 1 to 4 carbon atoms and substituted by at least one substituent selected from the group consisting of a hydroxy group, a halogen atom and an alkoxy group having from 1 to 6 carbon atoms; a cycloalkyl group having from 3 to 6 carbon atoms; an aryl group which has from 6 to 10 ring carbon atoms and which is unsubstituted or is substituted by at least one substituent selected from the group consisting of a hydroxy group, a halogen atom, an alkoxy group having from 1 to 6 carbon atoms, an alkyl group having from 1 to 6 carbon atoms and which is unsubstituted or substituted by at least one halogen atom and a cycloalkyloxy group having from 3 to 8 carbon atoms; and an aralkyl group having from 1 to 4 carbon atoms, in the alkyl part and containing at least one said aryl group.

13. The compound of claim 1, wherein:

R represents a hydrogen atom, a halogen atom or an alkyl group having from 1 to 4 carbon atoms;

$R^1$ represents a methyl group, an amino group or an acetylamino group;

$R^2$ represents an unsubstituted phenyl group or a phenyl group which is substituted by at least one substituent selected from the group consisting of a halogen atom: an alkoxy group having from 1 to 4 carbon atoms; an alkylthio group having from 1 to 4 carbon atoms; an unsubstituted alkyl group having from 1 to 4 carbon atoms; an alkyl group having from 1 to 4 carbon atoms which is substituted by at least one substituent selected from the group consisting of a halogen atom, an alkoxy group having from 1 to 4 carbon atoms and an alkylthio group having from 1 to 4 carbon atoms; a mercapto group; an alkanoyl group having from 1 to 4 carbon atoms; a haloalkyl group having from 1 to 4 carbon atoms; and an alkylenedioxy group having from 1 to 4 carbon atoms;

$R^3$ represents a hydrogen atom, a halogen atom, an unsubstituted alkyl group having from 1 to 4 carbon atoms or a substituted alkyl group having from 1 to 4 carbon atoms and substituted by at least one substituent selected from the group consisting of a halogen atom, an alkoxy group having from 1 to 4 carbon atoms and an alkylthio group having from 1 to 4 carbon atoms;

$R^4$ represents a hydrogen atom;

an unsubstituted alkyl group having from 1 to 4 carbon atoms;

a substituted alkyl group having from 1 to 4 carbon atoms and substituted by at least one substituent selected from the group consisting of a hydroxy group, a halogen atom, an alkoxy group having from 1 to 6 carbon atoms and an alkylthio group having from 1 to 6 carbon atoms;

a cycloalkyl group having from 3 to 6 carbon atoms;

an aryl group which has from 6 to 10 ring carbon atoms and which is unsubstituted or is substituted by at least one substituent selected from the group consisting of a halogen atom; an alkoxy group having from 1 to 4 carbon atoms; an alkylthio group having from 1 to 4 carbon atoms; an unsubstituted alkyl group having from 1 to 6 carbon atoms; an alkyl group having from 1 to 6 carbon atoms and substituted by at least one substituent selected from the group consisting of a halogen atom, an alkoxy group having 1 to 4 carbon atoms and an alkylthio group having 1 to 4 carbon atoms; and a cycloalkoxy group having 3 to 8 carbon atoms; and an aralkyl group having from 1 to 4 carbon atoms in the alkyl part and containing at least one said aryl group.

14. The compound of claim 1, wherein

R represents a hydrogen atom, a fluorine atom, a chlorine atom or a methyl group;

$R^1$ represents an amino group or an acetylamino group;

$R^2$ represents an unsubstituted phenyl group or a phenyl group which is substituted by at least one substituent selected from the group consisting of a halogen atom, an alkoxy group having from 1 to 4 carbon atoms, an alkylthio group having 1 to 4 carbon atoms, an alkyl group having from 1 to 4 carbon atoms, a haloalkyl group having from 1 to 4 carbon atoms, a mercapto group, an alkanoylthio group having from 1 to 4 carbon atoms, a haloalkoxy group having from 1 to 4 carbon atoms and an alkylenedioxy group having from 1 to 4 carbon atoms;

$R^3$ represents a hydrogen atom, a halogen atom, an alkyl group having from 1 to 4 carbon atoms or a haloalkyl group having from 1 to 4 carbon atoms;

$R^4$ represents a hydrogen atom; an unsubstituted alkyl group having from 1 to 4 carbon atoms; a substituted alkyl group having from 1 to 4 carbon atoms and substituted by at least one substituent selected from the group consisting of a hydroxy group, a halogen atom and alkoxy group having from 1 to 6 carbon atoms; a cycloalkyl group having from 3 to 6 carbon atoms, an aryl group which has from 6 to 10 ring carbon atoms and which is unsubstituted or is substituted by at lest one substituent selected from the group consisting of a hydroxy group, a halogen atom, an alkoxy group having from 1 to 6 carbon atoms, an alkyl group having from 1 to 6 carbon atoms and which is unsubstituted or substituted by at least one halogen atom, and a cycloalkyloxy group having from 3 to 8 carbon atoms; and an aralkyl group having from 1 to 4 carbon atoms in the alkyl part and containing at least one said aryl group.

15. The compound of claim 1, wherein:

R represents a hydrogen atom;

$R^1$ represents an amino group or an acetylamino group;

$R^2$ represents an unsubstituted phenyl group or a phenyl group which is substituted by at least one substituent selected from the group consisting of a halogen atom, an alkoxy group having from 1 to 4 carbon atoms, an alkylthio group having from 1 to 4 carbon atoms, an alkyl group having from 1 to 4 carbon atoms, a haloalkyl group having from 1 to 4 carbon atoms, a mercapto group, an alkanoylthio group having from 1 to 4 carbon atoms, a haloalkoxy group having from 1 to 4 carbon atoms and an alkylenedioxy group having from 1 to 4 carbon atoms;

$R^3$ represents a hydrogen atom, a halogen atom, an alkyl group having from 1 to 4 carbon atoms or a haloalkyl group having from 1 to 4 carbon atoms;

$R^4$ represents a hydrogen atom;

an unsubstituted alkyl group having from 1 to 4 carbon atoms;

a substituted alkyl group having from 1 to 4 carbon atoms and substituted by at least one substituent selected from the group consisting of a hydroxy group, a halogen atom and an alkoxy group having from 1 to 6 carbon atoms;

a cycloalkyl group having from 3 to 6 carbon atoms;

an aryl group which has from 6 to 10 ring carbon atoms and which is unsubstituted or is substituted by at least one substituent selected from the group consisting of a hydroxy group, a halogen atom, an alkoxy group having from 1 to 6 carbon atoms, an alkyl group having from 1 to 6 carbon atoms and which is unsubstituted or substituted by at least one halogen atom, and a cycloalkyloxy group having from 3 to 8 carbon atoms; and an aralkyl group having from 1 to 4 carbon atoms in the alkyl part and containing at least one said aryl group.

16. The compound of claim 1, which is 4-methyl-2-(4-methylphenyl)-1-(4-sulfamoylphenyl)pyrrole.

17. The compound of claim 1, which is 2-(4-methoxyphenyl)-4-methyl-1-(4-sulfamoylphenyl)pyrrole.

18. The compound of claim 1, which is 2-(4-chlorophenyl)-4-methyl-1-(4-sulfamoylphenyl)pyrrole.

19. The compound of claim 1, which is 4-methyl-2-(4-methylthiophenyl)-1-(4-sulfamoylphenyl)pyrrole.

20. The compound of claim 1, which is 2-(4-ethoxyphenyl)-4-methyl-1-(4-sulfamoylphenyl)pyrrole.

21. The compound of claim 1, which is 2-(4-methoxy-3-methylphenyl)-4-methyl-1-(4-sulfamoylphenyl)pyrrole.

22. The compound of claim 1, which is 2-(3-fluoro-4-methoxyphenyl)-4-methyl-1-(4-sulfamoylphenyl)pyrrole.

23. The compound of claim 1, which is 2-(3,4-dimethylphenyl)-4-methyl-1-(4-sulfamoylphenyl)pyrrole.

24. The compound of claim 1, which is 4-methyl-1-(4-methylthiophenyl)-2-(4-sulfamoylphenyl)pyrrole.

25. The compound of claim 1, which is 1-(4-acetylaminosulfonylphenyl)-4-methyl-2-(4-methoxyphenyl)pyrrole.

26. The compound of claim 1, which is 1-(4-acetylaminosulfonylphenyl)-4-methyl-2-(3,4-dimethylphenyl)pyrrole.

27. A method of treating or relieving pain or inflammation in a mammal suffering comprising administering to a mammal in need thereof an effective anti-inflammatory amount or effective analgesic amount of a compound selected from the group consisting of the compound of formula (I), the compound of formula (II), and a pharmaceutically acceptable salt of said compounds as claimed in claim 1.

28. The method of claim 27, wherein:

R represents a hydrogen atom, a halogen atom or an alkyl group having from 1 to 4 carbon atoms;

$R^1$ represents a methyl group, an amino group or an acetylamino group;

R² represents an unsubstituted phenyl group or;

a phenyl group which is substituted by at least one substituent selected from the group consisting of a halogen atom; an alkoxy group having from 1 to 4 carbon atoms; an alkylthio group having from 1 to 4 carbon atoms; an unsubstituted alkyl group having from 1 to 4 carbon atoms; an alkyl group having from 1 to 4 carbon atoms and which is substituted by at least one substituent selected from the group consisting of a halogen atom, an alkoxy group having from 1 to 4 carbon atoms and an alkylthio group having from 1 to 4 carbon atoms; a mercapto group; an alkanoylthio group having from 1 to 4 carbon atoms; a haloalkoxy group having from 1 to 4 carbon atoms; and an alkylenedioxy group having from 1 to 4 carbon atoms;

R³ represents a hydrogen atom, a halogen atom, an unsubstituted alkyl group having from 1 to 4 carbon atoms or a substituted alkyl group having from 1 to 4 carbon atoms and substituted by at least one substituent selected from the group consisting of a halogen atom, an alkoxy group having from 1 to 4 carbon atoms and an alkylthio group having from 1 to 4 carbon atoms;

R⁴ represents a hydrogen atom;

an unsubstituted alkyl group having from 1 to 4 carbon atoms;

a substituted alkyl group having from 1 to 4 carbon atoms and substituted by at least one substituent selected from the group consisting of a hydroxy group, a halogen atom, an alkoxy group having from 1 to 6 carbon atoms and an alkylthio group having from 1 to 6 carbon atoms;

a cycloalkyl group having from 3 to 6 carbon atoms;

an aryl group which has from 6 to 10 ring carbon atoms and which is unsubstituted or is substituted by at least one substituent selected from the group consisting of a halogen atom; an alkoxy group having from 1 to 4 carbon atoms; an alkylthio group having from 1 to 4 carbon atoms; an unsubstituted alkyl group having from 1 to 3 carbon atoms; an alkyl group having from 1 to 3 carbon atoms and substituted by at least one substituent selected from the group consisting of a hydroxy group, a halogen atom, an alkoxy group having from 1 to 6 carbon atoms and an alkylthio group having from 1 to 6 carbon atoms; and a cycloalkyloxy group having from 3 to 8 carbon atoms; and an aralkyl group having from 1 to 4 carbon atoms in the alkyl part and containing at least one said aryl group.

29. The method of claim 27, wherein:

R represents a hydrogen atom, a fluorine atom, a chlorine atom or a methyl group;

R¹ represents an amino group or an acetylamino group;

R² represents an unsubstituted phenyl group or a phenyl group which is substituted by at least one substituent selected from the group consisting of a halogen atom, an alkoxy group having from 1 to 4 carbon atoms, an alkylthio group having from 1 to 4 carbon atoms, an unsubstituted alkyl group having from 1 to 4 carbon atoms, a haloalkyl group having from 1 to 4 carbon atoms, a mercapto group, an alkanoylthio group having from 1 to 4 carbon atoms, a haloalkoxy group having from 1 to 4 carbon atoms and an alkenedioxy group having from 1 to 4 carbon atoms;

R³ represents a hydrogen atom, a halogen atom, an alkyl group having from 1 to 4 carbon atoms or a haloalkyl group having from 1 to 4 carbon atoms;

R⁴ represents a hydrogen atom;

an unsubstituted alkyl group having from 1 to 4 carbon atoms;

a substituted alkyl group having from 1 to 4 carbon atoms and substituted by at least one substituent selected from the group consisting of a hydroxy group, a halogen atom and an alkoxy group having from 1 to 6 carbon atoms;

a cycloalkyl group having from 3 to 6 carbon atoms;

an aryl group which has from 6 to 10 ring carbon atoms and which is unsubstituted or is substituted by at least one substituent selected from the group consisting of a hydroxy group; a halogen atom; an alkoxy group having from 1 to 6 carbon atoms; an alkyl group having from 1 to 6 carbon atoms and which is unsubstituted or substituted by at least one halogen atom; and a cycloalkyl group having from 3 to 8 carbon atoms; and an aralkyl group having from 1 to 4 carbon atoms in the alkyl part and containing at least one said aryl group.

30. The method of claim 27, wherein said anti-inflammatory and analgesic compound is selected from the group consisting of:

4-methyl-2-(4-methylphenyl)-1-(4-sulfamoylphenyl) pyrrole;

2-(4-methoxyphenyl)-4-methyl-1-(4-sulfamoylphenyl) pyrrole;

2-(4-chlorophenyl)-4-methyl-1-(4-sulfamoylphenyl) pyrrole;

4-methyl-2-(4-methylthiophenyl)-1-(4-sulfamoylphenyl) pyrrole;

2-(4-ethoxyphenyl)-4-methyl-1-(4-sulfamoylphenyl) pyrrole;

2-(4-methoxy-3-methylphenyl)-4-methyl-1-(4-sulfamoylphenyl)pyrrole;

2-(3-fluoro-4-methoxyphenyl)-4-methyl-1-(4-sulfamoylphenyl)pyrrole;

2-(3,4-dimethylphenyl)-4-methyl-1-(4-sulfamoylphenyl) pyrrole;

4-methyl-1-(4-methylthiophenyl)-2-(4-sulfamoylphenyl) pyrrole;

1-(4-acetylaminosulfonylphenyl)-4-methyl-2-(4-methoxyphenyl)pyrrole; and 1-(4-acetylaminosulfonylphenyl)-4-methyl-2-(3,4-dimethylphenyl)pyrrole.

31. A method of inhibiting bone resorption in a mammal comprising administering to a mammal in need thereof a pharmaceutically effective amount of a compound selected from the group consisting of the compound of formula (I), the compound of formula (II), and a pharmaceutically acceptable salt of said compounds as claimed in claim 1.

32. The method of claim 31, wherein:

R represents a hydrogen atom, a halogen atom or an alkyl group having from 1 to 4 carbon atoms;

R¹ represents a methyl group, an amino group or an acetylamino group;

R² represents an unsubstituted phenyl group or a phenyl group which is substituted by at least one substituent selected from the group consisting of a halogen atom; an alkoxy group having from 1 to 4 carbon atoms; an alkylthio group having from 1 to 4 carbon atoms; an unsubstituted alkyl group having from 1 to 4 carbon atoms; an alkyl group having from 1 to 4 carbon atoms and which is substituted by at least one substituent selected from the group consisting of a halogen atom, an alkoxy group having 1 to 4 carbon atoms and an alkylthio group having from 1 to 4 carbon atoms; a mercapto group; an alkanoylthio group having from 1 to 4 carbon atoms; a haloalkoxy group having from 1 to 4 carbon atoms and an alkylenedioxy group having from 1 to 4 carbon atoms;

$R^3$ represents a hydrogen atom, a halogen atom, an unsubstituted alkyl group having from 1 to 4 carbon atoms or a substituted alkyl group having from 1 to 4 carbon atoms and substituted by at least one substituent selected from the group consisting of a halogen atom, an alkoxy group having from 1 to 4 carbon atoms and an alkylthio group having from 1 to 4 carbon atoms;

$R^4$ represents a hydrogen atom;

an unsubstituted alkyl group having from 1 to 4 carbon atoms;

a substituted alkyl group having from 1 to 4 carbon atoms and substituted by at least one substituent selected from the group consisting of a hydroxy group, a halogen atom, an alkoxy group having from 1 to 6 carbon atoms and an alkylthio group having from 1 to 6 carbon atoms;

a cycloalkyl group having from 3 to 6 carbon atoms;

an aryl group which has from 6 to 10 ring carbon atoms and which is unsubstituted or is substituted by at least one substituent selected from the group consisting of a halogen atom; an alkoxy group having from 1 to 4 carbon atoms; an alkylthio group having from 1 to 4 carbon atoms; an unsubstituted alkyl group having from 1 to 6 carbon atoms and an alkyl group having from 1 to 6 carbon atoms and substituted by at least one substituent selected from the group consisting of a hydroxy group, a halogen atom, an alkoxy group having from 1 to 6 carbon atoms and an alkylthio group having from 1 to 6 carbon atoms; and an aralkyl group having from 1 to 4 carbon atoms in the alkyl part and containing at least one said aryl group.

33. The method of claim 31, wherein:

R represents a hydrogen atom, a fluorine atom, a chlorine atom or a methyl group;

$R^1$ represents an amino group or an acetylamino group;

$R^2$ represents an unsubstituted phenyl group or a phenyl group which is substituted by at least one substituent selected from the group consisting of a halogen atom, an alkoxy group having from 1 to 4 carbon atoms, an alkylthio group having from 1 to 4 carbon atoms, an alkyl group having from 1 to 4 carbon atoms, a haloalkyl group having from 1 to 4 carbon atoms, a mercapto group, an alkanoylthio group having from 1 to 4 carbon atoms, a haloalkoxy group having from 1 to 4 carbon atoms and an alkenedioxy group having from 1 to 4 carbon atoms;

$R^3$ represents a hydrogen atom, a halogen atom, an alkyl group having from 1 to 4 carbon atoms or a haloalkyl group having from 1 to 4 carbon atoms;

$R^4$ represents a hydrogen atom, an unsubstituted alkyl group having from 1 to 4 carbon atoms, a substituted alkyl group having from 1 to 4 carbon atoms and substituted by at least one substituent selected from the group consisting of a hydroxy group, a halogen atom and an alkoxy group having from 1 to 6 carbon atoms, a cycloalkyl group having from 3 to 6 carbon atoms, an aryl group which has from 6 to 10 ring carbon atoms and which is unsubstituted or is substituted by at least one substituent selected from the group consisting of a hydroxy group, a halogen atom, an alkoxy group having from 1 to 4 carbon atoms, an alkyl group having from 1 to 6 carbon atoms and which is unsubstituted or substituted by at least one halogen atom, and a cycloalkyloxy group having from 3 to 8 carbon atoms, an aralkyl group having from 1 to 4 carbon atoms in the alkyl part and containing at least one said aryl group.

34. The method of claim 31, wherein said active compound is selected from the group consisting of:

4-methyl-2-(4-methylphenyl)-1-(4-sulfamoylphenyl) pyrrole;

2-(4-methoxyphenyl)-4-methyl-1-(4-sulfamoylphenyl) pyrrole;

2-(4-chlorophenyl)-4-methyl-1-(4-sulfamoylphenyl) pyrrole;

4-methyl-2-(4-methylthiophenyl)-1-(4-sulfamoylphenyl) pyrrole;

2-(4-ethoxyphenyl)-4-methyl-1-(4-sulfamoylphenyl) pyrrole;

2-(4-methoxy-3-methylphenyl)-4-methyl-1-(4-sulfamoylphenyl)pyrrole;

2-(3-fluoro-4-methoxyphenyl)-4-methyl-1-(4-sulfamoylphenyl)pyrrole;

2-(3,4-dimethylphenyl)-4-methyl-1-(4-sulfamoylphenyl) pyrrole;

4-methyl-1-(4-methylthiophenyl)-2-(4-sulfamoylphenyl) pyrrole;

1-(4-acetylaminosulfonylphenyl)-4-methyl-2-(4-methoxyphenyl)pyrrole; and 1-(4-acetylaminosulfonylphenyl)-4-methyl-2-(3,4-dimethylphenyl)pyrrole.

35. A method of inhibiting leukotriene production in a mammal comprising administering to a mammal in need thereof a compound selected from the group consisting of the compound of formula (I), the compound of formula (II) and a pharmaceutically acceptable salt of said compound as claimed in claim 1.

36. The method of claim 35, wherein:

R represents a hydrogen atom, a halogen atom or an alkyl group having from 1 to 4 carbon atoms;

$R^2$ represents a methyl group, an amino group or an acetylamino group;

$R^2$ represents an unsubstituted phenyl group or a phenyl group which is substituted by at least one substituent selected from the group consisting of a halogen atom; an alkoxy group having from 1 to 4 carbon atoms; an alkylthio group having from 1 to 4 carbon atoms; an unsubstituted alkyl group having from 1 to 4 carbon atoms; an alkyl group having from 1 to 4 carbon atoms and which is substituted by at least one substituent selected from the group consisting of a halogen atom, an alkoxy group having from 1 to 4 carbon atoms and an alkylthio group having from 1 to 4 carbon atoms; a mercapto group; an alkanoythio group having from 1 to 4 carbon atoms; a haloalkoxy group having from 1 to 4 carbon atoms; and an alkylenedioxy group having from 1 to 4 carbon atoms;

$R^3$ represents a hydrogen atom, a halogen atom, an unsubstituted alkyl group having from 1 to 4 carbon atoms or a substituted alkyl group having from 1 to 4 carbon atoms and substituted by at least one substituent selected from the group consisting of a halogen atom, an alkoxy group having from 1 to 4 carbon atoms and an alkylthio group having from 1 to 4 carbon atoms;

$R^4$ represents a hydrogen atom;

an unsubstituted alkyl group having from 1 to 4 carbon atoms;

a substituted alkyl group having from 1 to 4 carbon atoms and substituted by at least one substituent selected from the group consisting of a hydroxy group, a halogen atom, an alkoxy group having from 1 to 6 carbon atoms and an alkylthio group having from 1 to 6 carbon atoms;

a cycloalkyl group having from 3 to 6 carbon atoms;

an aryl group which has from 6 to 10 ring carbon atoms and which is unsubstituted or is substituted by at least one substituent selected from the group consisting of a halogen atom; an alkoxy group having from 1 to 4 carbon atoms; an alkylthio group having from 1 to 4 carbon atoms; an unsubstituted alkyl group having from 1 to 6 carbon atoms; an alkyl group having from 1 to 6 carbon atoms and substituted by at least one substituent selected from the group consisting of a hydroxy group, a halogen atom, an alkoxy group having from 1 to 6 carbon atoms and an alkylthio group having from 1 to 6 carbon atoms; and a cycloalkyloxy group having from 3 to 8 carbon atoms; an aralkyl group having from 1 to 4 carbon atoms in the alkyl part and containing at least one said aryl group.

37. The method of claim 35, wherein:

R represents a hydrogen atom, a fluorine atom, a chlorine atom or a methyl group;

$R^1$ represents an amino group or an acetylamino group;

$R^2$ represents an unsubstituted phenyl group or a phenyl group which is substituted by at least one substituent selected from the group consisting of a halogen atom, an alkoxy group having from 1 to 4 carbon atoms, an alkylthio group having from 1 to 4 carbon atoms, an alkyl group having from 1 to 4 carbon atoms, a haloalkyl group having from 1 to 4 carbon atoms, a mercapto group, an alkanoylthio group having from 1 to 4 carbon atoms, a haloalkoxy group having from 1 to 4 carbon atoms and a alkylenedioxy group having from 1 to 4 carbon atoms;

$R^3$ represents a hydrogen atom, a halogen atom, an alkyl group having from 1 to 4 carbon atoms or a haloalkyl group having from 1 to 4 carbon atoms;

$R^4$ represents a hydrogen atom;

an unsubstituted alkyl group having from 1 to 4 carbon atoms;

a substituted alkyl group having from 1 to 4 carbon atoms and substituted by at least one substituent selected from the group consisting of a hydroxy group and an alkoxy group having from 1 to 6 carbon atoms;

a cycloalkyl group having from 3 to 6 carbon atoms;

an aryl group which has from 6 to 10 ring carbon atoms and which is unsubstituted or is substituted by at least one substituent selected from the group consisting of a hydroxy group; a halogen atom; an alkoxy group having from 1 to 6 carbon atoms; an unsubstituted alkyl group having from 1 to 6 carbon atoms; an alkyl group having from 1 to 6 carbon atoms and which is unsubstituted or substituted by at least one halogen atom; and a cycloalkyloxy group having from 3 to 8 carbon atoms; and an aralkyl group having from 1 to 4 carbon atoms in the alkyl part and containing at least one said aryl group.

38. The method of claim 35, wherein said active compound is selected from the group consisting of:

4-methyl-2-(4-methylphenyl)-1-(4-sulfamoylphenyl) pyrrole;

2-(4-methoxyphenyl)-4-methyl-1-(4-sulfamoylphenyl) pyrrole;

2-(4-chlorophenyl)-4-methyl-1-(4-sulfamoylphenyl) pyrrole;

4-methyl-2-(4-methylthiophenyl)-1-(4-sulfamoylphenyl) pyrrole;

2-(4-ethoxyphenyl)-4-methyl-1-(4-sulfamoylphenyl) pyrrole;

2-(4-methoxy-3-methylphenyl)-4-methyl-1-(4-sulfamoylphenyl)pyrrole;

2-(3-fluoro-4-methoxyphenyl)-4-methyl-1-(4-sulfamoylphenyl)pyrrole;

2-(3,4-dimethylphenyl)-4-methyl-1-(4-sulfamoylphenyl) pyrrole;

4-methyl-1-(4-methylthiophenyl)-2-(4-sulfamoylphenyl) pyrrole;

1-(4-acetylaminosulfonylphenyl)-4-methyl-2-(4-methoxyphenyl)pyrrole; and 1-(4-acetylaminosulfonylphenyl)-4-methyl-2-(3,4-dimethylphenyl)pyrrole.

39. A method of selectively inhibiting the activity of COX-2 in a mammal comprising administering to said mammal a pharmaceutically effective amount of a compound selected from the group consisting of the compound of formula (I), the compound of formula (II) and a pharmaceutically acceptable salt of said compounds as claimed in claim 1.

40. The method of claim 39, wherein:

R represents a hydrogen atom, a halogen atom or an alkyl group having from 1 to 4 carbon atoms;

$R^1$ represents a methyl group, an amino group or an acetylamino group;

$R^2$ represents an unsubstituted phenyl group or a phenyl group which is substituted by at least one substituent selected from the group consisting of a halogen atom; an alkoxy group having 1 to 4 carbon atoms; an alkylthio group having from 1 to 4 carbon atoms; an unsubstituted alkyl group having from 1 to 4 carbon atoms; an alkyl group having from 1 to 4 carbon atoms and which is substituted by at least one substituent selected from the group consisting of a halogen atom, an alkoxy group having 1 to 4 carbon atoms and an alkylthio group having from 1 to 4 carbon atoms; a mercapto group; an alkanoylthio group having from 1 to 4 carbon atoms; a haloalkoxy group having from 1 to 4 carbon atoms; and an alkylenedioxy group having from 1 to 4 carbon atoms;

$R^3$ represents a hydrogen atom, a halogen atom, an unsubstituted alkyl group having from 1 to 4 carbon atoms or a substituted alkyl group having from 1 to 4 carbon atoms and substituted by at least one substituent selected from the group consisting of a halogen atom, an alkoxy group having from 1 to 4 carbon atoms and an alkylthio group having from 1 to 4 carbon atoms;

$R^4$ represents a hydrogen atom;

an unsubstituted alkyl group having from 1 to 4 carbon atoms;

a substituted alkyl group having from 1 to 4 carbon atoms and substituted by at least one substituent selected from the group consisting of a hydroxy group, a halogen atom, an alkoxy group having from 1 to 6 carbon atoms and an alkylthio group having from 1 to 6 carbon atoms;

a cycloalkyl group having from 3 to 6 carbon atoms;

an aryl group which has from 6 to 10 ring carbon atoms and which is unsubstituted or is substituted by at least one substituent selected from the group consisting of a halogen atom; an alkoxy group having from 1 to 4 carbon atoms; an alkylthio group having from 1 to 4 carbon atoms; an unsubstituted alkyl group having from 1 to 6 carbon atoms; an alkyl group having from 1 to 6 carbon atoms and substituted by at least one substituent selected from the group consisting of a hydroxy group, a halogen atom, an alkoxy group having from 1 to 6 carbon atoms and an alkylthio group having from 1 to 6 carbon atoms; and a cycloalkyloxy group having from 3 to 8 carbon atoms; and an aralkyl group having from 1 to 4 carbon atoms in the alkyl part and containing at least one said aryl group.

41. The method of claim 39, wherein:

R represents a hydrogen atom, a fluorine atom, a chlorine atom or a methyl group;

$R^1$ represents an amino group or an acetylamino group;

$R^2$ represents an unsubstituted phenyl group or a phenyl group which is substituted by at least one substituent selected from the group consisting of a halogen atom, an alkoxy group having from 1 to 4 carbon atoms, an alkylthio group having from 1 to 4 carbon atoms, an alkyl group having from 1 to 4 carbon atoms, a haloalkyl group having from 1 to 4 carbon atoms, a mercapto group, an alkanoylthio group having from 1 to 4 carbon atoms, a haloalkoxy group having from 1 to 4 carbon atoms and a alkylenedioxy group having from 1 to 4 carbon atoms;

$R^3$ represents a hydrogen atom, a halogen atom, an alkyl group having from 1 to 4 carbon atoms or a haloalkyl group having from 1 to 4 carbon atoms;

$R^4$ represents a hydrogen atom;

an unsubstituted alkyl group having from 1 to 4 carbon atoms;

a substituted alkyl group having from 1 to 4 carbon atoms and substituted by at least one substituent selected from the group consisting of a hydroxy group, a halogen atom, and an alkoxy group having from 1 to 6 carbon atoms;

a cycloalkyl group having from 3 to 6 carbon atoms;

an aryl group which has from 6 to 10 ring carbon atoms and which is unsubstituted or is substituted by at least one substituent selected from the group consisting of a hydroxy group, a halogen atom; an alkoxy group having from 1 to 6 carbon atoms; an alkyl group having from 1 to 6 carbon atoms which is unsubstituted or substituted by at least one halogen atom; and cycloalkyloxy group having from 3 to 8 carbon atoms; and an aralkyl group having from 1 to 4 carbon atoms in the alkyl part and containing at least one said aryl group.

42. The method of claim 39, wherein said active compound is selected from the group consisting of:

4-methyl-2-(4-methylphenyl)-1-(4-sulfamoylphenyl) pyrrole;

2-(4-methoxyphenyl)-4-methyl-1-(4-sulfamoylphenyl) pyrrole;

2-(4-chlorophenyl)-4-methyl-1-(4-sulfamoylphenyl) pyrrole;

4-methyl-2-(4-methylthiophenyl)-1-(4-sulfamoylphenyl) pyrrole;

2-(4-ethoxyphenyl)-4-methyl-1-(4-sulfamoylphenyl) pyrrole;

2-(4-methoxy-3-methylphenyl)-4-methyl-1-(4-sulfamoylphenyl)pyrrole;

2-(3-fluoro-4-methoxyphenyl)-4-methyl-1-(4-sulfamoylphenyl)pyrrole;

2-(3,4-dimethylphenyl)-4-methyl-1-(4-sulfamoylphenyl) pyrrole;

4-methyl-1-(4-methylthiophenyl)-2-(4-sulfamoylphenyl) pyrrole;

1-(4-acetylaminosulfonylphenyl)-4-methyl-2-(4-methoxyphenyl)pyrrole; and 1-(4-acetylaminosulfonylphenyl)-4-methyl-2-(3,4-dimethylphenyl)pyrrole.

43. The compound of claim 8, wherein the phenyl group is substituted with 1 to 3 of said substituents.

* * * * *